United States Patent
Mills et al.

[11] Patent Number: 5,962,462
[45] Date of Patent: Oct. 5, 1999

[54] SPIRO-SUBSTITUTED AZACYCLES AS MODULATORS OF CHEMOKINE RECEPTOR ACTIVITY

[75] Inventors: Sander G. Mills, Scotch Plains; Malcolm Maccoss, Freehold; Martin S. Springer, Westfield, all of N.J.

[73] Assignee: Merck & Co., Inc., Rahway, N.J.

[21] Appl. No.: 08/989,947

[22] Filed: Dec. 12, 1997

Related U.S. Application Data

[60] Provisional application No. 60/032,735, Dec. 13, 1996, and provisional application No. 60/033,558, Dec. 20, 1996.

[51] Int. Cl.$^6$ .................. A61K 31/44; A61K 31/435; C07D 209/54; C07D 209/56
[52] U.S. Cl. .................. 514/278; 514/277; 546/15; 546/16; 546/17; 546/18
[58] Field of Search .................. 546/17, 18; 514/278

[56] References Cited

U.S. PATENT DOCUMENTS

| | | | |
|---|---|---|---|
| 4,233,307 | 11/1980 | Ono et al. | 424/267 |
| 5,091,387 | 2/1992 | Evans et al. | 546/17 |
| 5,536,716 | 7/1996 | Chen et al. | 514/215 |

FOREIGN PATENT DOCUMENTS

| | | |
|---|---|---|
| WO 94/17045 | 8/1994 | WIPO. |
| WO 94/29309 | 12/1994 | WIPO. |
| WO 96/10568 | 4/1996 | WIPO. |

Primary Examiner—José G. Dees
Assistant Examiner—Sabiha N. Qazi
Attorney, Agent, or Firm—J. Eric Thies; David L. Rose

[57] ABSTRACT

The present invention is directed to spiro-substituted azacycles of the Formula 1:

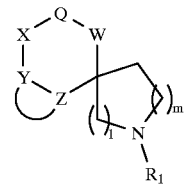

(wherein $R_1$, l, m, Q, W, X, Y, and Z are defined herein) which are useful as modulators of chemokine receptor activity. In particular, these compounds are useful as modulators of the chemokine receptors CCR-1, CCR-2, CCR-2A, CCR-2B, CCR-3, CCR-4, CCR-5, CXCR-3, and/or CXCR-4.

10 Claims, No Drawings

SPIRO-SUBSTITUTED AZACYCLES AS MODULATORS OF CHEMOKINE RECEPTOR ACTIVITY

CROSS REFERENCE TO RELATED APPLICATIONS

This application claims priority under 35 U.S.C. § 119(e) from U.S. Ser. No. 60/032/735, filed Dec. 13, 1996, and U.S. Ser. No. 60/033,558, filed Dec. 20, 1996.

BACKGROUND OF THE INVENTION

Chemokines are chemotactic cytokines that are released by a wide variety of cells to attract macrophages, T cells, eosinophils, basophils and neutrophils to sites of inflammation (reviewed in Schall, *Cytokine*, 3, 165–183 (1991) and Murphy, *Rev. Immun.*, 12, 593–633 (1994)). There are two classes of chemokines, C-X-C ($\alpha$) and C-C ($\beta$), depending on whether the first two cysteines are separated by a single amino acid (C-X-C) or are adjacent (C-C). The $\alpha$-chemokines, such as interleukin-8 (IL-8), neutrophil-activating protein-2 (NAP-2) and melanoma growth stimulatory activity protein (MGSA) are chemotactic primarily for neutrophils, whereas $\beta$-chemokines, such as RANTES, MIP-1$\alpha$, MIP-1$\beta$, monocyte chemotactic protein-1 (MCP-1), MCP-2, MCP-3 and eotaxin are chemotactic for macrophages, T-cells, eosinophils and basophils (Deng, et al., *Nature*, 381, 661–666 (1996)).

The chemokines bind specific cell-surface receptors belonging to the family of G-protein-coupled seven-transmembrane-domain proteins (reviewed in Horuk, *Trends Pharm. Sci.*, 15,159–165 (1994)) which are termed "chemokine receptors." On binding their cognate ligands, chemokine receptors transduce an intracellular signal though the associated trimeric G protein, resulting in a rapid increase in intracellular calcium concentration. There are at least seven human chemokine receptors that bind or respond to $\beta$-chemokines with the following characteristic pattern: CCR-1 (or "CKR-1" or "CC-CKR-1") [MIP-1$\alpha$, MIP-1$\beta$, MCP-3, RANTES] (Ben-Barruch, et al.,*J. Biol. Chem.*, 270, 22123–22128 (1995); Beote, et al, *Cell*, 72, 415–425 (1993)); CCR-2A and CCR-2B (or "CXR-2A"/"CKR-2A" or "CC-CKR-2A"/"CC-CKR-2A") [MCP-1, MCP-3, MCP-4]; CCR-3 (or "CKR-3" or "CC-CKR-3") [eotaxin, RANTES, MCP-3] (Combadiere, et al.,*J. Biol. Chem.*, 270, 16491–16494 (1995); CCR-4 (or "CKR-4" or "CC-CKR-4") [MIP-1$\alpha$, RANTES, MCP-1] (Power, et al., *J. Biol. Chem.*, 270,19495–19500 (1995)); CCR-5 (or "CKR-5" or "CC-CKR-5") [MIP-1$\alpha$, RANTES, MIP-1$\beta$](Sanson, et al., *Biochemistry* 36, 3362–3367 (1996)); and the Dufly blood-group antigen [RANTES, MCP-1] (Chaudhun, et al.,*J. Biol. Chem.*, 269, 7835–7838 (1994)). The $\beta$-chemokines include eotaxin, MIP ("macrophage inflammatory protein"), MCP ("monocyte chemoattractant protein") and RANTES ("regulation-upon-activation, normal T expressed and secreted").

Chemokine receptors, such as CCR-1, CCR-2, CCR-2A, CCR-2B, CCR-3, CCR-4, CCR-5, CXCR-3, CXCR-4, have been implicated as being important mediators of inflammatory and immunoregulatory disorders and diseases, including asthma and allergic diseases, as well as autoimmune pathologies such as rheumatoid arthritis and atherosclerosis. For example, the chemokine receptor COR-3 plays a pivotal role in attracting eosinophils to sites of allergic inflammation. Accordingly, agents which modulate chemokine receptors would be useful in such disorders and diseases.

A retrovirus designated human immunodeficiency virus (HIV-1) is the etiological agent of the complex disease that includes progressive destruction of the immune system (acquired immune deficiency syndrome; AIDS) and degeneration of the central and peripheral nervous system. This virus was previously known as LAV, HTLV-III, or ARV.

Certain compounds have been demonstrated to inhibit the replication of HIV, including soluble CD4 protein and synthetic derivatives (Smith, et al., *Science*, 238, 1704–1707 (1987)), dextran sulfate, the dyes Direct Yellow 50, Evans Blue, and certain azo dyes (U.S. Pat. No. 5,468,469). Some of these antiviral agents have been shown to act by blocking the binding of gp120, the coat protein of HIV, to its target, the CD4 gyycoprotein of the cell.

Entry of HIV-1 into a target cell requires cell-surface CD4 and additional host cell cofactors. Fusin has been identified as a cofactor required for infection with virus adapted for growth in transformed T-cells, however, fusin does not promote entry of macrophagetropic viruses which are believed to be the key pathogenic strains of HIV in vivo. It has recently been recognized that for efficient entry into target cells, human immunodeficiency viruses require the chemokine receptors CCR-5 and CXCR-4, as well as the primary receptor CD4 (Levy, *N. Engl. J. Med.*, 335(20), 1528–1530 (Nov. 14, 1996). The principal cofactor for entry mediated by the envelope glycoproteins of primary macrophage-trophic strains of HIV-1 is CCR5, a receptor for the $\beta$-chemokines RANTES, MIP-1$\alpha$ and MIP-1$\beta$ (Deng, et al., *Nature*, 381, 661–666 (1996)). HIV attaches to the CD4 molecule on cells through a region of its envelope protein, gp120. It is believed that the CD-4 binding site on the gp120 of HIV interacts with the CD4 molecule on the cell surface, and undergoes conformational changes which allow it to bind to another cell-surface receptor, such as CCR5 and/or CXCR-4. This brings the viral envelope closer to the cell surface and allows interaction between gp41 on the viral envelope and a fusion domain on the cell surface, fusion with the cell membrane, and entry of the viral core into the cell. Macrophage-tropic HIV and SIV envelope proteins have been shown to induce a signal through CCR-5 on CD4+ cells resulting in chemotaxis of T cells which may enhance the replication of the virus (Weissman, et al., *Nature*, 389, 981–985 (1997)). It has been shown that $\beta$-chemokine ligands prevent HIV-1 from fusing with the cell (Dragic, et al., *Nature*, 381, 667–673 (1996)). It has further been demonstrated that a complex of gp120 and soluble CD4 interacts specifically with CCR-5 and inhibits the binding of the natural CCR-5 ligands MIP-1$\alpha$ and MIP-1$\beta$ (Wu, et al., *Nature*, 384, 179–183 (1996); Trkola, et al., *Nature*, 384,184–187 (1996)).

Humans who are homozygous for mutant CCR-5 receptors which do not serve as co-receptors for HIV-1 in vitro apper to be unusually resistant to HIV-1 infection and are not immunocompromised by the presence of this genetic variant (*Nature*, 382, 722–725 (1996)). Similarly, an alteration in the CCR-2 gene, CCR2-641, can prevent the onset of full-blown AIDS (Smith, et al., *Science*, 277, 959–965 (1997). Absence of CCR-5 appears to confer protection from HIV-1 infection (*Nature*, 382, 668–669 (1996)). An inherited mutation in the gene for CCR5, Delta 32, has been shown to abolish functional expression of the gene and individuals homozygous for the mutation are apparently not susceptible to HIV infection. Other chemokine receptors may be used by some strains of HIV-1 or may be favored by non-sexual routes of transmission. Although most HIV-1 isolates studied to date utilize CCR-5 or fusin, some can use both as well as the related CCR-2B and CCR-3 as co-receptors (*Nature Medicine*, 2(11), 1240–1243 (1996)). Nevertheless, drugs targeting chemokine receptors may not be unduly compromised by the genetic diversity of HIV-1 (Zhang, et al., Nature, 383, 768 (1996)). The β-chemokine macrophage-derived chemokine (MDC) has been shown to inhibit HIV-1 infection (Pal, et al., Science, 278 (5338), 695–698 (1997). The chemokines RANTES, MIP-1 , MIP-1β, vMIP-I, vMIP-II, SDF-1 have also been shown to suppress HIV. A derivative of RANTES, (AOP)-RANTES, is a subnanomolar antagonist of CCR-5 function in monocytes (Simmons, et al., Science, 276, 276–279 (1997)). Monoclonal antibodies to CCR-5 have been reported to block infection of cells by HIV in vitro. Accordingly, an agent which could block chemokine receptors in humans who possess normal chemokine receptors should prevent infection in healthy individuals and slow or halt viral progression in infected patients (see Science, 275, 1261–1264 (1997)). By focusing on the host's cellular immune response to HIV infection, better therapies towards all subtypes of HIV may be provided. These results indicate that inhibition of chemokine receptors presents a viable method for the prevention or treatment of infection by HIV V and the prevention or treatment of AIDS.

The peptides eotaxin, RANTES, MIP-1α, MIP-1β, MCP-1, and MCP-3 are known to bind to chemokine receptors. As noted above, the inhibitors of HIV-1 replication present in supernatants of CD8+ T cells have been characterized as the β-chemokines RANTES, MIP-1α and MIP-1β. PCT Patent Publications WO 94/17045 (published Aug. 4, 1994), WO 94/29309 (published Dec. 22, 1994), and WO 96/10568 (published Apr. 11, 1996) disclose certain azacycles as tachykinin antagonists.

SUMMARY OF THE INVENTION

The present invention is directed to compounds which are modulators of chemokine receptor activity and are useful in the prevention or treatment of certain inflammatory and immunoregulatory disorders and diseases, including asthma and allergic diseases, as well as autoimmune pathologies such as rheumatoid arthritis and atherosclerosis. The invention is also directed to pharmaceutical compositions comprising these compounds and the use of these compounds and compositions in the prevention or treatment of such diseases in which chemokine receptors are involved.

The present invention is further concerned with compounds which inhibit the entry of human immunodeficiency virus (HIV) into target cells and are of value in the prevention of infection by HIV, the treatment of infection by HIV and the prevention and/or treatment of the resulting acquired immune deficiency syndrome (AIDS). The present invention also relates to pharmaceutical compositions containing the compounds and to a method of use of the present compounds and other agents for the prevention and treatment of AIDS and viral infection by HIV.

DETAILED DESCRIPTION OF THE INVENTION

The present invention is directed to compounds of Formula I:

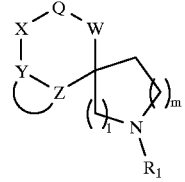

wherein the nitrogen expressly shown above is optionally quaternized with $C_{1-4}$alkyl or phenyl $C_{1-4}$alkyl or is optionally present as the N-oxide (N+O−), and
wherein:
l and m are each independently 0, 1, 2, 3, 4, or 5, with the proviso that the sum of l+m is equal to 1, 2, 3, 4, or 5;
$R_1$ is selected from a group consisting of:
(1) hydrogen, and
(2) linear or branched $C_{1-8}$ alkyl, linear or branched $C_{2-8}$ alkenyl, or linear or branched $C_{2-8}$ alkynyl, wherein the $C_{1-8}$ alkyl, $C_{2-8}$ alkenyl or $C_{2-8}$ alkynyl is optionally mono, di, tri or tetra substituted, wherein the substitutents are independently selected from:
(a) hydroxy,
(b) oxo,
(c) cyano,
(d) halogen, which is —Br, —Cl, —I, or —F,
(e) trifluoromethyl,
(f) phenyl or mono, di or trisubstituted phenyl, wherein the substitutents are independently selected from:
(1') phenyl,
(2') hydroxy,
(3') $C_{1-3}$alkyl,
(4') cyano,
(5') halogen,
(6') trifluoromethyl,
(7') —$NR_6COR_7$, wherein $R_6$ and $R_7$ are independently selected from:
(i) hydrogen,
(ii) $C_{1-6}$ alkyl, or mono or disubstituted $C_{1-6}$ alkyl, the substitutents independently selected from:
(a') phenyl,unsubstituted or substituted with hydroxy, $C_{1-3}$alkyl, cyano, halogen, trifluoromethyl or $C_{1-4}$alkoxy,
(b') hydroxy,
(c') oxo,
(d') cyano,
(e') halogen, and
(f') trifluoromethyl,
(iii) phenyl, pyridinyl or thiophene, or mono, di or trisubstituted phenyl, pyridinyl or thiophene, wherein the substitutents are independently selected from:
(a') hydroxy,
(b') $C_{1-4}$alkyl,
(c') cyano,
(d') halogen, and
(e') trifluoromethyl,
(iv) $C_{1-3}$alkyloxy,
or $R_6$ and $R_7$ are joined together to form a 5-, 6-, or 7-membered monocyclic saturated ring containing 1 or 2 heteroatoms independently selected from nitrogen, oxygen, and sulfur, and in which the ring is unsubstituted or mono or disubstituted, wherein the substituents are independently selected from:

(a') hydroxy,
(b') oxo,
(c') cyano,
(d') halogen, and
(e') trifluoromethyl,
(8') —NR$_6$CO$_2$R$_7$,
(9') —NR$_6$CONHR$_7$,
(10') —NR$_6$S(O)jR$_7$, wherein j is 1 or 2,
(11') —CONR$_6$R$_7$,
(12') —COR$_6$,
(13') —CO$_2$R$_6$,
(14') —OR$_6$,
(15') —S(O)$_k$R$_6$ wherein k is 0, 1 or 2,
(16') heteroaryl, wherein heteroaryl is selected from the group consisting of:
(a') benzimidazolyl,
(b') benzofuranyl,
(c') benzoxazolyl,
(d') furanyl,
(e') imidazolyl,
(f') indolyl,
(g') isoxazolyl,
(h') isothiazolyl,
(i') oxadiazolyl,
(i') oxazolyl,
(k') pyrazinyl,
(l') pyrazolyl,
(m') pyridyl,
(n') pyrimidyl,
(o') pyrrolyl,
(p') quinolyl,
(q') tetrazolyl,
(r') thiadiazolyl,
(s') thiazolyl,
(t') thienyl, and
(u') triazolyl,
wherein the heteroaryl is unsubstituted or mono, di or trisubstituted, wherein the substituents are independently selected from:
(i') hydroxy,
(ii') oxo,
(iii') cyano,
(iv') halogen, and
(v') trifluoromethyl,
(g) —NR$_6$R$_7$,
(h) —NR$_6$COR$_7$,
(i) —NR$_6$CO$_2$R$_7$,
(j) —NR$_6$CONHR$_7$,
(k) —NR$_6$S(O)jR$_7$,
(l) —CONR$_6$R$_7$,
(m) —COR$_6$,
(n) —CO$_2$R$_6$,
(o) —OR$_6$,
(p) —S(O)$_k$R$_6$,
(q) —NR$_6$CO-heteroaryl, wherein heteroaryl is defined above,
(r) —NR$_6$S(O)j-heteroaryl, wherein heteroaryl is defined above,
(s) heteroaryl, wherein heteroaryl is defined above;
wherein the nitrogen of definition R$_1$ 2(g) as defined above is optionally quaternized with C$_{1-4}$alkyl or phenyl C$_{1-4}$alkyl or is optionally present as the N-oxide (N+O—);

W is selected from the group consisting of:
(1) a covalent bond
(2) C$_{1-3}$ alkyl, unsubstituted or substituted with a substituent selected from:
(a) oxo,
(b) hydroxy
(c) —OR$_6$,
(d) halogen,
(e) trifluoromethyl,
(f) phenyl or mono, di or trisubstituted phenyl, wherein the substitutents are independently selected from:
(1') hydroxy,
(2') cyano,
(3') halogen,
(4') trifluoromethyl,
(5') —S(O)$_k$,
(6') —(C$_{1-3}$ alkyl)—S(O)$_k$,
(7') —S(O)$_k$—(C$_{1-2}$ alkyl),
(8') —S(O)k—NH,
(9') —S(O)j—NE(C$_{1-2}$ alkyl),
(10') —S(O)j—NR$_6$,
(11') —S(O)j—NR$_6$—(C$_{1-2}$ alkyl),
(12') —CONH,
(13') —CONH—(C$_{1-2}$ alkyl),
(14') —CONR$_6$,
(15') —CONR$_6$—(C$_{1-2}$ alkyl),
(16') —CO$_2$, and
(17') —CO$_2$—(C$_{1-2}$ alkyl);
Q is selected from:
—NR$_2$—, —O—, —S—, —S(O)—, and —SO$_2$—,
with the proviso that when W is a covalent bond and X is C$_{1-3}$alkyl, then Q must be —NR$_2$—;
R$_2$ is selected from a group consisting of:
(1) hydrogen,
(2) C$_{1-8}$ linear or branched alkyl, unsubstituted, monosubstituted or multiply substituted with a substituent independently selected from:
(a) —OR$_6$,
(b) oxo,
(c) —NHCOR$_6$,
(d) —NR$_6$R$_7$,
(e) —CN,
(f) halogen,
(g) —CF$_3$,
(h) -phenyl, unsubstituted or substituted, wherein the substitutents are independently selected from:
(1') hydroxy,
(2') cyano,
(3') halogen, and
(4') trifluoromethyl,
(3) —S(O)R$_8$, wherein R$_8$ is C$_{1-6}$ linear or branched alkyl, unsubstituted, mono di or trisubstituted with a substituent independently selected from:
(a) hydroxy,
(b) oxo,
(c) cyano,
(d) —OR$_6$,
(e) —NR$_6$R$_7$,
(f) —NR$_6$COR$_7$,
(g) halogen,
(h) —CF$_3$,
(i) -phenyl, or mono, di or trisubstituted phenyl, wherein the substituents are independently selected from:

(1') hydroxy,
(2') oxo,
(3') cyano,
(4') —NHR$_6$,
(5') —NR$_6$R$_7$,
(6') —NR$_6$COR$_7$,
(7') halogen,
(8') —CF$_3$, and
(9') C$_{1-3}$ alkyl,
(4) —SO$_2$R$_8$,
(5) —COR$_8$,
(6) —CO$_2$R$_8$, and
(7) —CONR$_7$R$_8$;
X is selected from the group consisting of:
(1) a covalent bond,
(2) C$_{1-3}$ alkyl, unsubstituted or substituted with a substituent selected from:
  (a) oxo,
  (b) —OR$_6$,
  (c) halogen,
  (d) trifluoromethyl, and
  (e) phenyl or mono, di or trisubstituted phenyl, wherein the substitutents are independently selected from:
    (1') —OR$_6$,
    (2') halogen, and
    (3') trifluoromethyl,
(3) —S(O)$_k$—,
(4) —(C$_{1-3}$ alkyl)S(O)$_k$—,
(5) —S(O)$_k$(C$_{1-2}$ alkyl)—,
(6) —NHS(O)j—,
(7) —NH(C$_{1-2}$ alkyl)S(O)j—,
(8) —S(O)jNR$_6$—,
(9) —S(O)j—NR$_6$—(C$_{1-2}$ alkyl)—,
(10) —NHCO—,
(11) —NHCO—(C$_{1-2}$ alkyl)—,
(12) —NR$_6$CO—,
(13) —NR$_6$—(C$_{1-2}$ alkyl)CO—,
(14) —O(CO)—, and
(15) —(C$_{1-2}$ alkyl)O(CO)—,
Y-Z considered together are 2 adjoining atoms of the ring

wherein the ring is phenyl, naphthyl or heteroaryl, wherein the heteroaryl is as defined above;
and pharmaceutically acceptable salts thereof.

Preferred compounds for use in the present invention include those of Formula I wherein:
the sum of l+m is equal to 2, 3, or 4;
R$_1$ is selected from a group consisting of:
  C$_1$, C$_2$, C$_3$, C$_4$, C$_6$ or C$_6$ linear or branched alkyl, di or tri substituted, wherein the substitutents are independently selected from:
    (a) hydroxy,
    (b) —Cl or —F,
    (c) phenyl or mono, di or trisubstituted phenyl, wherein the substitutents are independently selected from:
      (1') phenyl,
      (2') hydroxy,
      (3') C$_{1-3}$alkyl,
      (4') cyano,
      (5') halogen,
      (6') trifluoromethyl, (d) —NR$_6$COR$_7$, wherein:
      R$_6$ is hydrogen or C$_{1-3}$ alkyl, and
      R$_7$ is selected from: phenyl, pyridinyl, thiophene, phenylC$_{1-3}$alkyl, pyridinylC$_{1-3}$alkyl and thiopheneC$_{1-3}$alkyl, wherein the phenyl, pyridinyl or thiophene, phenylC$_{1-3}$alkyl, pyridinylC$_{1-3}$alkyl or thiophenelC$_{1-3}$alkyl, is optionally substituted with a substitutent selected from:

—Cl, —F, —CF$_3$ and C$_{1-3}$alkyl, (e) —NR$_6$S(O)$_j$R$_7$,
    (f) —COR$_6$,
    (h) —OR$_6$;
W is selected from the group consisting of:
(1) a covalent bond, and
(2) C$_{1-3}$ alkyl, unsubstituted or substituted with oxo;
Q is selected from:
  —NR$_2$—, —O—, —S—, —S(O)—, and —SO$_2$—;
R$_2$ is selected from a group consisting of:
(1) hydrogen,
(2) C$_1$, C$_2$, C$_3$ or C$_4$ linear or branched alkyl, unsubstituted, monosubstituted or disubstituted with a substituent independently selected from:
  (a) —OR$_6$,
  (b) oxo,
  (c) -phenyl,
  (d) —NR$_6$R$_7$,
(3) —SO$_2$R$_8$, wherein R$_8$ is unsubstituted C$_{1-6}$ linear or branched alkyl,
(4) —COR$_8$,
(5) —CO$_2$R$_8$, and
(6) —CONR$_7$R$_8$;
X is selected from the group consisting of
(1) a covalent bond, and
(2) methylene or 1-ethylene or 2-ethylene;
Y-Z considered together are 2 adjoining atoms of the ring

wherein the ring is phenyl;
and pharmaceutically acceptable salts thereof.

More preferred compounds for use in the present invention include those compounds of Formula I wherein:
the sum of 1+m is equal to 2 or 3; and
Q is —NR$_2$—;
and pharmaceutically acceptable salts thereof.

More preferred compounds for use in the present invention also include those compounds of Formula I wherein:
the sum of l+m is 3;
R$_1$ is selected from:

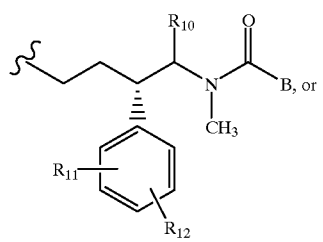

-continued

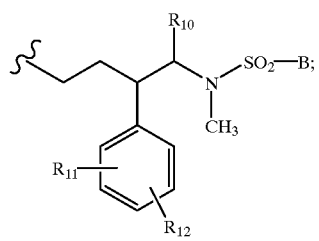

where B is selected from:
(1) phenyl, or mono di or trisubstituted pheny,l wherein the substitutents are independently selected from:
chloro, fluoro, methyl, phenyl, and —CF₃;
(2) —CH₂-phenyl, or mono or disubstituted —CH₂phenyl, wherein the substitutents on phenyl are independently selected from:
chloro, fluoro, methyl, phenyl, and —CF₃;
(3) pyridyl, or mono di or trisubstituted pyridyl, wherein the substitutents on pyridyl are independently selected from:
chloro, fluoro, methyl, phenyl, and —CF₃; and
(4) thiophene, or mono or disubstituted thiophene, wherein the substitutents on thiophene are independently selected from:
chloro, fluoro, methyl, phenyl, and —CF₃;
$R_{10}$ is selected from: hydrogen, $C_{1-3}$alkyl, and phenyl;
$R_{11}$ and $R_{12}$ are independently selected from:
hydrogen, halogen, methyl, phenyl or CF₃;
and pharmaceutically acceptable salts thereof.

More preferred compounds for use in the present invention also include those compounds of Formula I wherein:
B is phenyl, or mono di or trisubstituted phenyl wherein the substitutents on phenyl are independently selected from:
chloro, methyl, phenyl and —CF₃.

Even more preferred compounds for use in the present invention include those of Formula I wherein B is unsubstituted phenyl, 3-chlorophenyl, 3-fluorophenyl or unsubstituted thiophene.

Preferred compounds for use in the present invention also include those compounds of Formula I:

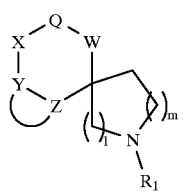

I wherein the group:

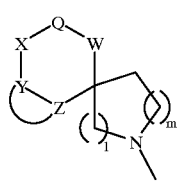

is an optionally mono di or trisubstituted structure selected from the group consisting of:

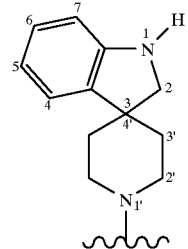

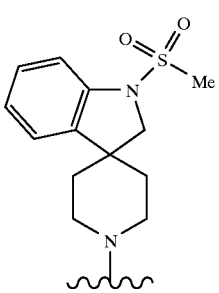

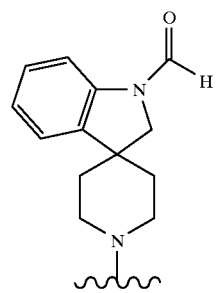

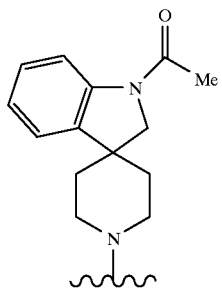

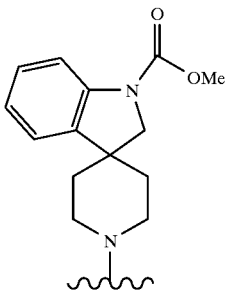

-continued
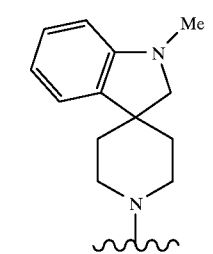
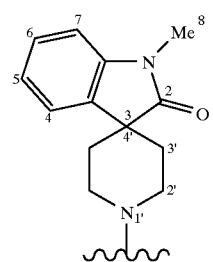
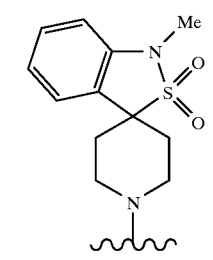
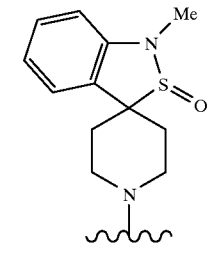
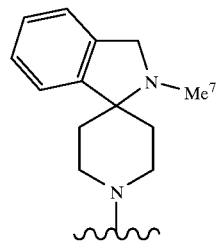
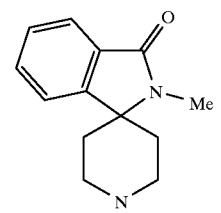
-continued
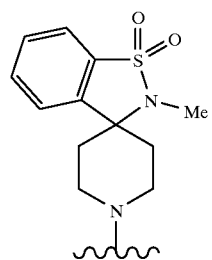
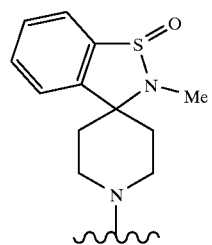
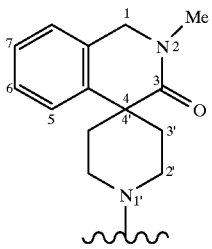
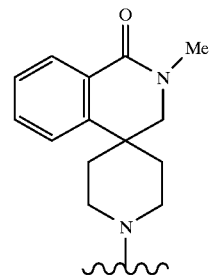
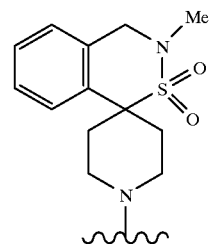
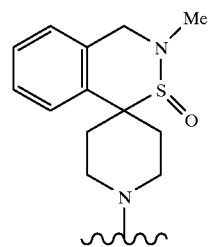

-continued
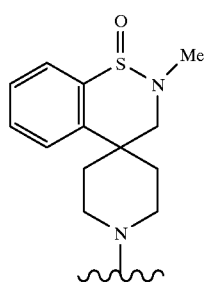
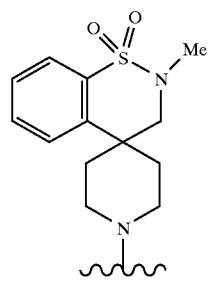
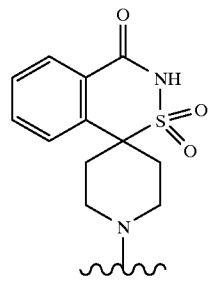
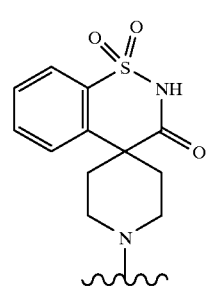
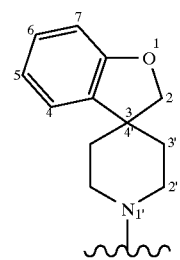
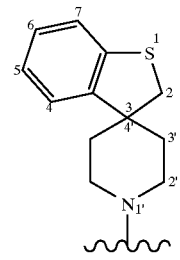
-continued
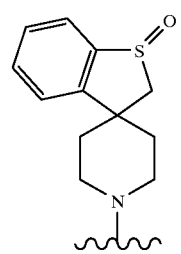
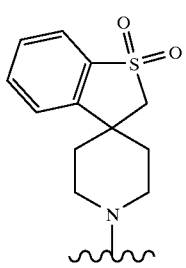
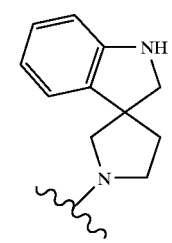
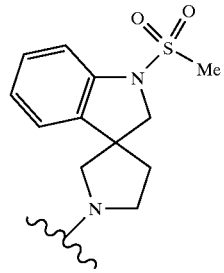
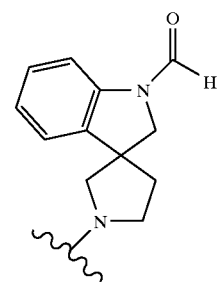
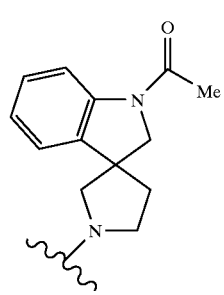

-continued
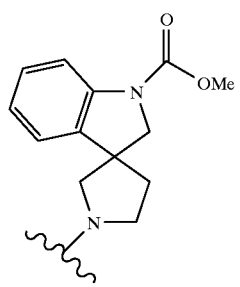
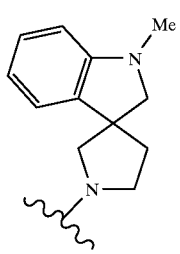
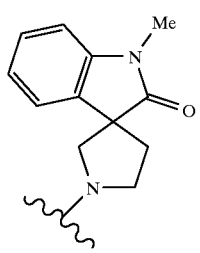
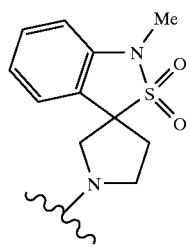
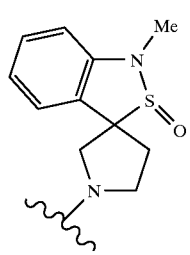
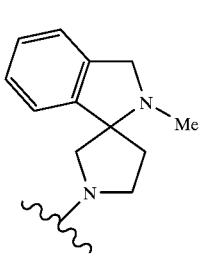
-continued
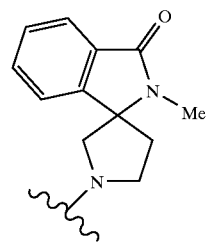
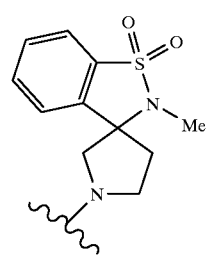
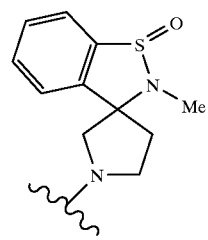
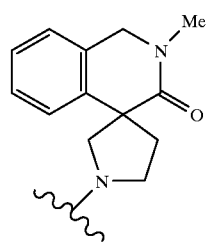
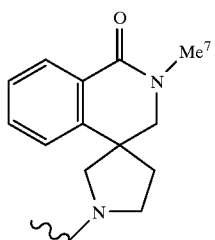
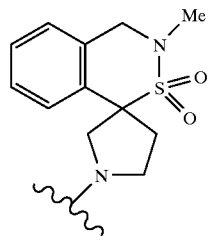

-continued
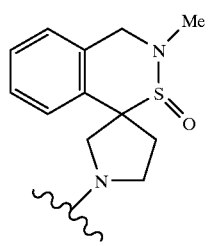
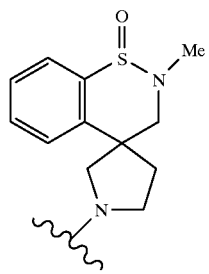
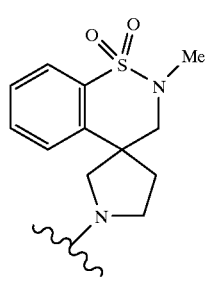
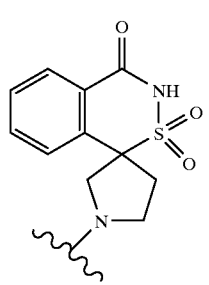
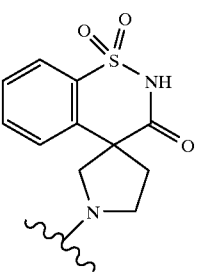
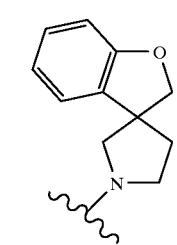
-continued
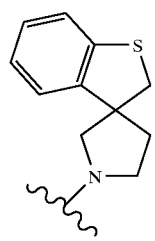
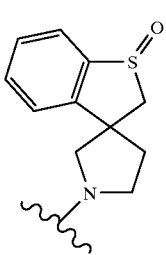
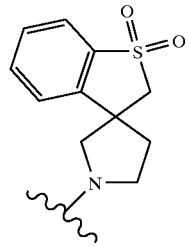
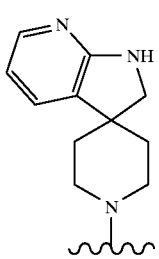
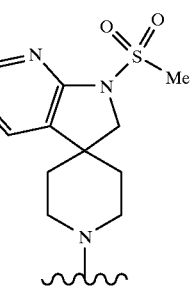
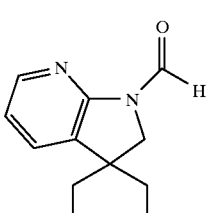

-continued
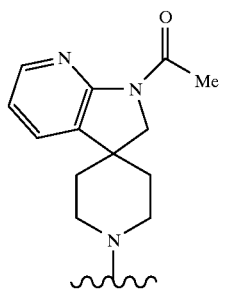
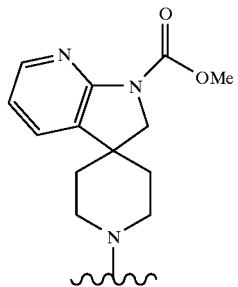
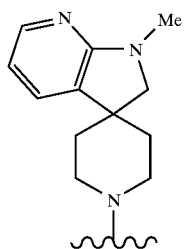
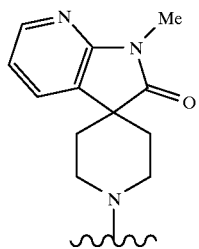
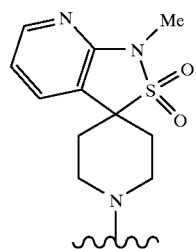
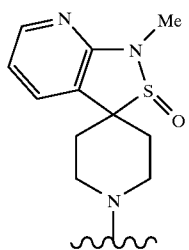
-continued
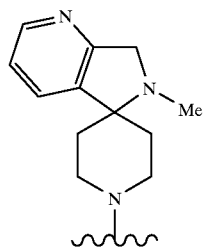
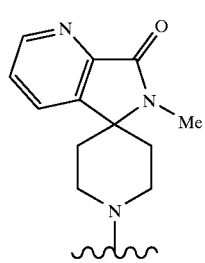
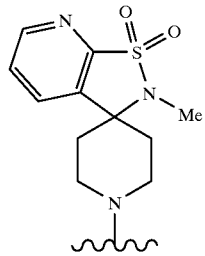
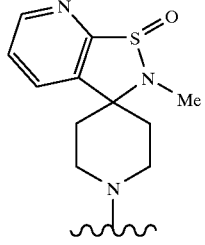
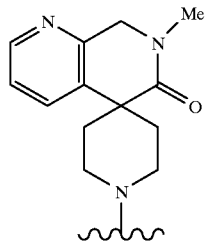
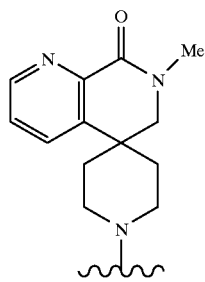

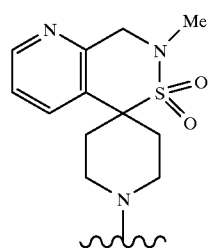
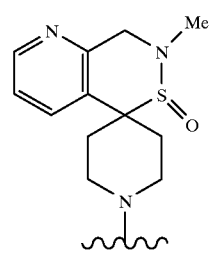
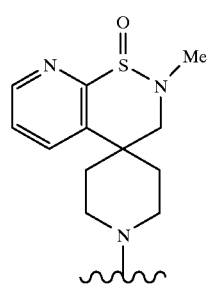
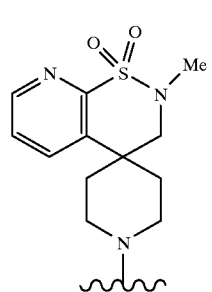
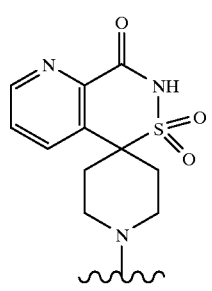
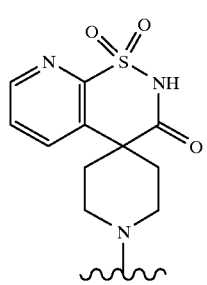
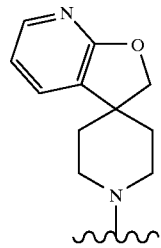
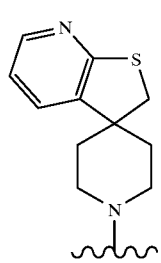
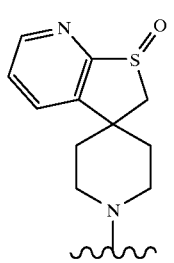
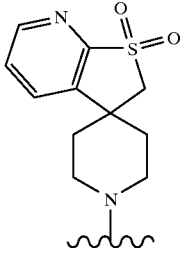

-continued
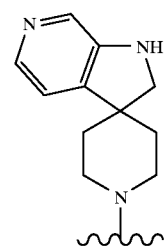
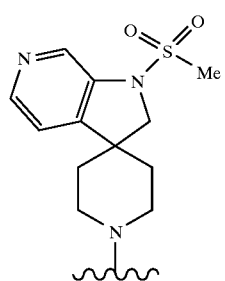
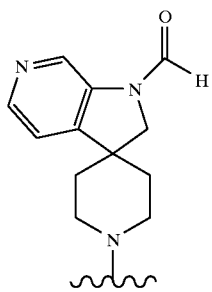
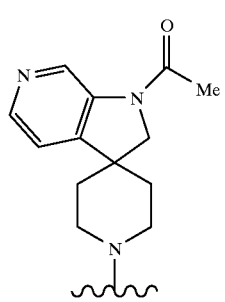
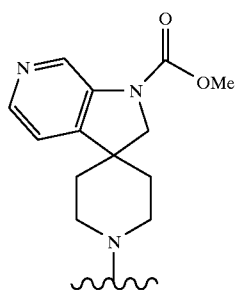
-continued
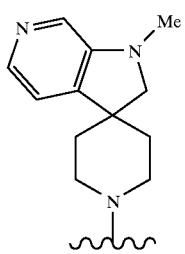
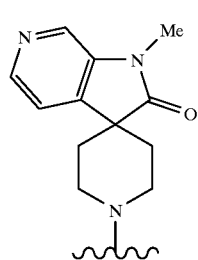
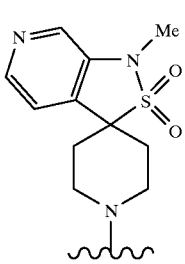
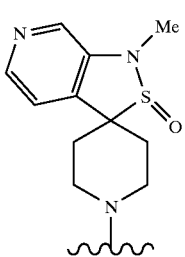
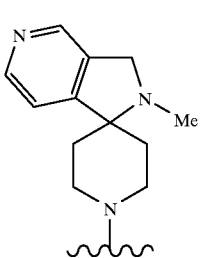

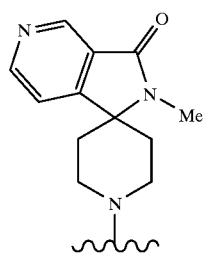
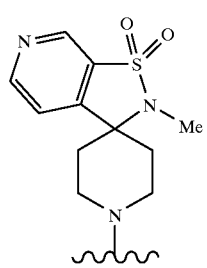
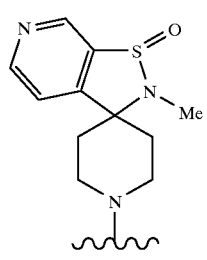
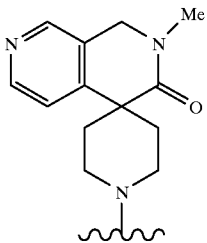
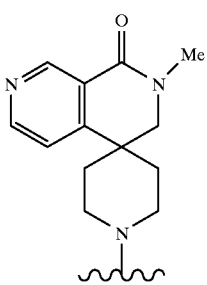
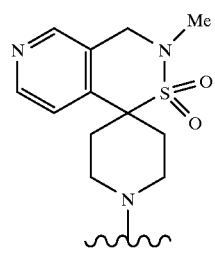
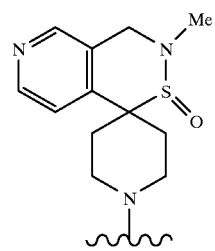
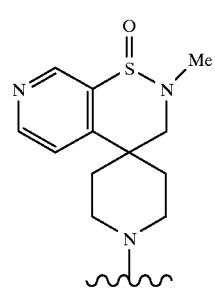
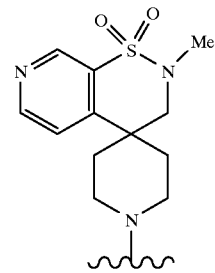
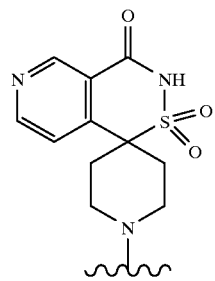

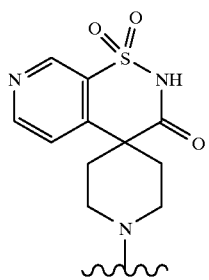
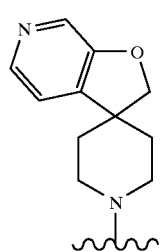
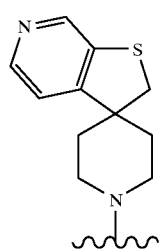
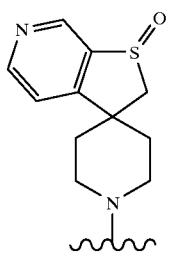
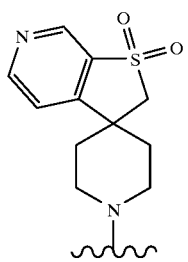
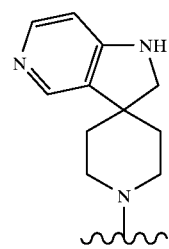
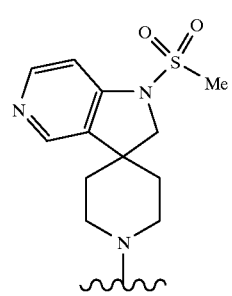
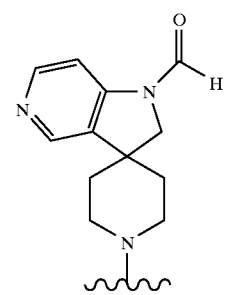
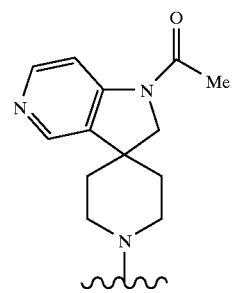
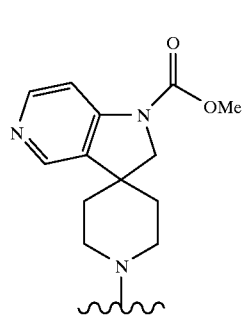

-continued
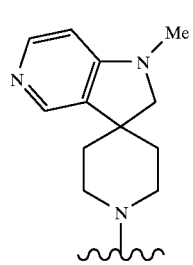
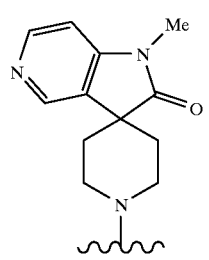
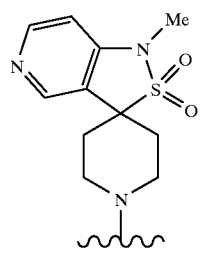
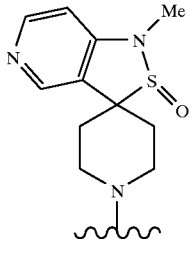
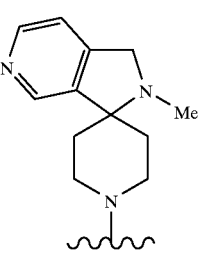
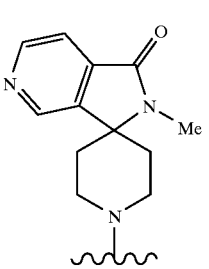
-continued
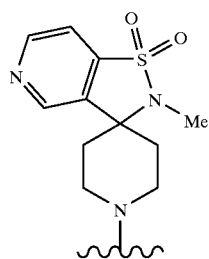
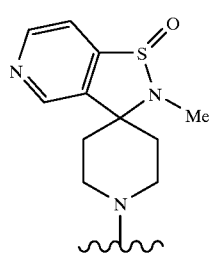
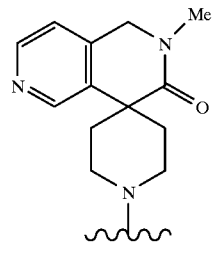
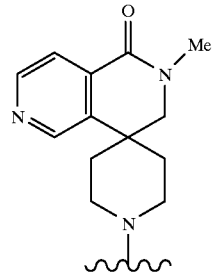
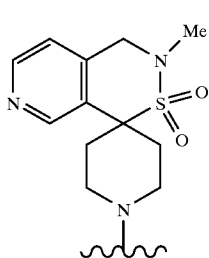
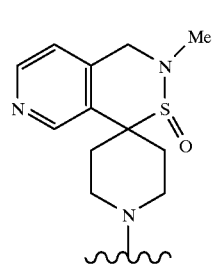

31
-continued
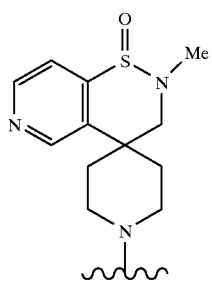
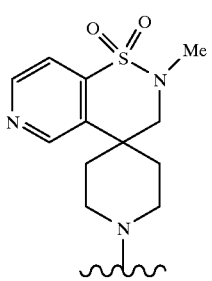
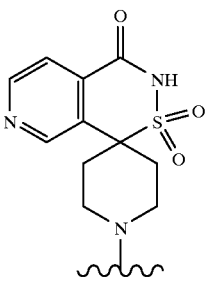
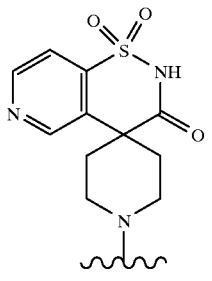
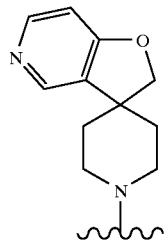
32
-continued
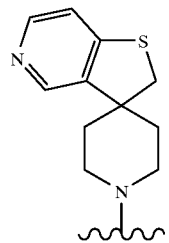
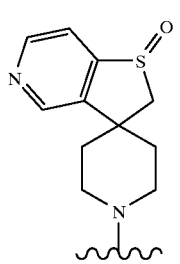
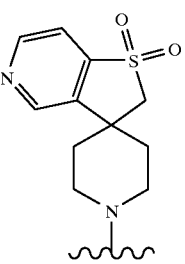
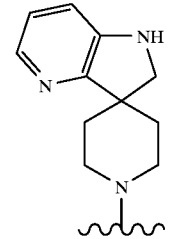
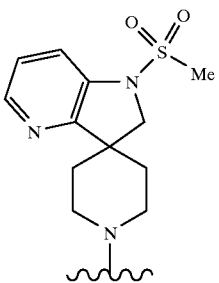

-continued
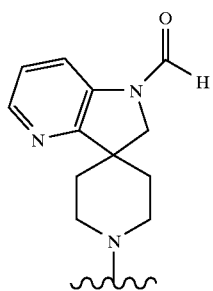
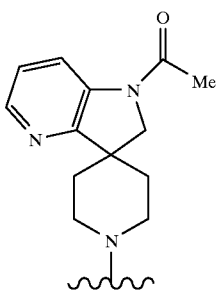
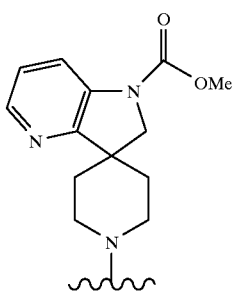
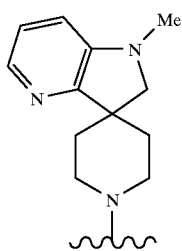
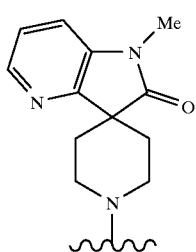
-continued
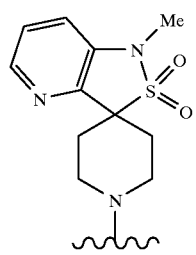
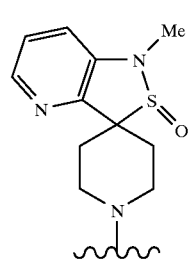
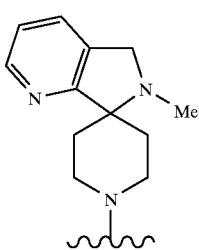
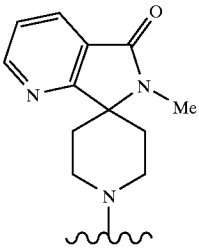
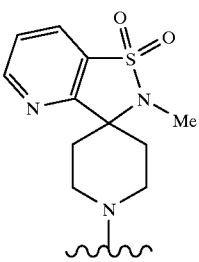

-continued
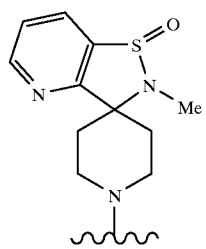
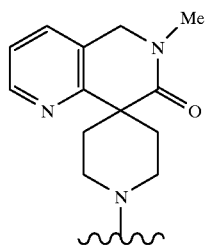
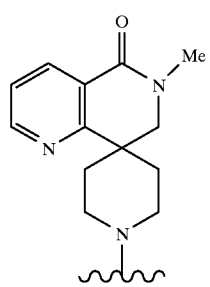
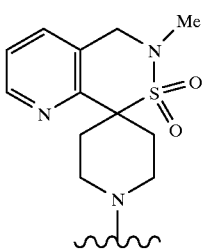
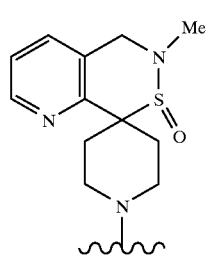
-continued
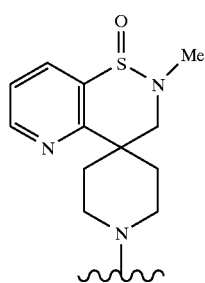
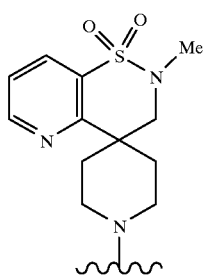
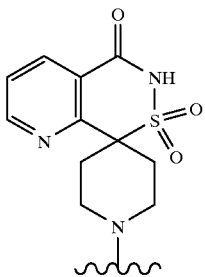
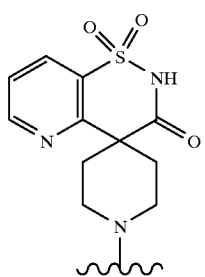
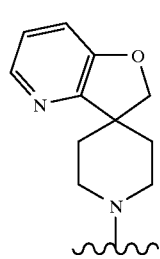

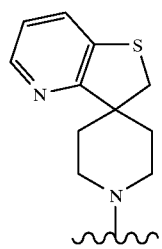
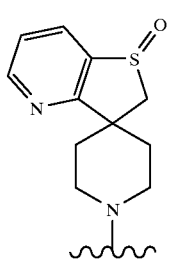
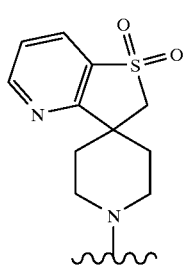
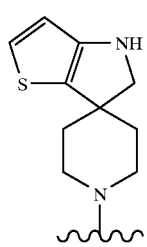
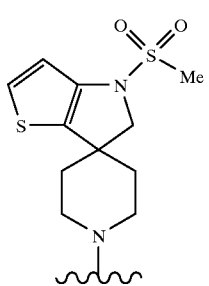
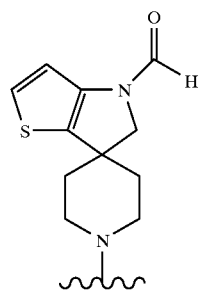
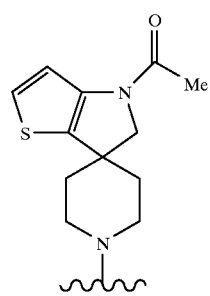
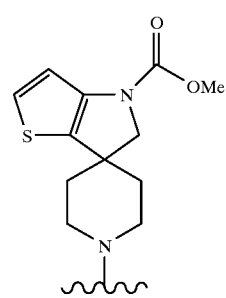
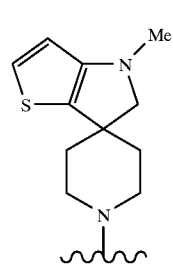
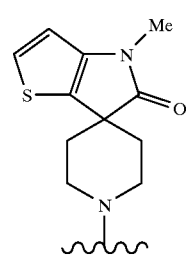

-continued
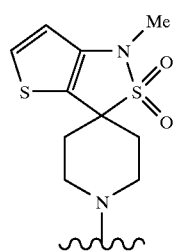
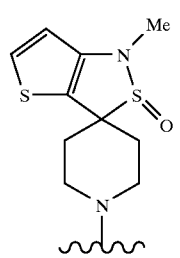
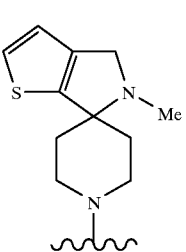
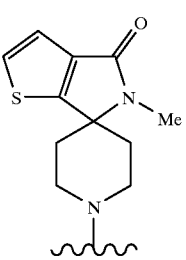
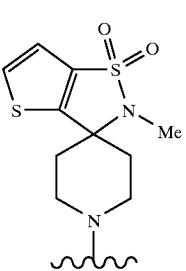
-continued
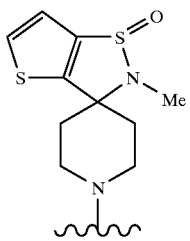
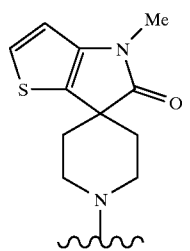
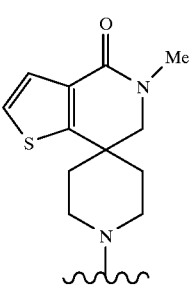
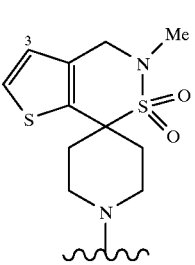
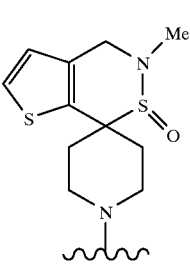

41
-continued
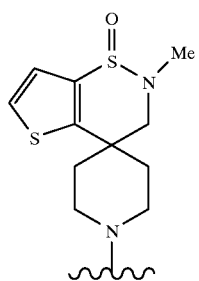
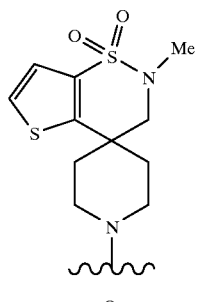
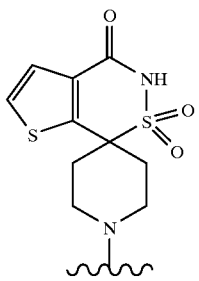
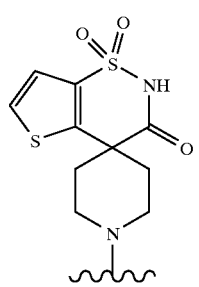
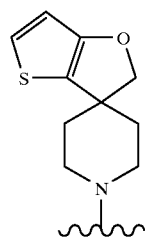
42
-continued
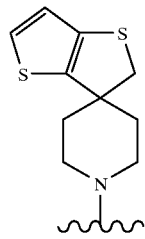
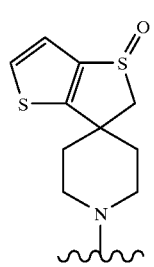
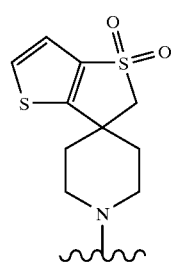
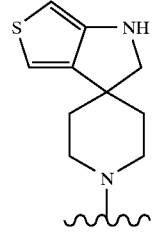
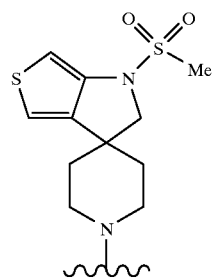

-continued
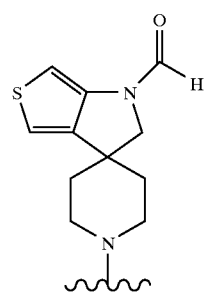
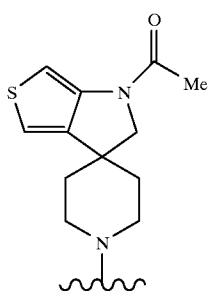
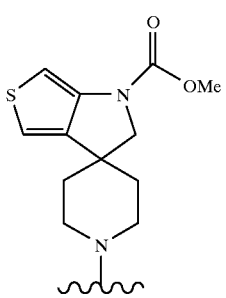
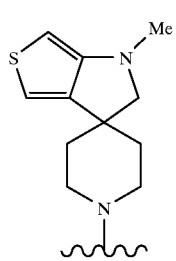
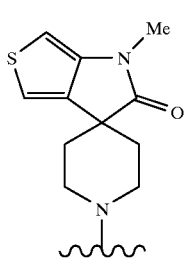
-continued
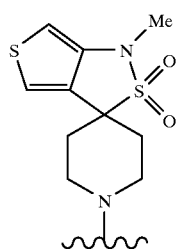
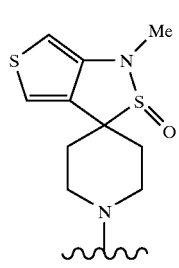
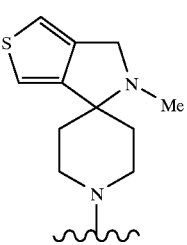
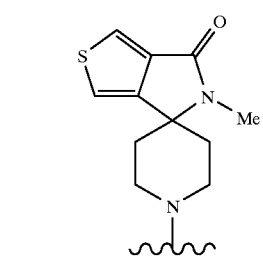
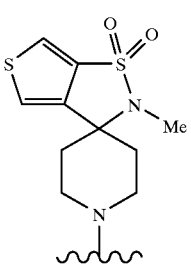

-continued
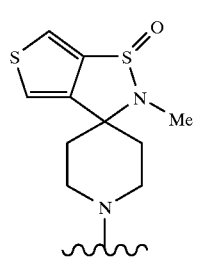
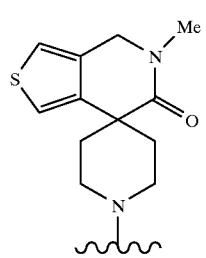
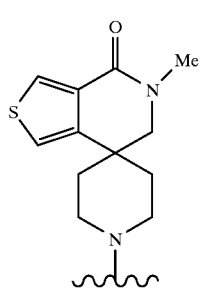
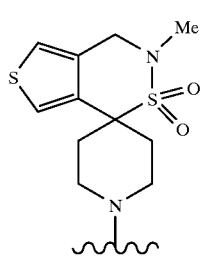
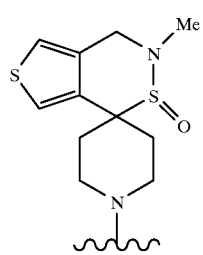
-continued
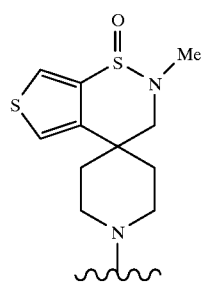
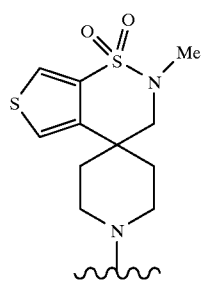
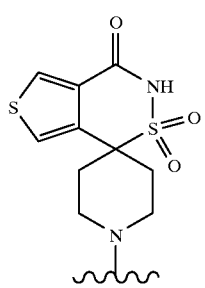
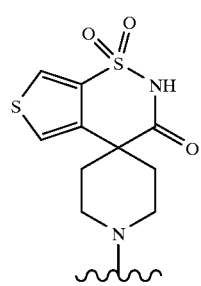
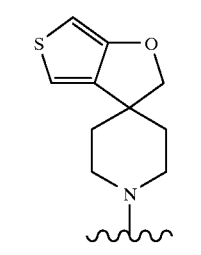

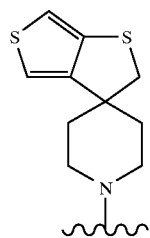
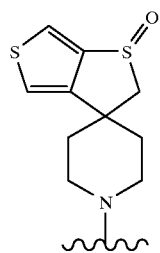
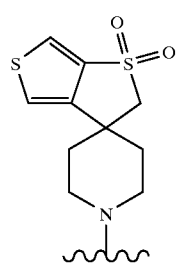
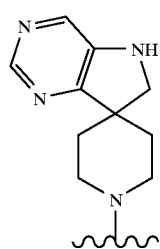
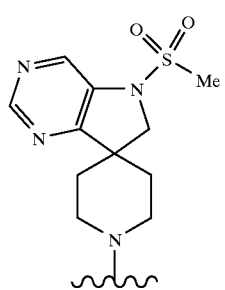
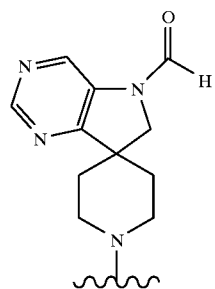
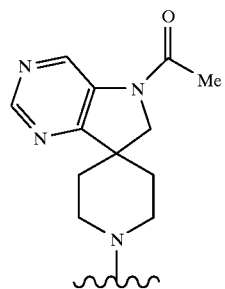
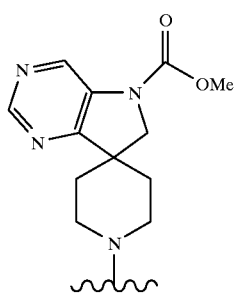
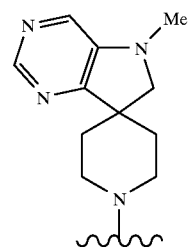
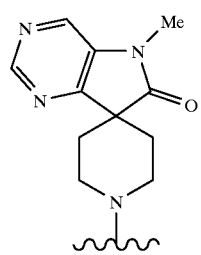

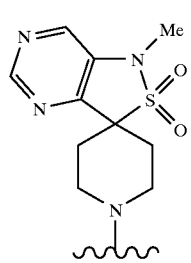
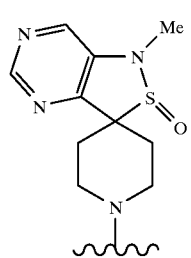
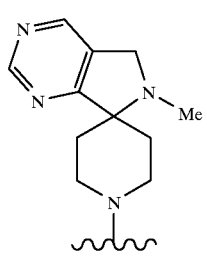
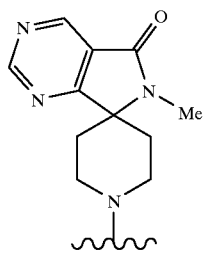
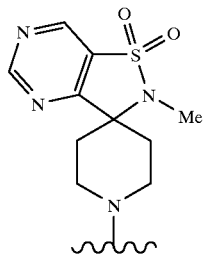
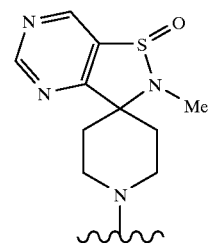
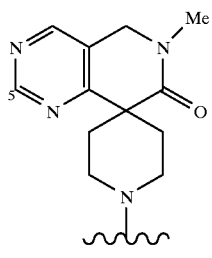
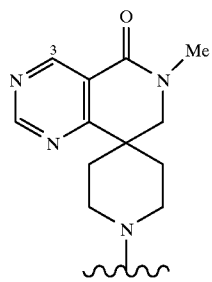
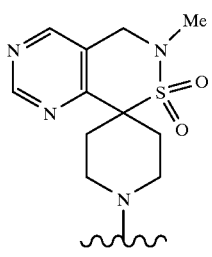
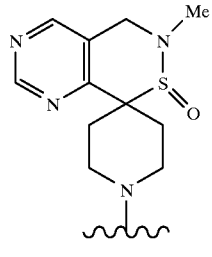

-continued

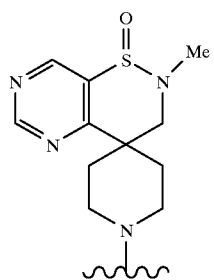

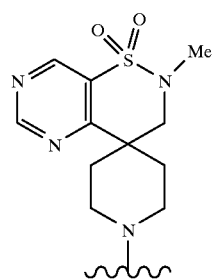

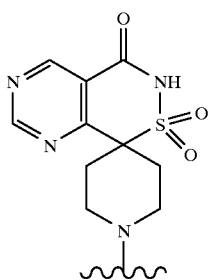

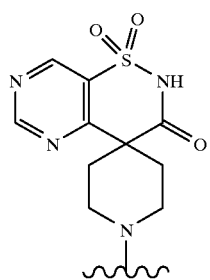

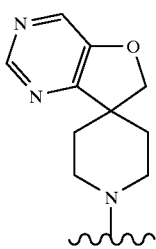

-continued

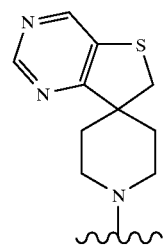

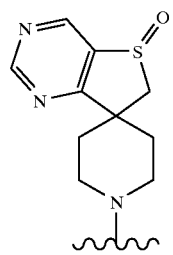

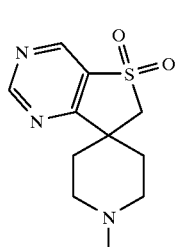

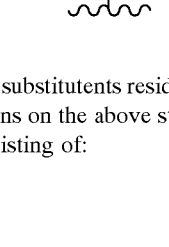

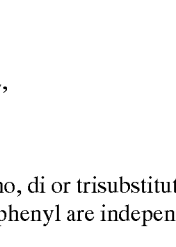

wherein the optional substitutents residing at 1, 2, or 3 of the unsubstituted positions on the above structures, are selected from the group consisting of:

(a) hydroxy,
(b) oxo,
(c) cyano,
(d) —NR$_6$R$_7$,
(e) —NHCOR$_6$R$_7$,
(f) halogen,
(g) —CF$_3$,
(h) -phenyl or mono, di or trisubstituted phenyl, where the substituents on phenyl are independently selected from:
   (1) hydroxy,
   (2) oxo,
   (3) cyano,
   (4) —NR$_6$R$_7$,
   (5) —NHCOR$_6$R$_7$,
   (6) -halogen,
   (7) —CF$_3$, and
   (8) —C$_{1-3}$ alkyl;

and pharmaceutically acceptable salts thereof.

More preferred compounds for use in the present invention also include those compounds of Formula I:

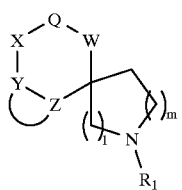

wherein the group:

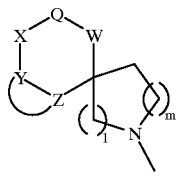

is a structure selected from the group consisting of:

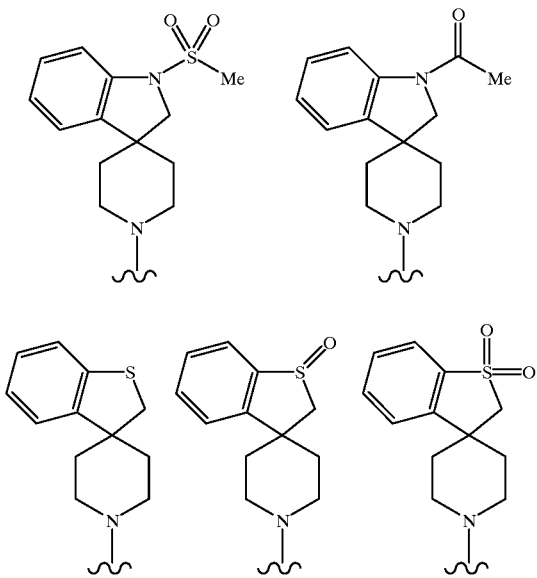

Preferred compounds for use in the present invention also include those compounds of Formula I wherein:
$R_1$ is selected from a group consisting of:
$C_1$, $C_2$, $C_3$, $C_4$, $C_6$ or $C_6$ linear or branched alkyl, di or tri substituted, wherein the substitutents are independently selected from:
(a) hydroxy,
(b) —Cl or —F,
(c) phenyl or mono, di or trisubstituted phenyl, wherein the substitutents are independently selected from:
 (1') phenyl,
 (2') hydroxy,
 (3') $C_{1-3}$alkyl,
 (4') cyano,
 (5') halogen,
 (6') trifluoromethyl,
(d) —$NR_6COR_7$, wherein:
 $R_6$ and $R_7$ are independently selected from:
  (i) hydrogen,
  (ii) $C_{1-6}$ alkyl, or mono or disubstituted $C_{1-6}$ alkyl, the substitutents are independently selected from:
   (a') phenyl, unsubstituted or substituted with hydroxy, $C_{1-3}$alkyl, cyano, halogen, trifluoromethyl or $C_{1-4}$alkoxy,
   (b') hydroxy,
   (c') oxo,
   (d') cyano,
   (e') halogen, and
   (f') trifluoromethyl,
  (iii) phenyl, pyridinyl or thiophene, or mono, di or trisubstituted phenyl, pyridinyl or thiophene, wherein the substitutents are independently selected from:
   (a') hydroxy,
   (b') $C_{1-4}$alkyl,
   (c') cyano,
   (d') halogen, and
   (e') trifluoromethyl,
  (iv) $C_{1-3}$alkyloxy,
 or $R_6$ and $R_7$ are joined together to form a 5-, 6-, or 7-membered monocyclic saturated ring containing 1 or 2 heteroatoms independently selected from nitrogen, oxygen, and sulfur, and in which the ring is unsubstituted or mono or disubstituted, wherein the substituents are independently selected from:
   (a') hydroxy,
   (b') oxo,
   (c') cyano,
   (d') halogen, and
   (e') trifluoromethyl,
(8') —$NR_6CO_2R_7$,
(9') —$NR_6CONHR_7$,
(10') —$NR_6S(O)jR_7$, wherein j is 1 or 2,
(11') —$CONR_6R_7$,
(12') —$COR_6$,
(13') —$CO_2R_6$,
(14') —$OR_6$,
(15') —$S(O)_kR_6$ wherein k is 0, 1 or 2,
(16') heteroaryl, wherein heteroaryl is selected from the group consisting of:
 (a') benzimidazolyl,
 (b') benzofuranyl,
 (c') benzoxazolyl,
 (d') furanyl,
 (e') imidazolyl,
 (f') indolyl,
 (g') isoxazolyl,
 (h') isothiazolyl,
 (i') oxadiazolyl,
 (j') oxazolyl,
 (k') pyrazinyl,
 (l') pyrazolyl,
 (m') pyridyl,
 (n') pyrimidyl,
 (o') pyrrolyl,
 (p') quinolyl,
 (q') tetrazolyl,
 (r') thiadiazolyl,
 (s') thiazolyl,
 (t') thienyl, and
 (u') triazolyl,
wherein the heteroaryl is unsubstituted or mono, di or trisubstituted, wherein the substitutents are independently selected from:
 (i') hydroxy,
 (ii') oxo,
 (iii') cyano,
 (iv') halogen, and (v') trifluoromethyl,
(g) —NE$_6$R$_7$,
(h) —NR$_6$COR$_7$,
(i) —NR$_6$CO$_2$R$_7$,
(j) —NR$_6$CONHR$_7$,
(k) —NR$_6$S(O)jR$_7$,
(l) —CONR$_6$R$_7$,
(m) —COR$_6$,
(n) —CO$_2$R$_6$,
(o) —OR$_6$,
(p) —S(O)$_k$R$_6$,
(q) —NR$_6$CO-heteroaryl, wherein heteroaryl is defined above,
(r) —NR$_6$S(O)j-heteroaryl, wherein heteroaryl is defined above,
(s) heteroaryl, wherein heteroaryl is defined above; and pharmaceutically acceptable salts thereof.

Preferred compounds for use in the present invention also include those compounds of Formula I wherein:

R$_1$ is selected from a group consisting of-:

C$_1$, C$_2$, C$_3$, C$_4$, C$_5$ or C$_6$ linear or branched alkyl, di or tri substituted, wherein the substitutents are independently selected from:
(a) hydroxy,
(b) —Cl or —F,
(c) phenyl or mono, di or trisubstituted phenyl, wherein the substitutents are independently selected from:
 (1') phenyl,
 (2') hydroxy,
 (3') C$_{1-3}$alkyl,
 (4') cyano,
 (5') halogen,
 (6') trifluoromethyl,
(d) —NR$_6$COR$_7$, wherein:
 R$_6$ is hydrogen or C$_{1-3}$ alkyl, and
 R$_7$ is selected from: phenyl, pyridinyl, thiophene, phenylC$_{1-3}$alkyl, pyridinylC$_{1-3}$alkyl and thiopheneC$_{1-3}$alkyl, wherein the phenyl, pyridinyl or thiophene, phenylC$_{1-3}$alkyl, pyridinylC$_{1-3}$alkyl or thiophenelC$_{1-3}$alkyl, is optionally substituted with a substitutent selected from:
 —Cl, —F, —CF$_3$ and C$_{1-3}$alkyl,
(e) —NR$_6$S(O)jR$_7$, wherein j is 1 or 2,
(f) —COR$_6$,
(h) —OR$_6$;

and pharmaceutically acceptable salts thereof.

More preferred compounds for use in the present invention include those compounds of Formula I wherein the group

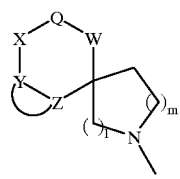

is an optionally mono di or trisubstituted structure selected from the group consisting of:

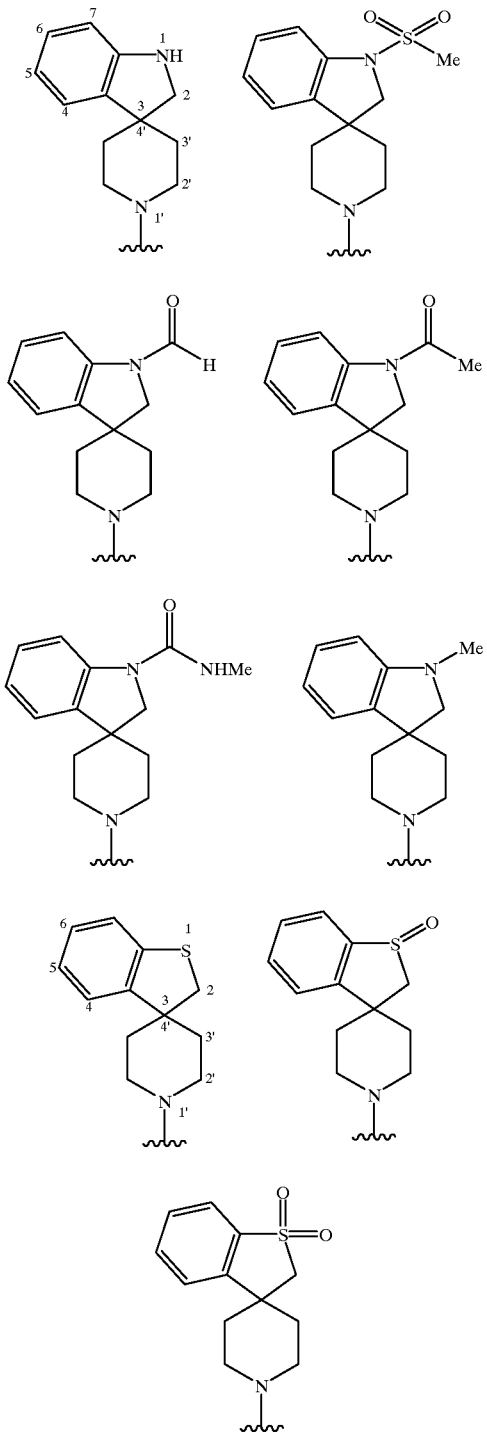

wherein the optional substitutents residing at 1, 2, or 3 of the positions numbered #1, #2, #2', #3', #4, #5, #6 or #7 on the above structures, are independently selected from the group consisting of:
(a) hydroxy,
(b) oxo,
(c) cyano,
(d) —NHR$_6$,
(e) —NR$_6$R$_7$,
(f) —NHCOR$_6$R$_7$, (g) halogen,
(h) —CF$_3$,
(h) -phenyl or mono, di or trisubstituted phenyl, where the substituents on phenyl are independently selected from:
(1) hydroxy,
(2) oxo,
(3) cyano,
(4) —NHR$_6$,
(5) —NR$_6$R$_7$,
(6) —NHCOR$_6$R$_7$,
(7) -halogen,
(8) —CF$_3$, and
(9) —C$_{1-3}$ alkyl;

and pharmaceutically acceptable salts thereof.

Even more preferred compounds for use in the present invention include those compounds of Formula I wherein the group

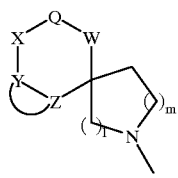

is an optionally mono di or trisubstituted structure selected from the group consisting of:

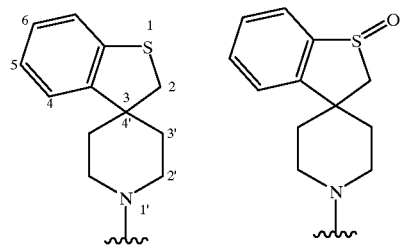

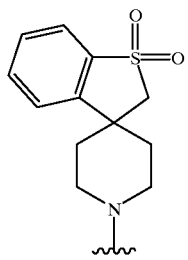

wherein the optional substitutents residing at 1, 2, or 3 of the positions numbered #2, #2', #3', #4, #5, #6 or #7 on the above structures, are independently selected from the group consisting of:
(a) hydroxy,
(b) oxo,
(c) cyano,
(d) —NHR$_6$,
(e) —NR$_6$R$_7$,
(f) —NHCOR$_6$R$_7$,
(g) halogen,
(h) —CF$_3$,
(h) -phenyl or mono, di or trisubstituted phenyl, where the substituents on phenyl are independently selected from:
(1) hydroxy,
(2) oxo,
(3) cyano,
(4) —NHR$_6$,
(5) —NR$_6$R$_7$,
(6) —NHCOR$_6$R$_7$,
(7) -halogen,
(8) —CF$_3$, and
(9) —C$_{1-3}$ alkyl;

and pharmaceutically acceptable salts thereof.

More preferred compounds for use in the present invention also include those compounds of Formula I wherein:
R$_1$ is selected from a group consisting of:
C$_1$, C$_2$, C$_3$, C$_4$, C$_5$ or C$_6$ linear or branched alkyl, di or tri substituted, wherein the substitutents are independently selected from:
(a) hydroxy,
(b) —Cl or —F,
(c) phenyl or mono, di or trisubstituted phenyl, wherein the substitutents are independently selected from:
(1') phenyl,
(2') hydroxy,
(3') C$_{1-3}$alkyl,
(4') cyano,
(5') halogen,
(6') trifluoromethyl,
(d) —NR$_6$COR$_7$, wherein:
R$_6$ is hydrogen or C$_{1-3}$ alkyl, and
R$_7$ is selected from: phenyl, pyridinyl, thiophene, phenylC$_{1-3}$alkyl, pyridinylC$_{1-3}$alkyl and thiopheneC$_{1-3}$alkyl, wherein the phenyl, pyridinyl or thiophene, phenylC$_{1-3}$alkyl, pyridinylC$_{1-3}$alkyl or thiophenelC$_{1-3}$alkyl, is optionally substituted with a substitutent selected from:
—Cl, —F, —CF$_3$ and C$_{1-3}$alkyl, and pharmaceutically acceptable salts thereof.

More preferred compounds for use in the present invention also include those compounds of Formula I wherein:
R$_1$ is selected from:

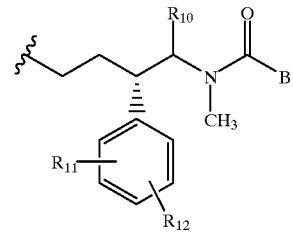, or

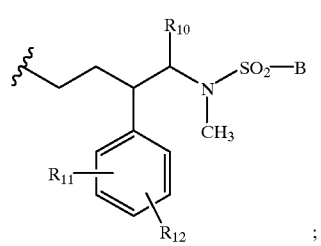;

where B is selected from:
(1) phenyl, or mono di or trisubstituted pheny,l wherein the substituents are independently selected from:
chloro, fluoro, methyl, phenyl, and —CF$_3$;
(2) —CH$_2$-phenyl, or mono or disubstituted —CH$_2$phenyl, wherein the substitutents on phenyl are independently selected from:

chloro, fluoro, methyl, phenyl, and —CF₃;

(3) pyridyl, or mono di or trisubstituted pyridyl, wherein the substitutents on pyridyl are independently selected from:
chloro, fluoro, methyl, phenyl, and —CF₃; and (4) thiophene, or mono or disubstituted thiophene, wherein the substitutents on thiophene are independently selected from:
chloro, fluoro, methyl, phenyl, and —CF₃;

$R_{10}$ is selected from: hydrogen, $C_{1-3}$alkyl, and phenyl;

$R_{11}$ and $R_{12}$ are independently selected from:

hydrogen, halogen, methyl, phenyl or CF₃;

and pharmaceutically acceptable salts thereof.

More preferred compounds for use in the present invention also include those compounds of Formula I wherein:

B is phenyl, or mono di or trisubstituted phenyl, wherein the substitutents on phenyl are independently selected from:
chloro, fluoro, methyl, phenyl or CF₃;

and pharmaceutically acceptable salts thereof.

Even more preferred compounds for use in the present invention include those of Formula I wherein B is unsubstituted phenyl, 3-chlorophenyl, 3-fluorophenyl or unsubstituted thiophene.

Especially preferred compounds of the present invention include those of Formula Ia:

Ia wherein the group:

is an optionally mono di or trisubstituted structure selected from the group consisting of:

-continued wherein the optional substitutents residing at 1, 2, or 3 of the positions numbered #2, #2', #3', #4, #5, #6 or #7 on the above structures, are independently selected from the group consisting of:
(a) hydroxy,
(b) oxo,
(c) cyano,
(d) chloro,
(e) fluoro,
(f) —CF₃,
(g) -phenyl;

$R_1$ is:

where B is phenyl, or mono di or trisubstituted phenyl, wherein the substitutents on phenyl are independently selected from:
chloro, fluoro, methyl, phenyl or CF₃;

$R_{10}$ is selected from: hydrogen, $C_{1-3}$alkyl, and phenyl;

$R_{11}$ and $R_{12}$ are independently selected from:
hydrogen, halogen, methyl, phenyl or CF₃;
and pharmaceutically acceptable salts thereof.

As is clear from the examples and schemes, the designation:

in formula I is interchangeable with $(CH_2)_l$ or $(CH_2)_m$ respectively. As appreciated by those of skill in the art, halo as used herein are intended to include chloro, fluoro, bromo and iodo.

Specific compounds of use in the present invention include:

(a) 1'-(3-(S)-(3,4-dichlorophenyl)-4-(t-butoxycarbonyl (methylamino)) butyl)-1-methanesulfonyl-spiro(indoline-3,4'-piperidine);

(b) 1'-(3-((S)-(3,4-dichlorophenyl))-4-(N-(3,5-dimethyl-benzoyl) methylamino))butyl)-1-methanesulfonyl-spiro (indoline-3,4'-piperidine);

(c) 1'-(3-((S)-(3,4-dichlorophenyl))-4-(N-(benzoyl)(methylamino))butyl)-1-methanesulfonyl-spiro(indoline-3,4'-piperidine);

(d) 1'-(3-((S)-(3,4-dichlorophenyl))-4-(N-(3,5-bistrifluoromethylbenzoyl)(methylamino))butyl)-1-methanesulfonyl-spiro(indoline-3,4'-piperidine);

(e) 1'-(3-((S)-(3,4-dichlorophenyl))-4-(N-(3-methylbenzoyl)(methylamino))butyl)-1-methanesulfonyl-spiro(indoline-3,4'-piperidine);

(f) 1'-(3-((S)-(3,4-dichlorophenyl))-4-(N-(3-chlorobenzoyl)(methylamino))butyl)-1-methanesulfonyl-spiro(indoline-3,4'-piperidine);

(g) 1'-(3-((S)-(3,4-dichlorophenyl))-4-(N-(3-trifluoromethyl-benzoyl)(methylamino))butyl)-1-methanesulfonyl-spiro(indoline-3,4'-piperidine);

(h) 1'-(3-((S)-(3,4-dichlorophenyl))-4-(N-(3,5-dichlorobenzoyl) methylamino))butyl)-1-rmethanesulfonyl-spiro(indoline-3,4'-piperidine);

(i) 1'-(3-((S)-(3,4-dichlorophenyl))-4-(N-(3-trifluoromethyl-phenylacetyl)(methylamino))butyl)-1-methanesulfonyl-spiro(indoline-3,4'-piperidine);

(j) 1'-(3-((S)-(3,4-dichlorophenyl))-4-(N-(3-isopropyloxy-phenylacetyl) methylamino))butyl)-1-methanesulfonyl-spiro(indoline-3,4'-piperidine);

(k) 1'-(3-((S)-(3,4-dichlorophenyl))-4-(N-(benzenesulfonyl)(methylamino))butyl)-1-methanesulfonyl-spiro(indoline-3,4'-piperidine);

(l) 1'-(3-((S)-(3,4-dichlorophenyl))-4-(N-(3,5-dimethyl-benzoyl) methylamino))butyl)-1-benzyoxycarbonyl-spiro(indoline-3,4'-piperidine);

(m) 1'-(3-((S)-(3,4-dichlorophenyl))-4-(N-(3,5-dimethyl-benzoyl)(methylamino))butyl)-spiro(indoline-3,4'-piperidine);

(n) 1'-(3-((S)-(3,4-dichlorophenyl))-4-(N-(3,5-dimethyl-benzoyl)(methylamino))butyl)-1-propionyl-spiro(indoline-3,4'-piperidine);

(o) 1'(3-((S)-(3,4-dichlorophenyl))-4-(N-(3,5-dimethyl-benzoyl)(methylamino)) butyl)-1-formyl-spiro(indoline-3,4'-piperidine);

(p) 1'-(3-((S)-(3,4-dichlorophenyl))-4-(N-(3,5-dimethyl-benzoyl)(methylamino))butyl)-1-t-butylcarbonyl-spiro(indoline-3,4'-piperidine);

(q) 1'-(3-((S)-(3,4-dichlorophenyl))-4-(N-(3,5-dimethyl-benzoyl)(methylamino))butyl)-1-methylaminocarbonyl-spiro(indoline-3,4-piperidine);

(r) 1'(3-((S)-(3,4-dichlorophenyl))-4-(N-(3,5-dimethyl-benzoyl)(methylamino))butyl)-1-ethoxycarbonyl-spiro(indoline-3,4'-piperidine);

(s) 1'(3-((S)-(3,4-dichlorophenyl))-4-(N-(3,5-dimethyl-benzoyl)(methylamino))butyl)-1-ethanesulfonyl-spiro(indoline-3,4'-piperidine);

(t) 1'(3-((S)-(3,4-dichlorophenyl))-4-(N-(3,5-dimethyl-benzoyl)(methylamino))butyl)-1-i-propanesulfonyl-spiro(indoline-3,4'-piperidine);

(u) 1'(3-((S)-(3,4-dichlorophenyl))-4-(N-(3,5-dimethyl-benzoyl)(methylamino))butyl)-1'-methyl-1-methanesulfonyl-spiro-indoline-3,4'-piperidinium iodide;

(v) 1'-(3-(S)-(3,4-dichlorophenyl)-4-(N-(R or S)-(3-methylbenzoyl)(methylamino))pentyl)-1-methanesulfonyl-spiro(indoline-3,4'-piperidine);

(w) 1'-(3-(S)-(3,4-dichlorophenyl)-4-(N-(R or S)-(3,5-bis(trifluoromethyl)benzoyl)(methylamino))pentyl)-1-methanesulfonyl-spiro(indoline-3,4'-piperidine);

(x) 1'-(3-(S)-(3,4-dichlorophenyl)-4-(N-(R or S)-(3,5-dimethylbenzoyl)(methylamino)pentyl)-1-methanesulfonyl-spiro-(indoline-3,4'-piperidine);

(y) 1'-(3-(S)-(3,4-dichlorophenyl)-4-(N-(R or S)-(3,5-dichlorobenzoyl)(methylamino)pentyl)-1-methanesulfonyl-spiro-(indoline-3,4'-piperidine);

(aa) 1'-(3-((S)-(3,4-dichlorophenyl))-4-(N-(3,5-difluorobenzoyl)(methylamino))butyl)-1-methanesulfonyl-spiro-(indoline-3,4'-piperidine);

(ab) 1'-(3-((S)-(3,4-dichlorophenyl))-4-(N-(3-fluoro-5-(trifluoromethyl)benzoyl)(methylamino))butyl)-1methanesulfonyl-spiro(indoline-3,4'-piperidine);

(ac) 1'-(3-((S)-(3,4-dichlorophenyl))-4-(N-(1-naphthoyl)-(methylamino))butyl)-1-methanesulfonyl-spiro(indoline-3,4'-piperidine);

(ad) 1'-(2-((S)-(3,4-dichlorophenyl))-1-(N-(2-chloro-phenylsulfonyl)-(methylamino))-4-butyl)-1-methylsulfonyl-spiro-(indoline-3,4'-piperidine);

(ae) 1'-(2-((S)-(3,4-dichlorophenyl))-1-(N-(3-chloro-phenylsulfonyl)-(methylamino))-4-butyl)-1-methylsulfonyl-spiro-(indoline-3,4'-piperidine);

(af) 1'-(2-((S)-(3,4-dichlorophenyl))-1-(N-(4-chloro-phenylsulfonyl)-(methylamino))-4-butyl)-1-methylsulfonyl-spiro(indoline-3,4'-piperidine);

(ag) 1'-(2-((S)-(3,4-dichlorophenyl))-1-(N-(3,5-dichloro-phenylsulfonyl)-(methylamino))-4-butyl)-1-methylsulfonyl-spiro-(indoline-3,4'-piperidine);

(ah) 1'-(3-((S)-(3,4-dichlorophenyl))-4-(N-(3-fluoro-5-(trifluoromethyl)benzoyl)(rethylamino))butyl)-1-acetyl-spiro(indoline-3,4'-piperidine);

(ai) 1'-(3-((S)-(3,4-dichlorophenyl))-4-(N-(3,5-dimethyl-benzoyl)(methylamino))butyl)-1-acetyl-spiro(indoline-3,4'-piperidine).

(aj) 1'-(3-((S)-(3,4-dichlorophenyl))-4-(N-(3-bromo-5-methylbenzoyl)(methylamino))butyl)-1-methanesulfonyl-spiro(indoline-3,4'-piperidine);

(ak) 1'-(3-((S)-(3,4-dichlorophenyl))-4-(N-(3,5-dimethylbenzoyl)(methylamino))butyl)-1-(2-aminoacetyl)-spiro-(indoline-3,4-piperidine);

(al) 1'-(3-((S)-(3,4-dichlorophenyl))-4-(N-(3,5-dimethylbenzoyl)(methylamino))butyl)-1-methyl-spiro(indol-2-one-3,4'-piperidine);

(am) 1'-(3-((S)-(3,4-dichlorophenyl))-4-(N-(3,5-dichlorobenzoyl)(methylamino))butyl)-1-methyl-spiro(isoindol-1-one-3,4'-piperidine);

(an) 1'-(3-((S)-(3,4-dichlorophenyl))-4-(N-(3,5-dimethylbenzoyl)(methylamino))butyl)-spiro(2-oxo-tetrahydroquinoline-4,4'-piperidine); and (ao) 1'-(3-((S)-(3,4-dichlorophenyl))-4-(N-(3,5-dichlorobenzoyl)(methylamino))butyl)-1-methyl-spiro(2-oxo-tetrahydro-quinoline-4,4'-piperidine);

and pharmaceutically acceptable salts thereof.

Specific compounds of use in the present invention further include:

(a) 1'-(3-(S)-(4-fluorophenyl)-4-(N-(3,5-bistrifluoromethylbenzoyl)(methylamino))butyl)-1-acetyl-spiro(indoline-3,4'-piperidine), (b) 1'-(3-(S)-(3-chlorophenyl)-4-(N-(3,5-bistrifluoromethylbenzoyl)(methylamino))butyl)-1-acetyl-spiro(indoline-3,4'-piperidine), (c) 1'-(3-(S)-(4-chlorophenyl)-4-(N-(3,5-bistrifluoromethylbenzoyl)(methylamino))butyl)-1-acetyl-spiro(indoline-3,4'-piperidine), (d) 1'-(3-(S)-(3,4-difluorophenyl)-4-(N-(3,5-bistrifluoromethylbenzoyl)(methylamino))butyl)-1-acetyl-spiro(indoline-3,4'-piperidine), (e) 1'-(3-(S)-(3,4-methylenedioxyphenyl)-4-(N-(3,5-bistrifluoromethylbenzoyl)(methylamino))butyl)-1-methanesulfonyl-spiro(indoline-3,4'-piperidine), (f) 1'-(3-(RS)-(3,5-dichlorophenyl)-4-(N-(3,5-bistrifluoromethylbenzoyl)(methylamino))butyl)-1-methanesulfonyl-spiro(indoline-3,4'-piperidine), (g) 1'-(3-(S)-(4-chlorophenyl)-4-(N-(3,5-bistrifluoromethylbenzoyl)(methylamino))butyl)-spiro(2,3-dihydrobenzothiophene-3,4'-piperidine), (h) 1'-(3-(RS)-(4-pyridyl)-4-(N-(3,5-bistrifluoromethylbenzoyl)(methylamino))butyl)-1-acetyl-spiro(indoline-3,4'-piperidine), (i) 1'-(3-(S)-(3,4-dichlorophenyl)-4-(N-(3,5-dimethylbenzoyl)(ethylamino))butyl)-1-methanesulfonyl-spiro(indoline-3,4'-piperidine), (j) 1'-(3-((S)-(3,4-dichlorophenyl))-4-(N-(3,5-dichlorobenzoyl)(methylamino))butyl)-5-fluoro-spiro(2,3-dihydrobenzofuran-3,4'-piperidine), (k) 1'-(3-((S)-(3,4-dichlorophenyl))-4-(N-(3-chlorobenzoyl)(methylamino))butyl)-5-fluoro-spiro(2,3-dihydrobenzofuran-3,4'-piperidine), (l) 1'-(3-((S)-(3,4-dichlorophenyl))-4-(N-(3,5-dimethylbenzoyl)(methylamino))butyl)-5-fluoro-spiro(2,3-dihydrobenzofuran-3,4'-piperidine), (m) 1'-(3-((S)-(3,4-dichlorophenyl))-4-(N-(3-methylbenzoyl)(methylamino))butyl)-5-fluoro-spiro(2,3-dihydrobenzofuran-3,4'-piperidine), (n) 1'-(3-((S)-(3,4-dicliiorophenyl))-4-(N-(benzoyl)(methylamino))butyl)-5-filuoro-spiro(2,3-dihydrobenzofuran-3,4'-piperidine), (o) 1'-(3-((S)-(3,4-dichlorophenyl))-4-(N-(benzoyl)(methylamino))butyl)-spiro(2,3-dihydrobenzofuran-3,4'-piperidine), (p) 1'-(3-((S)-(3,4-dichlorophenyl))-4-(N-(3-methylbenzoyl)(methylamino))butyl)-spiro(2,3-dihydrobenzofuran-3,4'-piperidine), (q) 1'-(3-((S)-(3,4-dichlorophenyl))-4-(N-(3,5-dimethylbenzoyl)(methylamino))butyl)-spiro(2,3-dihydrobenzofuran-3,4'-piperidine), (r) 1'-(3-((S)-(3,4-dichlorophenyl))-4-(N-(3-chlorobenzoyl)(methylamino))butyl)-spiro(2,3-dihydrobenzofuran-3,4'-piperidine), (s) 1'-(3-((S)-(3,4-dichlorophenyl))-4-(N-(3,5-dichlorobenzoyl)(methylamino))butyl)-spiro(2,3-dihydrobenzofuran-3,4'-piperidine), (t) 1'-(3-((S)-(3,4-dichlorophenyl))-4-(N-(4-fluoro-1-napthoyl)(methylamino))butyl)-spiro(2,3-dihydrobenzofuran-3,4'-piperidine), (u) 1'-(3-((S)-(3,4-dichlorophenyl))-4-(N-(t-butoxycarbonyl)(methylamino))butyl)-spiro(2,3-dihydrobenzothiophene-3,4'-piperidine), (v) 1'-(3-((S)-(3,4-dichlorophenyl))-4-(N-(3,5-dimethylbenzoyl)(methylamino))butyl)-spiro(2,3-dihydrobenzothiophene-3,4'-piperidine), (w) 1'-(3-(S)-(4-chlorophenyl)-4-(N-(3,5-dimethylbenzoyl)(methylamino))butyl)-spiro(2,3-dihydrobenzothiophene-3,4'-piperidine), (x) 1'-(3-((S)-(3,4-dichlorophenyl))-4-(N-(t-butoxycarbonyl)(methylamino))butyl)-spiro(2,3-dihydrobenzothiophene-3,4'-piperidine)-1-oxide, (y) 1'-(3-((S)-(3,4-dichlorophenyl))-4-(N-(4-fluoro-1-napthylmethyl)(methylamino))butyl)-spiro(2,3-dihydrobenzothiophene-3,4'-piperidine)-1-oxide, (z) 1'-(3-((S)-(3,4-dichlorophenyl))-4-(N-(t-butoxycarbonyl)(methylamino))butyl)-spiro(2,3-dihydrobenzothiophene-3,4'-piperidine)-1,1-dioxide, (aa) 1'-(3-((S)-(3,4-dichlorophenyl))-4-(N-(3,5-dimethylbenzoyl)(methylamino))butyl)-spiro(2,3-dihydrobenzothiophene-3,4'-piperidine)-1,1-dioxide, (ab) 1'-(3-((S)-(3,4-dichlorophenyl))-4-(N-(3,5-dimethylbenzoyl)(methylamino))butyl)-spiro(2,3-dihydrobenzothiophene-3,4'-piperidine)-1,1-dioxide, (ac) 1'-(3-((S)-(4-chlorophenyl))-4-(N-(3,5-dimethylbenzoyl)(methylamino))butyl)-spiro(2,3-dihydrobenzothiophene-3,4'-piperidine)-1,1-dioxide, (ad) 1'-(3-((S)-(4-chlorophenyl))-4-(N-(3,5-dimethylbenzoyl)(methylamino))butyl)-spiro(2,3-dihydrobenzothiophene-3,4'-piperidine)-1-oxide, (ae) 1'-(3-(S)-(4-chlorophenyl)-4-(N-(3,5-bistrifluoromethylbenzoyl)(methylamino))butyl)-spiro(2,3-dihydrobenzothiophene-3,4'-piperidine), 1-oxide, (af) 1'-(3-(S)-(4-chlorophenyl)-4-(N-(3,5-bistrifluoromethylbenzoyl)(methylamino))butyl)-spiro(2,3-dihydrobenzothiophene-3,4'-piperidine), 1,1-dioxide, (ag) 1'-benzyloxycarbonyl-5-fluoro-1-methanesulfonyl-spiro(indoline-3,4'-piperidine), (ah) 1'-(3-((S)-(3,4-dichlorophenyl))-4-(methylamino)butyl)-1-methanesulfonyl-5-methoxy-spiro(indoline-3,4'-piperidine), (ai) 1'-(3-((S)-(3,4-dichlorophenyl))-4-(methylamino)butyl)-1-methanesulfonyl-5-methyl-spiro(indoline-3,4'-piperidine), 5-chloro-1'-(3-((S)-(3,4-dichlorophenyl))-4-(methylamino)butyl)-1-methanesulfonyl-spiro(indoline-3,4'-piperidine), (ak) 1'-(3-((S)-(3,4-dichlorophenyl))-4-(methylamino)butyl)-5-fluoro-1-methanesulfonyl-spiro(indoline-3,4'-piperidine), (al) 1'-(3-((S)-(3,4-dichlorophenyl))-4-(methylamino)butyl)-7-fluoro-1-methanesulfonyl-spiro(indoline-3,4'-piperidine), (am) 1'-(3-((S)-(3,4-dichlorophenyl))-4-(N-(3,5-dimethylbenzoyl)(methylamino))butyl)-1-methanesulfonyl-5-methyl-spiro(indoline-3,4'-piperidine), (an) 5-chloro-1'-(3-((S)-(3,4-dichlorophenyl))-4-(N-(3-methylbenzoyl)(methylamino))butyl)-1-methanesulfonyl-spiro(indoline-3,4'-piperidine), (ao) 1'-(3-((S)-(3,4-dichlorophenyl))-4-(N-(3,5-dimethylbenzoyl)(methylamino))butyl)-1-methanesulfonyl-5-methoxy-spiro(indoline-3,4'-piperidine), (ap) 1'-(3-((S)-(3,4-dichlorophenyl))-4-(N-(3-methylbenzoyl)(methylamino))butyl)-5-fluoro-1-methanesulfonyl-spiro(indoline-3,4'-piperidine), (aq) 1'-(3-((S)-(3,4-dichlorophenyl))-4-(N-(3,5-dichlorobenzoyl)(methylamino))butyl)-5-fluoro-1-methanesulfonyl-spiro(indoline-3,4'-piperidine), (ar) 1'-(3-((S)-(3,4-dichlorophenyl))-4-(N-(3,5-dimethylbenzoyl)(methylamino))butyl)-5-fluoro-1-methanesulfonyl-spiro(indoline-3,4'-piperidine), (as) 1'-(3-((S)-(3,4-dichlorophenyl))-4-(N-(3-chlorobenzoyl)(methylamino))butyl)-5-fluoro-1-methanesulfonyl-spiro(indoline-3,4'-piperidine), (at) 1'-(3-((S)-(3,4-dichlorophenyl))-4-(N-(3,5-bis(trifluoromethyl)benzoyl)-(methylamino))butyl)-5-fluoro-1-methanesulfonyl-spiro(indoline-3,4'-piperidine), (au) 1'-(3-((S)-(3,4-dichlorophenyl))-4-(N-(3,5-dimethylbenzoyl)(methylamino))butyl)-7-fluoro-1-methanesulfonyl-spiro(indoline-3,4'-piperidine), (av) 1-acetyl-1'-(3-((S)-(3,4-dichlorophenyl))-4-(N-t-butoxycarbonyl)(methylamino))butyl)-5-fluoro-spiro(indoline-3,4'-piperidine), (aw) 1-acetyl-5-chloro-1'-(3-((S)-(3,4-dichlorophenyl))-4-(methylamino)butyl)-spiro(indoline-3,4'-piperidine), (ax) 1-acetyl-1-(3-((S)-(3,4-dichlorophenyl))-4-(methylamino)butyl)-5-methyl-spiro(indoline-3,4'-piperidine), (ay) 1-acetyl-1'-(3-((S)-(3,4-dichlorophenyl))-4-(methylamino)butyl)-5-fluoro-spiro(indoline-3,4'-piperidine), (az) 1-acetyl-1'-(3-((S)-(3,4-dichlorophenyl))-4-(methylamino)butyl)-6-fluoro-spiro(indoline-3,4'-piperidine), (ba) 1-acetyl-1'-(3-((S)-(3,4-dichlorophenyl))-4-(methylamino)butyl)-4-fluoro-spiro(indoline-3,4'-piperidine), (bb) 1-acetyl-1'-(3-((S)-(3,4-dichlorophenyl))-4-(N-(benzoyl)(methylamino))butyl)-4-fluoro-spiro(indoline-3,4'-piperidine),
(bc) 1-acetyl-1'-(3-((S)-(3,4-dichlorophenyl))-4-(N-(3,5,-dimethylbenzoyl)(methylamino))butyl)-6-fluoro-spiro(indoline-3,4'-piperidine),
(bd) 1-acetyl-1'-(3-((S)-(3,4-dichlorophenyl))-4-(N-(benzoyl)(methylamino))butyl)-6-fluoro-spiro(indoline-3,4'-piperidine),
(be) 1-acetyl-1'-(3-((S)-(3,4-dichlorophenyl))-4-(N-(3,5'-dimethylbenzoyl)(methylamino))butyl)-4-fluoro-spiro(indoline-3,4'-piperidine),
(bf) 1-acetyl-1'-(3-((S)-(3,4-dichlorophenyl))-4-(N-(benzoyl)(methylamino))butyl)-5-fluoro-spiro(indoline-3,4'-piperidine),
(bg) 1-acetyl-1'-5-chloro-(3-((S)-(3,4-dichlorophenyl))-4-(N-(3,5'-dimethylbenzoyl)(methylamino))butyl)-spiro(indoline-3,4'-piperidine),
(bh) 1-acetyl-1'-(3-((S)-(3,4-dichlorophenyl))-4-(N-(3-chlorobenzoyl)(methylamino))butyl)-5-fluoro-spiro(indoline-3,4'-piperidine),
(bi) 1-acetyl-1'-(3-((S)-(3,4-dichlorophenyl))-4-(N-(3,5-dichlorobenzoyl)(methylamino))butyl)-5-fluoro-spiro(indoline-3,4'-piperidine),
(bj) 1-acetyl-1'-(3-((S)-(3,4-dichlorophenyl))-4-(N-(3-methylbenzoyl)(methylamino))butyl)-5-fluoro-spiro(indoline-3,4'-piperidine),
(bk) 1-acetyl-1'-(3-((S)-(3,4-dichlorophenyl))-4-(N-(3,5-dimethylbenzoyl)(methylamino))butyl)-5-fluoro-spiro(indoline-3,4'-piperidine),
(bl) 1-acetyl-1'-(3-((S)-(3,4-dichlorophenyl))-4-(N-(3-isopropoxybenzoyl)(methylamino))butyl)-5-fluoro-spiro(indoline-3,4'-piperidine),
(bm) 1-acetyl-1'-(3-((S)-(3,4-dichlorophenyl))-4-(N-(3,5-bis(trifluoromethyl)(methylamino))butyl)-5-fluoro-spiro(indoline-3,4'-piperidine),
(bn) 1-acetyl-1'-(3-((S)-(3,4-dichlorophenyl))-4-(N-(3,5-dimethylbenzoyl)(methylamino))butyl)-5-methyl-spiro(indoline-3,4'-piperidine),
(bo) 1-acetyl-1'-(3-((S)-(3,4-dichlorophenyl))-4-(N-(4-fluoro-1-napthoyl)(methylamino))butyl)-5-fluoro-spiro(indoline-3,4'-piperidine),
(bp) 1-acetyl-1'-(3-((S)-(3,4-dichlorophenyl))-4-(N-(1-napthoyl)(methylamino))butyl)-5-fluoro-spiro(indoline-3,4'-piperidine),
(bq) 1'-(3-((S)-(3,4-dichlorophenyl))-4-(N-(1-napthoyl)-(methylamino))butyl)-5-fluoro-1-methanesulfonyl-spiro(indoline-3,4'-piperidine),
(br) 1'-(3-((S)-(3,4-dichlorophenyl))-4-(N-(4-fluoro-1-napthoyl)(methylamino))butyl)-5-fluoro-1-methanesulfonyl-spiro(indoline-3,4'-piperidine),
(bs) 1'-(3-((S)-(3,4-dichlorophenyl))-4-(N-(4-fluoro-1-napthoyl)(methylamino))butyl)-spiro(2,3-dihydrobenzothiophene-3,4'-piperidine),
(bt) 1'-(3-((S)-(3,4-dichlorophenyl))-4-(N-(4-fluoro-1-napthoyl)(methylamino))butyl)-spiro(2,3-dihydrobenzothiophene-3,4'-piperidine) sulfone,
(bu) 1'-(3-((S)-(3,4-dichlorophenyl))-4-(N-(4-fluoro-1-napthoyl)(methylamino))butyl)-spiro(2,3-dihydrobenzothiophene-3,4'-piperidine),
(bv) 1'-(3-((S)-(3,4-dichlorophenyl))-4-(N-(4-fluoro-1-napthyl)(methylamino))butyl)-5-fluoro-spiro(2,3-dihydrobenzofuran-3,4'-piperidine),
(bw) 1'-(3-((S)-(3,4-dichlorophenyl))-4-(N-(4-fluoro-1-napthyl)(methylamino))butyl)-spiro(2,3-dihydrobenzofuran-3,4'-piperidine),
(bx) 1-acetyl-1'-(3-((S)-(3,4-dichlorophenyl))-4-(N-(4-fluoro-1-napthoyl)(methylamino))butyl)-6-fluoro-spiro(indoline-3,4'-piperidine),
(by) 1-acetyl-1'-(3-((S)-(3,4-dichlorophenyl))-4-(N-(4-fluoro-1-napthoyl)(methylamino))butyl)-4-fluoro-spiro(indoline-3,4'-piperidine),
(bz) 1'-(3-((S)-(3,4-dichlorophenyl))-4-(N-(4-fluoro-1-napthylmethyl)(methylamino))butyl)-5-fluoro-1-methanesulfonyl-spiro(indoline-3,4'-piperidine),
(ca) 1'-(3-((S)-(3,4-dichlorophenyl))-4-(N-(4-fluoro-1-napthylmethyl)(methylamino))butyl)-5-fluoro-spiro(indoline-3,4'-piperidine),
(cb) 1-acetyl-1'-(3-((S)-(3,4-dichlorophenyl))-4-(N-(4-fluoro-1-napthylmethyl)(methylamino))butyl)-5-fluoro-spiro(indoline-3,4'-piperidine),
(cd) 1'-(5-fluoroindolyl-3-(2-ethanoyl))-1-methanesulfonyl-spiro(indoline-3,4'-piperidine),
(ce) 1'-(2-(3-(5-fluoroindolyl))ethyl)-1-methanesulfonyl-spiro(indoline-3,4'-piperidine),
(cf) 1'-(3-((S)-(3,4-dichlorophenyl))-4-(N-(3-chloro-4-fluorobenzoyl)(methylamino))butyl)-1-methanesulfonyl-spiro(indoline-3,4'-piperidine),
(cg) 1'-(3-((S)-(3,4-dichlorophenyl))-4-(N-(3-chloro-4-fluorobenzoyl)(methylamino))butyl)-5-fluoro-1-methanesulfonyl-spiro(indoline-3,4'-piperidine),
(ch) 1'-(3-((S)-(3,4-dichlorophenyl))-4-(N-(4-fluorobenzoyl)(methylamino))butyl)-1-methanesulfonyl-spiro(indoline-3,4'-piperidine),
(ci) 1'-(3-((S)-(3,4-dichlorophenyl))-4-(N-(4-fluorobenzoyl)(methylamino))butyl)-5-fluoro-1-acetyl-spiro(indoline-3,4'-piperidine),
(cj) 1'-(3-((S)-(3,4-dichlorophenyl))-4-(N-(3-chloro-4-fluorobenzoyl)(methylamino))butyl)-5-fluoro-1-acetyl-spiro(indoline-3,4'-piperidine),
(ck) 1'-(3-((S)-(3,4-dichlorophenyl))-4-(N-(4-fluoro-3,5-dimethylbenzoyl)(methylamino))butyl)-5-fluoro-1-acetyl-spiro(indoline-3,4'-piperidine),
(cl) 1'-(3-((S)-(3,4-dichlorophenyl))-4-(N-(4-fluoro-3,5-dimethylbenzoyl)(methylamino))butyl)-1-methanesulfonyl-spiro(indoline-3,4'-piperidine),
(cm) 1'-(3-((S)-(3,4-dichlorophenyl))-4-(N-(4-fluoro-3-trifluoromethylbenzoyl)(methylamino))butyl)-1-methanesulfonyl-spiro(indoline-3,4'-piperidine),
(cn) 1'-(3-((S)-(3,4-dichlorophenyl))-4-(N-(4-fluoro-3,5-dimethylbenzoyl)(methylamino))butyl)-1-acetyl-spiro(indoline-3,4'-piperidine),
(co) 1'-(3-((S)-(3,4-dichlorophenyl))-4-(N-(4-fluoro-3-trifluoromethylbenzoyl)(methylamino))butyl)-1-acetyl-spiro(indoline-3,4'-piperidine),
(cp) 1'-(3-((S)-(3,4-dichlorophenyl))-4-(N-(4-fluoro-naphthoyl)(methylamino))butyl)-1-acetyl-spiro(indoline-3,4'-piperidine),
(cq) 1'-(3-((S)-(3,4-dichlorophenyl))-4-(N-(4-fluoro-1-naphthoyl)(methylamino))butyl)-1-methanesulfonyl-spiro(indoline-3,4'-piperidine),
(cr) 1'-(3-((S)-(3,4-dichlorophenyl))-4-(N-(1-naphthoyl)(methylamino))butyl)-1-acetyl-spiro(indoline-3,4'-piperidine),
(cs) 1'-(3-((S)-(3,4-dichlorophenyl))-4-(N-(3,5-dimethylbenzoyl)(methylamino))-4-phenyl-butyl)-1-methanesulfonyl-spiro(indoline-3,4'-piperidine),
(ct) 1'-(4-(N-(3,5-dimethylbenzoyl)(methylamino))-4-(phenyl)butyl)-l-acetyl-spiro(indoline-3,4'-piperidine),
(cu) 1'-(3-((S)-(3,4-dichlorophenyl))-4-(1-(2-phenylimidazolo))butyl)-1-methanesulfonyl-spiro(indoline-3,4'-piperidine),
(cv) 1'-(3-((S)-(3,4-dichlorophenyl))-4-((N-(3,5-dimethylbenzoyl)(methylamino))-4-(methyl)butyl)-1-acetyl-spiro(indoline-3,4'-piperidine),
(cw) 1'-(3-((S)-(3,4-dichlorophenyl))-4-((N-(4-fluoro-1-napthyl)(methylamino))-4-(methyl)butyl)-1-acetyl-spiro(indoline-3,4'-piperidine), (cx) 1'-(3-((S)-(3,4-dichlorophenyl))-4-(R and S)-(N-(3,5-dimethylbenzoyl)(methylamino))hexyl)-1-acetyl-spiro (indoline-3,4'-piperidine), (cy) 1'-(3-((S)-(3,4-dichlorophenyl))-4-(R and S)-(N-(3,5-dimethylbenzoyl)(methylamino))hexyl)-1-acetyl-5-fluoro-spiro(indoline-3,4'-piperidine), (cz) 1L-(3-(S)-(3,4-dichlorophenyl)-4-(R and S)-(N-(3,5-dimethylbenzoyl)(methylamino))heptyl)-1-acetyl-spiro (indoline-3,4'-pipperidine), (da) 1'-(3-(S)-(3,4-dichlorophenyl)-4-(R and S)-(N-(3,5-dimethylbenzoyl)(methylamino))heptyl)-1-acetyl-5-fluoro-spiro(indoline-3,4'-piperidine), (db) 1'-(3-((S)-(3,4-dichlorophenyl))-4-(R and S)-hydroxy-5-(3,5-dimethylphenyl)pentyl)-1-methanesulfonyl-spiro (indoline-3,4'-piperidine), (dc) 1'-(3-(R)-(3,4-dichlorophenyl)-5-(N-(3,5-dimethylphenyl)(methylamino))-5-oxo-pentyl)-1-methanesulfonyl-spiro(indoline-3,4'-piperidine), (dd) 1'-(3-(R)-(3,4-dichlorophenyl))-5-(3,5-dimethylphenyl)-5-oxo-pentyl)-1-methanesulfonyl-spiro (indoline-3,4'-piperidine), (de) 1'-(3-(R)-(3,4-dichlorophenyl)-6-(3,5-dimethylphenyl)-5-oxo-hexyl)-1-methanesulfonyl-spiro(indoline-3,4'-piperidine), (df) 1'-(3-(S)-(3,4-dichlorophenyl)-6-(3,5-dimethylphenyl)-6-oxo-hexyl)-1-methanesulfonyl-spiro(indoline-3,4'-piperidine), (dg) 1'-(3-(S)-(3,4-dichlorophenyl)-6-(3,5-dimethylphenyl)-5-(R&S)-methyl-6-oxo-hexyl)-1-methanesulfonyl-spiro (indoline-3,4'-piperidine); and (dh) 1'-(3-(S)-(3,4-dichlorophenyl)-4-(3,5-(bistrifluoromethyl)benzyloxy)-1-acetyl-spiro(indoline-3,4'-piperidine);

and pharmaceutically acceptable salts thereof.

The subject compounds are useful in a method of modulating chemokine receptor activity in a patient in need of such modulation comprising the administration of an effective amount of the compound.

The present invention is directed to the use of the foregoing spiro-substituted azacycles as modulators of chemokine receptor activity. In particular, these compounds are useful as modulators of the chemokine receptors, including CCR-1, CCR-2, CCR-2A, CCR-2B, CCR-3, CCR-4, CCR-5, CXCR-3, and/or CXCR-4. In particular, the compounds of the present invention are preferred as modulators of the chemokine receptor CCR-5.

The present invention is further directed to the use of compounds of this general structure which are disclosed as being antagonists of neurokinin receptors. Such compounds are disclosed, for example, in: U.S. Pat. No. 5,317,020; U.S. Pat. No. 5,534,525; U.S. Pat. No. 5,350,852; U.S. Pat. No. 5,411,971; U.S. Pat. No. 5,446,052; U.S. Pat. No. 5,560,700; EP 0 559 538, Sep. 8, 1993; EP 0 591 040, Apr. 6, 1994; EP 0 698 601, Feb. 28, 1996; EP 0 625 509, Nov. 23, 1994; 3P 0 630 887, Dec. 28, 1994; EP 0 680 962, Nov. 8, 1995; EP 0 709 375, May 1, 1996; EP 0 709 376, May 1, 1996; EP 0 723 959, Jul. 31, 1996; EP 0 739 891; WO 94/10146, May 11, 1994; WO 94/17045, Aug. 4, 1994; WO 94/26735, Nov. 24, 1994; WO 94/29309, Dec. 22, 1994; WO 95/05377, Feb. 23, 1995; WO 95/12577, May 11, 1995; WO 95/15961, Jun. 15, 1995; WO 95/16682, Jun. 22, 1995; WO 95/21187; WO 95/26335, Oct. 5, 1995; WO 95/26338, Oct. 5, 1995; WO 95/35279; WO 96/06094, Feb. 29, 1996; WO 96/10568, Apr. 11, 1996; WO 96/23787, Aug. 8, 1996; WO 96/24582, Aug. 15, 1996; WO 96/28441; and WO 96/32385. Accordingly, the present invention embraces the use of a compound disclosed in these publications as a modulator of chemokine receptor activity.

The utility of the compounds in accordance with the present invention as modulators of chemokine receptor activity may be demonstrated by methodology known in the art, such as the assay for CCR-1 and/or CCR-5 binding as disclosed by Van Riper, et al., *J. Exp. Med.*, 177, 851–856 (1993), and the assay for CCR-2 and/or CCR-3 binding as disclosed by Daugherty, et al., *J. Exp. Med.*, 183, 2349–2354 (1996). Cell lines for expressing the receptor of interest include those naturally expressing the receptor, such as EOL-3 or THP-1, or a cell engineered to express a recombinant receptor, such as CHO, RBL-2HR3, HEK-293. For example, a CCR3 transfected AML14.3D10 cell line has been placed on restricted deposit with American Type Culture Collection in Rockville, Md. as ATCC No. CR[]L-12079, on Apr. 5, 1996. The utility of the compounds in accordance with the present invention as inhibitors of the spread of HIV infection in cells may be demonstrated by methodology known in the art, such as the HIV quantitation assay disclosed by Nunberg, et al., *J. Virology*, 65 (9), 4887–4892 (1991).

In particular, the compounds of the following examples had activity in binding to either the CCR-5 receptor or the CCR-3 receptor in the aforementioned assays. Such a result is indicative of the intrinsic activity of the compounds in use as modulators of chemokine receptor activity.

Mammalian chemokine receptors provide a target for interfering with or promoting eosinophil and/or lymphocyte function in a mammal, such as a human. Compounds which inhibit or promote chemokine receptor function, are particularly useful for modulating eosinophil and/or lymphocyte function for therapeutic purposes. Accordingly, the present invention is directed to compounds which are useful in the prevention and/or treatment of a wide variety of inflammatory and immunoregulatory disorders and diseases, including asthma and allergic diseases, as well as autoimmune pathologies such as rheumatoid arthritis and atherosclerosis.

For example, an instant compound which inhibits one or more functions of a mammalian chemokine receptor (e.g., a human chemokine receptor) may be administered to inhibit (i.e., reduce or prevent) inflammation. As a result, one or more inflammatory processes, such as leukocyte emigration, chemotaxis, exocytosis (e.g., of enzymes, histamine) or inflammatory mediator release, is inhibited. For example, eosinophilic infiltration to inflammatory sites (e.g., in asthma) can be inhibited according to the present method.

Similarly, an instant compound which promotes one or more functions of a mammalian chemokine receptor (e.g., a human chemokine) is administered to stimulate (induce or enhance) an inflammatory response, such as leukocyte emigration, chemotaxis, exocytosis (e.g., of enzymes, histamine) or inflammatory mediator release, resulting in the beneficial stimulation of inflammatory processes. For example, eosinophils can be recruited to combat parasitic infections.

In addition to primates, such as humans, a variety of other mammals can be treated according to the method of the present invention. For instance, mammals including, but not limited to, cows, sheep, goats, horses, dogs, cats, guinea pigs, rats or other bovine, ovine, equine, canine, feline, rodent or murine species can be treated. However, the method can also be practiced in other species, such as avian species (e.g., chickens).

Diseases and conditions associated with inflammation and infection can be treated using the method of the present invention. In a preferred embodiment, the disease or condition is one in which the actions of eosinophils and/or lymphocytes are to be inhibited or promoted, in order to modulate the inflammatory response.

Diseases or conditions of humans or other species which can be treated with inhibitors of chemokine receptor function, include, but are not limited to: inflammatory or allergic diseases and conditions, including respiratory allergic diseases such as asthma, allergic rhinitis, hypersensitivity lung diseases, hypersensitivity pneumonitis, eosinophilic pneumonias (e.g., Loeffler's syndrome, chronic eosinophilic pneumonia), delayed-type hypersentitivity, interstitial lung diseases (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); systemic anaphylaxis or hypersensitivity responses, drug allergies (e.g., to penicillin, cephalosporins), insect sting allergies; autoimmune diseases, such as rheumatoid arthritis, psoriatic arthritis, multiple sclerosis, systemic lupus erythematosus, myasthenia gravis, juvenile onset diabetes; glomerulonephritis, autoimmune thyroiditis, Behcet's disease; graft rejection (e.g., in transplantation), including allograft rejection or graft-versus-host disease; inflammatory bowel diseases, such as Crohn's disease and ulcerative colitis; spondyloarthropathies; scleroderma; psoriasis (including T-cell mediated psoriasis) and inflammatory dermatoses such an dermatitis, eczema, atopic dermatitis, allergic contact dermatitis, urticaria; vasculitis (e.g., necrotizing, cutaneous, and hypersensitivity vasculitis); eosinphilic myositis, eosinophilic fasciitis; cancers with leukocyte infiltration of the skin or organs. Other diseases or conditions in which undesirable inflammatory responses are to be inhibited can be treated, including, but not limited to, reperfusion injury, atherosclerosis, certain hematologic malignancies, cytokine-induced toxicity (e.g., septic shock, endotoxic shock), polymyositis, dermatomyositis.

Diseases or conditions of humans or other species which can be treated with promoters of chemokine receptor function, include, but are not limited to: immunosuppression, such as that in individuals with immunodeficiency syndromes such as AIDS, individuals undergoing radiation therapy, chemotherapy, therapy for autoimmune disease or other drug therapy (e.g., corticosteroid therapy), which causes immunosuppression; immunosuppression due congenital deficiency in receptor function or other causes; and infectious diseases, such as parasitic diseases, including, but not limited to helminth infections, such as nematodes (round worms); (Trichuriasis, Enterobiasis, Ascariasis, Hookworm, Strongyloidiasis, Trichinosis, filariasis); trematodes (flukes) (Schistosomiasis, Clonorchiasis), cestodes (tape worms) (Echinococcosis, Taeniasis saginata, Cysticercosis); visceral worms, visceral larva migrans (e.g., Toxocara), eosinophilic gastroenteritis (e.g., Anisaki spp., *Phocanema* ssp.), cutaneous larva migrans (*Ancylostona braziliense, Ancylostoma caninum*).

The compounds of the present invention are accordingly useful in the prevention and treatment of a wide variety of inflammatory and immunoregulatory disorders and diseases.

In another aspect, the instant invention may be used to evaluate putative specific agonists or antagonists of chemokine receptors, including CCR-1, CCR-2, CCR-2A, CCR-2B, CCR-3, CCR-4, CCR-5, CXCR-3, and CXCR-4. Accordingly, the present invention is directed to the use of these compounds in the preparation and execution of screening assays for compounds which modulate the activity of chemokine receptors. For example, the compounds of this invention are useful for isolating receptor mutants, which are excellent screening tools for more potent compounds. Furthermore, the compounds of this invention are useful in establishing or determining the binding site of other compounds to chemokine receptors, e.g., by competitive inhibition. The compounds of the instant invention are also useful for the evaluation of putative specific modulators of the chemokine receptors, including CCR-1, CCR-2, CCR-2A, CCR-2B, CCR-3, CCR-4, CCR-5, CXCR-3, and CXCR-4. As appreciated in the art, thorough evaluation of specific agonists and antagonists of the above chemokine receptors has been hampered by the lack of availability of non-peptidyl (metabolically resistant) compounds with high binding affinity for these receptors. Thus the compounds of this invention are commercial products to be sold for these purposes.

The present invention is further directed to a method for the manufacture of a medicament for modulating chemokine receptor activity in humans and animals comprising combining a compound of the present invention with a pharmaceutical carrier or diluent.

The present invention is further directed to the use of these compounds in the prevention or treatment of infection by a retrovirus, in particular, the human immunodeficiency virus (HIV) and the treatment of, and delaying of the onset of consequent pathological conditions such as AIDS. Treating AIDS or preventing or treating infection by HIV is defined as including, but not limited to, treating a wide range of states of HIV infection: AIDS, ARC (AIDS related complex), both symptomatic and asymptomatic, and actual or potential exposure to HIV. For example, the compounds of this invention are useful in treating infection by HIV after suspected past exposure to HIV by, e.g., blood transfusion, organ transplant, exchange of body fluids, bites, accidental needle stick, or exposure to patient blood during surgery. In addition, a compound of the present invention may be used for the prevention of infection by HIV and the prevention of AIDS, such as in post-coital prophylaxis or in the prevention of maternal transmission of the HIV virus to a fetus or a child upon birth.

In a preferred aspect of the present invention, a subject compound may be used in a method of inhibiting the binding of a human immunodeficiency virus to a chemokine receptor, such as CCR-5 and/or CXCR-4, of a target cell, which comprises contacting the target cell with an amount of the compound which is effective at inhibiting the binding of the virus to the chemokine receptor.

The subject treated in the methods above is a mammal, preferably a human being, male or female, in whom modulation of chemokine receptor activity is desired. "Modulation" as used herein is intended to encompass antagonism, agonism, partial antagonism and/or partial agonism. The term "therapeutically effective amount" means the amount of the subject compound that will elicit the biological or medical response of a tissue, system, animal or human that is being sought by the researcher, veterinarian, medical doctor or other clinician.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The terms "administration of" and or "administering a" compound should be understood to mean providing a compound of the invention or a prodrug of a compound of the invention to the individual in need of treatment.

Combined therapy to modulate chemokine receptor activity and thereby prevent and treat inflammatory and immunoregulatory disorders and diseases, including asthma and allergic diseases, as well as autoimmune pathologies such as rheumatoid arthritis and atherosclerosis, and those pathologies noted above is illustrated by the combination of the compounds of this invention and other compounds which are known for such utilities.

For example, in the treatment or prevention of inflammation, the present compounds may be used in conjunction with an antiinflammatory or analgesic agent such as an opiate agonist, a lipoxygenase inhibitor, such as an inhibitor of 5-lipoxygenase, a cyclooxygenase inhibitor, such as a cyclooxygenase-2 inhibitor, an interleukin inhibitor, such as an interleukin-1 inhibitor, an NMDA antagonist, an inhibitor of nitric oxide or an inhibitor of the synthesis of nitric oxide, a non-steroidal antiinflammatory agent, or a cytokine-suppressing antiinflammatory agent, for example with a compound such as acetaminophen, asprin, codiene, fentanyl, ibuprofen, indomethacin, ketorolac, morphine, naproxen, phenacetin, piroxicam, a steroidal analgesic, sufentanyl, sunlindac, tenidap, and the like. Similarly, the instant compounds may be administered with a pain reliever; a potentiator such as caffeine, an H2-antagonist, simethicone, aluminum or magnesium hydroxide; a decongestant such as phenylephrine, phenylpropanolamine, pseudophedrine, oxymetazoline, ephinephrine, naphazoline, xylometazoline, propylhexedrine, or levo-desoxy-ephedrine; an antiitussive such as codeine, hydrocodone, caramiphen, carbetapentane, or dextramethorphan; a diuretic; and a sedating or non-sedating antihistamine. Likewise, compounds of the present invention may be used in combination with other drugs that are used in the treatment/prevention/suppression or amelioration of the diseases or conditions for which compounds of the pressent invention are useful. Such other drugs may be administered, by a route and in an amount commonly used therefor, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention. Examples of other active ingredients that may be combined with a compound of the present invention, either administered separately or in the same pharmaceutical compositions, include, but are not limited to: (a) VLA-4 antagonists such as those described in U.S. Pat. No. 5,510,332, WO97/03094, WO97102289, WO96/40781, WO96/22966, WO96/20216, WO96/01644, WO96/06108, WO95/15973 and WO96/31206; (b) steroids such as beclomethasone, methylprednisolone, betamethasone, prednisone, dexamethasone, and hydrocortisone; (c) immunosuppressants such as cyclosporin, tacrolimus, rapamycin and other FK-506 type immunosuppressants; (d) antihistamines (H1-histamine antagonists) such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (e) non-steroidal anti-asthmatics such as β2-agonists (terbutaline, metaproterenol, fenoterol, isoetharine, albuterol, bitolterol, and pirbuterol), theophylline, cromolyn sodium, atropine, ipratropium bromide, leukotriene antago-
nists (zafirlukast, montelukast, pranlukast, iralukast, pobilukast, SKB-106,203), leukotriene biosynthesis inhibitors (zileuton, BAY-1005); (f) non-steroidal antiinflammatory agents (NSAIDs) such as propionic acid derivatives (alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone); (g) cyclooxygenase-2 (COX-2) inhibitors; (h) inhibitors of phosphodiesterase type IV (PDE-IV); (i) other antagonists of the chemokine receptors, especially CCR-1, CCR-2, CCR-3 and CCR-5; (j) cholesterol lowering agents such as HMG-CoA reductase inhibitors (lovastatin, simvastatin and pravastatin, fluvastatin, atorvastatin, and other statins), sequestrants (cholestyramine and colestipol), nicotinic acid, fenofibric acid derivatives (gemfibrozil, clofibrat, fenofibrate and benzafibrate), and probucol; (k) anti-diabetic agents such as insulin, sulfonylureas, biguanides (metformin), α-glucosidase inhibitors (acarbose) and glitazones (troglitazone and pioglitazone); (l) preparations of interferon beta (interferon beta-la, interferon beta-1β); (m) other compounds such as 5-aminosalicylic acid and prodrugs thereof, anitimetabolites such as azathioprine and 6-mercaptopurine, and cytotoxic cancer chemotherapeutic agents. The weight ratio of the compound of the compound of the present invention to the second active ingredient may be varied and will depend upon the effective dose of each ingredient. Generally, an effective dose of each will be used. Thus, for example, when a compound of the present invention is combined with an NSAID the weight ratio of the compound of the present invention to the NSAID will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

The present invention is further directed to combinations of the present compounds with one or more agents useful in the prevention or treatment of AIDS. For example, the compounds of this invention may be effectively administered, whether at periods of pre-exposure and/or post-exposure, in combination with effective amounts of the AIDS antivirals, immunomodulators, anti-infectives, or vaccines known to those of ordinary skill in the art.

ANTIVIRALS

| Drug Name | Manufacturer | Indication |
|---|---|---|
| 097 | Hoechst/Bayer | HIV infection, AIDS, ARC (non-nucleoside reverse transcriptase (RT) |

| Drug Name | Manufacturer | Indication |
|---|---|---|
| 141 W94 | Glaxo Wellcome | inhibitor) HIV infection, AIDS, ARC (protease inhibitor) |
| 1592U89 | Glaxo Wellcome | HIV infection, AIDS, ARC (protease inhibitor) |
| Abacavir (1592U89) | Glaxo Wellcome | HIV infection, AIDS, ARC (RT inhibitor) |
| Acemannan | Carrington Labs (Irving, TX) | ARC |
| Acyclovir | Burroughs Wellcome | HIV infection, AIDS, ARC, in combination with AZT |
| AD-439 | Tanox Biosystems | HIV infection, AIDS, ARC |
| AD-519 | Tanox Biosystems | HIV infection, AIDS, ARC |
| Adefovir dipivoxil | Gilead Sciences | HIV infection |
| AL-721 | Ethigen (Los Angeles, CA) | ARC, PGL HIV positive, AIDS |
| Alpha Interferon | Glaxo Wellcome | Kaposi's sarcoma, HIV in combination w/Retrovir |
| Ansamycin LM 427 | Adria Laboratories (Dublin, OH) Erbamont (Stamford, CT) | ARC |
| Antibody which neutralizes pH labile alpha aberrant Interferon | Advanced Biotherapy Concepts (Rockville, MD) | AIDS, ARC |
| AR177 | Aronex Pharm | HIV infection, AIDS, ARC |
| beta-fluoro-ddA | Nat'l Cancer Institute | AIDS-associated diseases |
| BMS-232623 (CGP-73547) | Bristol-Myers Squibb/ Novartis | HIV infection, AIDS, ARC (protease inhibitor) |
| BMS-234475 (CGP-61755) | Bristol-Myers Squibb/ Novartis | HIV infection, AIDS, ARC (protease inhibitor) |
| (−)6-Chloro-4(S)-cyclopropylethynyl-4(S)-trifluoro-methyl-1,4-dihydro-2H-3,1-benzoxazin-2-one | Merck | HIV infection, AIDS, ARC (non-nucleoside reverse transcriptase inhibitor) |
| CI-1012 | Warner-Lambert | HIV-1 infection |
| Cidofovir | Gilead Science | CMV retinitis, herpes, papillomavirus |
| Curdlan sulfate | AJI Pharma USA | HIV infection |
| Cytomegalovirus immune globin | MedImmune | CMV retinitis |
| Cytovene Ganciclovir | Syntex | sight threatening CMV peripheral CMV retinitis |
| Delaviridine | Pharmacia-Upjohn | HIV infection, AIDS, ARC (RT inhibitor) |
| Dextran Sulfate | Ueno Fine Chem. Ind. Ltd. (Osaka, Japan) | AIDS, ARC, HIV positive asymptomatic |
| ddC Dideoxycytidine | Hoffman-La Roche | HIV infection, AIDS, ARC |
| ddI Dideoxyinosine | Bristol-Myers Squibb | HIV infection, AIDS, ARC; combination with AZT/d4T |
| DMP-450 | AVID (Camden, NJ) | HIV infection, AIDS, ARC (protease inhibitor) |
| Efavirenz (DMP 266) | DuPont Merck | HIV infection, AIDS, ARC (non-nucleoside RT inhibitor) |

| Drug Name | Manufacturer | Indication |
|---|---|---|
| EL10 | Elan Corp, PLC (Gainesville, GA) | HIV infection |
| Famciclovir | Smith Kline | herpes zoster, herpes simplex |
| FTC | Emory University | HIV infection, AIDS, ARC (reverse transcriptase inhibitor) |
| GS 840 | Gilead | HIV infection, AIDS, ARC (reverse transcriptase inhibitor) |
| GW 141 | Glaxo Welcome | HIV infection, AIDS, ARC (protease inhibitor) |
| GW 1592 | Glaxo Welcome | HIV infection, AIDS, ARC (reverse transcriptase inhibitor) |
| HBY097 | Hoechst Marion Roussel | HIV infection, AIDS, ARC (non-nucleoside reverse transcriptase inhibitor) |
| Hypericin | VIMRx Pharm. | HIV infection, AIDS, ARC |
| Recombinant Human Interferon Beta | Triton Biosciences (Almeda, CA) | AIDS, Kaposi's sarcoma, ARC |
| Interferon alfa-n3 | Interferon Sciences | ARC, AIDS |
| Indinavir | Merck | HIV infection, AIDS, ARC, asymptomatic HIV positive, also in combination with AZT/ddI/ddC |
| ISIS 2922 | ISIS Pharmaceuticals | CMV retinitis |
| KNI-272 | Nat'l Cancer Institute | HIV-assoc. diseases |
| Lamivudine, 3TC | Glaxo Wellcome | HIV infection, AIDS, ARC (reverse transcriptase inhibitor); also with AZT |
| Lobucavir | Bristol-Myers Squibb | CMV infection |
| Nelfinavir | Agouron Pharmaceuticals | HIV infection, AIDS, ARC (protease inhibitor) |
| Nevirapine | Boeheringer Ingleheim | HIV infection, AIDS, ARC (RT inhibitor) |
| Novapren | Novaferon Labs, Inc. (Akron, OH) | HIV inhibitor |
| Peptide T Octapeptide Sequence | Peninsula Labs (Belmont, CA) | AIDS |
| Trisodium Phosphonoformate | Astra Pharm. Products, Inc | CMV retinitis, HIV infection, other CMV infections |
| PNU-140690 | Pharmacia Upjohn | HIV infection, AIDS, ARC (protease inhibitor) |
| Probucol | Vyrex | HIV infection, AIDS |
| RBC-CD4 | Sheffield Med. Tech (Houston TX) | HIV infection, AIDS, ARC |
| Ritonavir | Abbott | HIV infection, AIDS, ARC (protease inhibitor) |
| Saquinavir | Hoffmann-LaRoche | HIV infection, AIDS, ARC (protease inhibitor) |
| Stavudine; d4T Didehydrodeoxy-thymidine | Bristol-Myers Squibb | HIV infection, AIDS, ARC |
| Valaciclovir | Glaxo Wellcome | genital HSV & CMV infections |
| Virazole Ribavirin | Viratek/ICN (Costa Mesa, CA) | asymptomatic HIV positive, LAS, ARC |

-continued

| Drug Name | Manufacturer | Indication |
|---|---|---|
| VX-478 | Vertex | HIV infection, AIDS, ARC |
| Zalcitabine | Hoffmann-La Roche | HIV infection, AIDS, ARC, with AZT |
| Zidovudine; AZT | Glaxo Wellcome | HIV infection, AIDS, ARC, Kaposi's sarcoma, in combination with other therapies |

IMMUNO-MODULATORS

| Drug Name | Manufacturer | Indication |
|---|---|---|
| AS-101 | Wyeth-Ayerst | AIDS |
| Bropirimine | Pharmacia Upjohn | advanced AIDS |
| Acemannan | Carrington Labs, Inc. (Irving, TX) | AIDS, ARC |
| CL246,738 | American Cyanamid Lederle Labs | AIDS, Kaposi's sarcoma |
| EL10 | Elan Corp, PLC (Gainesville, GA) | HIV infection |
| FP-21399 | Fuki ImmunoPharm | blocks HIV fusion with CD4 + cells |
| Gamma Interferon | Genentech | ARC, in combination w/TNF (tumor necrosis factor) |
| Granulocyte Macrophage Colony Stimulating Factor | Genetics Institute Sandoz | AIDS |
| Granulocyte Macrophage Colony Stimulating Factor | Hoeschst-Roussel Immunex | AIDS |
| Granulocyte Macrophage Colony Stimulating Factor | Schering-Plough | AIDS, combination w/AZT |
| HIV Core Particle Immunostimulant | Rorer | seropositive HIV |
| IL-2 Interleukin-2 | Cetus | AIDS, in combination w/AZT |
| IL-2 Interleukin-2 | Hoffman-La Roche Immunex | AIDS, ARC, HIV, in combination w/AZT |
| IL-2 Interleukin-2 (aldeslukin) | Chiron | AIDS, increase in CD4 cell counts |
| Immune Globulin Intravenous (human) | Cutter Biological (Berkeley, CA) | pediatric AIDS, in combination w/AZT |
| IMREG-1 | Imreg (New Orleans, LA) | AIDS, Kaposi's sarcoma, ARC, PGL |
| IMREG-2 | Imreg (New Orleans, LA) | AIDS, Kaposi's sarcoma, ARC, PGL |
| Imuthiol Diethyl Dithio Carbamate | Merieux Institute | AIDS, ARC |
| Alpha-2 Interferon | Schering Plough | Kaposi's sarcoma w/AZT, AIDS |
| Methionine-Enkephalin | TNI Pharmaceutical (Chicago, IL) | AIDS, ARC |
| MTP-PE Muramyl-Tripeptide | Ciba-Geigy Corp. | Kaposi's sarcoma |
| Granulocyte Colony Stimulating Factor | Amgen | AIDS, in combination w/AZT |
| Remune | Immune Response Corp. | immunotherapeutic |
| rCD4 Recombinant Soluble Human CD4 | Genentech | AIDS, ARC |
| rCD4-IgG hybrids | | AIDS, ARC |
| Recombinant Soluble Human CD4 | Biogen | AIDS, ARC |
| Interferon Alfa 2a | Hoffman-La Roche | Kaposi's sarcoma AIDS, ARC, in combination w/AZT |
| SK&F106528 Soluble T4 | Smith Kline | HIV infection |
| Thymopentin | Immunobiology Research Institute (Annandale, NJ) | HIV infection |
| Tumor Necrosis Factor; TNF | Genentech | ARC, in combination w/gamma Interferon |

ANTI-INFECTIVES

| Drug Name | Manufacturer | Indication |
|---|---|---|
| Clindamycin with Primaquine | Pharmacia Upjohn | PCP |
| Fluconazole | Pfizer | cryptococcal meningitis, candidiasis |
| Pastille Nystatin Pastille | Squibb Corp. | prevention of oral candidiasis |
| Ornidyl Eflornithine | Merrell Dow | PCP |
| Pentamidine Isethionate (IM & IV) | LyphoMed (Rosemont, IL) | PCP treatment |
| Trimethoprim | | antibacterial |
| Trimethoprim/sulfa | | antibacterial |
| Piritrexim | Burroughs Wellcome | PCP treatment |
| Pentamidine isethionate for inhalation | Fisons Corporation | PCP prophylaxis |
| Spiramycin | Rhone-Poulenc | cryptosporidial diarrhea |
| Intraconazole-R51211 | Janssen Pharm. | histoplasmosis; cryptococcal meningitis |
| Trimetrexate | Warner-Lambert | PCP |

OTHER

| Drug Name | Manufacturer | Indication |
|---|---|---|
| Daunorubicin | NeXstar, Sequus | Karposi's sarcoma |
| Recombinant Human Erythropoietin | Ortho Pharm. Corp. | severe anemia assoc. with AZT therapy |
| Recombinant Human Growth Hormone | Serono | AIDS-related wasting, cachexia |
| Megestrol Acetate | Bristol-Myers Squibb | treatment of anorexia assoc. w/AIDS |
| Testosterone | Alza, Smith Kline | AIDS-related wasting |
| Total Enteral Nutrition | Norwich Eaton Pharmaceuticals | diarrhea and malabsorption related to AIDS |

It will be understood that the scope of combinations of the compounds of this invention with AIDS antivirals, immunomodulators, anti-infectives or vaccines is not limited to the list in the above Table, but includes in principle any combination with any pharmaceutical composition useful for the treatment of AIDS.

Preferred combinations are simultaneous or alternating treatments of with a compound of the present invention and an inhibitor of HIV protease and/or a non-nucleoside inhibitor of HIV reverse transcriptase. An optional fourth component in the combination is a nucleoside inhibitor of HIV reverse transcriptase, such as AZT, 3TC, ddC or ddI. A preferred inhibitor of HIV protease is indinavir, which is the sulfate salt of N-(2(IR)-hydroxy-1(S)-indanyl)-2(R)-phenylmethyl-4-(S)-hydroxy-5-(1-(4-(3-pyridyl-methyl)-2(S)-N'-(t-butylcarboxamido)-piperazinyl))-pentaneamide ethanolate, and is synthesized according to U.S. Pat. No. 5,413,999. Indinavir is generally administered at a dosage of 800 mg three times a day. Other preferred protease inhibitors are nelfinavir and ritonavir. Another preferred inhibitor of HIV protease is saquinavir which is administered in a dosage of 600 or 1200 mg tid. Preferred non-nucleoside inhibitors of HIV reverse transcriptase include efavirenz. The preparation of ddC, ddI and AZTF are also described in EPO 0,484,071. These combinations may have unexpected effects on limiting the spread and degree of infection of HIV. Preferred combinations include those with the following (1) indinavir with efavirenz, and, optionally, AZT and/or 3TC and/or ddE and/or ddC; (2) indinavir, and any of AZTI and/or ddI and/or ddC and/or 3TC, in particular, indinavir and AZT and 3TC; (3) stavudilne and 3TC and/or zidovudine; (4) zidovudine and lamivudine and 141W94 and 1592U89; (5) zidovudine and lamivudine.

In such combinations the compound of the present invention and other active agents may be administered separately or in conjunction. In addition, the administration of one element may be prior to, concurrent to, or subsequent to the administration of other agent(s).

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention are effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl- pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally- occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of The present invention are employed. (For purposes of this application, topical application shall include mouth washes and gargles.)

The pharmaceutical composition and method of the present invention may further comprise other therapeutically active compounds as noted herein which are usually applied in the treatment of the above mentioned pathological conditions.

In the treatment or prevention of conditions which require chemokine receptor modulation an appropriate dosage level will generally be about 0.001 to 100 mg per kg patient body weight per day which can be administered in single or multiple doses. Preferably, the dosage level will be about 0.01 to about 25 mg/kg per day; more preferably about 0.05 to about 10 mg/kg per day. A suitable dosage level may be about 0.01 to 25 mg/kg per day, about 0.05 to 10 mg/kg per day, or about 0.1 to 5 mg/kg per day. Within this range the dosage may be 0.005 to 0.05, 0.05 to 0.5 or 0.5 to 5.0 mg/kg per day. For oral administration, the compositions are preferably provided in the form of tablets containing 1.0 to 1000 milligrams of the active ingredient, particularly 1.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Several methods for preparing the compounds of this invention are illustrated in the following Schemes and Examples.

The compounds of the present invention are prepared by alkylating azacycle 1, in which $R_1=H$, under appropriate conditions (Scheme 1). The required azacycle starting materials are prepared using methods described in the literature; such as described in Ong, H. H. et al, Journal of Medicinal Chemistry, 1983,26, 981–986, and Nargund, R. et al, U.S. Ser. No. 08/147,226 (Nov. 3, 1993), EP 93309867.5.

Thus, azacycle 1 ($R_1=H$) is combined with the appropriate aldehyde and the intermediate imine is reduced to the tertiary amine chemically (e.g. using sodium cyanoborohydride) or catalytically (e.g. using hydrogen and palladium on carbon or Raney nickel catalyst) (Scheme 1). The aldehyde needed for this reaction can be prepared by methods generally known in the chemical literature; for the purposes of the present invention the preparation of a representative aldehyde is described in Hale, J. J.; Finke, P. E.; MacCoss, M. *Bioorganic & Medicinal Chemistry Letters* 2993,3, 319–322.

In an alternative embodiment of the present invention, azacycle 1 ($R_1=H$) can be alkylated with an alkyl halide or alkyl sulfonate ester (with or without an added base to neutralize the mineral acid or sulfonic acid by-product) to give the desired compound (Scheme 1). The alkyl halide or alkyl sulfonate needed for this reaction can be prepared by methods generally known in the chemical literature; for the purposes of the present invention an aldehyde, prepared as described above, can be reduced to an alcohol with sodium borohydride, diisobutylaluminum hydride or lithium aluminum hydride, and the product alcohol converted to either the alkyl halide using methods described in March J. "Advanced Organic Chemistry", 3rd ed., John Wiley & Sons, New York, pp. 382–384 (1985), or alkyl sulfonate ester using methods described in March J. "Advanced Organic Chemistry", 3rd ed., John Wiley & Sons, New York, p. $4^{44}$ (1985).

In an alternative embodiment of the present invention, 1 ($R_1=H$) can be acylated to give the tertiary amide and subsequent reduction with a strong reducing agent (e.g. diborane including borane dimethylsulfide; and, lithium aluminum hydride) will give the desired compound (Scheme 1). The acylating agent needed for this reaction can be prepared by methods generally known in the chemical literature; for the purposes of the present invention an aldehyde, prepared as described above, can be oxidized using such commonly used reagents as permanganate in acid or silver oxide, and the resulting acid activated as an acid chloride or mixed anhydride which can be used to acylate I ($R_1=H$). The product amide can be reduced with a strong reducing agent, such as diborane or lithium aluminum hydride, to give the tertiary amine.

Optionally, compound f formed in the alkylation step may be further modified in subsequent reactions. In one illustration of such an approach, the aldehyde fragment contained a t-butoxycarbonylamino group (Example 2). After-reductive amination, the t-butoxycarbonyl protecting group is removed by treatment with a strong acid such as trifluoroacetic acid or formic acid and the resulting amine is acylated to furnish the desired compounds (Example 3). Alternatively, the protecting group may also be present in the azacycle portion as illustrated with a benzyloxycarbonyl group in Example 6. Thus an azacycle containing a benzyloxycarbonylindoline (prepared in Example 4) is alkylated with an aldehyde in the presence of a reducing agent. Next, the protecting group is removed to liberate a free amine (Example 7) and the amine is further reacted to provide additional analogs (Example 8).

presence of palladium on carbon or by exposure to trimethylsilyl iodide, to give the deprotected substituted spiro (indoline-3,4'-piperidine).

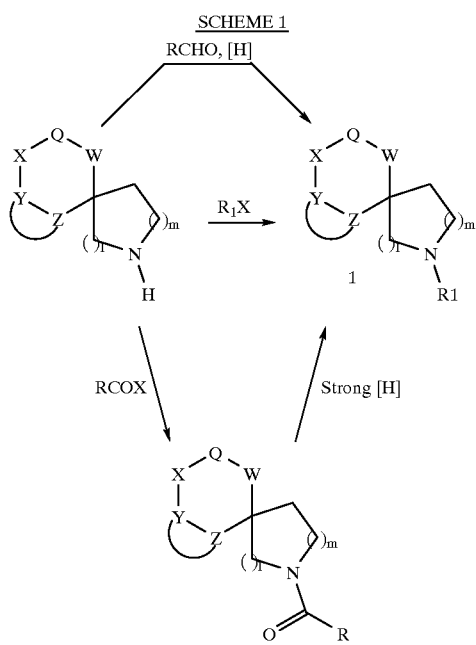

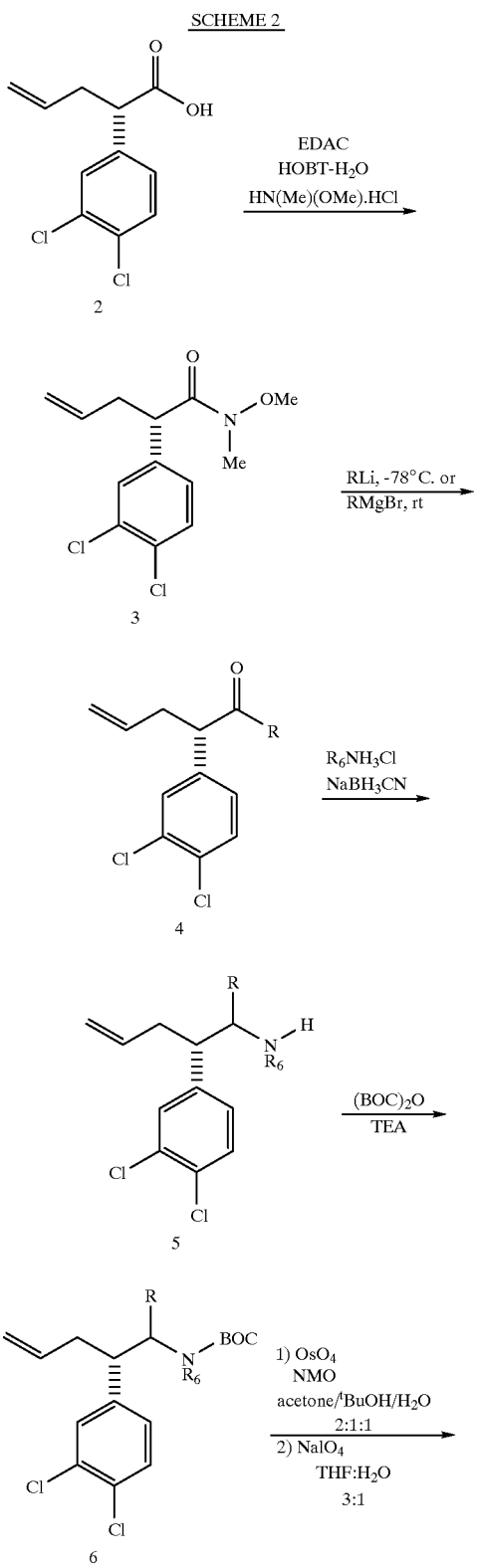

In an alternative embodiment of the present invention, the allyl acid 2 (described in Hale et al; see above) can be converted into the N-methyl methoxy amide 3, which is then treated with an alkyl or aryl metal reagent, for example methyllithium or butyllithium, to provide the ketone 4 (Scheme 2). The ketone can be converted into an imine which can then be reduced to secondary amine 5 chemically, (e.g using sodium cyanoborohydride or sodium borohydride), or catalytically (e.g. using hydrogen and palladium on carbon or Raney nickel catalyst). Acylation under standard conditions, for example with an acid chloride, provides amide 6. The allyl group in 6 can be oxidatively cleaved to aldehyde 7 with osmium tetroxide followed by sodium periodate or with ozone at low temperature. Reductive amination of aldehyde 7 with azacycle 1 can then be carried out under the conditions described above.

Substituted spiro(indoline-3,4'-piperidine) derivatives can be prepared as shown in Scheme 3 starting from the appropriately substituted phenylhydrazines. Following the Fischer indole reaction and reduction of the intermediate imine with a mild reducing agent such as sodium borohydride, the indoline nitrogen can be reacted with an electrophile such as an acyl chloride or a sulfonyl chloride. The protecting group on the piperidine nitrogen, for example a benzyloxycarbonyl group, can be removed by treatment with hydrogen in the -continued

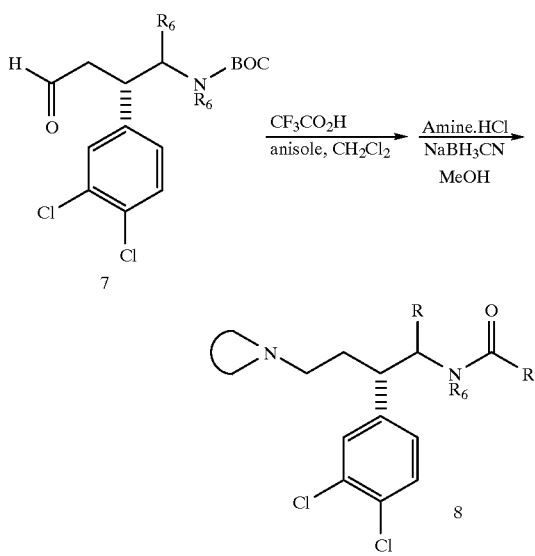

vides the allylic sulfide, which can be cyclized under radical conditions to give the illustrated spiro(2,3-dihydrobenzothiophene-3,4'-piperidine). Cleavage of the t-butoxycarbonyl group under standard conditions, such as trifluoroacetic acid, then provides the desired spirocycle.

SCHEME 4

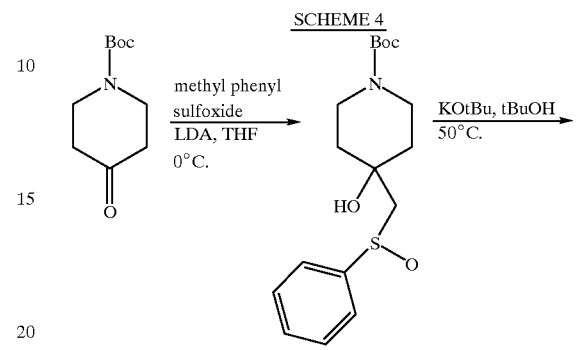

SCHEME 3

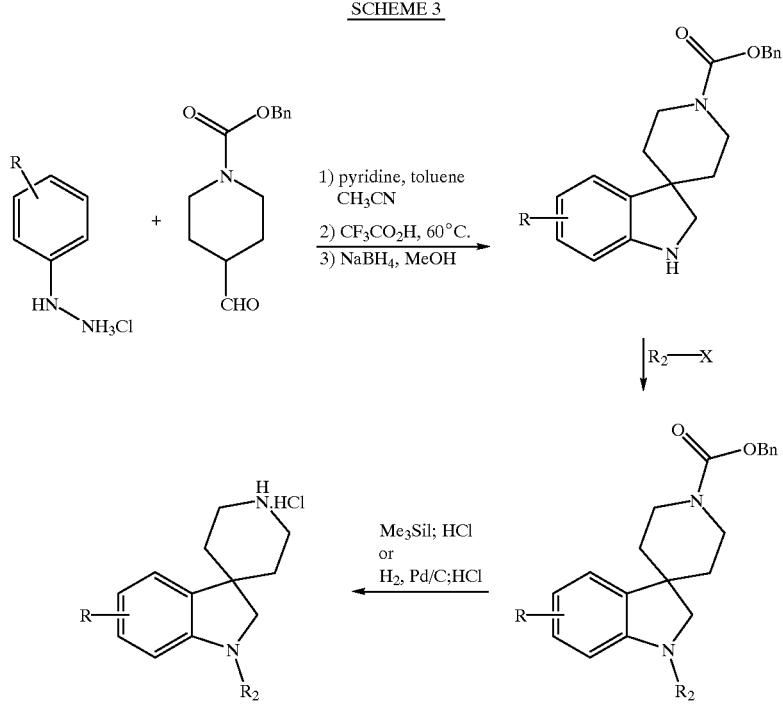

Preparation of spiro(2,3-dihydrobenzothiophene-3,4'-piperidine) derivatives is shown in Scheme 4. Reaction of N-Boc protected 4-piperidone with the lithium salt of methyl phenyl sulfoxide followed by base-mediated elimination-rearrangement and basic cleavage provides the indicated allylic alcohol. The alcohol can be converted to the rearranged allylic chloride with thionyl chloride in toluene in the presence of 2,6-lutidine as a proton scavenger. Displacement of the chloride with functionalized 2-bromothiophenol pro- -continued

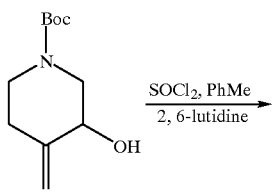

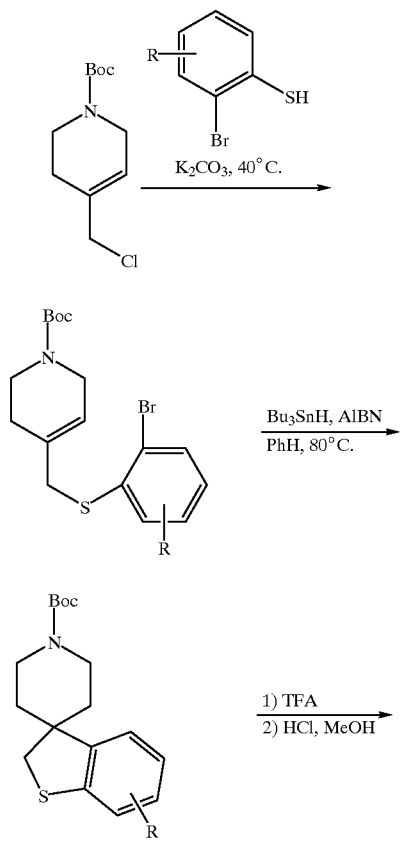

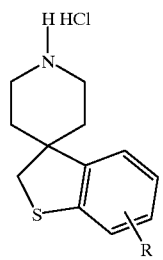

Spiro(2,3-dihydrobenzofuran-3,4'-piperidine) derivatives can be prepared as illustrated in Scheme 5. Treatment of an appropiately substituted ester of 2-fluorophenylacetate with mechlorethamine hydrochloride under basic conditions provides the piperidine product, which on treatment with a strong reducing agent such as lithium aluminum hydride produces the corresponding 4-(hydroxymethyl) compound. Cyclization with base provides the benzofuran derivative, and cleavage of the N-methyl group can then be carried out using 1-chloroethyl chloroformate or other suitable N-demethylating agents.

SCHEME 5

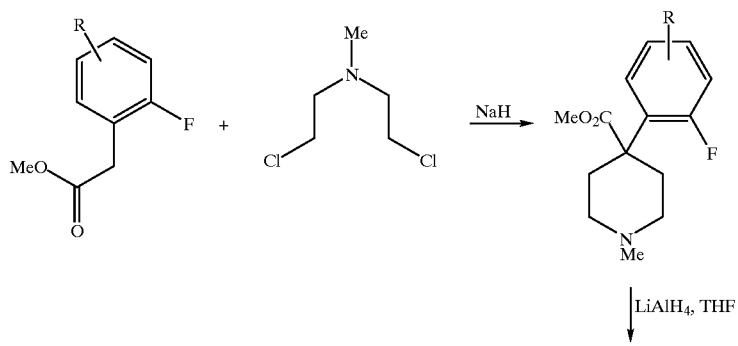

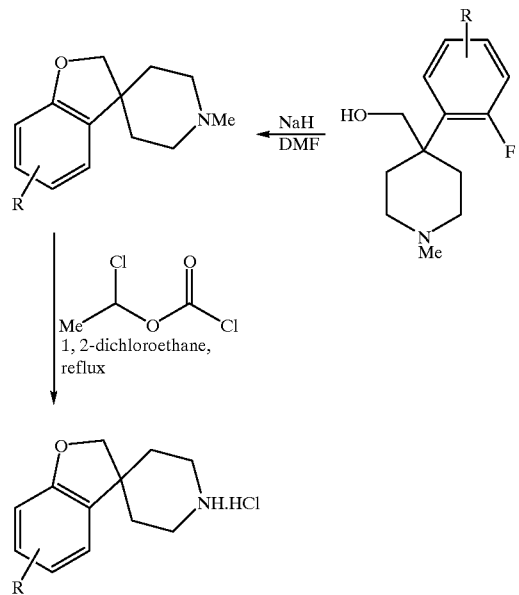

Compounds with alternate arrangements of the amide bond can be prepared as shown in Scheme 6. The illustrated acid can be homologated under Arndt-Eistert conditions to give the chain-extended acid, which can be derivatized under standard acylating conditions with, for example, an aniline derivative, to give the corresponding amide. Oxidative cleavage of the olefin with osmium tetroxide or ozone then provides the aldehyde intermediate suitable for coupling as described earlier.

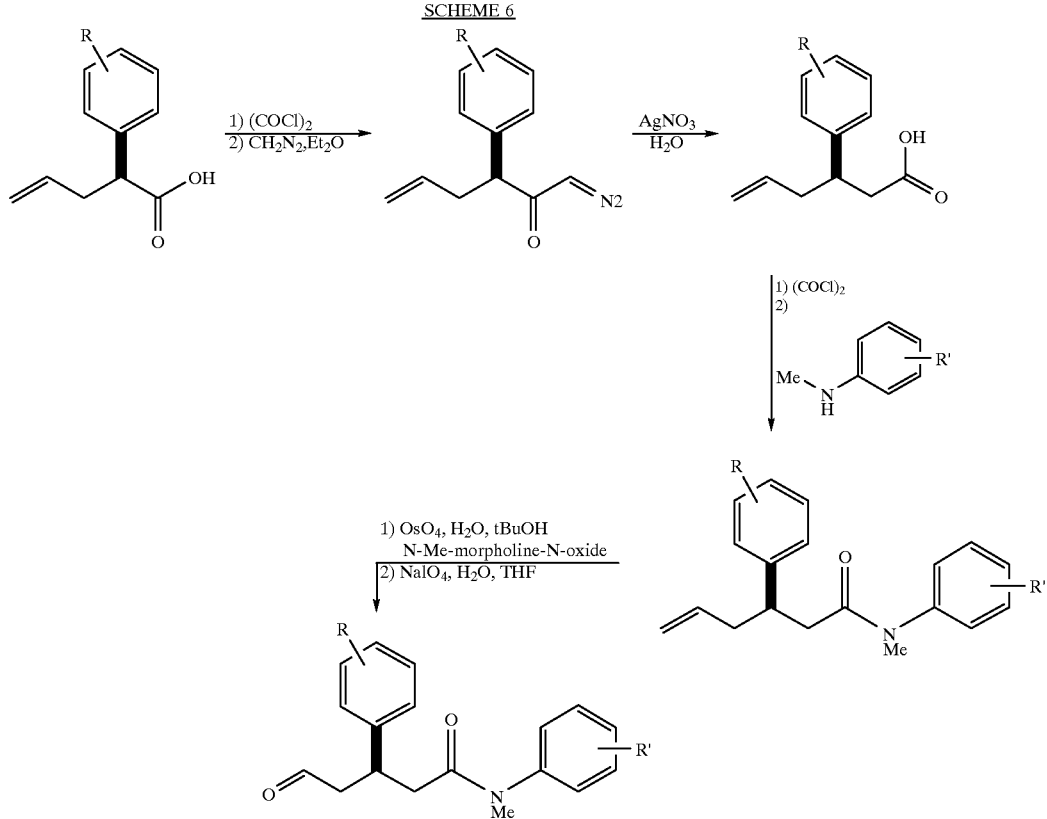

In addition, ketone derivatives can be prepared by an extension of the chemistry given above, as shown in Scheme 7. A second Arndt-Eistert chain extension provides the illustrated heptenoic acid derivative, which after conversion into its N-methoxy-N-methyl amide, can be reacted with an aryl organometallic reagent, such as an aryl magnesium bromide, to provide the ketone. Routine oxidative cleavage then gives the desired aldehyde, which can be coupled with a spiro-piperidine derivative as described above.

SCHEME 7

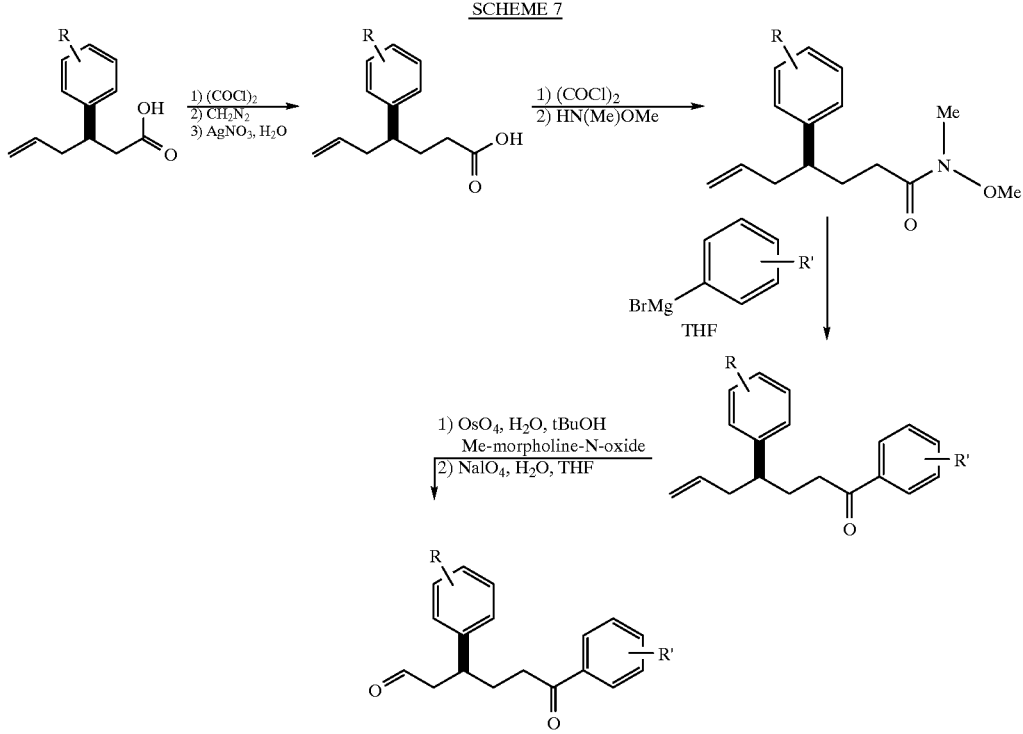

Alcohol containing antagonists can be prepared according to procedures given in Scheme 8. Formation of the N-methyl-N-methoxy amide of the indicated acid followed by oxidative cleavage of the olefin provides the intermediate aldehyde. Coupling with a spiro(indoline-3,4'-piperidine) derivative followed by addition of an organometallic reagent to the amide provides the illustrated ketone. Treatment with a hydride reducing agent, such as sodium borohydride, then yields the desired alcohol derivatives.

SCHEME 8

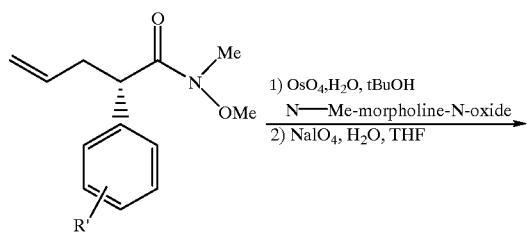

-continued

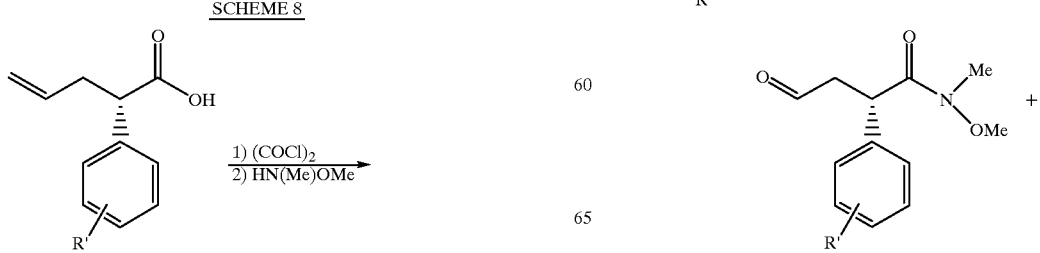

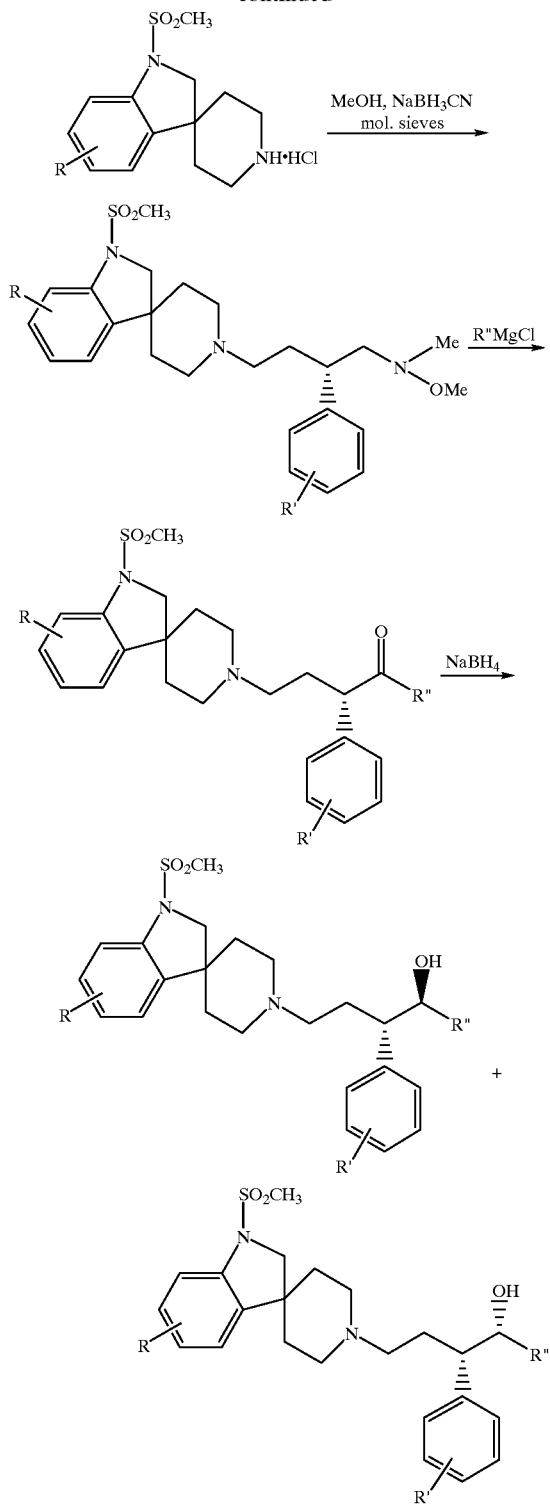

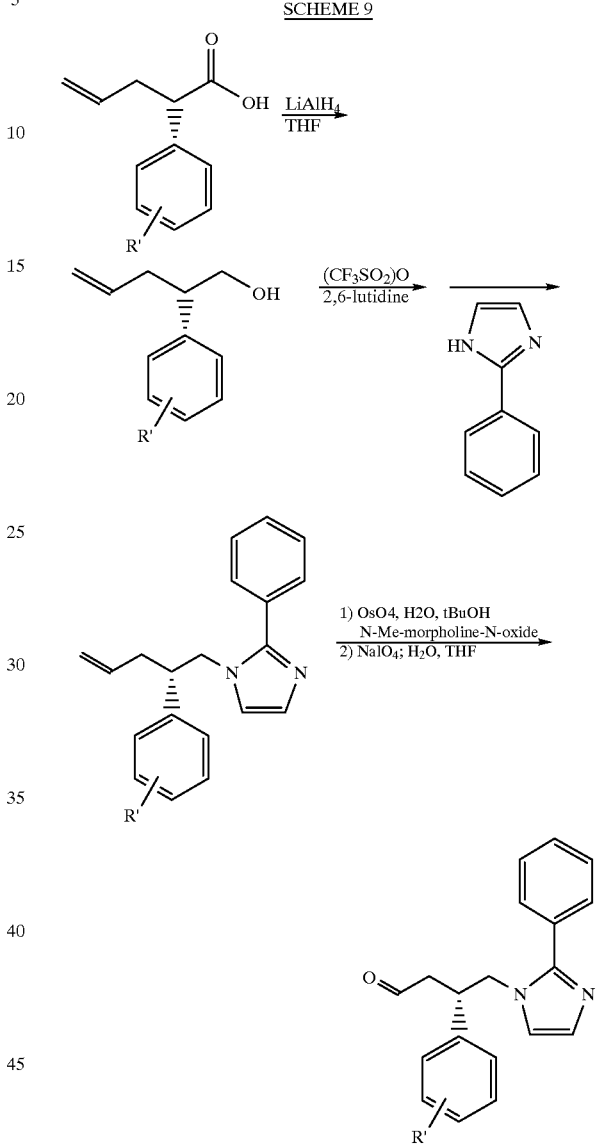

SCHEME 9

Formation of heterocycle substituted antagonists can be carried out according to the procedure given in Scheme 9 for substituted imidazoles. Reduction of the allyl acid with a strong reducing agent such as lithium aluminum hydride followed by in situ formation of the trifluoromethane-sulfonate of the formed alcohol allows for displacement of the triflate with a nucleophile such as 2-phenylimidazole. Oxidative cleavage under standard conditions provides the indicated aldehyde which can then be coupled under the conditions described above to the appropriate spiro derivative.

Spiro(2-oxo-1,2,3,4-tetrahydroquinoline-4,4'-piperidine) and spiro(1-oxo-1,2,3,4-tetrahydroisoquinoline-4,4'-piperidine) can be prepared as shown in Scheme 10. Starting from the indicated spiro(2-oxoindane-3,4'-piperidine) (described in Claremon, D. A. et al, European Patent 0 431 943 943 A2, Evans, B. E. et al, U.S. Pat. No. 5,091,387, Davis, L. et al, U.S. Pat. No. 4,420,485, all of which are incorporated by reference, and Parham et al, *Journal of Organic Chemistry*, 41, 2628 (1976)), deprotection of the piperidine nitrogen is carried out by treatment with acid, for example trifluoroacetic acid, followed by protection as the trifluoroacetamide, and the product is exposed to hydrazoic acid in the presence of sulfuric acid. Heating of this mixture effects a Schmidt rearrangement, to provide both the tetrahydroquinoline and the tetrahydroisoquinoline derivatives. These spiro compounds can then be separated and coupled to functionalized aldehydes by the methodology given above.

SCHEME 10

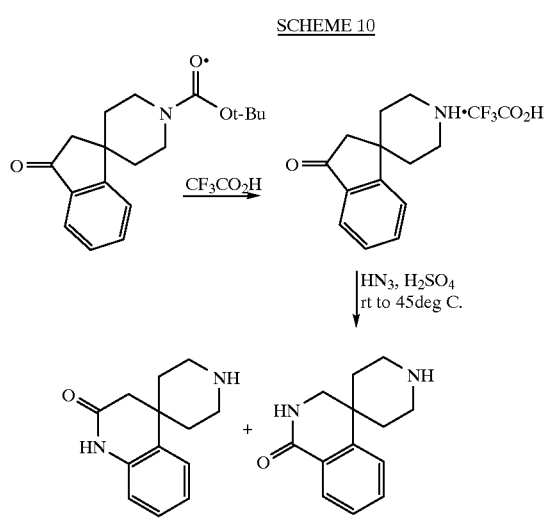

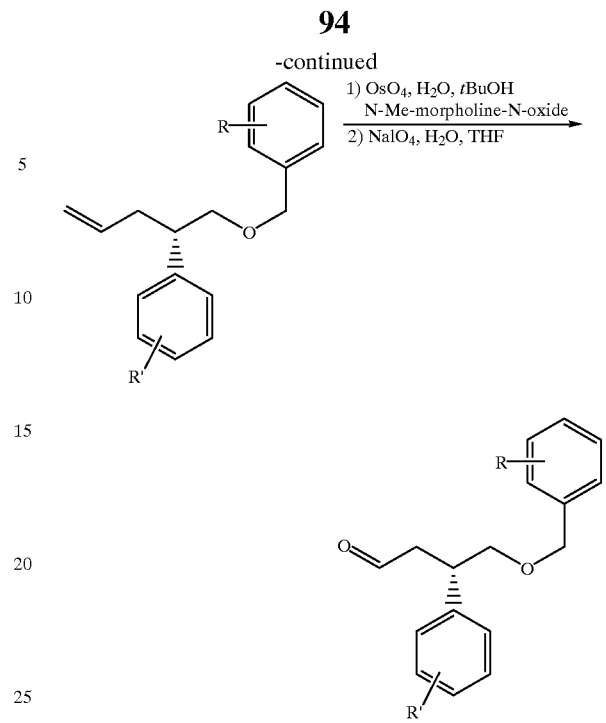

Compounds with ether substituents can also be prepared by the route shown in Scheme 11. Thus, the allyl acid discussed earlier can be reduced to the corresponding alcohol with, for example, lithium aluminum hydride. This alcohol can be alkylated by a Williamson ether synthesis, by deprotonation with a strong base such as sodium hydride or sodium hexamethyldisilazide followed by reaction with a benzyl halide such as benzyl bromide. The product can be processed through the oxidative cleavage steps described earlier to provide the aldehyde, which can then be coupled with a spirocycle kunder reductive amination conditions or else by reduction to the corresponding alcohol and conversion to the bromide. the bromide can then be used to alkylate a spirocycle under the conditions detailed above.

SCHEME 11

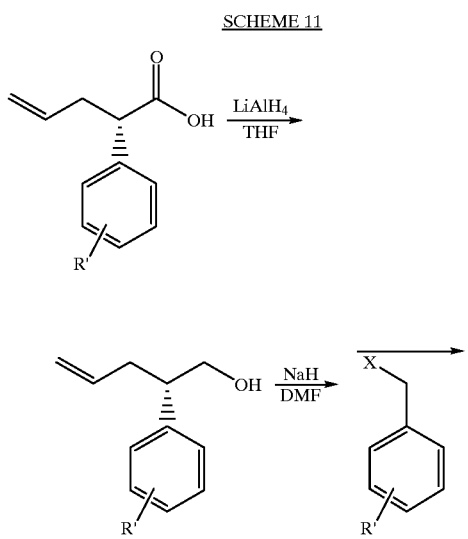

In some cases the order of carrying out the foregoing reaction schemes may be varied to facilitate the reaction or to avoid unwanted reaction products.

The following examples are provided for the purpose of further illustration only and are not intended to be limitations on the disclosed invention.

EXAMPLE 1

3-(S)-(3,4-Dichlorophenyl)-4-(N-(t-butoxycarbonyl) methylamino) butanal

A solution of 10 g (41 mmol) of 3-(S)-(3,4-dichlorophenyl)-4-methylamino-1-pentene in 100 mL of $CH_2Cl_2$ was cooled in an ice bath and treated with 5.8 mL (41 mmol) of triethylamine ($Et_3N$) and 9 g (41 mmol) of di-t-butyl dicarbonate. The cold bath was removed after 5 min and the stirring was continued for 1 h. The reaction mixture was diluted with $CH_2Cl_2$ and washed with water, 1.2 N HCl, saturated $NaHCO_3$ and brine. The solution was dried over $Na_2SO_4$ and concentrated to give 14.58 g of residual oil. $^1H$ NMR ($CDCl_3$, ppm ranges are given because of amide rotamers and line broadening) δ 1.36 (s, 9H), 2.33 (m, 2H), 2.60 & 2.70 (2s, 3H), 2.8–3.6 (m, 3H), 4.94 (m, 2H), 5.59 (m, 1H), 6.9–7.4 (m, 3H).

The residue was dissolved in 80 mL of acetone, 40 mL of t-butanol and 40 mL of water. To this solution 1 mL of osmium tetroxide (4% solution in water) and 5.15 g (44 mmol) of 4-methylmorpholine N-oxide were added. After stirring for 26 h, the reaction was quenched with approximately 5 g of $Na_2SO_3$ and concentrated to 25% of the original volume. The residue was partitioned between water and 1:1 ether ($Et_2O$), ethyl acetate (EtOAc), the layers were separated and the aqueous layer was extracted with $Et_2O$:EtOAc. Each organic layer was washed with water, brine and dried by filtering through $Na_2SO_4$. The filtrate was concentrated to afford the crude diol.

A solution of the diol in 120 mL of tetrahydrofuran (THF) and 40 mL of water was treated with 9.42 g (44 mmol) of sodium periodate. After stirring for 2 h, the reaction was diluted with Et$_2$O:EtOAc and washed with water and brine. The organic layer was dried (Na$_2$SO$_4$) and the filtrate was concentrated. The residue was purified by prepLC using 30% EtOAc/hexane to furnish 11.74 g (83% yield for three steps) of the title compound as a thick oil. 1H NMR (CDCl$_3$, ppm ranges are given because of amide rotamers and line broadening) δ 1.38 (s, 9H), 2.69 & 2.75 (2s, 3H), 2.6–3.65 (m, 51H), 6.95–7.4 (m, 31H), 9.67 (s, 11).

EXAMPLE 2

1'-(3-(S)-(3,4-Dichlorophenyl)-4-(N-(t-butoxycarbonyl)(methyl-amino))butyl)-1-methanesulfonyl-spiro(indoline-3,4'-piperidine)

To a solution of 0.76 g (2.2 mmol) of 3-(S)-(3,4-dichlorophenyl)-4-(N-(t-butoxycarbonyl)methylamino) butanal (from Example 1) in 4 mL of methanol were added 0.608 g (2 mmol) of 1-methane-sulfonyl-spiro(indoline-3,4'-piperidine) hydrochloride and 0.6 g of powdered 4 Å molecular sieves. After 15 min a solution of 0.554 g (8.8 mmol) of NaCNBH$_3$ in 8 mL of THF was dropwise added. Some gas evolution was observed. After 2 h, when the reaction was complete by TLC, the mixture was filtered through a pad of celite, the reaction flask and the pad were rinsed with methanol. The filtrate was concentrated to approximately 5 ml and the residue was partitioned between saturated NaECO$_3$ and Et$_2$O:EtOAc. The organic layer was washed with water, brine and dried over Na$_2$SO$_4$. The filtrate was concentrated and the residue was chromatographed on a flash column using a gradient of 49:49:2 to 74:24:2 EtOAc:hexane: triethylamine to furnish 0.94 g (72%) of the title compound as a foam. $^1$H NME (CDCl3, ppm ranges are given because of amide rotamers and line broadening) δ 1.37 (s, 9H), 1.6–3.6 (m, 15H), 2.61 & 2.72 (2s, 3H), 2.86 (s, 3H), 3.74 (s, 2H), 6.95–7.4 (m, 7H).

EXAMPLE 3

1'-(3-((S)-(3,4-Dichlorophenyl))-4-(N-(3,5-dimethylbenzoyl)(methyl-amino)) butyl)-1-methanesulfonyl-spiro(indoline-3,4'-piperidine)

Step A: 1'-(3-((S)-(3,4-dichlorophenyl))-4-(methylamino) butyl)-1-methanesulfonyl-spiro(indoline-3,4'-piperidine)

Cold trifluoroacetic acid (TFA, 4 mL) and 0.2 mL of anisole were added to 0.94 g (1.57 mmol) of 1'-(3-(S)-(3, 4-dichlorophenyl)-4-(N-(t-butoxycarbonyl)(methylamino)) butyl)-1-methanesulfonyl-spiro(indoline-3,4'-piperidine) and the mixture was stirred in an ice bath until all the foam dissolved. After stirring the resulting solution at room temperature for 30 min, it was concentrated in vacuo. The residue was partitioned between 0.5 N NaOH and CH$_2$Cl$_2$ and the layers were separated. The organic layer was washed with brine, dried over Na$_2$SO$_4$ and concentrated to give 0.7 g of foam which was used in the next step without purification.

1H NMR (CDCl$_3$, ppm ranges are given because of amide rotamers and line broadening) δ 1.7–2.7 (m, 10H), 2.64 (s, 3H), 2.88 (s, 3H), 2.9–3.4 (m, 5H), 3.70 (s, 2H), 6.8–7.4 (m, 7H).

Step B: 1'-(3-((S)-(3,4-Dichlorophenyl))-4-(N-(3,5-dimethylbenzoyl)(methylamino))butyl)-1-methanesulfonyl-spiro(indoline-3,4'-piperidine)

A solution of 0. 12 g (0.52 mmol) of 3,5-dimethylbenzoic acid in 2 mL of CH$_2$Cl$_2$ containing 1 drop of DMF was treated with 85 ul of oxalyl chloride. (Caution-gas evolution!) After 20 min the solution was concentrated in vacuo and the residue was mixed with 0.2 g (0.4 mmol) of 1'-(3-((S)-(3,4-dichlorophenyl))-4-(methylamino)butyl)-1-methane-sulfonyl-spiro(indoline-3,4'-piperidine) obtained from Step A, and 0.14 mL (1 mmol) of Et$_3$N in 2 mL of CH$_2$Cl$_2$. After 1 h the reaction mixture was diluted with CH$_2$Cl$_2$ and washed with saturated NaHCO$_3$, water, and brine. The CH$_2$Cl$_2$ solution was dried over Na$_2$SO$_4$, filtered and concentrated. Purification of the residue by prep TLC using 2% Et3N/EtOAc afforded 0.238 g (93% yield) of the title compound as a foam. $^1$H NMR (CDCl$_3$, ppm ranges are given because of amide rotamers and line broadening) δ 1.6–2.4 (m, 10H), 2.27 (s, 6H), 2.6–3.9 (m, 10H), 2.86 (s, 3H), 6.6–7.5 (m, 10H).

The following compounds were prepared by substituting the required acid chloride for 3,5-dimethylbenzoyl chloride in Step B.

1'-(3-((S)-(3,4-dichlorophenyl))-4-(N-(benzoyl) (methylamino)) butyl)-1-methanesulfonyl-spiro(indoline-3,4'-piperidine)

Mass Spectrum (FAB) 602 ($^{37}$Cl+$^{35}$Cl isotope), 600 ($^{35}$Cl+$^{35}$Cl isotope).

1'-(3-((S)-(3,4-Dichlorophenyl))-4-(N-(3,5-bistrifluoromethylbenzoyl)(methylamino))butyl)-1-methanesulfonyl-spiro(indoline-3,4'-piperidine)

Mass Spectrum (FAB) 738 ($^{37}$Cl+$^{35}$Cl isotope), 736 ($^{35}$Cl+$^{35}$Cl isotope).

1'-(3-((S)-(3,4-Dichlorophenyl))-4-(N-(3-methylbenzoyl) (methylamino))-butyl)-1-methanesulfonyl-spiro (indoline-3,4'-piperidine) $^1$H NME (CDCl$_3$, ppm ranges are given because of amide rotamers and line broadening) δ 1.6–2.4 (m, 10H), 2.32 (s, 3H), 2.6–3.9 (m, 10H), 2.86 (s, 3H), 6.75–7.5 (m, 11H).

Mass Spectrum (FAB) 616 ($^{37}$Cl+$^{35}$Cl isotope), 614 ($^{35}$Cl+$^{35}$Cl isotope).

1'-(3-((S)-(3,4-Dichlorophenyl))-4-(N-(3-chlorobenzoyl) (methylamino))-butyl)-1-methanesulfonyl-spiro (indoline-3,4'-piperidine) $^1$H NMR (CDCl$_3$, ppm ranges are given because of amide rotamers and line broadening) δ 1.6–2.4 (m, 10H), 2.6–3.9 (m, 10H), 2.86 (s, 3H), 6.75–7.5 (m, 11H).

Mass Spectrum (FAB) 635 ($^{37}$Cl+$^{35}$Cl isotope), 633 ($^{35}$Cl+$^{35}$Cl isotope).

1'-(3-((S)-(3,4-Dichlorophenyl))-4-(N-(3-trifluoromethylbenzoyl) (methyl-amino))butyl)-1-methanesulfonyl-spiro(indoline-3,4'-piperidine)

Mass Spectrum (FAB) 669 ($^{37}$Cl+$^{35}$Cl isotope), 667 ($^{35}$CL+$^{35}$Cl isotope).

1'-(3-((S)-(3,4-Dichlorophenyl))-4-(N-(3,5-dichlorobenzoyl) (methylamino))-butyl)-1-methanesulfonyl-spiro(indoline-3,4'-piperidine) $^1$H NMR (CDCl$_3$, ppm ranges are given because of amide rotamers and line broadening) δ 1.6–2.4 (m, 10H), 2.6–3.9 (m, 10H), 2.86 (s, 3H), 6.75–7.5 (m, 10H). Mass Spectrum (FAB) 671 ($^{37}$Cl+$^{35}$Cl isotope), 669 ($^{35}$Cl+$^{35}$Cl isotope).

1'-(3-((S)-(3,4-Dichlorophenyl))-4-(N-(3-trifluoromethylphenylacetyl) (methylamino))butyl)-1-methanesulfonyl-spiro(indoline-3,4'-piperidine)

Mass Spectrum (FAB) 684 ($^{37}$Cl+$^{35}$Cl isotope), 682 ($^{35}$Cl+$^{35}$Cl isotope).

1'-(3-((S)-(3,4-Dichlorophenyl))-4-(N-(3-isopropyloxyphenylacetyl) (methyl-amino))butyl)-1-methanesulfonyl-spiro(indoline-3,4'-piperidine)

1'-(3-((S)-(3,4-Dichlorophenyl))-4-(N-(benzenesulfonyl) (methylamino))-butyl)-1-methanesulfonyl-spiro (indoline-3,4'-piperidine)

$^1$H NMR (CDCl$_3$, ppm ranges are given because of amide rotomers and line broadening) δ 1.65 (m, 3H), 1.8–2.3 (m, 7H), 2.62 (s, 3H), 2.7–3.05 (m, 4H), 2.86 (s, 3H), 3.3 (m, 2H), 3.74 (s, 2H), 7.0–7.7 (m, 12H).

Mass Spectrum (lFAB) 637 ($^{37}Cl+^{35}Cl$ isotope), 635 ($^{35}Cl+^{35}Cl$ isotope).

The following compounds were also prepared by using the appropriate acid chloride under the conditions given in Step B above:

1'-(3-((S)-(3,4-dichlorophenyl))-4-(N-(3,5-difluorobenzoyl)(methyl-amino))butyl)-1-methanesulfonyl-spiro(indoline-3,4'-piperidine)

Mass Spectrum (FAB) 638($^{37}Cl+^{35}Cl$ isotope), 636($^{35}Cl+^{35}Cl$ isotope).

1'-(3-((S)-(3,4-Dichlorophenyl))-4-(N-(3-fluoro-5-(trifluoromethyl)-benzoyl)(methylamino))butyl)-1-methanesulfonyl-spiro(indoline-3,4'-piperidine) Mass Spectrum (CI) 688 ($^{37}Cl+^{35}Cl$ isotope), 686 ($^{35}Cl+^{35}Cl$ isotope).

1'-(3-((S)-(3,4-Dichlorophenyl))-4-(N-(1-naphthoyl)(methylamino))-butyl)-1-methanesulfonyl-spiro(indoline-3,4'-piperidine) $^1H$ NMR (CDCl$_3$, ppm ranges are given because of amide rotomrers and line broadening) d Mass Spectrum (FAB) ($^{37}Cl+^{35}Cl$ isotope), ($^{35}Cl+^{35}Cl$ isotope).

1'-(3-((S)-(3,4-Dichlorophenyl))-4-(N-(2-chlorophenylsulfonyl)-(methylamino))butyl)-1-methylsulfonyl-spiro(indoline-3,4'-piperidine)

Mass Spectrum: 200, 202, 228, 230, 279, 308, 310, 494, 496, 670, 672 (cluster).

1'-(3-((S)-(3,4-Dichlorophenyl))-1-(N-(3-chlorophenylsulfonyl)-(methylamino))-4-butyl)-1-methylsulfonyl-spiro(indoline-3,4'-piperidine)

Mass Spectrum: 200, 202, 228, 230, 279, 308, 310, 494, 496, 670, 672 (cluster).

1'-(3-((S)-(3,4-Dichlorophenyl))-4-(N-(4-chlorophenylsulfonyl)-(methylamino))butyl)-1-methylsulfonyl-spiro(indoline-3,4'-piperidine)

Mass Spectrum: 200, 228, 230, 279, 494, 496, 669 (cluster).

1'-(3-((S)-(3,4-Dichlorophenyl))-4-(N-(3,5-dichlorophenylsulfonyl)-(methylamino))butyl)-1-methylsulfonyl-spiro(indoline-3,4'-piperidine)

Mass Spectrum: 228, 230, 279, 494, 496, 703, 705 (cluster).

EXAMPLE 4

1-Benzyloxycarbonyl-spiro(indoline-3,4'-piperidinium) hydrochloride

A solution of 99 g (489 mmol) of 1'-methylspiro(indoline-3,4'-piperidine) (prepared according to Ong, H. H. et al, J. Med. Chem., 1983, 26, 981–986) in 1 L of CH$_2$Cl$_2$ and 82 mL (539 mmol) of Et$_3$N was cooled to 0–5° C. with an ice bath and 77 mL (539 mmol) of benzyl chloroformate was added over 30 min keeping the reaction temperature below 10° C. After stirring for 2 h 19 mL (136 mmol) of Et$_3$N and 15 mL (105 mmol) of benzyl chloroformate were added since the reaction was incomplete and stirred for 2 h. At this time, additional 19 mL (136 mmol) of Et$_3$N and 15 mL (105 mmol) of benzyl chloroformate were added. After 1 h, when a TLC indicated a complete reaction, the solution was concentrated in vacuo and the residue was partitioned between ether and saturated NaHCO$_3$. The layers were separated, the organic layer was washed with saturated NaHCO$_3$ and brine, and dried over MgSO$_4$. The filtrate was concentrated and the residue was chromatographed on 2 kg of silica gel using 1–5% MeOH/CH$_2$Cl$_2$ to obtain 117 g (71%) of 1-benzyloxycarbonyl-1'-methylspiro(indoline-3,4'-piperidine) as a yellow oil. The yellow oil was dissolved in 800 mL of 1,2-dichloroethane and cooled in ice bath as 50 mL (463 mmol) of 1-chloroethyl chloroformate keeping the temperature below 10° C. The resulting solution was heated to reflux. Gas evolution was noticed when the reaction temperature reached 70–75° C. After 1 h the solution was cooled, concentrated to ca. 250 mL in vacuo and 700 mL of methanol was added. The mixture was refluxed for 1.5 h and gas evolution was observed. The reaction was cooled to room temperature and concentrated in vacuo to a wet solid. The solid was slurried with cold methanol, the solid was filtered, washed with cold methanol and dried. The filtrates and the washing were combined and concentrated to a brown foam. The brown foam and the filtered solid were suspended in CH$_2$Cl$_2$, washed with 2.5 N NaOH and the CH$_2$Cl$_2$ solution was dried. The residue was chromatographed on 2 kg of silica gel using a gradient of 94:5:1 to 89:10:1 CH$_2$Cl$_2$, methanol, NH$_4$OH to isolate 91.3 g of free base as a brown oil. The oil was dissolved in 1 L of EtOAc by adding methanol (ca. 10 mL) and HCl gas was passed through the solution. After stirring the acidic solution for 10 min, it was concentrated to a foam. The foam was triturated with ether and the solid was filtered, washed with more ether and dried to furnish 91.5 g (73%) of title compound as a light yellow solid.

EXAMPLE 5

3-((S)-(3,4-Dichlorophenyl))-4-((3,5-dimethylbenzoyl)methylamino)-butanal

The title compound was prepared using the procedures described in Example 1 by substituting 3,5-dimethylbenzoyl chloride for di-t-butyl dicarbonate. $^1H$ NMR (CDCl$_3$, ppm ranges are given because of amide rotomers and line broadening) δ 2.27 (s, 6H), 2.6–3.9 (m, 8H), 6.5–7.5 (m, 6H), 9.73 (s, 1H).

EXAMPLE 6

1'-(3-((S)-(3,4-Dichlorophenyl))-4-(N-(3,5-dimethylbenzoyl)(methyl-amino))butyl)-1-benzyoxycarbonyl-spiro(indoline-3,4'-piperidine)

The title compound was prepared from 3-((S)-(3,4-dichlorophenyl))-4-((3,5-dimethylbenzoyl)methylamino) butanal (Example 5) and 1-benzyloxycarbonyl-spiro(indoline-3,4'-piperidinium) hydrochloride (Example 4) following the procedure of Example 2. 1 H NMR (CDCl$_3$, ppm ranges are given because of amide rotomers and line broadening) δ 1.6–2.35 (m, 10H), 2.27 (s, 6H), 2.6–3.9 (m, 10H), 5.23 & 5.3 (2 s, 2H), 6.6–7.6 (m, 15H). Mass Spectrum (FAB) 686 ($^{37}Cl+^{35}Cl$ isotope), 684 ($^{35}Cl+^{35}Cl$ isotope).

EXAMPLE 7

1'-(3-((S)-(3,4-Dichlorophenyl))-4-(N-(3,5-dimethylbenzoyl) (methylamino))butyl)-spiro (indoline-3,4'-piperidine)

To a solution of 1.23 g (1.8 mmol) of 1'-(3-((S)-(3,4-dichlorophenyl))-4-(3,5-dimethylbenzoyl(methylamino)) butyl)-1-benzyoxycarbonyl-spiro(indoline-3,4'-piperidine) (Example 6) in 10 mL of ethanol and 0.8 mL of acetic acid (HOAc) was added 0.15 g of 10% Pd/C. The resulting mixture was hydrogenated on a Parr apparatus for 20 h. The catalyst was filtered and washed with EtOH. The combined filtrate was concentrated in vacuo and the residue was dissolved in CH$_2$Cl$_2$. The CH$_2$Cl$_2$ solution was washed with dilute (ca 0.5 N) NaOH and brine, and dried by filtering through $Na_2SO_4$. The filtrate was concentrated to furnish 1.03 g (quantitative) of the title compound as a foam which was used in the next reaction without purification. $^1$H NMR ($CDCl_3$, ppm ranges are given because of amide rotamers and line broadening) δ 1.6–2.45 (m, 10H), 2.27 (s, 6H), 2.6–3.9 (m, 10H), 6.5–7.5 (m, 10H).

Mass Spectrum (FAB) 552 ($^{37}Cl+^{35}Cl$ isotope), 550 ($^{35}Cl+^{35}Cl$ isotope).

EXAMPLE 8

1'-(3-((S)-(3,4-Dichlorophenyl))-4-(N-(3,5-dimethylbenzoyl) (methylamino))butyl)-1-acetyl-spiro(indoline-3,4'-piperidine)

Acetyl chloride (16 uL) was added to a solution of 0.1 g (0.18 mmol) of 1'-(3-((S)-(3,4-dichlorophenyl))-4-(N-(3,5-dimethyl-benzoyl)(methyl amino))butyl)-spiro(indoline-3,4'-piperidine) (Example 7) in 4 mL of $CH_2Cl_2$ containing 30 mL of pyridine. After stirring for 2 h, the reaction mixture was diluted with $CH_2Cl_2$ and washed with saturated $NaHCO_3$, water, brine and dried. The residue after concentration of the filtrate was purified by prep TLC using 5% $Et_3$N/EtOAc as an eluent to afford 90 mg (84%) of the title compound. $^1$H NMR ($CDCl_3$, ppm ranges are given because of amide rotamers and line broadening) δ 1.55–2.5 (m, 10H), 2.22 (s, 3H), 2.27 (s, 6H), 2.6–3.9 (m, 10H), 6.6–7.5 (m, 9H), 8.17 (d, 1H, J=12 Hz). Mass Spectrum (FAB) 594 ($^{37}Cl+^{35}Cl$ isotope), 592 ($^{35}Cl+^{35}Cl$ isotope).

The following analogs were prepared by substituting the appropriate acylation reagent for acetyl chloride in the above procedure.

1'-(3-((S)-(3,4-Dichlorophenyl))-4-(N-(3,5-dimethylbenzoyl)(methyl-amino))butyl)-1-propionyl-spiro(indoline-3,4'-piperidine)

Mass Spectrum (FAB) 608 ($^{37}Cl+^{35}Cl$ isotope), 606 ($^{35}Cl+^{35}Cl$ isotope).

1'-(3-((S)-(3,4-Dichlorophenyl))-4-(N-(3,5-dimethylbenzoyl) (methylamino)) butyl)-1-formyl-spiro(indoline-3,4'-piperidine)

Mass Spectrum (FAB) 580 ($^{37}Cl+^{35}Cl$ isotope), 578 ($^{35}Cl+^{35}Cl$ isotope).

1'-(3-((S)-(3,4-Dichlorophenyl))-4-(N-(3,5-dimethylbenzoyl) (methylamino)) butyl)-1-t-butylcarbonyl-spiro(indoline-3,4'-piperidine)

Mass Spectrum (FAB) 636 ($^{37}Cl+^{35}Cl$ isotope), 634 ($^{35}Cl+^{35}Cl$ isotope).

1'-(3-((S)-(3,4-Dichlorophenyl))-4-(N-(3,5-dimethylbenzoyl) (methylamino)) butyl)-1-methylaminocarbonyl-spiro(indoline-3,4'-piperidine)

Mass Spectrum (FAB) 609 (M+E, $^{37}Cl+^{35}Cl$ isotope), 607 (M+H, $^{35}Cl+^{35}Cl$ isotope).

1'-(3-((S)-(3,4-Dichlorophenyl))-4-(N-(3,5-dimethylbenzoyl) (methylamino)) butyl)-1-ethoxycarbonyl-spiro(indoline-3,4'-piperidine)

Mass Spectrum (FAB) 624 ($^{37}Cl+^{35}Cl$ isotope), 622 ($^{35}Cl+^{35}Cl$ isotope).

1'-(3-((S)-(3,4-Dichlorophenyl))-4-(N-(3,5-dimethylbenzoyl) (methylamino)) butyl)-1-ethanesulfonyl-spiro(indoline-3,4'-piperidine)

Mass Spectrum (FAB) 643 ($^{37}Cl+^{35}Cl$ isotope), 641 ($^{35}Cl+^{35}Cl$ isotope).

1'-(3-((S)-(3,4-Dichlorophenyl))-4-(N-(3,5-dimethylbenzoyl) (methylamino)) butyl)-1-i-propanesulfonyl-spiro(indoline-3,4'-piperidine)

Mass Spectrum (FAB) 657 ($^{37}Cl+^{35}Cl$ isotope), 655 ($^{35}Cl+^{35}Cl$ isotope).

The following compound can also be prepared under the conditions given above:

1'-(3-((S)-(3,4-Dichlorophenyl))-4-(N-(3-fluoro-5-(trifluoromethyl)-benzoyl)(methylamino))butyl)-1-acetyl-spiro(indoline-3,4'-piperidine)

Mass Spectrum (FAB) (CI) 652 ($^{37}Cl+^{35}Cl$ isotope), 650 ($^{35}Cl+^{35}Cl$ isotope).

An alternative method (method B) is given below: 1'-(3-((S)-(3,4-Dichlorophenyl))-4-(N-(3,5-dimethylbenzoyl) (methyl-amino))butyl)-1-acetyl-spiro(indoline-3,4'-piperidine)

1-Acetyl-spiro(indoline-3,4'-piperidine)

Acetyl chloride (1.4 mL, 19.9 mmol) was added to a solution of 5.35 g (16.6 mmol) of 1'-benzyloxycarbonyl-spiro(indoline-3,4'-piperidine) in 33 mL of $CH_2Cl_2$ and 3.2 mL (23.2 mmol) of $Et_3$N keeping the temperature between 0–5° C. by cooling in ice bath. After 10 min the cold bath was removed and reaction was stirred for 30 min at which time a TLC indicated complete reaction. The solution was diluted with $CH_2Cl_2$ and washed with water, brine and dried over $Na_2SO_4$. The filtrate was concentrated to a thick oil and the oil was dissolved in 40 mL of EtOH. Acetic acid (3 mL) and 0.8 g of 10% Pd/C were added to the solution and the resulting mixture was hydrogenated on a Parr apparatus for 3 h. The catalyst was filtered and washed with EtOAc and the combined filtrate was concentrated. The residue was partitioned between $CH_2Cl_2$ and water and 2N NaOH was added to this mixture until the aqueous layer was basic. The layers were separated and the aqueous layer was extracted with $CH_2Cl_2$. The combined organic layer was washed with brine, dried over $Na_2SO_4$ and the filtrate was concentrated to give 2.93 g (77%) of the title compound sufficiently pure for use in the next reaction.

1'-(3-((S)-(3,4-Dichlorophenyl))-4-(N-(3,5-dimethylbenzoyl)(methyl-amino)) butyl)-1-acetyl-spiro(indoline-3,4'-piperidine)

To a solution of 0.284 g (0.75 mmol)of 3-((S)-(3,4-dichlorophenyl))-4-(N-(3,5-dimethylbenzoyl) (methylamino))butanal (Example 5) in 2 mL of MeOH were added 0.166 g (0.72 mmol) of 1-acetyl-spiro(indoline-3,4'-piperidine), 0.5 g of powdered 4 Å molecular sieves and 10 drops (ca. 0.1 mL) of acetic acid. After stirring the mixture for 1.5 h a solution of 0.189 g (3 mmol) of $NaCNBH_3$ in 3 mL of THF was added. Some gas evolution was observed. After 30 min when the reaction was complete by TLC the mixture was filtered through a pad of celite, the reaction flask and the pad were rinsed with MeOH. The filtrate was concentrated to approximately 3 mL and the residue was diluted with EtOAc. The EtOAc solution was washed with water, brine and dried over $Na_2SO_4$. The filtrate was concentrated and the residue was chromatographed on a flash column using 50% EtOAc-hexane followed by 2% Et3N-EtOAc and finally 93:5:2 EtOAc: MeOH: $Et_3$N to isolate 0.317 g (74%) of the title compound as a white foam.

EXAMPLE 9

1'-(3-((S)-(3,4-Dichlorophenyl))-4-(3,5-dimethylbenlzoyl(methyl-amino)) butyl)-1'-methyl-1-methanesulfonyl-spiro(indoline-3,4'-piperidinium) iodide A solution of 53 mg (0.084 mmol) of 1'-(3-((S)-(3,4-dichlorophenyl))-4-(3,5-dimethylbenzoyl(methylamino)) butyl)-1-methanesulfonyl-spiro(indoline-3,4'-piperidine) in 5 drops of MeOH was diluted with 1 mL of ether and 0.5 mL of methyl iodide was added. The reaction mixture was stirred overnight while a solid was formed. The yellowish solid was allowed to settle and the supernatent was removed. The solid was washed with ether and dried to furnish 51 mg (78%) of the title compound.

EXAMPLE 10

1'-(3-(S)-(3,4-Dichlorophenyl)-4-(N-(R or S)-(3-methylbenzoyl) (methyl-amino))pentyl)-1-methanesulfonyl-spiro(indoline-3,4'-piperidine)

Step 1: N-Methoxy-N-methyl-2-(S)-(3,4-dichlorophenyl)-4-pentenamide

A mixture of 306 mg (1.25 mmol) of (2S)-(3,4-dichlorophenyl)-4-pentenoic acid (prepared according to the procedure of Hale, J. J.; Finke, P. E.; MacCoss, M. *Bioorganic & Medicinal Chemistry Letters* 1993,3, 319–322) and 202 mg (1.50 mmol) of 1-hydroxybenzotriazole hydrate in 10 mL of methylene chloride was cooled to 0° C. and treated with 287 mg (1.50 mmol) of 1-(3-dimethyl-aminopropyl)-3-ethylcarbodiimide. The cooling bath was removed and after 45 min. a solution of 365 mg (3.75 mmol) of N,O-dimethyl-hydroxylamine hydrochloride and 522 µl (3.75 mmol) of triethylamine in 10 mL of methylene chloride was added via cannula. The mixture was then stirred at 22° C. for 4 hours and then quenched with 10 mL of water and diluted with 8 mL of methylene chloride. The layers were separated and the aqueous layer was extracted with methylene chloride (2×10 mL). The combined organic layers were washed with 10 mL of brine, dried over anhydrous sodium sulfate, filtered, and concentrated in vacuo. Flash chromatography on 75 g of silica gel using 1:9 v/v ethyl acetate/hexane as the eluant afforded 319 mg (89%) of the title compound as a clear oil. $^1$H NMR (400 MHz, CDCl$_3$) δ 2.40 (pentet, 1H), 2.75 (pentet, 1H), 3.13 (s, 3H), 3.52 (s, 3H), 3.99–4.01 (m, 1H), 4.96–5.05 (m, 2H), 5.63–5.70 (m, 1H), 7.15 (dd, 1H), 7.35 (d, 1H), 7.41 (d, 1H). Mass Spectrum (FAB): m/z 290 (M+H, $^{37}$Cl+$^{35}$Cl isotope, 50%), 288 (M+H, $^{37}$Cl+$^{37}$Cl isotope, 100%).

Step 2: 3-(S)-(3,4-dichlorophenyl)-5-hexen-2-one

A solution of 319 mg (1.11 mmoL) of N-methoxy-N-methyl-2-(S)-(3,4-dichlorophenyl)-4-pentenamide (from Step 1 above) in 10 mL of dry tetrahydrofuran was cooled to −70° C. and treated with 1.0 mL (1.40 mmol) of methyllithium and stirred between −70° C to −40° C. After 3 hours, the reaction was quenched with 5 mL of water, and diluted with 10 mL of ethyl acetate. The layers were separated and the organic layer was washed with water (3×10 mL). The aqueous layers were extracted with 10 mL of ethyl acetate. The combined organic layers were washed with 10 mL of saturated aqueous sodium chloride solution, dried over anhydrous sodium sulfate, filtered, and concentrated in vacuo. Flash chromatography on 44 g of silica gel using 1:3 v/v ethyl acetate/hexane as the eluant afforded 250 mg (93%) of the title compound as a clear oil. $^1$H NMR (400 MHz, CDCl$_3$) δ 2.07 (s, 3H), 2.36 (pentet, 1H), 2.72 (pentet, 1H), 3.64 (t, 1H), 4.95–5.01 (m, 2H), 5.55–5.65 (m, 1H), 7.03 (dd, 1H), 7.30 (d, 1H), 7.39 (d, 1H).
Mass Spectrum (FAB): m/z 245 (M+H, $^{37}$Cl+$^{35}$Cl isotope, 30%), 243 (M+H, $^{37}$Cl+$^{37}$Cl isotope, 50%), 155 (60%), 119 (100%).

Step 3: N-Methyl 3-(S)-(3,4-dichlorophenyl)-5-hexen-2-(RS)-amine

A mixture of 102 mg (0.42 mmol) of 3-(S)-(3,4-dichlorophenyl)-5-hexen-2-one (from Step 2 above), 170 mg (2.52 mmol) of methylamine hydrochloride, and 234 µl (1.68 mmol) of triethylamine in 4.0 mL of methanol was treated with 16 mg (0.25 mmol) of sodium cyanoborohydride and stirred at 22° C. for 20 hours. Saturated aqueous sodium bicarbonate solution (1.0 mL) was added and the resulting milky mixture was diluted with 5.0 mL of ethyl acetate and 5.0 mL of water. The layers were separated and the organic layer was washed with water (3×5 mL). The aqueous layers were extracted with 10 mL of ethyl acetate. The combined organic layers were washed with 10 mL of saturated aqueous sodium chloride solution, dried over anhydrous sodium sulfate, filtered, and concentrated in vacuo. Flash chromatography on 42 g of silica gel using 10:1 v/v ether/ hexane as the eluant afforded 64 mg of the higher R$_f$ isomer (Isomer A) and 22 mg of a lower R$_f$ isomer (Isomer B) both as yellow oils. $^1$H NMR (400 MHz, CDCl$_3$); Isomer A: δ 1.04 (d, 3H), 2.29–2.35 (m, 4H), 2.50–2.68 (m, 3H), 4.86–4.95 (m, 2H), 5.48–5.56 (m, 1H), 7.01 (dd, 1H), 7.26 (d, 1H), 7.34 (d, 1H); Isomer B: δ 0.86 (d, 3H), 2.32–2.50 (m, 4H), 2.51–2.53 (m, 1H), 2.68–2.73 (m, 2H), 4.88–4.98 (m, 2H), 5.54–5.61 (m, 1H), 6.97 (dd, 1H), 7.22 (d, 1H), 7.33 (d, 1H). Mass Spectrum (Isomer A) (FAB): m/z 260 (M+H, $^{37}$Cl+$^{35}$Cl isotope, 70%), 258 (M+H, $^{35}$Cl+$^{35}$Cl isotope, 100%).

Step 4: N-Methyl-N-t-butoxycarbonyl-3-(S)-(3,4-dichlorophenyl)-5-hexen-2-(RS)-amine.

A solution of 1.1 g (4.1 mmol) of N-methyl-(3-(S)-(3,4-dichlorophenyl)-5-hexen-2-(R or S)-amine (Isomer B from Step 3 above) in 10 mL of dry methylene chloride was cooled to 0° C. and treated with 690 µl (5.0 mmol) of triethylamine and 1.2 g (5.3 mmol) of di-tert-butyl dicarbonate. The cooling bath was removed and the reaction was stirred at 22° C. for 20 hours. The reaction was quenched with 10 mL of water and diluted with 25 mL of methylene chloride. The layers were separated and the aqueous layer was extracted with methylene chloride (2×10 mL). The combined organic layers were washed with 15 mL of brine, dried over anhydrous sodium sulfate, filtered, and concentrated in vacuo. Flash chromatography on 72 g of silica gel using 1:3 v/v ethyl acetate/ hexane as the eluant afforded 1.4 g (95%) of the title compound as a yellow oil. $^1$H NMR (400 MHz, CDCl$_3$, ranges are given due to amide rotamers and line broadening) δ 1.24–5.70 (22H), 6.88–7.40 (3H), 1.50 (s, 3H, N—CH$_3$). Mass Spectrum (FAB): m/z 358 (M+H, $^{37}$Cl+$^{35}$Cl isotope, 30%), 302 (100%).

Step 5: N-Methyl-N-t-butoxycarbonyl-3-(S)-(3,4-dichlorophenyl)-4-(RS )-amino-pentanal A solution of 1.4 g (3.9 mmol) of N-methyl-N-t-butoxycarbonyl-3-(S)-(3,4-dichlorophenyl)-5-hexen-2-(RS)-amine (from Step 4 above) in 20 mL of 2:1:1 v/v/v acetone/t-butanol/water was treated with 30 mg (0.12 mmol) of osmium tetroxide. After 5 min., 691 mg (5.90 mmol) of N-methylmorpholine N-oxide was added and the resulting mixture was stirred at 22° C. for 4 hours. The reaction was quenched with 491 mg of sodium bisulfite and concentrated in vacuo to 25% of the original volume. The residue was partitioned between 20 mL of methylene chloride and 10 mL of water and the layers were separated. The aqueous layer was extracted with methylene chloride (2×10 mL). The combined organic layers were dried over anhydrous sodium sulfate, filtered, and concentrated in vacuo.

A solution of the crude diol in 24 mL of 3:1 v/v tetrahydrofuran/water was treated with 1.1 g (5.1 mmol) of sodium periodate and stirred at 22° C. for 20 hours. The reaction mixture was partitioned between 20 mL of ethyl ether and 10 mL of water and the layers were separated. The organic layer was washed with water (2×15 mL), dried over anhydrous sodium sulfate, filtered, and concentrated in vacuo. Flash chromatography on 68 g of silica gel using 4:1 v/v ethyl ether/hexane as the eluant afforded 372 mg of the higher R$_f$ isomer (Isomer A) and 879 mg of a lower Rf isomer (Isomer B) both as yellow oils. $^1$H NMR (400 MHz, CDCl$_3$) Isomer B: δ 1.19–1.34 (m, 13H), 2.45 (s, 3H, N—CH$_3$), 2.68–2.81 (m, 2H), 3.28–3.34 (m, 1H), 4.20–4.50 (m, 1H), 6.98–7.32 (m, 3[), 9.60 (s, 1H, —CHO). Mass Spectrum (Isomer B) (1FAB): m/z 360 (M+H, $^{37}$Cl+$^{35}$Cl isotope, 20%), 242 (100%).

Step 6: 1'-(3-(S)-(3,4-Dichlorophenyl)-4-(N-(REt or S)-(t-butoxy-carbonyl)(methylamino))pentyl)-1-methanesulfonyl-spiro(indoline-3,4'-piperidine)

A mixture of 217 mg (0.60 mmol) of N-methyl-N-t-butoxycarbonyl-3-(S)-(3,4-dichlorophenyl)-4-(RS)-aminopentanal (from Step 5 above) and 262 mg (0.86 mmol) of 1-methanesulfonyl-spiro(indoline-3,4'-piperidine) hydrochloride in 13 mL of methanol was treated with 115 mg (1.83 mmol) of sodium cyanoborohydride and stirred at 22° C. for 20 hours. Saturated sodium bicarbonate solution (1.0 ml) was added and the resulting milky mixture was concentrated to 50% of its original volume. The residue was partitioned between 25 mL of ethyl acetate and 15 mL of water and the layers were separated. The organic layer was washed with water (3×10 mL). The aqueous layers were extracted with 20 mL of ethyl acetate. The combined organic layers were washed with 15 mL of brine, dried over anhydrous sodium sulfate, filtered, and concentrated in vacuo. Flash chromato-graphy on 42 g of silica gel using 5:95 v/v methanol/methylene chloride as the eluant afforded 329 mg (89%) of the title compound as a white foam. $^1$H NMR (400 MHz, CDCl$_3$, ranges are given due to amide rotamers and line broadening) δ 1.20–2.90 (31H), 3.74 (s, 3H, N—SO$_2$CH$_3$), 7.05–7.41 (m, 8H). Mass Spectrum (FAB): m/z 612 (M+H, $^{37}$Cl+$^{35}$Cl isotope, 70%), 610 (M+H, $^{37}$Cl+$^{37}$Cl isotope, 100%).

Step 7: 1'-(3-(S)-(3,4-Dichlorophenyl)-4-(N-(R or S)-(methyl-amino))pentyl)-1-methanesulfonyl-spiro(indoline-3,4'-piperidine)

To a solution of 329 mg (0.54 mmol) of 1'-(3-(S)-(3,4-dichlorophenyl)-4-N((R or S)-(t-butoxycarbonyl)(methylamino))pentyl)-1-methanesulfonyl-spiro(indoline-3,4'-piperidine) (from Step 6 above) in 8.0 mL of dry methylene chloride at 0° C. was added 117 μl (1.1 mmol) of anisole and 2.0 mL of trifluoroacetic acid. The cooling bath was removed and the reaction was stirred at 22° C. for 20 minutes. The reaction was concentrated in vacuo. The residue was partitioned between 10 mL of methylene chloride and 5.0 mL of water. The organic layer was washed with 2N NaOH (3×5 mL), dried over anhydrous sodium sulfate, filtered, and concentrated in vacuo. Flash chromatography on 42 g of silica gel using 5:95:0.5 v/v/v methanol/methylene chloride/ammonium hydroxide as the eluant afforded 221 mg (80%) of the title compound as a clear oil. $^1$H NMR (400 MHz, CDCl$_3$) δ 1.05 (d, 3H, J=6.2 Hz), 1.62–2.85 (m, 17H), 2.30 (s, 3H, N—CH$_3$), (7.03–7.37 (m, 17H). Mass Spectrum (1FAB): m/z 512 (M+H, $^{37}$Cl+$^{35}$Cl isotope, 70%), 510 (M+H, $^{37}$Cl+$^{37}$Cl isotope, 100%).

Step 8: 1'-(3-(S)-(3,4-Dichlorophenyl)-4-(N-(R or S)-(3-methyl-benzoyl)(methylamino))pentyl)-1-methanesulfonyl-spiro(indoline-3,4-piperidine)

The title compound was prepared from 1'-(3-(S)-(3,4-dichlorophenyl)-4-(R or S)-(methylamino)pentyl)-1-methanesulfonyl-spiro(indoline-3,4'-piperidine) (from Step 7 above) using a procedure identical to Example 3, Step (b), substituting m-toluoyl chloride for 3,5-dimethylbenzoyl chloride. $^1$H NMR (400 MHz, CDCl$_3$, ranges are given due to amide rotamers and line broadening) δ 1.42 (δ, 3H, J=6.7 Hz), 1.60–2.30 (16H), 2.54 (s, 3H, Ph-CH$_3$), 2.87 (s, 3H, N-CH$_3$), 3.74 (s, 3H, N—SO$_2$CH$_3$), 7.05–7.79 (m, 11H). Mass Spectrum (FAB): m/z 630 (M+H, $^{37}$Cl+$^{35}$Cl isotope, 70%), 628 (M+H, $^{37}$Cl+$^{37}$Cl isotope, 100%).

EXAMPLE 11

1'-(3-(S)-(3,4-Dichlorophenyl)-4-(N-(R or S)-(3,5-bis(trifluoromethyl)-benzoyl)(methylamino))pentyl)-1-methanesulfonyl-spiro(indoline-3,4'-piperidine)

The title compound was prepared from 1'-(3-(S)-(3,4-dichlorophenyl)-4-(R or S)-(methylamino)pentyl)-1-methanesulfonyl-spiro(indoline-3,4'-piperidine) (from Example 1, Step 7 above) using a procedure identical to Example 3 Step (b), substituting 3,5-bis(trifluoromethyl)benzoyl chloride for 3,5-dimethylbenzoyl chloride. $^1$H NMR (400 MHz, CDCl$_3$, ranges are given due to amide rotamers and line broadening) δ 1.38–3.00 (22H), 3.74 (s, 3HR[, N—SO$_2$CH$_3$), 6.40–7.41 (m, 10H). Mass Spectrum (FAB): m/z 752 (M+H, $^{37}$Cl+$^{35}$Cl isotope, 40%), 750 (M+H, $^{37}$Cl+$^{37}$Cl isotope, 60%), 241 (100%).

EXAMPLE 12

1'-(3-(S)-(3,4-Dichlorophenyl)-4-(R or S)-(3,5-dimethylbenzoyl-(methylamino))pentyl)-1-methanesulfonyl-spiro(indoline-3,4'-piperidine)

The title compound was prepared from 1'-(3-(S)-(3,4-dichlorophenyl)-4-(R or S)-(methylamino)pentyl)-1-methanesulfonyl-spiro(indoline-3,4'-piperidine) (from Example 1, Step 7 above) using a procedure identical to Example 3, Step (b). $^1$H NMR (400 MEz, CDCl$_3$, ranges are given due to amide rotamers and line broadening) δ 1.37–2.86 (28H), 3.74 (s, 3H, N—SO$_2$CH$_3$), 6.24–7.41 (m, 10H). Mass Spectrum (FAB): m/z 642 (M+H, $^{37}$Cl+35Cl isotope, 70%), 644 (M+H, $^{37}$Cl+$^{37}$Cl isotope, 100%).

EXAMPLE 13

(1'-(3-(S)-(3,4-Dichlorophenyl)-4-(R or S)-(3,5-dichlorobenzoyl-(methyl-amino))pentyl)-1-methanesulfonyl-spiro(indoline-3,4'-piperidine)

The title compound was prepared from 1'-(3-(S)-(3,4-dichlorophenyl)-4-(R or S)-(methylamino)pentyl)-1-methanesulfonyl-spiro(indoline-3,4'-piperidine) (from Example 1, Step 7 above) using a procedure identical to Example 3, Step (b), substituting 3,5-dichloro-benzoyl chloride for 3,5-dimethylbenzoyl chloride. $^1$H NMR (400 MHz, CDCl$_3$, ranges are given due to amide rotamers and line broadening) δ 1.38–2.93 (22H), 3.73 (s, 3H, N—SO$_2$CH$_3$), 6.53–7.42 (m, 10H). Mass Spectrum (FAB): m/z 684 (M+H, $^{37}$Cl+$^{35}$Cl isotope, 70%), 686 (M+H, $^{37}$Cl+$^{37}$Cl isotope, 100%).

EXAMPLE 14

1'-(3-((S)-(3,4-dichlorophenyl))-4-(N-(3-bromo-5-methylbenzoyl)-(methylamino))butyl)-1-methanesulfonyl-spiro(indoline-3,4'-piperidine)

Step A: 3-Bromo-5-methylbenzoic acid

To a solution of 0.38 g (1.44 mmol) of 3-bromo-5-methyl-benzyl bromide (prepared by NBS bromination of 3,5-dimethyl-bromobenzene) in 22 mL of MeCN and 50 mL of water was added 7.8 mL (28.8 mmol) of aqueous sodium hypochlorite (13% active Cl). The mixture was allowed to stand in an ultrasonic cleaning bath for 14 h. The reaction was acidified with HCl to pHR 3 and extracted with CH$_2$Cl$_2$. The organic layer was washed with water, brine and dried with Na$_2$SO$_4$. The filtrate was concentrated and the residue which was a mixture of the desired acid and the aldehyde was dissolved in 3 mL of acetone. The solution was treated with 6 N Jones reagent until the orange color persisted. After stirring for 20 min the excess reagent was destroyed by adding few drops of i-PrOH. The solution was diluted with water and extracted with CH$_2$Cl$_2$. The CH$_2$Cl$_2$ layer was washed with brine, dried and the filtrate was concentrated. The residue was purified by prep TLC using 0.5:30:69.5 of HOAc:EtOAc:hexane to isolate 0.14 g (45%) of 3-bromo-5-methylbenzoic acid.

Step B: 1'-(3-((S)-(3,4-dichlorophenyl))-4-(N-(3-bromo-5-methylbenzoyl)(methylamino))butyl)-1-methanesulfonyl-spiro(indoline-3,4'-piperidine)

3-Bromo-5-methylbenzoic acid was used in the acylation reaction according to the procedure of Example 3, Step B to obtain the title compound. Mass Spectrum (CI) 696 ($^{37}$Cl+ $^{35}$Cl isotope), 694 ($^{35}$Cl+$^{35}$Cl isotope).

EXAMPLE 15

1'-(3-((S)-(3,4-Dichlorophenyl))-4-(N-(3,5-dimethylbenzoyl)-(methylamino))butyl)-1-(2-aminoacetyl)-spiro(indoline-3,4'-piperidine)

A solution of 65 mg (0.31 mmol) of carbobenzyl-oxyglycine in 3 mL of $CH_2Cl_2$ was treated with 82 mg (0.41 mmol) of 1-ethyl-3-(3-dimethylaminopropyl)carbodiimide and 56 mg (0.41 mmol) of 1-hydroxybenzotriazole and 42 mg (0.41 mmol) of N-methylmorpholine. After 10 min 123 mg (0.21 mmol) of 1'-(3-((S)-(3,4-dichlorophenyl))-4-(N-(3,5-dimethylbenzoyl)(methylamino))-butyl)-spiro(indoline-3,4'-piperidine) (Example 7) was added and the reaction was stirred for 2 h. The mixture was diluted with $CH_2Cl_2$ and washed with water, brine, dried and concentrated to give 0.184 g of residue. The residue in 10 drops of HOAc was dissolved in 3 mL of EtOH and the solution was hydrogenated on a Parr apparatus for 16 h. The catalyst was filtered and washed with EtOAc. The filtrate was washed with 10% $Na_2CO_3$, brine and concentrated. The residue was purified by prep TLC using 30% MeOH-EtOAc to give 80 mg (59%) of the title compound. Mass Spectrum (CI) 651 ($^{37}$Cl+$^{35}$Cl isotope), 649 ($^{35}$Cl+$^{35}$Cl isotope).

EXAMPLE 16

1'-(3-((S)-(3,4-Dichlorophenyl))-4-(N-(3,5-dimethylbenzoyl)-(methylamino))butyl)-1-methyl-spiro(indol-2-one-3,4'-piperidine)

Step A: 1,1'-Dimethyl-spiro(indol-2-one-3,4'-piperidine)

A solution of 0.1 g (0.68 mmol) of N-methyl-2-oxo-indole in 2 mL of THF was added to a well stirred suspension of 0.14 g (3.4 mmol) of NaH in 2 mL of THF with cooling in ice bath. After the gas evolution had stopped the cold bath was removed and the mixture was heated in a 50° C. bath for another 15 min. The reaction was allowed to cool to room temperature and 0.68 mL of DMSO was added and more gas evolution was observed. After stirring for 10 min, the reaction mixture was cooled in ice bath and 0.144 g of mechlorethamine hydro-chloride was added. The mixture was warmed to room temperature and stirred overnight. Next morning, the reaction was quenched with water and extracted with EtOAc. The EtOAc extact was washed with brine, dried with $Na_2SO_4$ and filtered. The filtrate was concentrated and the residue was purified by prep TLC using 89:10:1 EtOAc:MeOH:$Et_3$N to furnish 25 mg (15%) of the title compound.

Step B: 1-Methyl-spiro(indol-2-one-3,4'-piperidine)

A solution of 25 mg (0.11 mmol) of 1,1'-dimethyl-spiro (indol-2-one-3,4'-piperidine) (from Step A above) in 1 mL of dry dichloroethane was treated with 0.023 mL (0.22 mmol) of 1-chloroethyl chloroformate (ACECl) under a dry $N_2$ atmosphere. After 30 mim at room temperature, the solution was kept in a 50° C. bath for 30 min. The reaction mixture was cooled to room temperature, 2 mL of MeOH was added and reheated to 60° C. After 30 min the solution was cooled and concentrated in vacuo. The residue was partitioned between water and EtOAc and the aqueous phase was adjusted to pH 9 by adding 1N NaOH. The layers were separated and the combined EtOAc solution was washed with brine and dried. The filtrate upon concentration gave 34 mg of a residue which was a mixture of the desired compound and the starting material, but was sufficiently pure to be used in the next reaction.

Step C: 1'-(3-((S)-(3,4-Dichlorophenyl))-4-(N-(3,5-dimethyl-benzoyl)(methylamino))butyl)-1-methyl-spiro(indol-2-one-3,4'-piperidine)

A reaction of 49 mg (0.13 mmol) of 3-((S)-(3,4-dichlorophenyl))-4-(N-(3,5-dimethylbenzoyl)methylamino)butanal (Example 5) with 34 mg of impure 1-methyl-spiro(indol-2-one-3,4'-piperidine) (from Step B) according to the procedure of Example 8, method B furnished 32 mg of the title compound after purification by prep TLC.
Mass Spectrum (CI) 580 ($^{37}$Cl+$^{35}$Cl isotope), 578 ($^{35}$Cl+ $^{35}$Cl isotope).

EXAMPLE 17

1'-(3-((S)-(3,4-Dichlorophenyl))-4-(N-(3,5-dichlorobenzoyl)-(methylamino))butyl)-1-methyl-spiro(isoindol-1-one-3,4'-piperidine)

Mass Spectrum (CI) 622 ($^{37}$Cl+$^{35}$Cl isotope), 620 ($^{35}$Cl+ $^{35}$Cl isotope).

EXAMPLE 18

1'-(3-((S)-(3,4-Dichlorophenyl))-4-(N-(3,5-dimethylbenzoyl)-(methylamino))butyl)-spiro(2-oxo-tetrahydroquinoline-4,4'-piperidine)

Step A: 1'-Trifluoroacetyl-spiro(1-indanone-3,4'-piperidine)

Cold trifluoroacetic acid (15 mL) and 0.6 mL of anisole were added to 2 g (6.6 mmol) of 1'-t-butoxycarbonyl-spiro (1-indanone-3,4'-piperidine) and the resulting solution was stirred in ice bath for 1 h. The reaction mixture was concentrated in vacuo and the residue was partitioned between $CH_2Cl_2$ and 0.5 N NaOH. The organic layer was washed with brine, dried with $Na_2SO_4$ and concentrated. The residual orange oil was dissolved in 10 mL of $CH_2Cl_2$ and 1.92 mL (13.7 mmol) of $Et_3$N, 1 mL (7.1 mmol) of trifluoroacetic anhydride and 3 crystals of DMAP were added. After stirring for 4 h, the reaction mixture was diluted with $CH_2Cl_2$ and washed with water, brine and dried. The solution was filtered and the filtrate was concentrated to yield 2.0 g (quantitative) of the desired product as a solid. $^1$H NMR (CDCl$_3$) δ 1.65 (d, 2H, J=14 Hz), 2.05 (m, 2H), 2.67 (ABq, 2H), 2.89 (m, 1H), 3.28 (m, 1H), 4.11(d, 1H, J=14 Hz), 4.67 (dt, 1H, J=14 and 2 Hz), 7.5–7.8 (m, 4H).

Step B: 1'-Trifluoroacetyl-spiro-(2-oxo-1,2,3,4-tetrahydro-quinoline-4,4'-piperidine) and 1'-trifluoroactyl-spiro-(1-oxo-1,2,3,4-tetrahydroisoquinoline-4,4'-piperidine)

To a mixture of 1.09 g (16.8 mmol) of Sodium azide in 1.2 mL of water and 6.6 mL of CHCl$_3$ was added 0.46 mL of concentrated $H_2SO_4$ (36 N) keeping the temperature between 0–5° C. (Caution!) After 10 min the cold bath was removed and the reaction was stirred for 3 h, at which time the CHCl$_3$ layer was separated from the aqueous layer. The CHCl$_3$ layer containing HN$_3$ was dried and the filtrate was added to a solution of 2 g (6.7 mmol) of 1'-trifluoroacetyl-spiro(1-indanone-3,4'-piperidine) (from Step A) in 7 mL of CHCl$_3$. Concentrated $H_2SO_4$ (1.8 mL) was added to this solution and the reaction was allowed to age for 30 min. The mixture was heated in a 45° C. bath for 45 min and then stirred at room temperature for 16 h. Next morning, the reaction mixture was poured into ice and the layers were separated. The aqueous layer was neutralized with aq. NaOH and extracted with EtOAc. The combined organic phases were washed with brine, dried and concentrated. The residue was chromatographed using 50–80% EtOAc-CH$_2$Cl$_2$ to isolate 0.34 g (16%) of 1'-trifluoroactyl-spiro(2-oxo-1,2,3,4-tetrahydroquinoline-4,4'-piperidine) and 0.13 g of 1'-trifluoroactyl-spiro(1-oxo-1,23,4-tetrahydroisoquinoline-4,4'-piperidine). In addition, 0.72 g (36%) of the starting indanone was recovered. $^1$H NMR (CDCl$_3$) Isomer A: δ 1.82 (m, 2H), 1.96 (m, 2H), 2.75 (ABq, 2H, J=14 Hz), 3.16 (t, 1H), 3.46 (t, 1H), 3.9 (d, 1H), 4.42 (d, 1H), 6.8–7.3 (m, 4H), 8.49 (br s, 1H); Isomer B: δ 1.9–2.1 (m, 4H), 3.09 (t, 1H), 3.42 (m, 1H), 3.61 (ABq, 2H), 3.94 (d, 1H), 4.45 (d, 1H), 6.72 (br s, 1H), 7.3–7.6 (m, 3H), 8.11 (d, 1H).

Step C: Spiro-(2-oxo-1,2,3,4-tetrahydroquinoline-4,4'-piperidine)

To a solution of 0.3 g (0.97 mmol) of 1'-trifluoroacetyl-spiro-(2-oxo-1,2,3,4-tetrahydroquinoline-4,4'-piperidine) (from Step B) in 4 mL of MeOH was added 0.16 g (2.9 mmol) of KOH in 1 mL of water. After stirring the reaction for 16 H the solution was concentrated and the residue was partitioned between EtOAc and water. The EtOAc layer was washed with brine, dried with Na$_2$SO$_4$ and concentrated to give 0.16 g (76%) of the title compound as a white solid. $^1$H NMR (CDCl$_3$) δ 1.6–2.0 (m, 4H), 2.72 (s, 2H), 2.95 (m, 4H), 6.7–7.4 (m, 4H), 8.4 (br s, 1H).

Step D: 1'-(3-((S)-(3,4-Dichlorophenyl))-4-(N-(3,5-dimethyl-benzoyl)(methylamino))butyl)-spiro(2-oxo-tetrahydroguinoline-4,4'-piperidine)

The title compound was obtained by reductive amination of 3-((S)-(3,4-dichlorophenyl))-4-((3,5-dimethylbenzoyl) methylamino)-butanal (Example 5) by spiro-(2-oxo-1,2,3,4-tetrahydroquinoline-4,4'-piperidine) obtained in Step C according to the procedure of Example 8, method B. Mass Spectrum (CI) 580 ($^{37}$Cl+$^{35}$Cl isotope), 578($^{35}$Cl+$^{35}$Cl isotope).

EXAMPLE 19

1'-(3-((S)-(3,4-Dichlorophenyl))-4-(N-(3,5-dichlorobenzoyl)(methyl-amino))butyl)-1-methyl-spiro(2-oxo-tetrahydroquinoline-4,4'-piperidine)

Step A: 1-Methyl-spiro-(2-oxo-1,2,3,4-tetrahydroquinoline-4,4'-piperidine)

To a solution of 0.15 g (0.48 mmol) of 1'-trifluoroacetyl-spiro-(2-oxo-1,2,3,4-tetrahydroquinoline-4,4'-piperidine) (from Example 18, Step B) in 1.7 mL of DMF was added 19 mg (0.77 mmol) of 95% NaH at 0° C. After 15 min 0.063 mL (1 mmol) of methyl iodide was added and the reaction was allowed to warm to room temperature. After stirring for 16 H the reaction was not complete, so an additional 0.015 mL of methyl iodide was added and the solution was heated in a 45° C. bath. After 2 H the reaction was cooled to room temperature and partitioned between EtOAc and water. The EtOAc layer was washed with brine, dried and the filtrate was concentrated. The residue was purified by prep TLC using 33% EtOAc-hexane to provide 1-methyl-1'-trifluoroacetyl-spiro-(2-oxo-1,2,3,4-tetrahydroquinoline-4, 4'-piperidine). Hydrolysis of this trifluoroacetamide as described in Example 55, Step C furnished 71 mg (64%) of the title compound.
$^1$H NMR (CDCl$_3$) δ 1.61 (d, 2H), 1.92 (m, 2H), 2.74 (s, 2H), 2.98 (m, 4H), 3.36 (s, 3H), 7.0–7.4 (m, 4H).

Step B: 1'-(3-((S)-(3,4-dichlorophenyl))-4-(N-(3,5-dichloro-benzoyl)(methylamino))butyl)-1-methyl-spiro(2-oxo-tetrahydroquinoline-4,4'-piperidine The title compound was prepared by reaction of the amine from Step A and 3-((S)-(3,4-dichlorophenyl))-4-((3,5-dichlorobenzoyl)-methylamino)butanal as described in Example 18, Step D.

Mass Spectrum (CI) 636 ($^{37}$Cl+$^{35}$Cl isotope), 634 ($^{35}$Cl+$^{35}$Cl isotope).

EXAMPLE 20

4-Bromo-2-(S)-(4-fluorophenyl)-1-(N-(3,5-bistrifluoromethylbenzoyl)-methylamino)butane Step A: 3-(S)-(4-Fluorophenyl)-4-(N-(3,5-bistrifluoromethylbenzoyl)methylamino)butanol A solution of 1.67 g (3.84 mmol) of 3-((S)-(4-fluorophenyl)-4-(N-(3,5-(bistrifluoromethyl)benzoyl)-(methylamino))-butanal (prepared from 4-fluorophenylacetic acid as described by J. Hale et. al., Bioorganic & Medicinal Chemistry Letters 1993,3, 319–322) in 16 mL of absolute ethanol at 0° C. was treated with 172 mg (4.55 mmol) of sodium borohydride. After stirring for 1 h at room temperature, the reaction was quenched with saturated NH$_4$Cl and extracted twice with ethyl acetate. The combined organic layers were washed with brine, dried (MgSO$_4$) and evaporated to give 1.59 of residual oil. Purification on a silica gel flash column (30:70 then 50:50 ethyl acetate:hexanes) provided 1.21 g (72%) of the title compound as a viscous oil. Mass Spectrum (CI/NH$_3$) M+H=438.

Step B: 4-Bromo-2-(S)-(4-fluorophenyl)-1-(N-(3,5-bistrifluoromethylbenzoyl)methylamino)butane To a solution of 1.19 g (2.72 mmol) of 3-(S)-(4-fluorophenyl)-4-(N-(3,5-bistrifluoromethylbenzoyl)methyl-amino)butanol in 20 mL of acetonitrile was added 1.49 g (3.53 mmol) of triphenylphosphine dibromide. After 1.5 h the reaction was partitioned between ethyl acetate and water. The organic layer was washed with brine, dried (MgSO4) and concentrated to give 2.33 g of crude white solid. Purification on a silica gel flash column (30:70 ethyl acetate:hexanes) gave 944 mg (69%) of the desired bromide as a viscous oil. Mass Spectrum (CI/NH3) M+H=500, 502 ($^{79,81}$Br isotope).

EXAMPLE 21

1'-(3-(S)-(4-Fluorophenyl)-4-(N-(3,5-bistrifluoromethylbenzoyl)-(methylamino))butyl)-1-acetyl-spiro(indoline-3,4'-piperidine).

To 40 mg (0.08 mmol) of the bromide prepared in Example 20, Step B and 0.21 ul (0.12 mmol) of N,N-diisopropylethylamine in 0.5 mL of acetonitrile was added 37 mg (0.16 mmol) of 1-acetyl-spiro(indoline-3,4'-piperidine). The resultant mixture was heated in a tightly capped vial at 50° C. for four days. The solvent was evaporated and the residue was purified on a 1000 micron silica gel prep plate (93:5:2 ethyl acetate:methanol:triethylamine) to furnish 46.6 mg (90%) of the title compound as a white foam.

Mass Spectrum (CI/NH3) M+H=650.

The compounds in Examples 22–26 were prepared as in Example 21 from the requisite bromide, prepared from the corresponding phenylacetic acid as described in Example 20, and the required 1-substituted-spiro(indoline-3,4'-piperidine).

EXAMPLE 22

1'-(3-(S)-(3-Chlorophenyl)-4-(N-(3,5-bistrifluoromethylbenzoyl)-(methylamino))butyl)-1-acetyl-spiro(indoline-3,4'-piperidine)

Mass Spectrum (CI/NH3) M+H=666, 668 ($^{35,37}$Cl-isotope).

EXAMPLE 23

1'-(3-(S)-(4-Chlorophenyl)-4-(N-(3,5-bistrifluoromethylbenzoyl)-(methylamino))butyl)-1-acetyl-spiro(indoline-3,4'-piperidine)
Mass Spectrum (CI/NH3) M+H=666, 668 ($^{35,37}$Cl-isotope).

EXAMPLE 24

1'-(3-(S)-(3,4-Difluorophenyl)-4-(N-(3,5-bistrifluoromethylbenzoyl)-(methylamino))butyl)-1-acetyl-spiro(indoline-3,4'-piperidine)
Mass Spectrum (CI/NH3) M+H=668.

EXAMPLE 25

1'-(3-(S)-(3,4-Methylenedioxyphenyl)-4-(N-(3,5-bistrifluoromethylbenzoyl)-(methylamino))butyl)-1-methanesulfonyl-spiro(indoline-3,4'-piperidine)
Mass Spectrum (CI/NH3) M+H=712.

EXAMPLE 26

1'-(3-(RS)-(3,5-Dichlorophenyl)-4-(N-(3,5-bistrifluoromethylbenzoyl)-(methylamino))butyl)-1-methanesulfonyl-spiro(indoline-3,4'-piperidine).
Mass Spectrum (CI/NH3) M+H=736, 738 ($^{35,37}$Cl-isotope).

EXAMPLE 27

1'-(3-(S)-(4-Chlorophenyl)-4-(N-(3,5-bistrifluoromethylbenzoyl)-(methylamino))butyl)-spiro(2,3-dihydrobenzothiophene-3,4'-piperidine).

The title compound was prepared as in Example 21 from 4-bromo-2-(S)-(4-chlorophenyl)-1-(N-(3,5-bistrifluoromethylbenzoyl)-methylamino)butane and spiro(2,3-dihydrobenzothiophene-3,4'-piperidine) hydrochloride except that 3 eq. of diisopropylethylamine were used.
Mass Spectrum (CI/NH3) M+H=641,643 ($^{35,37}$Cl-isotope).

EXAMPLE 28

1'-(3-(RS)-(4-Pyridyl)-4-(N-(3,5-bistrifluoromethylbenzoyl)-(methylamino))butyl)-1-acetyl-spiro(indoline-3,4'-piperidine)

The title compound was prepared from 3-(S)-(4-pyridyl)-4-(N-(3,5-bistrifluoromethyl-benzoyl)methylamino)butanal (prepared from 4-pyridylacetic acid as described by J. Hale et. al., *Bioorganic & Medicinal Chemistry Letters* 1993,3, 319–322) by reductive amination as described in Example 2.
Mass Spectrum (CI/NH3) M+H=633.

EXAMPLE 29

1'-(3-(S)-(3,4-Dichlorophenyl)-4-(N-(3,5-dimethylbenzoyl)-(ethylamino))butyl)-1-methanesulfonyl-spiro(indoline-3,4'-piperidine)

Step A: 4-Bromo-2-(S)-(3,4-dichlorophenyl)-1-(N-(3,5-dimethylbenzoyl)methylamino)butane The title compound was prepared as in Example 20, Steps A and B, from 3-(S)-(3,4-dichlorophenyl)-4-(N-(3,5-dimethyl-benzoyl)ethylamino)butanal (prepared from 3,4-dichlorophenylacetic acid as described by J. Hale et. al., (*Bioorganic & Medicinal Chemistry Letters* 1993,3, 319–322) using ethylamine rather than methylamine to form the intermediate amide). Mass Spectrum (CI/NH$_3$) M=454, 456 ($^{79,81}$Br isotope).

Step B: 1'-(3-(S)-(3,4-Dichlorophenyl)-4-(N-(3,5-dimethyl-benzoyl)-(ethylamino))butyl)-1-methanesulfonyl-spiro (indoline-3,4'-piperidine)

The title compound was prepared from the bromide prepared in Step A and 1-acetyl-spiro(indoline-3,4'-piperidine) as described in Example 21. Mass Spectrum (CI/NH3) M+H=641, 643 ($^{35,37}$Cl-isotope).

EXAMPLE 30

5-Fluoro-spiro(2,3-dihydrobenzofuran-3,4'-piperidine) hydrochloride

Step 1: 4-(2,5-Difluorophenyl)-4-methoxycarbonyl-1-methylpiperidine

Methyl 2,5-difluorophenylacetate (4.8 g, 26 mmol) and mechlorethamine hydrochloride (5.0 g, 26 mmol) in DMSO (15 mL) and THF (50 mL) at 0° C. was carefully treated with NaH (2.5 g, 104 mmol). The reaction was gradually warmed to reflux over 1 h and refluxed further for 1 h. The reaction was cooled to 0° C., and 6N HCl (25 mL) was slowly added. The reaction was diluted with 1N HCl (200 mL) and washed with hexane (200 mL). The aqueous layer was cooled to 0° C. and adjusted to pHE 12 with solid K$_2$CO$_3$. The product was extracted with ethyl acetate (200 mL), washed with brine (100 mL), dried (MgSO$_4$), and concentrated to 4.1 g (59%) of the title compound as an oil. $^1$H NMR (400 MHz, CDCl$_3$) δ 7.34 (dq, 1H), 6.88 (m, 1H) 6.78 (ddd, 1H) 6.69 (minor NMe invertomer, dm), 6.59 (minor NMe invertomer, dd), 3.69 (s, 3H), 3.80 (minor invertomer, s), 2.71 (d, 2H), 2.48 (d, 2H), 2.38 (t, 2H), 2.25 (s, 3H), 2.10 (t, 2H) ppm.

Step 2) 4-(2,5-Difluorophenyl)-4-hydroxymethyl-1-methylpiperidine

EtOH (5.1 mL, 86 mmol) was added to 0.5 M LAlH$_4$ in glyme (82 mL, 41 mmol) at 0° C. 4-(2,5-difluorophenyl)-4-methoxycarbonyl-1-methylpiperidine (3.45 g, 12.8 mmol) in glyme (4 mL) was added. Saturated aqueous sodium potassium tartrate (50 mL) was added along with Celite (10 g), and the mixture was mechanically stirred 1 h at room temp. The slurry was filtered, and the organic layer was extracted with 1N HCl. The HCl was washed with EtOAc and then basified with 3N NaOH. The product was extracted with CH$_2$Cl$_2$, washed with 20% brine, dried (MgSO$_4$), and concentrated to a crude solid, which was recrystallized (EtOAc) to yield 1.46 g (52%) of the title compound as colorless crystals. $^1$H NMR (400 MHz, CDCl$_3$) δ 7.28 (dt, 1H, J=7,9 Hz), 6.88 (ddd, 1H, J=3,9,9 Hz), 6.81 (ddd, J=3,9,13 Hz), 3.76 (s, 2H), 2.59 (m, 2H), 2.32–2.20 (m, 4H), 2.23 (s, 3H), 1.96 (t, 2H, J=5 Hz) ppm.

Step 3) 5-Fluoro-1'-methyl-spiro(2,3-dihydrobenzofuran-3,4'-piperidine)

NaH (158 mg, 6.56 mmol) was added to 4-(2,5-difluorophenyl)-4-hydroxymethyl-1-methylpiperidine (1.45 g, 6.56 mmol) in DMF (20 mL). The slurry was heated to 90° C. for 6 h. The reaction was diluted with hexane (200 mL), washed with water (200 mL), brine (50 mL), dried (MgSO$_4$), and concentrated to yield 1.21 g (92%) of the title compound as a white crystalline solid; $^1$H NMR (400 MHz, CDCl$_3$) δ 6.98 (dd, 1H), 6.54 (dt, 1H), 6.48 (dd, 1H), 4.37 (s, 2H), 2.84 (m, 2H), 2.31 (s, 3H), 1.97 (4H, pentuplet), 1.71 (m, 2H) ppm.

Step 4) 5-Fluoro-spiro(2,3-dihydrobenzofuran-3,4'-piperidine) hydrochloride salt 5-fluoro-1'-methyl-spiro(2,3-dihydrobenzofuran-3,4'-piperidine) (1.21 g, 5.48 mmol) in 1,2-dichloroethane (12 mL) at room temp was treated with 2-chloroethyl chloroformate (1 mL, 9 mmol). A white precipitate formed, and the reaction was refluxed 2 h. MeOH (12 mL) was added and refluxing was continued for 2 h. The reaction was concentrated to a crude solid, which was triturated with EtOAc (5 mL) and filtered to yield 1.27 g (95%) of the title compound as a white crystalline solid.

¹H NMR (400 MHz, d₆-DMSO) δ 9.12 (s, 1H), 9.04 (s, 1H), 7.11 (dd, 1H), 7.74–7.66 (m, 2H), 4.53 (s, 2H), 3.26 (d, 2H), 2.95 (t, 2H), 2.08 (t, 2H), 1. 79 (d, 2H) ppm.

Reaction of 5-fluoro-spiro(2,3-dihydrobenzofuran-3,4'-piperidine) hydrochloride with 3-((S)-(3,4-dichlorophenyl))-4-(N-(t-butoxycarbonyl)-(methylamino)) butanal according to the procedure given in Example 8, Method B gave 1'-(3-((S)-(3,4-dichlorophenyl))-4-(N-(t-butoxycarbonyl)-(methylamino))butyl)-5-fluoro-spiro(2,3-dihydrobenzofuran-3,4'-piperidine). Removal of the BOC group and benzamide formation according to the procedure given in Example 3, Steps A and B afforded the compounds listed in Examples 31–36:

EXAMPLE 31

1'-(3-((S)-(3,4-Dichlorophenyl))-4-(N-(3,5-dichlorobenzoyl)-(methyl-amino))butyl)-5-fluoro-spiro(2,3-dihydrobenzofuran-3,4'-piperidine)
Mass spectrum (CI): m/z=611.2 ($^{35}$Cl+$^{35}$Cl isotope+H$^+$), 613.2 ($^{37}$Cl+$^{35}$Cl isotope+H$^+$).

EXAMPLE 32

1'-(3-((S)-(3,4-Dichlorophenyl))-4-(N-(4-fluoro-1-napthoyl)-(methyl-amino))butyl)-5-fluoro-spiro(2,3-dihydrobenzofuran-3,4'-piperidine)
Mass spectrum (CI): m/z=609.3 ($^{35}$Cl+$^{35}$Cl isotope+H$^+$), 611.3 ($^{37}$Cl+$^{35}$Cl isotope+H$^+$).

EXAMPLE 33

1'-(3-((S)-(3,4-Dichlorophenyl))-4-(N-(3-chlorobenzoyl)-(methyl-amino))butyl)-5-fluoro-spiro(2,3-dihydrobenzofuran-3,4'-piperidine)
Mass spectrum (CI): m/z=575.2 ($^{35}$Cl+$^{35}$Cl isotope+H$^+$), 577.2 ($^{37}$Cl+$^{35}$Cl isotope+H$^+$), 579.2 ($^{37}$Cl+$^{37}$Cl isotope+H$^+$).

EXAMPLE 34

1'-(3-((S)-(3,4-Dichlorophenyl))-4-(N-(3,5-dimethylbenzoyl)-(methyl-amino))butyl)-5-fluoro-spiro(2,3-dihydrobenzofuran-3,4'-piperidine)
Mass spectrum (CI): m/z=569.3 ($^{35}$Cl+$^{35}$Cl isotope+H$^+$), 571.3 ($^{37}$Cl+$^{35}$Cl isotope+H$^+$).

EXAMPLE 35

1'-(3-((S)-(3,4-Dichlorophenyl))-4-(N-(3-methylbenzoyl)-(methyl-amino))butyl)-5-fluoro-spiro(2,3-dihydrobenzofuran-3,4'-piperidine)
Mass spectrum (CI): m/z=555.3 ($^{35}$Cl+$^{35}$Cl isotope+H$^+$), 557.3 ($^{37}$Cl+$^{35}$Cl isotope+H$^+$).

EXAMPLE 36

1'-(3-((S)-(3,4-Dichlorophenyl))-4-(N-(benzoyl)-(methylamino))butyl)-5-fluoro-spiro(2,3-dihydrobenzofuran-3,4'-piperidine)
Mass spectrum (CI): m/z=541.3 ($^{35}$Cl+$^{35}$Cl isotope+H$^+$), 543.3 ($^{37}$Cl+$^{35}$Cl isotope+H$^+$).

Preparation of spiro(2,3-dihydrobenzofuran-3,4'-piperidine) hydrochloride was carried out by analogy to the procedure given in Example 30, starting with methyl 2-fluorophenylacetate. Reaction of spiro(2,3-dihydrobenzofuran-3,4'-piperidine) hydrochloride with 3-(S)-(3,4-dichlorophenyl)-4-(t-butoxycarbonyl-methylamino)butanal according to the procedure given in Example 8, Step B gave 1'-(3-((S)-(3,4 -dichlorophenyl))-4-(N-(t-butoxycarbonyl)-(methylamino))butyl)-spiro(2,3-dihydrobenzofuran-3,4'-piperidine). Removal of the BOC group and benzamide formation according to the procedure given in Example 3, Steps A and B afforded the compounds listed in Examples 37–43:

EXAMPLE 37

1'-(3-((S)-(3,4-Dichlorophenyl))-4-(N-(benzoyl)-(methylamino))butyl)-spiro(2,3-dihydrobenzofuran-3,4'-piperidine)
Mass spectrum (CI): m/z=523.1 ($^{35}$Cl+$^{35}$Cl isotope+H$^+$).

EXAMPLE 38

1'-(3-((S)-(3,4-Dichlorophenyl))-4-(N-(3-methylbenzoyl)-(methyl-amino))butyl)-spiro(2,3-dihydrobenzofuran-3,4'-piperidine)
Mass spectrum (CI): m/z=537.2 ($^{35}$Cl+$^{35}$Cl isotope+H$^+$), 539.2 ($^{37}$Cl+$^{35}$Cl isotope+H$^+$).

EXAMPLE 39

1'-(3-((S)-(3,4-Dichlorophenyl))-4-(N-(3,5-dimethylbenzoyl)-(methylamino))butyl)-spiro(2,3-dihydrobenzofuran-3,4'-piperidine)
Mass spectrum (CI): m/z=551.2 ($^{35}$Cl+$^{35}$Cl isotope+H$^+$), 553.2 ($^{37}$Cl+$^{35}$Cl isotope+H$^+$).

EXAMPLE 40

1'-(3-((S)-(3,4-Dichlorophenyl))-4-(N-(3-chlorobenzoyl)-(methylamino))butyl)-spiro(2,3-dihydrobenzofuran-3,4'-piperidine)
Mass spectrum (CI): m/z=557.0 ($^{35}$Cl+$^{35}$Cl isotope+H$^+$).

EXAMPLE 41

1'-(3-((S)-(3,4-Dichlorophenyl))-4-(N-(3,5-dichlorobenzoyl)-(methylamino))butyl)-spiro(2,3-dihydrobenzofuran-3,4'-piperidine)
Mass spectrum (CI): m/z=591.0 ($^{35}$Cl+$^{35}$Cl isotope+H$^+$), 593.1 ($^{37}$Cl+$^{35}$Cl isotope+H$^+$).

EXAMPLE 42

1'-(3-((S)-(3,4-Dichlorophenyl))-4-(N-(4-fluoro-1-napthoyl)-(methylamino))butyl)-spiro(2,3-dihydrobenzofuran-3,4'-piperidine)
Mass spectrum (CI): m/z=591.3 ($^{35}$Cl+$^{35}$Cl isotope+H$^+$), 593.2 ($^{37}$Cl+$^{35}$Cl isotope+H$^+$).

EXAMPLE 44

1'-(3-((S)-(3,4-Dichlorophenyl))-4-(N-(t-butoxycarbonyl)-(methylamino))butyl)-spiro(2,3-dihydrobenzothiophene-3,4'-piperidine)

Step 1) 1-t-Butoxycarbonyl-3-hydroxy-4-methylenepiperidine n-Butyl lithium (9.57 mL, 2.45M in hexane, 23.7 mmol) was added to a −78° C. solution of diisopropylamine (3.32 mL, 23.7 mmol) in TEF (15 mL). After 30 min at −78° C., methyl phenyl sulfoxide (3.32 g, 23.7 mmol) in THF (4 mL) was added. The solution was warmed to 0° C. and cooled back down to −78° C. 1-t-butoxycarbonyl-4-piperidinone (4.69 g, 23.7 mmol) in TXF (20 mL) was added. The reaction was warmed to room temp, quenched by addition of solid NH₄Cl, concentrated in vacuo, and partitioned between H₂O (100 mL) and EtOAc (100 mL). The organic layer was washed with H₂O (50 mL) brine (50 mL), dried (MgSO₄), and concentrated in vacuo. The resultant oil was heated at 80° C. in t-butanol (50 mL) with potassium t-butoxide (3.4g, 30 mmol) for 2 h. Solid NH$_4$Cl was added, and the reaction was concentrated in vacuo and partitioned between H$_2$O (100 mL) and EtOAc (100 mL). The EtOAc was washed with brine (50 mL), dried (MgSO$_4$), concentrated in vacuo and purified by column chromatography (silica gel 60, 0–50% EtOAc/hexane) to yield 4.47 g (79%) of the title compound as a crystalline solid. $^1$H NMR (400 MHz, DMSO-d$_6$) δ 5.21 (d,1H), 4.96 (s, 1H), 4.77 (s, 1H), 3.82 (t, 2H), 3.67 (dt, 1H), 2.83 (dt, 1H), 2.77–2.50 (brd d, 1H), 2.26 (dt, 1H), 2.01 (ddd, 1H), 1.38 (s, 9H) ppm.

Step 2) 1-t-Butoxycarbonyl-3,4-didehydro-4-(chloromethyl)piperidine

To 1-t-butoxycarbonyl-3-hydroxy-4-methylenepiperidine (5.329 g, 25.1 mmol) in toluene (120 mL) and 2,6-lutidine (3.1 mL, 26 mmol) at 0° C. was added SOCl$_2$ (2.0 mL, 26 mmol). The reaction was heated at 40° C. for 30 min, cooled to 0° C., washed with 0° C. 1N HCl (100 mL), 0.1 N HCl (100 mL), H$_2$O (100 mL), brine (50 mL), dried (MgSO$_4$), and concentrated in vacuo to afford 5.18 g (89%) of allylic chloride as a yellow oil. $^1$H NMR (400 MHz, CDCl$_3$) δ 5.78 (s, 1H), 4.04 (s, 2H), 3.95 (s, 2H), 3.55 (t, 2H, J=6 Hz), 2.24 (s, 2H), 1.45 (s, 9H) ppm.

Step 3) 1-t-Butoxycarbonyl-4-((2-bromophenyl)thio)methyl-1,2,5,6-tetrahydropyridine The allylic chloride (330 mg, 1.43 mmole) was dissolved in acetone (10 mL) and 2-bromothiophenol (172 ml, 1.43 mmole) and K$_2$CO$_3$ (390 mg, 2.86 mmole) were added. The reaction mixture was heated to 60° C. for 1 h and then filtered though silica gel (ether). The organic layer was concentrated in vacuo and purified by column chromatography (silica gel 60, hexanes/ethyl acetate 10/1) to give the title compound in 84% yield (460 mg).

Step 4) 1'-t-Butoxycarbonyl-spiro(2,3-dihydrobenzothiophene-3,4'-piperidine).

The intermediate adduct from step 3 above (450 mg, 1.17 mmole) was dissolved in benzene (60 mL) and AIBN (10 mg) and tributyltin hydride (644 mL, 2.39 mmole) were added. This mixture was refluxed for 2 h and concentrated. The residue was dissolved in Et$_2$O and Br$_2$ was added until the reaction solution turned to a brownish color. To this brownish solution at room temp was added DBU (650 mL) dropwise. The resulting cloudy solution was filtered though silica gel and washed with Et$_2$O. The Et$_2$O solution was concentrated and the residue was purified by radial chromatography (silic gel 60, 10/1 hexanes/EtOAc) to give the title compound (157 mg) in 43% yield. $^1$H NMR (400 MHz, CDCl$_3$) δ 7.18 (d, 7 Hz, 1H), 7.12 (t, 7 Hz, 1H), 7.06 (m, 2H), 4.11(m, 2H), 3.30 (s, 3H), 2.89 (m, 2H), 1.79 (m, 4H), 1.47 (s, 9H) ppm.

Removal of the BOC group according to the procedure given in Example 3, Step A followed by reaction with 3-((S)-(3,4-dichlorophenyl))-4-(N-(t-butoxycarbonyl)-(methylamino))butanal according to the procedure given in Example 8, Method B gave 1'-(3-((S)-(3,4-dichlorophenyl))-4-(N-(t-butoxycarbonyl)-(methylamino))butyl)-spiro(2,3-dihydrobenzothiophene-3,4'-piperidine). Removal of the BOC group and benzamide formation according to the procedures described in Example 3, Steps A and B gave the compounds listed in Examples 45–46:

EXAMPLE 45

1'-(3-((S)-(3,4-Dichlorophenyl))-4-(N-(3,5-dimethylbenzoyl)-(methylamino))butyl)-spiro(2,3-dihydrobenzothiophene-3,4'-piperidine)
Mass spectrum (CI): m/z=567.2 ($^{35}$Cl+$^{35}$Cl isotope+H$^+$), 569.2 ($^{37}$Cl+$^{35}$Cl isotope+H$^+$).

EXAMPLE 46

1'-(3-((S)-(4-Chlorophenyl))-4-(N-(3,5-dimethylbenzoyl)-(methylamino))butyl)-spiro(2,3-dihydrobenzothiophene-3,4'-piperidine)
Mass spectrum (CI): m/z=533 ($^{35}$Cl+$^{35}$Cl isotope+H$^+$), 535 ($^{37}$Cl+$^{35}$Cl isotope+H$^+$).

EXAMPLE 47

1'-(3-((S)-(3,4-Dichlorophenyl))-4-(N-(t-butoxycarbonyl)-(methylamino))-butyl)-spiro(2,3-dihydrobenzothiophene-3,4'-piperidine)-1-oxide 1'-(3-((S)-(3,4-Dichlorophenyl))-4-(N-(t-butoxycarbonyl)-(methylamino))butyl)-spiro(2,3-dihydrobenzothiophene-3,4'-piperidine) (222 mg, 415 μmol) in CH$_2$Cl$_2$ (500 μL) at −78° C. was treated with a solution of m-chloroperbenzoic acid (86 mg, 498 μmol) in CH$_2$Cl$_2$ (1 mL). The reaction was poured into 0° C. saturated aqueous NaHSO$_3$. The organic layer was washed with saturated aqueous NaHCO$_3$ (1 mL), brine (1 mL), dried (MgSO$_4$), concentrated in vacuo and purified by column chromatography (silica gel 60, 0–100% acetone/CH$_2$Cl$_2$) to yield 54.3 mg (24%) of the title compound as a white foam. $^1$H NMR (500 MHz, CDCl$_3$) δ 7.84 (d, 1H, J=7.5 Hz), 7.60 (t, 1H, J=7.5 Hz), 7.48 (t, 1H, J=7.5 Hz), 7.44 (m, 1H), 7.39 (dd, 1H, J=2.0, 8.5 Hz), 7.32 (m, 1H), 7.10–7.04 (rotamer multiplets, 1H), 3.6–3.2 (m, 2H), 3.34, 3.32 (two doublets of one diastereomer, 1H), 3.16, 3.14 (two doublets of other diastereomer, 1H), 3.1–2.8 (m, 3H), 2.75–2.65 (rotamer singlets, 3H), 2.3–1.7 (m, 10H), 1.42 (s, 9H) ppm.

EXAMPLE 48

1'-(3-((S)-(3,4-Dichlorophenyl))-4-(N-(4-fluoro-1-napthylmethyl)-(methylamino))butyl)-spiro(2,3-dihydrobenzothiophene-3,4'-piperidine)-1-oxide The title compound was prepared by oxidizing 1'-(3-((S)-(3,4-dichlorophenyl))-4-(N-(t-butoxycarbonyl)-(methylamino))butyl)-spiro(2,3-dihydrobenzothiophene-3,4'-piperidine) as described in Example 47 above, and then removing the BOC group and N-benzoylating according to the procedures given in Example 3, Steps A and B. Mass spectrum (CI). m/z=623.1 ($^{35}$Cl+$^{35}$Cl isotope+H$^+$).

EXAMPLE 49

1'-(3-((S)-(3,4-Dichlorophenyl))-4-(N-(t-butoxycarbonyl)-(methylamino))butyl)-spiro(2,3-dihydrobenzothiophene-3,4'-piperidine)-1,1-dioxide.

To 1'-(3-((S)-(3,4-dichlorophenyl))-4-(N-(t-butoxycarbonyl)-(methylamino))butyl)-spiro(2,3-dihydrobenzo-thiophene-3,4'-piperidine)(102 mg, 191 μmol) in MeOH (0.8 mL) at 0° C. was added Oxone®(176 mg, 287 ) in water (0.4 mL). After 30 min at room temp, the reaction was filtered through a plug of silica gel and concentrated to yield 39.5 mg (36%) of the title compound as a white foam. $^1$H NMR (500 MHz, CDCl$_3$) δ 7.72 (d, 1H, J=7.5 Hz), 7.66 (t, 1H, J=7.5 Hz), 7.51 (t, 1H, J=7.3 Hz), 7.39 (t, 1H, J=8.3 Hz), 3.65–3.25 (m, 2H), 3.38 (s, 2H), 3.15–2.85 (m, 3H), 2.76,2.66 (rotamer singlets, 3H), 2.25 (m, 2H), 2.15–1.95 (m, 3H), 1.95–1.65 (m, 5H), 1.40 (s, 9H) ppm.

EXAMPLE 50

1'-(3-((S)-(3,4-Dichlorophenyl))-4-(N-(3,5-dimethylbenzoyl)-(methyl-amino))butyl)-spiro(2,3-dihydrobenzothiophene-3,4'-piperidine)-1,1-dioxide The title compound was prepared by removing the BOC group and N-benzoylating (according to the procedures given in Example 3, Steps A and ]B) the product from Example 49.

Mass spectrum (CI): m/z=639.1 ($^{35}Cl+^{35}Cl$ isotope+$H^+$).

EXAMPLE 51

1'-(3-((S)-(3,4-Dichlorophenyl))-4-(N-(3,5-dimethylbenzoyl)-(methyl-amino))butyl)-spiro(2,3-dihydrobenzothiophene-3,4'-piperidine)-1,1-dioxide To 1'-(3-((S)-(3,4-dichlorophenyl))-4-(N-(3,5-dimethylbenzoyl)-(methylamino))butyl)-spiro(2,3-dihydrobenzothiophene-3,4'-piperidine) (10 mg, 20 μmol) in MeOH (0.1 mL) at 0° C. was added 0.4 M aqueous Oxone® (75 μL, 30 μmol). The reaction was warmed to room temp and stirred overnight. The reaction was concentrated in vacuo, partitioned between 1N NaOH (1 mL) and $CH_2Cl_2$ (1 mL). The organic layer was concentrated and purified by column chromatography (silica gel 60, 0–100% acetone/$CH_2Cl_2$) to yield 9.0 mg (90%) of the title compound as a clear film. Mass spectrum (CI): ml/z=599.1 ($^{35}Cl+^{35}Cl$ isotope+$H^+$), 601.1 ($^{37}Cl+^{35}Cl$ isotope+$H^+$).

EXAMPLE 52

1'-(3-((S)-(4-Chlorophenyl))-4-(N-(3,5-dimethylbenzoyl)-(methylamino))-butyl)-spiro(2,3-dihydrobenzothiophene-3,4'-piperidine)-1,1-dioxide This compound was prepared according to the procedure given in Example 51 above. Mass spectrum (CI): m/z=567 ($^{35}Cl+^{35}Cl$ isotope+$H^+$), 565 ($^{37}Cl+^{35}Cl$ isotope+$H^+$).

EXAMPLE 53

1'-(3-((S)-(4-Chlorophenyl))-4-(N-(3,5-dimethylbenzoyl)-(methylamino))-butyl)-spiro(2,3-dihydrobenzothiophene-3,4'-piperidine)-1-oxide To 1'-(3-((S)-(4-chlorophenyl))-4-(N-(3,5-dimethylbenzoyl)-(methylamino))butyl)-spiro(2,3-dihydrobenzothiophene-3,4'-piperidine) (25 mg, 47 μmol) in MeOH (1.0 mL) at 0° C. was added a solution of Oxone® (38 mg, 61 gmol) in $H_2O$ (1.0 mL). The reaction was stirred 2 min and quenched with 10% aqueous sodium bisulfite. The reaction mixture was diluted with $H_2O$ (10 mL), neutralized with sat. aqueous NaHCO3 (15 mL), extracted with $CH_2Cl_2$ (3×25 mL), washed with brine (10 mL), dried ($Na_2SO_4$), concentrated in vacuo, and purified by column chromatography (silica gel 60, 5–8% MeOH/$CH_2Cl_2$) to yield 25 mg (99%) of a colorless solid; Mass spectrum (CI): m/z=549 (35Cl+$^{35}$Cl isotope+$H^+$), 551 ($^{37}Cl+^{35}Cl$ isotope+$H^+$).

EXAMPLE 54

1'-(3-(S)-(4-Chlorophenyl)-4-(N-(3,5-bistrifluoromethylbenzoyl)-(methylamino))butyl)-spiro(2,3-dihydrobenzothiophene-3,4'-piperidine), 1-oxide The title compound was prepared by the Oxone® (oxidation method described in Example 53. Mass Spectrum (CI/NH3) M+H=657, 659 ($^{35,37}$Cl-isotope).

EXAMPLE 55

1'-(3-(S)-(4-Chlorophenyl))-4-(N-(3,5-bistrifluoromethylbenzoyl)-(methylamino))butyl)-spiro(2,3-dihydrobenzothiophene-3,4'-piperidine), 1, 1-dioxide The title compound was prepared by the Oxone®oxidation method described in Example 51. Mass Spectrum (CI/NH3) M+H=673, 675 ($^{35,37}$Cl-isotope).

Substituted indoline spiropiperidine derivatives were obtained by employing substituted phenyl hydrazines and 1-benzyloxycarbonylpiperidine-4-carboxyaldehyde in the Fisher indole synthesis. When regioisomers were formed, they were separated as the 1'-benzyloxycarbonyl-1-methanesulfonyl-spiro(indoline-3,4'-piperidine) derivative by chromatography (silica gel 60, THF/hexane). Preparation of a representative substituted spiro(indoline-3,4'-piperidinium) hydrochloride is described below:

EXAMPLE 56

1'-Benzyloxycarbonyl-5-fluoro-spiro(indoline-3,4'-piperidine)

A slurry of 4-fluorophenylhydrazine hydrochloride (6.504 g, 40 mmol), pyridine (6.56 ml, 80 mmol), toluene (360 mL), acetonitrile (40 mL), and N-benzylcarboxy-4-piperidine carboxyaldehyde (9.88g, 40 mmol) was maintained at 0° C. for 1 h. Trifluoroacetic acid (18.5 mL, 240 mmol) was added, and the reaction was heated 20 h at 60° C. The reaction was cooled to 0° C., and methanol (40 mL) was added followed by $NaBH_4$ (1.51 g, 40 mmol). The cooling bath was removed and 30% aqueous $NH_4OH$ (100 mL) was added. The organic layer was separated, washed with 5% aqueous $NH_4OH$ (100 mL) brine (50 mL), dried ($MgSO_4$), and concentrated to a crude oil which was purified by column chromatography (SG 60 silica, 0–5% acetone/$CH_2Cl_2$) to yield 6.48 g (48%) of the title compound as a clear oil. $^1$H NMR (400 MHz, $CDCl_3$): δ 7.23–7.36 (m, 5H), 6.76–6.71 (m, 2H), 6.58 (dd, 1H, J=4.4, 8.0 Hz), 5.14 (s, 2H), 4.12 (br s, 2H), 3.49 (s, 2H), 2.95 (br s, 2H) 1.73 (br s, 4H) ppm.

EXAMPLE 57

Step 1) 1'-]Benzyloxycarbonyl-5-fluoro-1-methanesulfonyl-spiro(indoline-3,4'-piperidine)

To a solution of 1'-benzyloxycarbonyl-5-fluoro-spiro(indoline-3,4'-piperidine) (6.48 g, 19.0 mmol) in $CH_2Cl_2$ (19 mL) and pyridine (38 mmol, 3.1 mL) at 0° C. was added methanesulfonyl chloride (19 mmol, 1.52 mL). The reaction was warmed to room temp., diluted with ethyl acetate (200 mL), washed with 1N aqueous HCl (100 mL) saturated aqeuous $NaHCO_3$ (100 mL) brine (50 mL), dried ($MgSO_4$), and concentrated to 7.81 g (98%) of the title compound as a red foam. $^1$H NMR (400 MHz, $CDCl_3$) δ 7.35 (m, 5H), 7.32 (dd, 1H, J=4.2, 9.0 Hz), 6.90 (dt, 1H, J=2.7, 8.8 Hz), 6.81 (1H, dd, J=2.6, 8.2 Hz), 5.14 (s, 2H), 4.22 (br s, 2H), 3.84 (s, 2H), 2.92 (br s, 2H), 2.88 (s, 3H), 1.79 (br s, 2H), 1.69 (d, 2H, 13 Hz) ppm.

Step 2) 5-Fluoro-1-methanesulfonyl-spiro(indoline-3,4'-piperidine) hydrochloride salt To 1'-benzyloxycarbonyl-5-fluoro-1-methanesulfonyl-spiro(indoline-3,4'-piperidine) (7.81 g, 18.7 mmol) in $CHCl_3$ (18 mL) at room temp. was added trimethylsilyl iodide (20.5 mmol, 2.93 ml). After 5 min, the rxn was cooled to 0° C., and a 5M solution of HCl in methanol/methyl acetate is added with vigorous stirring. The HCl solution was prepared by adding acetyl chloride (190 mmol, 14 ml) to methanol (20 mL) at 0° C. 40 ml of EtOAc was added, and the slurry was vigorously stirred at 0° C. for 4 h. The solid was filtered off under dry nitrogen, washed with 0° C. ethyl acetate (10 mL) and then with hexane (10 mL), and dried under vacuum to yield 4.77 g (80%) of the title compound as a light pink solid.

$^1$H NMR (400 MHz, DMSO-$d_6$) δ 8.85 (br s, 1H), 8.77 (br s, 1H), 7.26 (dd, 1H, J=4.4, 8.8 Hz), 7.11 (dt, 1H, J=2.8, 8.8 Hz), 7.02 (dd, 1H, J=2.8, 8.4 Hz), 3.97 (s, 3H), 3.30 (m, 2H), 3.06 (m, 2H), 3.06 (s, 3H), 2.04 (m, 2H), 1.83 (d 2H,J=14 Hz) ppm.

The substituted 1-methanesulfonyl-spiro(indoline-3,4'-piperidinium) hydrochlorides could be reductively aminated with 3-(S)-(3,4-dichlorophenyl)-4-(t-butoxycarbonyl-methylamino)butanal according to the procedure described in Example 8, Method B. Removal of the BOC group by the procedure given in Example 3, Step A provided intermediate secondary amine compounds described below which could then be benzoylated under conditions given in Example 3, Step B to give the indicated benzamide derivatives.

EXAMPLE 58

1'-(3-((S)-(3,4-Dichlorophenyl))-4-(methylamino)butyl)-1-methanesulfonyl-5-methoxy-spiro(indoline-3,4'-piperidine)
$^1$H NMR (CDCl$_3$, 400 MHz) δ 7.37 (d, 1H, J=8.2 Hz), 7.29 (d, 1H), 7.25 (d, 1H), 7.04 (dd, 1H, J=2.1, 8.3 Hz), 6.72 (m, 2H), 3.76 (s, 3H), 3.73 (s, 2H), 2.87 (m, 2H), 2.82 (s, 3H), 2.78 (d, 2H, J=7.1 Hz), 2.41 (s, 3H), 2.32–2.18 (m, 2H), 2.05–1.85 (m, 5H), 1.7 (m, 3H) ppm.

EXAMPLE 59

1'-(3-((S)-(3,4-Dichlorophenyl))-4-(methylamino)butyl)-1-methane-sulfonyl-5-methyl-spiro(indoline-3,4'-piperidine)
$^1$H NMR (CDCl$_3$, 400 MHz) δ 7.37 (d, 1H, J=6.2 Hz), 7.30 (d, 1H, J=2.0 Hz), 7.24 (d, 1H, J=10 Hz), 7.05 (dd, 1H, J=2.0, 8.2 Hz), 7.00 (d, 1H, J=8.8 Hz), 6.95 (s, 1H), 3.71 (dd, 2H, J=16, 5.4 Hz), 2.9 (m, 3H), 2.84 (s, 3H), 2.79 (d, 2H, J=7.4 Hz), 2.43 (s, 3H), 2.30 (s, 3H), 2.24 (m, 1H), 2.05–1.85 (m, 5H), 1.75–1.60 (m, 3H) ppm.

EXAMPLE 60

5-Chloro-1'-(3-((S)-(3,4-dichlorophenyl))-4-(methylamino)butyl)-1-methanesulfonyl-spiro(indoline-3,4'-piperidine)
$^1$H NMR (CDCl$_3$, 400 MHz) δ 7.39 (d, 1H, J=8.2 Hz), 7.29 (d, 1H, J=2.1), 7.24 (s, 1H), 7.17 (dd, 1H, J=2.2, 8.5 Hz), 7.11 (d, 1H, J=2.1 Hz), 7.05 (dd, 1H, J=2.0, 8.3 Hz), 3.76 (dd, 2H, J=4.5, 25 Hz), 3.18 (p, 1H), 2.10–2.85 (m, 4H), 2.87 (s, 3H), 2.61 (s, 3H), 2.47 (m, 1H), 2.34 (m, 1H), 2.15 (t, 1H), 2.04 (m, 2H), 1.95–1.70 (m, 5H) ppm.

EXAMPLE 61

1'-(3-((S)-(3,4-Dichlorophenyl))-4-(methylamino)butyl)-5-fluoro-1-methanesulfonyl-spiro(indoline-3,4'-piperidine)
$^1$H NMR (CDCl$_3$, 400 MHz) δ 7.38 (d, 1H), 7.3 (m, 2H), 7.05 (dd, 1H), 7.91–7.85 (m, 2H), 3.75 (dd, 2H), 3.0–2.8 (m, 3H), 2.81 (d, 2H), 2.43 (s, 3H), 2.42 (m, 1H), 2.34 (m, 1H), 2.1–1.8 (m, 5H), 1.7 (m, 3H) ppm.

EXAMPLE 62

1'-(3-((S)-(3,4-Dichlorophenyl))-4-(methylamino)butyl)-7-fluoro-1-methanesulfonyl-spiro(indoline-3,4'-piperidine)
$^1$H NMR (CDCl$_3$, 400 MHz) δ 7.38 (d, 1H), 7.29 (d, 1H), 7.05 (m, 2H), 6.95 (m, 2H), 3.99 (dd, 2H), 3.25 (s, 3H), 2.9 (m, 2H), 2.81 (t, 1H), 2.45 (s, 3H), 2.38 (m, 1H), 2.28 (m, 1H), 2.1–1.8 (m, 5H), 1.75 (m, 3H) ppm.

EXAMPLE 63

1'-(3-((S)-(3,4-Dichlorophenyl))-4-(N-(3,5-dimethylbenzoyl)-(methylamino))butyl)-1-methanesulfonyl-5-methyl-spiro(indoline-3,4'-piperidine)
Mass spectrum (FAB): m/z=642.0 ($^{35}$Cl+$^{35}$Cl isotope+H$^+$).

EXAMPLE 64

5-Chloro-1'-(3-((S)-(3,4-dichlorophenyl))-4-(N-(3-methylbenzoyl)-(methylamino))butyl)-1-methanesulfonyl-spiro(indoline-3,4'-piperidine)
Mass spectrum (FAB): ml/z=648.1 ($^{35}$Cl+$^{35}$Cl isotope+H$^+$).

EXAMPLE 65

1'-(3-((S)-(3,4-Dichlorophenyl))-4-(N-(3,5-dimethylbenzoyl)-(methylamino))butyl)-1-methanesulfonyl-5-methoxy-spiro(indoline-3,4'-piperidine)
Mass spectrum (FAB): m/z=658 ($^{35}$Cl+$^{35}$Cl isotope+H$^+$).

EXAMPLE 66

1'-(3-((S)-(3,4-Dichlorophenyl))-4-(N-(3-methylbenzoyl)-(methylamino))butyl)-5-fuoro-1-methanesulfonyl-spiro(indoline-3,4'-piperidine)
Mass spectrum (Cl): m/z=632.2 ($^{35}$Cl+$^{35}$Cl isotope+H$^+$), 634.2 ($^{37}$Cl+$^{35}$Cl isotope+H$^+$).

EXAMPLE 67

1'-(3-((S)-(3,4-Dichlorophenyl))-4-(N-(3,5-dichlorobenzoyl)-(methylamino))butyl)-5-fluoro-1-methanesulfonyl-spiro(indoline-3,4'-piperidine)
Mass spectrum (FAB): m/z=688.0 ($^{37}$Cl+$^{35}$Cl isotope+$^{35}$Cl+$^{35}$Cl isotope+H$^+$).

EXAMPLE 68

1'-(3-((S)-(3,4-Dichlorophenyl))-4-(N-(3,5-dimethylbenzoyl)-(methylamino))butyl)-5-fluoro-1-methanesulfonyl-spiro(indoline-3,4'-piperidine)
Mass spectrum (CH): m/z=646.1 ($^{35}$Cl+$^{35}$Cl isotope+H$^+$), 648.1 ($^{37}$Cl+$^{35}$Cl isotope+H$^+$).

EXAMPLE 69

1'-(3-((S)-(3,4-Dichlorophenyl))-4-(N-(3-chlorobenzoyl)-(methylamino))butyl)-5-fluoro-1-methanesulfonyl-spiro(indoline-3,4'-piperidine)
Mass spectrum (Cl): m/z=652.2 ($^{35}$Cl+$^{35}$Cl isotope+$^{35}$Cl+$^{35}$Cl isotope+H$^+$), 656.2 (37Cl+$^{35}$Cl isotope+$^{37}$Cl+$^{35}$Cl isotope+H$^+$), 657.2 ($^{37}$Cl+$^{37}$Cl isotope+$^{37}$Cl+$^{35}$Cl isotope+H$^+$),. 658.2 ($^{37}$Cl+$^{37}$Cl isotope+$^{37}$Cl+$^{37}$Cl isotope+H$^+$).

EXAMPLE 70

1'-(3-((S)-(3,4-Dichlorophenyl))-4-(N-(3,5-bis(trifluoromethyl)benzoyl)-(methylamino))butyl)-5-fluoro-1-methanesulfonyl-spiro(indoline-3,4'-piperidine)
Mass spectrum (CI): m/z=754.1 ($^{35}$Cl+$^{35}$Cl isotope+H$^+$), 756.1 ($^{37}$Cl+$^{35}$Cl isotope+H$^+$).

EXAMPLE 71

1'-(3-((S)-(3,4-Dichlorophenyl))-4-(N-(3,5-dimethylbenzoyl)-(methylamino))butyl)-7-fluoro-1-methanesulfonyl-spiro(indoline-3,4'-piperidine)
Mass spectrum (CI): m/z=646.1 ($^{35}$Cl+$^{35}$Cl isotope+H$^+$), 648.1 ($^{37}$Cl+$^{35}$Cl isotope+H$^+$).

EXAMPLE 72

1-Acetyl-1'-(3-((S)-(3,4-dichlorophenyl))-4-(N-t-butoxycarbonyl)-(methylamino))butyl)-5-fluoro-spiro(indoline-3,4'-piperidine)

To 1'-(3-((S)-(3,4-dichlorophenyl))-4-(N-t-butoxycarbonyl)-(methylamino))butyl)-5-fluoro-1- methanesulfonyl-spiro(indoline-3,4'-piperidine) (1.32 g 2.15 mmol) in toluene (5 mL) at 0° C was added 3.4M Red-Al/toluene (5.1 mL, 17.2 mmol). After 4 h at room temp, the reaction was cooled to 0° C. and quenched by cautious addition of 1N aqueous NaOH (2 mL). Cold saturated aqueous sodium potassium tartrate (30 mL) was added, and the biphasic mixture was mechanically stirred at 0° C. for 1 h. The product was extracted with toluene (3×10 mL), washed with 50% saturated aqueous sodium potassium tartrate (10 mL), $H_2O$ (10 mL), brine (10 mL), dried ($MgSO_4$), and concentrated to roughly 5 mL volume, and cooled to 0° C. Pyridine (705 mL, 8.6 mmol) and acetic anhydride (410 μL, 4.3 mmol) were added. After 16 hours at room temp, the reaction was concentrated and purified by column chromatography (silica gel 60, 0–50% acetone/ $CH_2Cl_2$) to yield 830 mg (72%) of the title compound as a white foam. $^1H$ NMR (400 MHz, $CDCl_3$) δ 8.14 (dd, 1H), 7.37 (d, 1H), 7.28 (m, 1H), 7.1–7.0 (m, 1H), 6.87 (m, 2H), 3.95, 3.81 (rotamer singlets, 2H), 3.53 (m, 1H), 3.36 (m, 2H), 3.22 (m, 1H), 3.01 (m, 1H), 2.90 (m, 1H), 2.82 (m, 1H), 2.74, 2.63 (rotamer singlets, 3H), 2.39, 2.20 (rotamer singlets, 3H), 1.89 (m, 4H), 1.65 (m, 4H) ppm.

The corresponding 1-acetyl-spiro(indoline-3,4'-piperidine) compounds were obtained by selectively removing the methanesulfonyl group with Red-Al and then treating with acetic anhydride/pyridine at the stage where the methylamino group is protected with BOC; a representative procedure is given in Example 72 above. The BOC group could be removed using the procedure given in Example 3, step A to give intermediate methylamino compounds which were benzoylated according to Example 3, step B to give the compounds in Examples 73–90:

EXAMPLE 73

1-Acetyl-5-chloro-1'-(3-((S)-(3,4-dichlorophenyl))-4-(methylamino)butyl)-spiro(indoline-3.4'-piperidine)

$^1H$ NMR ($CDCl_3$, 400 MHz) δ 7.83 (d, 1H, J=6.6 Hz), 7.12 (d, 1H, J=5.2 Hz), 7.09 (d, 1H, J=2.0 Hz), 6.87 (dd, 2H, J=2.0, 10.0 Hz), 6.84 (s, 1H), 2.81 (p, 1H0, 2.75–2.55 (m, 4H), 2.27 (s, 3H), 2.12 (m, 1H), 2.04 (m, 1H), 1.95 (s, 3H), 1.9–1.7 (m, 3H), 1.6 (t, 2H), 1.5–1.4 (m, 3H) ppm.

EXAMPLE 74

1-Acetyl-1'-(3-((S)-(3,4-dichlorophenyl))-4-(methylamino)butyl)-5-methyl-spiro(indoline-3,4'-piperidine)

$^1H$ NMR ($CDCl_3$, 400 MHz) δ 8.05 (d, 1H), 7.38 (d, 1H), 7.30 (d, 1H), 7.05 (dd, 1H), 7.00 (d, 1H), 6.92 (s, 1H), 3.79 (s, 2H), 3.01 (p, 2H), 2.9 (m, 3H), 2.52 (s, 3H), 2.5–2.1 (m, 2H), 2.29 (s, 3H), 2.20 (s, 3H), 2.1–1.7 (m, 6H),. 1.65 (m, 2H) ppm.

EXAMPLE 75

1-Acetyl-1'-(3-((S)-(3,4-dichlorophenyl))-4-(methylamino)butyl)-5-fluoro-spiro(indoline-3,4'-piperidine)

$^1H$ NMR ($CDCl_3$, 400 MHz) δ 8.14 (dd, 1H), 7.38 (d, 1H), 7.24 (s, 1H), 7.05 (dd, 1H), 6.88 (dt, 1H), 6.82 (dd, 1H). 3.96, 3.83 (rotamer singlets, 2H), 3.13 (p, 1H), 3.04 (dd, 2H), 2.92 (dd, 2H), 2.69, 2.66 (rotamer singlets, 3H), 2.50 (p, 1H), 2.33 (p, 1H), 2.38, 2.20 (rotamer singlets, 3H), 2.13 (t, 1H), 2.05 (m, 1H), 1.7 (m, 4H), 1.73 (dd, 2H) ppm.

EXAMPLE 76

1-Acetyl-1'-(3-((S)-(3,4-dichlorophenyl))-4-(methylamino)butyl)-6-fluoro-spiro(indoline-3,4'-piperidine)

$^1H$ NMR (DMSO-$d_6$, 500 MHz) δ 7.76 (dd, 1H), 7.58–7.53 (m, 2H), 7.26 (dd, 1H), 7.21 (dd, 1H), 6.80 (dt, 1H), 3.93 (s, 2H), 2.98–2.86 (m, 3H), 2.82 (d, 1H), 2.65 (d, 1H), 2.38 (s, 3H), 2.19 (m, 1H), 2.16 (s, 3H), 2.09 (m, 1H), 2.05 (t, 3H), 1.90 (t, 2H), 1.78–1.6 (m, 3H), 1.6–1.5 (m, 2H) ppm.

EXAMPLE 77

1-Acetyl-1'-(3-((S)-(3,4-dichlorophenyl))-4-(methylamino)butyl)-4-fluoro-spiro(indoline-3,4'-piperidine)

1H NMR (DMSO-$d_6$, 500 MHz) δ 7.88 (d, 1H), 7.63–7.58 (m, 2H), 7.29 (dd, 1H), 7.19 (q, 1H), 6.79 (t, 1H), 3.86 (s, 2H), 3.23–3.13 (m, 3H), 2.97 (m, 1H), 2.72 (m, 1H), 2.52 (s, 3H), 2.26 (m, 1H), 2.16 (s, 3H), 2.09 (t, 4H), 1.97 (p, 2H), 1.76–1.62 (m, 3H) ppm.

EXAMPLE 78

1-Acetyl-1'-(3-((S)-(3,4-dichlorophenyl))-4-(N-(benzoyl)-(methyl-amino))butyl)-4-fluoro-spiro(indoline-3,4'-piperidine)

Mass spectrum (CI): m/z=588.2 ($^{35}Cl+^{35}Cl$ isotope+$H^+$).

EXAMPLE 79

1-Acetyl-1'-(3-((S)-(3,4-dichlorophenyl))-4-(N-(3,5,-dimethylbenzoyl)-(methylamino))butyl)-6-fluoro-spiro(indoline-3,4'-piperidine)

Mass spectrum (Cl): m/z=610.2 ($^{35}Cl+^{35}Cl$ isotope+$H^+$), 612.2 ($^{37}Cl+^{35}Cl$ isotope+$H^+$).

EXAMPLE 80

1-Acetyl-1'-(3-((S)-(3,4-dichlorophenyl))-4-(N-(benzoyl)-(methyl-amino))butyl)-6-fluoro-spiro(indoline-3,4'-piperidine)

Mass spectrum (CI): m/z=582.3 ($^{35}Cl+^{35}Cl$ isotope+$H^+$).

EXAMPLE 81

1-Acetyl-1'-(3-((S)-(3,4-dichlorophenyl))-4-(N-(3,5,-dimethylbenzoyl)-(methylamino))butyl)-4-fluoro-spiro(indoline-3,4'-piperidine)

Mass spectrum (CI): m/z=610.3 ($^{35}Cl+^{35}Cl$ isotope+$H^+$)

EXAMPLE 82

1-Acetyl-1'-(3-((S)-(3,4-dichlorophenyl))-4-(N-(benzoyl)-(methyl-amino))butyl)-5-fluoro-spiro(indoline-3,4'-piperidine)

Mass spectrum (CI): m/z=582.2 ($^{35}Cl+^{35}Cl$ isotope+$H^+$).

EXAMPLE 83

1-Acetyl-1'-5-chloro-(3-((S)-(3,4-dichlorophenyl))-4-(N-(3,5-dimethyl-benzoyl)-(methylamino))butyl)-spiro(indoline-3,4'-piperidine)

Mass spectrum (FAB): m/z=626.0 ($^{35}Cl+^{35}Cl$ isotope+$H^+$), 628.1 ($^{37}Cl+^{35}Cl$ isotope+$H^+$).

EXAMPLE 84

1-Acetyl-1'-(3-((S)-(3,4-dichlorophenyl))-4-(N-(3-chlorobenzoyl)-(methylamino))butyl)-5-fluoro-spiro(indoline-3,4'-piperidine)

Mass spectrum (CI): m/z=616.2 ($^{35}Cl+^{35}Cl$ isotope+$H^+$).

EXAMPLE 85

1-Acetyl-1'-(3-((S)-(3,4-dichlorophenyl))-4-(N-(3,5-dichlorobenzoyl)-(methylamino))butyl)-5-fluoro-spiro(indoline-3,4'-piperidine)
Mass spectrum (CI): m/z=650.1 ($^{35}$Cl+$^{35}$Cl isotope+H$^+$).

EXAMPLE 86

1-Acetyl-1'-(3-((S)-(3,4-dichlorophenyl))-4-(N-(3-methylbenzoyl)-(methylamino))butyl)-5-fluoro-spiro(indoline-3,4'-piperidine)
Mass spectrum (CI): m/z=596.2 ($^{35}$Cl+$^{35}$Cl isotope+H$^+$), 598.3 ($^{37}$Cl+$^{35}$Cl isotope+H$^+$).

EXAMPLE 87

1-Acetyl-1'-(3-((S)-(3,4-dichlorophenyl))-4-(N-(3,5-dimethylbenzoyl)-(methylamino))butyl)-5-fluoro-spiro(indoline-3,4'-piperidine)
Mass spectrum (CI): m/z=610.2 ($^{35}$Cl+$^{35}$Cl isotope+H$^+$).

EXAMPLE 88

1-Acetyl-1'-(3-((S)-(3,4-dichlorophenyl))-4-(N-(3-isopropoxybenzoyl)-(methylamino))butyl)-5-fluoro-spiro(indoline-3,4'-piperidine)
Mass spectrum (CI): m/z=640.3 ($^{35}$Cl+$^{35}$Cl isotope+H$^+$), 642.3 ($^{37}$Cl+$^{35}$Cl isotope+H$^+$).

EXAMPLE 89

1-Acetyl-1'-(3-((S)-(3,4-dichlorophenyl))-4-(N-(3,5-bis(trifluoromethyl)-(methylamino))butyl)-5-fluoro-spiro(indoline-3,4'-piperidine)
Mass spectrum (CI): m/z=718.2 ($^{35}$Cl+35Cl isotope+H$^+$), 720.2 ($^{37}$Cl+$^{35}$Cl isotope+H$^+$).

EXAMPLE 90

1-Acetyl-1'-(3-((S)-(3,4-dichlorophenyl))-4-(N-(3,5-dimethylbenzoyl)-(methylamino))butyl)-5-methyl-spiro(indoline-3,4'-piperidine)
Mass spectrum (FAB): m/z=606.1 ($^{35}$Cl+$^{35}$Cl isotope+H$^+$), 608.2 ($^{37}$Cl+$^{35}$Cl isotope+H$^+$).

N-Napthoyl-methylamino derivatives (Examples 91–101) were prepared by analogy to the benzoyl derivatives, employing commercially available 1-napthoyl chlorides in place of benzoyl chlorides:

EXAMPLE 91

1-Acetyl-1'-(3-((S)-(3,4-dichlorophenyl))-4-(N-(4-fluoro-1-napthoyl)-(methylamino))butyl)-5-fluoro-spiro(indoline-3,4'-piperidine)
Mass spectrum (CI): m/z=650.3 ($^{35}$Cl+$^{35}$Cl isotope+H$^+$).

EXAMPLE 92

1-Acetyl-1'-(3-((S)-(3,4-dichlorophenyl))-4-(N-(1-napthoyl)-(methylamino))butyl)-5-fluoro-spiro(indoline-3,4'-piperidine)
Mass spectrum (CI): m/z=632.2 ($^{35}$Cl+$^{35}$Cl isotope+H$^+$), 634.2 ($^{37}$Cl+$^{35}$Cl isotope+H$^+$).

EXAMPLE 93

1'-(3-((S)-(3,4-Dichlorophenyl))-4-(N-(1-napthoyl)-(methylamino))butyl)-5-fluoro-1-methanesulfonyl-spiro(indoline-3,4'-piperidine)
Mass spectrum (CI): m/z=668.2 ($^{35}$Cl+$^{35}$Cl isotope+H$^+$).

EXAMPLE 94

1'-(3-((S)-(3,4-Dichlorophenyl))-4-(N-(4-fluoro-1-napthoyl)-(methyl-amino))butyl)-5-fluoro-1-methanesulfonyl-spiro(indoline-3,4'-piperidine)
Mass spectrum (CI): m/z=668.2 ($^{35}$Cl+$^{35}$Cl isotope+H$^+$).

EXAMPLE 95

1'-(3-((S)-(3,4-Dichlorophenyl))-4-(N-(4-fluoro-1-napthoyl)-(methyl-amino))butyl)-spiro(2,3-dihydrobenzothiophene-3,4'-piperidine)
Mass spectrum (CI): m/z=607.2 ($^{35}$Cl+$^{35}$Cl isotope+H$^+$).

EXAMPLE 96

1'-(3-((S)-(3,4-Dichlorophenyl))-4-(N-(4-fluoro-1-napthoyl)-(methyl-amino))butyl)-spiro(2,3-dihydrobenzothiophene-3,4'-piperidine) sulfone
Mass spectrum (CH): m/z=639.1 ($^{35}$Cl+$^{35}$Cl isotope+H$^+$).

EXAMPLE 97

1'-(3-((S)-(3,4-Dichlorophenyl))-4-(N-(4-fluoro-1-napthoyl)-(methyl-amino))butyl)-spiro(2,3-dihydrobenzothiophene-3,4'-piperidine)
Mass spectrum (CI): m/z=623.1 ($^{35}$Cl+$^{35}$Cl isotope+H$^+$).

EXAMPLE 98

1'-(3-((S)-(3,4-Dichlorophenyl))-4-(N-(4-fluoro-1-napthoyl)-(methyl-amino))butyl)-5-fluoro-spiro(2,3-dihydrobenzofuran-3,4'-piperidine)
Mass spectrum (CI): m/z=609.3 ($^{35}$Cl+$^{35}$Cl isotope+H$^+$), 611.3 ($^{37}$Cl+$^{35}$Cl isotope+H$^+$).

EXAMPLE 99

1'-(3-((S)-(3,4-Dichlorophenyl))-4-(N-(4-fluoro-1-napthoyl)-(methyl-amino))butyl)-spiro(2,3-dihydrobenzofuran-3,4'-piperidine)
Mass spectrum (CI): m/z=591.3 ($^{35}$Cl+$^{35}$Cl isotope+H$^+$), 593.3 ($^{37}$Cl+$^{35}$Cl isotope+H$^+$).

EXAMPLE 100

1-Acetyl-1'-(3-((S)-(3,4-dichlorophenyl))-4-(N-(4-fluoro-1-napthoyl)-(methylamino))butyl)-6-fluoro-spiro(indoline-3,4'-piperidine)
Mass spectrum (CI): m/z=650.3 ($^{35}$Cl+$^{35}$Cl isotope+H$^+$).

EXAMPLE 101

1-Acetyl-1'-(3-((S)-(3,4-dichlorophenyl))-4-(N-(4-fluoro-1-napthoyl)-(methylamino))butyl)-4-fluoro-spiro(indoline-3,4'-piperidine)
Mass spectrum (CI): m/z=650.3 ($^{35}$Cl+$^{35}$Cl isotope+H$^+$).

Benzylamine derivatives could be synthesized by reducing the benzamide of the 1-methanesulfonyl-spiro(indoline-3,4'-piperidine) derivatives described in some of the Examples. The methanesulfonyl group could be removed by heating with HBr/acetic acid/phenol and then be replaced with an acetyl group by treating with acetic anhydride/pyridine. Representative procedures and compounds are given in Examples 102 and 103 below:

EXAMPLE 102

1'-(3-((S)-(3,4-Dichlorophenyl))-4-(N-(4-fluoro-1-napthylmethyl)-(methylamino))butyl)-5-fluoro-1-methanesulfonyl-spiro(indoline-3,4'-piperidine)

1'-(3-((S)-(3,4-Dichlorophenyl))-4-(N-(4-fluoro-1-napthoyl)-(methylamino))butyl)-5-fluoro-1- methanesulfonyl-spiro(indoline-3,4'-piperidine) (96 mg) was dissolved in 1M Dibal-H in toluene (160 uL). After ½ h, saturated aqueous sodium potassium tartrate (5 mL) and EtOAc (5 mL) were added and stirred vigorously for 2 h. The organic layer was washed with $H_2O$ (5 mL), brine (5 mL), dried ($MgSO_4$), and concentrated to a crude oil, which was purified by column chromatography (silica gel 60, 0–10% acetone/$CH_2Cl_2$) to yield 55 mg (59%) of the title compound as a white foam; $^1H$ NMR (400 MHz, $CDCl_3$) δ 8.09 (d, 1H, J=8.5 Hz), 7.91 (d, 1H, J=8.5 Hz), 7.53 (t, 1H, J=7.5 Hz), 7.38 (t, 1H, J=7.5 Hz), 7.33 (dd, 1H, J=4.3, 8,8 Hz), 7.22 (dd, 1H, J=5.8, 7.8 Hz), 7.18 (d, 1H, J=8.5Hz), 7.09 (d, J=2.0 Hz), 7.04 (dd, 1h, J=7.5, 10. 0 Hz), 6.92 (dt, 1H, J=2.5, 8.5 Hz), 6.88 (d, 1H), 6.77 (dd, 1H, J=1.8, 8.3 Hz), 3.85 (dd, 1H, J=8.0 Hz), 3.76 (s, 2H), 3.75 (dd, 1H, J=8.0 Hz), 2.88 (s, 3H), 2.80–2.66 (m, 3H), 2.62 (dd, 1H, J=8.8, 12.3 Hz), 2.51 (dd, 1H, J=6.5, 12.5 Hz), 2.28 (s, 3H), 2.18–2.06 (m, 2H), 1.88–1.80 (m, 4H), 1.65 (d, 2H, J=10.5 Hz) ppm;
Mass spectrum (CI): m/z=672.4 (35Cl+$^{35}$Cl isotope+H$^+$).

EXAMPLE 103

1'-(3-((S)-(3,4-Dichlorophenyl))-4-(N-(4-fluoro-1-napthylmethyl)-(methylamino))butyl)-5-fluoro-spiro (indoline-3,4'-piperidine)

1'-(3-((S)-(3,4-dichlorophenyl))-4-(N-(4-fluoro-1-napthylmethyl)-(methylamino))butyl)-5-fluoro-1-methanesulfonyl-spiro(indoline-3,4'-piperidine) (45.6 mg) and phenol (19 mg) in 30% HBr/HOAc (270 μL) were heated to 70° C. for 6 h in a sealed vessel. The reaction was concentrated and partitioned between $CH_2Cl_2$ (1 ml) and 1N NaOH (2 mL). The organic layer was eluted through a 3×3 cm silica gel plug with 0–100% acetone/$CH_2Cl_2$ to yield 30 mg (74%) of the title compound as a yellow oil. $^1H$ NMR (400 MHz, $CDCl_3$) δ 8.09 (d, 1H, J=8.0 Hz), 7.93 (d, 1H, J=8.5 Hz), 7.52 (t, 1H, J=7.5 Hz), 7.43 (t, 1H, J=7.3 Hz), 7.22 (dd, 1H, J=5.5, 7.5 Hz), 7.17 (d, 1H, J=8.5 Hz), 7.06 (dd, 1H, J=8.8, 10.3 Hz), 7.02 (d, 1H, J=1.5 Hz), 6.87 (d, 1H, J=3.5 Hz) 6.78 (dd, 1H, J=2.3, 8.3 Hz), 6.75 (dd, 1H, J=2.3, 7.8 Hz), 6.56 (dd, 1H, J=4.0, 8.5 Hz) ppm; Mass spectrum (CI): m/z=594.3 ($^{35}$Cl+$^{35}$Cl isotope+H$^+$), 596.3 ($^{37}$Cl+$^{35}$Cl isotope+H$^+$).

EXAMPLE 104

1-Acetyl-1'-(3-((S)-(3,4-dichlorophenyl))-4-(N-(4-fluoro-1-napthylmethyl)-(methylamino))butyl)-5-fluoro-spiro(indoline-3,4'-piperidine)

1'-(3-((S)-(3,4-Dichlorophenyl))-4-(N-(4-fluoro-1-napthylmethyl)-(methylamino))butyl)-5-fluoro-spiro (indoline-3,4'-piperidine) (10 mg) in $CH_2Cl_2$ (100 μL) was treated with one drop acetic anhydride and 1 drop pyridine. After 30 min, the reaction was eluted through a 1×2 cm silica gel column using 0–100% acetone/$CH_2Cl_2$ plus 1% $NH_4OH$ to yield 10 mg (93%) of the title compound as a clear film. $^1H$ NMR ($CDCl_3$) δ 8.17 (dd, 1H, J=4.3, 8.8 Hz), 8.09 (d, 1H, J=8.5 Hz), 7.91 (d, 1H, J=8.0 Hz), 7.52 (t, 1H, 7.3 Hz), 7.38 (t, 1H, J=7.3 Hz), 7.22 (dd 1H, 6.8, 7.0 Hz), 7.18 (d, 1H, J=8.8 Hz), 7.07 (d, 1H, J=2.0 Hz), 7.04 (dd, 1H, J=8.0, 10.5 Hz), 6.91 (d, 1H, J=2.0, 9.0 Hz), 6.86 (dd, 1H, J=2.0, 7.5 Hz), 6.76 (dd, 1H, J=2.0, 8.5 Hz), 3.96, 3.81 (rotamer singlets, 3H), 3.85 (d, 1H, J=13 Hz), 3.75 (d, 1H, J=13 Hz), 2.84 (m, 2H), 2.74 (m, 1H), 2.61 (dd, 1H, J=8.5, 13Hz), 2.51 (dd, 1H, J=7.0, 13 Hz), 2.43, 2.35 (rotamer singlets, 3H), 2.24 (s, 3H), 2.3–2.2 (m, 3H), 2.0–1.85 (m, 4H), 1.65 (m, 2H), 1.50 (m, 1H) ppm;
Mass spectrum (CI): m/z=636.4 ($^{35}$Cl+$^{35}$Cl isotope+H$^+$), 638.4 ($^{37}$Cl+$^{35}$Cl isotope+H$^+$).

EXAMPLE 105

1'-(5-Fluoroindolyl-3-(2-ethanoyl))-1-methanesulfonyl-spiro(indoline-3,4'-piperidine)

To a solution of 1-methanesulfonyl-spiro(indoline-3,4'-piperidine) hydrochloride (373 mg, 1.23 mmol), 5-fluoroindole-3-acetic acid (500 mg, 2.59 mmol), in DMF (15 mL) at room temp. was added N-methyl morpholine (261 mg, 2.59 mmol), hyroxybenzotriazole (381 mg,, 2.82 mmol) and 1-(3-dimethylaminopropyl)-3-ethylcarbodiimide (473 mg, 2.47 mmol). The reaction was stirred 48 h, diluted with $H_2O$ (250 mL), extracted with EtOAc (3×100 mL), washed with $H_2O$ (2×150 mL), brine (150 mL), dried ($Na_2SO_4$), concentrated in vacuo and purified by column chromatography (SG 60 silica, 5% MeOV/$CH_2Cl_2$) to afford 486 mg (89%) of the title compound as a colorless oil. $^1H$ NMIR (500 MHz, $CDCl_3$) δ 8.39 (br s, 1H), 7.37 (d, 1H, J=8.2 Hz), 7.34 (dd, 1H, J=9.6, 2.3 Hz), 7.29 (dd, 1H, J=8.9, 4.4 Hz), 7.23 (dt, 1H, J=7.8, 1.2 Hz), 7.14 (d, 1H, J=2.3 Hz), 7.03 (t, 1H, J=7.3 Hz), 6.98 (dt, 1H, J=8.9, 2.5 Hz), 6.87 (d, 1H, J=7.5 Hz), 4.73 (d, 1H, J=13.7 Hz), 3.96 (d, 1H, J=14.0 Hz), 3.82–3.92 (m, 2H), 3.72–3.78 (m, 1H), 3.13 (t, 1H, J=13.4 Hz), 2.91 (s, 3H), 2.73 (t, 1H, J=13.5 Hz), 1.83 (dt, 1H, J=13.5, 4.4 Hz), 1.65–1.75 (m, 2H), 1.52–1.58 (m, 1H), 1.40 (dt, 1H, J=13.0, 4.3 Hz) ppm; Mass spec (CI) m/z 441 (M+H).

EXAMPLE 106

1'-(2-(3-(5-Fluoroindolyl))ethyl))-1-methanesulfonyl-spiro(indoline-3,4'-3piperidine)

To a solution of 1'-(5-fiuoroindolyl-3-(2-ethanoyl))-1-methanesulfonyl-spiro(indoline-3,4'-piperidine) (100 mg, .226 mmol) in $CH_2Cl_2$ (8 mL) at −70° C. was added Dibal-H (1M in THF, 0.91 mL, .906 mmol). After 2.5 h the mixture was quenched by addition of 1M NaOH (20 mL), diluted with $CH_2Cl_2$ and stirred vigorously for 15 min. The mixture was extracted with $CH_2C_{12}$ (3×50 mL), washed with brine (50 mL), dried ($Na_2SO_4$), concentrated in vacuo and purified by column chromatography (SG60 silica, 5% MeOH/$CH_2Cl_2$) to afford 66 mg (68%) of the title compound as a colorless solid.
$^1H$ NMR (500 MHz, $CDCl_3$) δ 8.20 (br s, 1H), 7.42 (d, 1H, J=8.0 Hz), 7.20–7.30 (m, 4H), 7.06–7.14 (m, 2H), 6.93–6.97 (m, 1H), 3.84 (s, 2H), 3.08 (d, 2H, J=11.7 Hz), 2.94–3.00 (m, 2H), 2.93 (s, 3H), 2.71–2.77 (m, 2H), 2.19 (t, 2H, J=12.3 Hz), 2.07 (dt, 2H, J=13.2, 3.9 Hz), 1.75 (d, 2H, J=13.0 Hz) ppm;
Mass spec (CI) m/z 428 (M+H).

EXAMPLE 107

4-Fluoro-3,5-dimethylbenzoic acid
Step 1) 1-Bromo-4-fluoro-3,5-dimethylbenzene
To a mixture of 4-Bromo-2,6-dimethylaniline (8.3 g, 42 mmol) at 5° C. and $H_2O$ (50 mL) was added conc $H_2SO_4$ (6.25 mL). $NaNO_2$ (4.1 g) was added in portions until an excess was indicated by starch iodide paper. Water (30 mL) was added to make the mixture homogeneous. After transferring to a plastic container, $HBF_4$ (50%, 13.7 g) was added dropwise with stirring. The resultant white precipitate was collected by vacuum filtration, washed with $H_2O$ (30 mL), MeOH (30 mL), and $Et_2O$ (60 mL), and dried over $P_2O_5$ under vacuum for 16 h. The solid was then heated in a glass flask with an open flame until all the solid had decomposed. The remaining liquid was diluted with $Et_2O$ (50 mL) and 0.5 M NaOH (30 mL). The organic layer was separated, washed with 0.5 M NaOH (25 mL), $H_2O$ (25 mL), brine (25 mL), dried ($MgSO_4$), and concentrated in vacuo yielding 6.06 g (72%) of 1-bromo-4-fluoro-3,5-dimethylbenzene as a pale yellow liquid.

$^1H$ NMR (500 MHZ, $CDCl_3$) δ 7.17 (d, 2H, J=6.2 Hz), 2.21 (s, 6H) ppm.

Step B) 4-Fluoro-3,5-dimethylbenzoic acid

To a mixture of magnesium shavings (120 mg, 4.92 mmol) in THF (2 mL) was added a crystal of iodine followed by slow addition of a solution of the bromide (1.0 g, 4.92 mmol) in THF (3 mL). The reaction mixture was heated to reflux for 1 h followed by cooling to room temp. and addition of $CO_2(s)$ (excess), stirred 1 h and quenched by addition of 1M HCl (10 mL). The mixture was extracted with $Et_2O$ (3×25 mL), washed with brine (25 mL), dried ($MgSO_4$), and concentrated in vacuo to afford 0.82 g (99%) of the title compound as a pale yellow solid. $^1H$ NMR (500 MHz, $CDCl_3$) δ 7.81 (d, 2H, J=6.7 Hz), 2.36 (s, 6H) ppm; Mass spec (CI) m/z 168 (M–H).

The compounds of Examples 108–120 were prepared as per Example 3 Step B utilizing the previously prepared amines and the appropriate benzoic or naphthoic acids:

EXAMPLE 108

1'-(3-((S)-(3,4-Dichlorophenyl))-4-(N-(3-chloro-4-fluorobenzoyl)-(methyl-amino))butyl)-1-methanesulfontl-spiro(indoline-3,4'-piperidine)

Mass spec (CI) 656 ($^{37}Cl+^{35}Cl$ isotope+$H^+$), 654 ($^{35}Cl+^{35}Cl$ isotope+$H^+$).

EXAMPLE 109

1'-(3-((S)-(3,4-Dichlorophenyl))-4-(N-(3-chloro-4-fluorobenzoyl)-(methylamino))butyl)-5-fluoro-1-methanesulfonyl-spiro(indoline-3,4'-piperidine)

Mass spec (CI) 674 ($^{37}Cl+^{35}Cl$ isotope+$H^+$), 672 ($^{35}Cl+^{35}Cl$ isotope+$H^+$).

EXAMPLE 110

1'-(3-((S)-(3,4-Dichlorophenyl))-4-(N-(4-fluorobenzoyl)-(methyl-amino))butyl)-1-methanesulfonyl-spiro(indoline-3,4'-piperidine)

Mass spec (CI) 620 ($^{37}Cl+^{35}Cl$ isotope+$H^+$), 618 ($^{35}Cl+^{35}Cl$ isotope+$H^+$).

EXAMPLE 111

1'-(3-((S)-(3,4-Dichlorophenyl))-4-(N-(4-fluorobenzoyl)-(methyl-amino))butyl)-5-fluoro-1-acetyl-spiro(indoline-3,4'-piperidine)

Mass spec (CI) 618 ($^{37}Cl+^{35}Cl$ isotope+$H^+$), 616 ($^{35}Cl+^{35}Cl$ isotope+$H^+$).

EXAMPLE 112

1'-(3-((S)-(3,4-Dichlorophenyl))-4-(N-(3-chloro-4-fluorobenzoyl)-(methylamino))butyl)-5-fluoro-1-acetyl-spiro(indoline-3,4'-piperidine)

Mass spec (CI) 636 ($^{37}Cl+^{35}Cl$ isotope+$H^+$), 634 ($^{35}Cl+^{35}Cl$ isotope+$H^+$).

EXAMPLE 113

1'-(3-((S)-(3,4-Dichlorophenyl))-4-(N-(4-fluoro-3,5-dimethylbenzoyl)-(methylamino))butyl)-5-fluoro-1-acetyl-spiro(indoline-3,4'-piperidine)

Mass spec (CI) 630 ($^{37}Cl+^{35}Cl$ isotope+$H^+$), 628 ($^{35}Cl+^{35}Cl$ isotope+$H^+$).

EXAMPLE 114

1'-(3-((S)-(3,4-Dichlorophenyl))-4-(N-(4-fluoro-3,5-dimethylbenzoyl)-(methylamino))butyl)-1-methanesulfonyl-spiro(indoline-3,4'-piperidine)

Mass spec (CI) 648 ($^{37}Cl+^{35}Cl$ isotope+$H^+$), 646 ($^{35}Cl+^{35}Cl$ isotope+$H^+$).

EXAMPLE 115

1'-(3-((S)-(3,4-Dichlorophenyl))-4-(N-(4-fluoro-3-trifluoromethylbenzoyl)-(methylamino))butyl)-1-methanesulfonyl-spiro(indoline-3,4'-piperidine)

Mass spec (CI) 688 ($^{37}Cl+^{35}Cl$ isotope+$H^+$), 686 ($^{35}Cl+35Cl$ isotope+$H^+$)

EXAMPLE 116

1'-(3-((S)-(3,4-Dichlorophenyl))-4-(N-(4-fluoro-3,5-dimethylbenzoyl)-(methylamino))butyl)-1-acetyl-spiro(indoline-3,4'-piperidine)

Mass spec (CI) 612 ($^{37}Cl+^{35}Cl$ isotope+$H^+$), 610 ($^{35}Cl+35Cl$ isotope+$H^+$).

EXAMPLE 117

1'-(3-((S)-(3,4-Dichlorophenyl))-4-(N-(4-fluoro-3-trifluoromethylbenzoyl)-(methylamino))butyl)-1-acetyl-spiro(indoline-3,4'-piperidine)

Mass spec (CI) 652 ($^{37}Cl+^{35}Cl$ isotope+$H^+$), 650 ($^{35}Cl+^{35}Cl$ isotope+$H^+$).

EXAMPLE 118

1'-(3-((S)-(3,4-Dichlorophenyl))-4-(N-(4-fluoro-1-naphthoyl)-(methyl-amino))butyl)-1-acetyl-spiro(indoline-3,4'-piperidine)

Mass spec (CI) 634 ($^{37}Cl+^{35}Cl$ isotope+$H^+$), 632 ($^{35}Cl+^{35}Cl$ isotope+$H^+$).

EXAMPLE 119

1'-(3-((S)-(3,4-Dichlorophenyl))-4-(N-(4-fluoro-1-naphthoyl)-(methyl-amino))butyl)-1-methanesulfonyl-spiro(indoline-3,4'-piperidine)

Mass spec (CI) 670 ($^{37}Cl+^{35}Cl$ isotope+$H^+$), 668 ($^{35}Cl+^{35}Cl$ isotope+$H^+$).

EXAMPLE 120

1'-(3-((S)-(3,4-Dichlorophenyl))-4-(N-(1-naphthoyl)-(methylamino))butyl)-1-acetyl-spiro(indoline-3,4'-piperidine)

Mass spec (CI) 616 ($^{37}Cl+^{35}Cl$ isotope+$H^+$), 614 ($^{35}Cl+^{35}Cl$ isotope+$H^+$)

EXAMPLE 121

1'-(3-((S)-(3,4-Dichlorophenyl))-4-(N-(3,5-dimethylbenzoyl)-(methylamino))-4-phenyl-butyl)-1-methanesulfonyl-spiro(indoline-3,4'-piperidine)

The title compound was prepared in 6 steps from 2-(S)-(3,4-dichlorophenyl)-4-pentenoic acid using procedures identical to those in Example 10, substituting phenyllithium for methyllithium in Example 10, Step 2. Mass Spectrum (FAB): m/z 704 (M+H, $^{37}Cl+^{35}Cl$ isotope, 100%), 706 (M+H, $^{37}Cl+^{37}Cl$ isotope, 80%).

EXAMPLE 122

1'-(4-(N-(3,5-Dimethylbenzoyl)-(methylamino))-4-(phenyl)butyl)-1-acetyl-spiro(indoline-3,4'-piperidine)

The title compound was prepared in 6 steps from 4-pentenoic acid using procedures identical to those in Example 10, substituting phenyllithium for methyllithium in Example 10, Step 2.
Mass Spectrum (FAB): m/z 524 (M+H, $^{37}$Cl+$^{35}$Cl isotope, 100%), 526 (M+H, $^{37}$Cl+$^{37}$Cl isotope, 50%).

EXAMPLE 123

1'-(3-((S)-(3,4-Dichlorophenyl))-4-(1-(2-phenylimidazolo))butyl)-1-methanesulfonvl-spiro (indoline-3,4'-piperidine)

Step 1) 1-(2-Phenylimidazolo)-2-((S)-(3,4-dichlorophenyl))-4-pentene

To a solution of 0.178 g (0.77 mmole) of 2-((S)-(3,4-dichlorophenyl))-4-penten-1-ol (prepared in Example 136, Step A) and 0.099 mL (0.85 mmole) of 2,6-lutidine in 1.5 mL of methylene chloride at −53 deg C. under nitrogen was added 0.136 mL (0.81 mmole) of trifluoromethanesulfonic anhydride. The solution was stirred between −30 deg C. and −40 deg C. for 15 min at which point 0.333 g (2.31 mmole) of 2-phenylimidazole was added. The temperature was allowed to warm to −20 deg C. briefly, and the mixture was then cooled to −60 deg C., stirred at that temperature for 1 hr, stirred at −20 deg C. for 2 hr, and then held at 4 deg C. for 16 hr. After stirring at room temperature for 8 hr, the mixture was treated with 10 mL of saturated sodium carbonate solution and 10 mL of ethyl acetate and the layers were separated. The aqueous phase was extracted with 2×15 mL of ethyl acetate and the combined aqueous layers were dried over sodium sulfate, filtered and concentrated in vacuo. The residue was partly purified by flash chromatography on 36 g of silica eluting with 500 mL of 3:100 methanol:methylene chloride then 300 mL of 5:100:0.1 methanol:methylene chloride: ammonia water. The partly purified product fractions were flash chromatographed on 66 g of silica eluting with 1.2 L of 83:17 methylene chloride-:ethyl acetate to give 85 mg (31%) of an oil.
$^1$H-NMR (400 MHz, CDCl$_3$) δ 2.26 (app. t, 2H), 2.85 (pentet, 1H), 4.08 (dd, 1H), 4.27 (dd, 1H), 4.9–5.0 (m, 2H), 5.45–5.55 (m, 1H), 6.59 (dd, 1H), 6.79 (s, 1H), 6.85 (d, 1H), 7.18 (d, 1H), 7.23–7.30 (m, 2H), 7.35–7.4 (m, 3H). Mass Spectrum (FAB): m/z 359 (M+H, 65%), 357 (M+H, 100%), 145 (7%).

Step 2) 1'-(2-((S)-(3,4-1Dichlorophenyl))-1-(1-(2-phenylimidazolo))-4-butyl)-1-methanesulfonyl-spiro (indoline-3,4'-piperidine)

The title compound was prepared by employing the chemistry outlined in Examples 1 and 2, using 1-(2-phenylimidazolo)-2-((S)-(3,4-dichlorophenyl))-3-butene in place of 3-(S)-(3,4-dichlorophenyl)-4-methylamino-1-pentene, and beginning with the osmium tetroxide step.
$^1$H-NMR (400 MHz, CDCl$_3$) δ 1.55–2 (m, 8H), 2.08 (t, J=7.3, 2H), 2.63 (br d, J=11, 1H), 2.70 (br d, J=8.3, 1H), 2.86 (s, 3H), 2.9–3.0 (m, 1H), 3.71 (s, 2H), 4.13 (dd, J=14, 8.8, 1H), 4.25 (dd, J=14, 6.2, 1H), 6.66 (dd, J=6.2, 2.1, 1H), 6.79 (d, J=1.3, 1H), 6.94 (d, J=2.1, 1H), 7.03 (d, J=1.3, 1H), 7.05 (d, J=6.4, 1H), 7.15 (d, J=6.5, 1H), 7.15–7.25 (m, 2H), 7.35–7.45 (m, 6H)
Mass Spectrum (FAB): m/z 609 (M+H, 25%), 279 (100%), 267 (50%), 212 (30%), 187 (35%).

EXAMPLE 124

1'-(3-((S)-(3,4-Dichlorophenyl))-4-((N-(R or S)-(3,5-dimethylbenzoyl)-(methylamino))pentyl)-1-acetyl-spiro(indoline-3,4'-piperidine)

The title compound was prepared in 6 steps from (2S)-(3,4-dichlorophenyl)-4-pentenoic acid using procedures identical to those in Example 10, substituting 1-acetyl-spiro (indoline-3,4'-piperidine) for 1-methanesulfonyl-spiro (indoline-3,4'-piperidine) in Example 10, Step 6.
Mass Spectrum (FAB): m/z 606 (M+H, $^{37}$Cl+$^{35}$Cl isotope, 100%), 608 (M+H, $^{37}$Cl+$^{37}$Cl isotope, 80%).

EXAMPLE 125

1'-(3-((S)-(3,4-Dichlorophenyl))-4-((N-(R or S)-(4-fluoro-1-napthyl)-(methylamino))pentyl)-1-acetyl-spiro(indoline-3,4'-piperidine)

The title compound was prepared in 6 steps from (2S)-(3,4-dichlorophenyl)-4-pentenoic acid using procedures identical to those in Example 10, substituting 1-acetyl-spiro (indoline-3,4'-piperidine) for 1-methanesulfonyl-spiro (indoline-3,4'-piperidine) in Example 10, Step 6, and substituting 4-fluoro-1-napthoyl chloride for benzoyl chloride.
Mass Spectrum (1FAB): m/z 646 (M+H, $^{37}$Cl+$^{35}$Cl isotope, 30%), 204 (100%).

The following compounds described in Examples 126–129 were prepared by the method described in Scheme II and in Example 10, except that in step 2 ethylmagnesium chloride or propylmagnesium chloride was used at room temperature instead of methyllithium at −78° C.

EXAMPLE 126

1'-(3-((S)-(3,4-Dichlorophenyl))-4-(R or S)-(N-(3,5-dimethylbenzoyl)-(methylamino))hexyl)-1-acetyl-spiro(indoline-3,4'-piperidine)
$^1$H-NMR (400 MHz, CDCl$_3$) δ 0.97 (t, 3H), 2.20 (s, 6H), 2.21 (s, 3H), 2.42–2.46 (s+m, 4H), 6.23 (s, 2H), 6.89 (s, 1H), 7.04 (t, 1H), 7.15–7.21 (m, 3H), 7.39 (t, 2H), 8.18 (d, 1H). Mass Spectrum (FAB) m/z 620 (m$^+$).

EXAMPLE 127

1'-(3-((S)-(3,4-Dichlorophenyl))-4-(R or S)-(N-(3,5-dimethylbenzoyl)-(methylamino))hexyl)-1-acetyl-5-fluoro-spiro(indoline-3,4'-piperidine)
$^1$H-NMR (400 MHz, CDCl$_3$) δ 0.96 (t, 3H), 2.20 (s, 9H), 2.45 (s, 3H), 3.81 (s, 2H), 6.24 (s, 2H), 6.84–6.89 (m, 3H), 7.19 (dd, 1H), 7.39 (t, 2H), 8.13 (dd, 1H). Mass Spectrum (FAB) m/z 638 (m$^+$).

EXAMPLE 128

1'-(3-(S)-(3,4-Dichlorophenyl)-4-(RE or S)-(N-(3,5-dimethylbenzoyl)-(methylamino))heptyl)-1-acetyl-spiro(indoline-3,4'-piperidine)
$^1$H-NMR (400 MHz, CDCl$_3$) δ 0.96 (t, 3H), 2.20 (s, 6H), 2.21 (s, 3H), 2.41–2.45 (s+m, 4H), 3.78 (s, 2H), 6.22 (s, 2H). 6.89 (s, 1H), 7.03 (t, 1), 7.15–7.21 (m, 3H), 7.39 (t, 2H), 8.18 (d, 1H).
Mass Spectrum (FAB): m/z 634 (m$^+$).

EXAMPLE 129

1'-(3-(S)-(3,4-Dichlorophenyl)-4-(R or S)-(N-(3,5-dimethylbenzoyl)-(methylamino))heptyl)-1-acetyl-5-fluoro-spiro(indoline-3,4'-piperidine)
$^1$H-NMR (400 MHz, CDCl$_3$) δ 0.97 (t, 3H), 2.20 (s, 9H), 2.44 (s, 3H), 3.81 (s, 2H), 6.22 (s, 2H), 6.83–6.88 (m, 3H), 7.18 (dd, 1H), 7.38 (t, 2H), 8.13 (dd, 1H). Mass Spectrum (FAB) m/z 652 (m$^+$).

EXAMPLE 130

1'-(3-((S)-(3,4-Dichlorophenyl))-4-(R or S)-hydroxy-5-(3,5-dimethylphenyl)pentyl)-1-methanesulfonyl-spiro(indoline-3,4'-piperidine)

To a THF (3 mL) solution of 3,5-dimethylbenzyl-magnesium chloride (generated from 290 mg (1.9 mmol) of 3,5-dimethylbenzyl chloride and 53 mg (2.2 mmol) of magnesium in THF) was added slowly 1'-(3-((S)-(3,4-dichlorophenyl))-3-(N-methoxy-N-methylaminocarbonyl) propyl)-1-methanesulfonyl-spiro(indoline-3,4-piperidine) (100 mg, 0.19 mmol, prepared by reacting the product obtained in Example 10, Step 1 under the oxidative cleavage conditions given in Example 1 followed by the coupling procedure given in Example 2) in 1 mL of THF. The reaction mixture was stirred at 60° C. for 40 min and poured into 20 mL of 1N HCl. The solution was extracted with 3×10 mL of EtOAc. The organic extracts were combined, dried, and concentrated. The product was purified by preparative TLC (30% EtOAc in $CH_2Cl_2$) to afford 20 mg of ketone. To a MeOH (3 mL) solution of ketone (19.4 mg) was added sodium borohydride (7 mg). The mixture was stirred at 55° C. for 1 h and concentrated. The residue was purified by preparative TLC (4% MeOH in $CH_2Cl_2$) to give 15 mg of the higher $R_f$ isomer (Isomer A) and 4 mg of a lower $R_f$ isomer (Isomer B).

$^1$H-NMR (400 MHz, $CDCl_3$) , Isomer A: d 1.71 (d, 2H), 1.92–2.12 (m, 6H), 2.23–2.29 (s+m, 9H), 2.50–2.60 (m, 2H), 2.72–2.76 (m, 1H), 2.88 (s, 3H). 2.95 (d, 2H), 3.76 (s, 2H), 4.00–4.06 (n, 1H), 6.69 (s, 2H), 6.83 (s, 1H), 7.05 (d, 1H), 7.19–7.24 (m, 3H), 7.37 (t, 2H), 7.44 (s, 1H). Mass spectrum (FAB) Isomer A, m/z 601 (m$^+$), 603 (m$^+$+2).$^1$H-NMR (400 MHz, $CDCl_3$) , Isomer B: d 1.69 (d, 2H), 1.74–1.79 (m, 1H), 1.83–1.90 (m, 1H), 1.93–2.05 (m, 2H), 2.07–2.20 (m, 2H), 2.24–2.36 (s+m, 8H), 2.42–2.47 (m, 1H), 2.55–2.58 (dd, 1H), 2.66–2.72 (d+dd, 2H), 2.87 (s, 3H), 2.86–3.00 (m, 2H), 3.76 (s, 2H), 3.91–3.95 (in, 1H), 6.72 (s, 2H), 6.82 (s, 2H), 7.13–7.19 (m, 2H), 7.18–7.21 (m, 2H), 7.36 (t, 2H). Mass spectrum (FAB) Isomer B, m/z 601 (m$^+$) 603 (m$^+$+2).

EXAMPLE 131

1'-(3-(R)-(3,4-Dichlorophenyl)-5-(N-3,5-dimethylphenyl-methylamino)-5-oxo-pentyl)-1-methanesulfonyl-spiro(indoline-3,4'-piperidine)

Step 1) Diazomethyl-(2-(S)-(3,4-dichlorophenyl)-pent-4-en-yl)-ketone.

To a solution of 2-(S)-(3,4-dichlorophenyl)-pent-4-enoic acid (5.04 g, 20.6 mmol) in 60 mL of dichloromethane was added oxalyl chloride 2.15 mL (24.6mmol) and dimethylformamide (0.1 mL) upon cooling in an ice-water bath. The cooling bath was then removed and the reaction mixture was stirred at rt overnight. The solvent was removed under reduced pressure. The resulting material was diluted in ethyl acetate and concentrated in vacuo in order to remove residual HCl. The residual crude acid chloride was dissolved in 70 mL of ether and was slowly added to a 100 mL ether solution of diazomethane (77 mmol). After stirring for 2 hr at rt, the solvent was removed under vacuum. The resulting yellow oil was chromatographed on silica gel column eluting with a gradient of hexane:ethyl acetate=20:1 to 3:1 to give 4.66g (84%) of diazomethyl-(2-(S)-(3,4-dichlorophenyl)-pent-4-en-yl)-ketone.

$^1$H-NMR (CDCl$_3$ 400 MHz): δ 2.44(app. quint. 1H), 2.82 (app. qunit. 1H), 3.43(br s. 1H), 4.98 & 5.02 (d of AB quart., 2H), 5.16 (br s, 1H), 5.63(m, 1H), 7.09 (dd, J=2.2 Hz, 8.3 Hz, 1H), 7.34(d, J=2.2 Hz, 1H), 7.38 (d J=8.3 Hz).

Step 2) 3-(R)-(3,4-Dichlorophenyl)-hex-4-en-oic acid

To a solution of the above diazoketone 4.56g (17.0 mmol) in 340 mL of tetrahydrofuran was added 170 mL aquous solution of silver nitrate 3.02 g (17.8 mmol). After stirring at rt overnight, tetrahydrofuran was removed under reduced pressure. The remaining aqueous layer was extracted with two 100 mL portions of dichloromethane. The combined organic phases were washed with brine, dried over anhydrous magnesium sulfate, filtered, and concentrated. The resulting material was purified by silica gel column chromatography. Elution with dichloromethane: methanol=10:1 gave 3.94g (90%) of 3-(R)-(3,4-dichlorophenyl)-hex-4-en-oic acid.

Step 3) (N-(3,5-Dimethylphenyl)-N-methyl)-((3-(R)-(3,4-dichlorophenyl)-hex-5-en-yl)-amide The carboxylic acid from Step 2 (300 mg, 1.16 mmol) was dissolved in 5 mL of dichloromethane. To it was added 0.131 mL (1.50 mmol) of oxalyl chloride followed by the addition of a drop of dimethylformamide upon cooling in an ice-water bath. The cooling bath was then removed and the reaction mixture was stirred at rt for 2hr. The solvent and residual HCl was removed as described above. The resulting crude acid chloride was then dissolved in 5 mL of dichloromethane. To it was added N-methyl-3,5-dimethylaniline 313mg (3.32mmol) (Prepared from 3,5-Dimethylaniline following the procedure of Barluenga J., Bayon A. M., and Asensio G. *J. Chem. Soc. Chem. Comm.* 1984 1334) followed by the addition of triethylamine 0.5mL (3.6mmol) upon cooling in an ice-water bath. Then the cooling bath was removed and the reaction mixture was stirred at rt overnight. The solvent was removed under reduced pressure. The residual solid material was dissolved in 15 mL of ethyl acetate and 5 mL of water. The organic phase was separated and aqueous phase was extracted with two 7 mL portions of ethyl acetate. The combined organic phases were washed with brine, dried over anhydrous magnesium sulfate, filtered, and concentrated. This crude material was chromatographed on silica gel eluting with a gradient of 10:1 to 3:1 hexane-ethyl acetate to give 386 mg of (N-(3,5 -dimethylphenyl)-N-methyl)-((3-(R)-(3,4-dichlorophenyl)-hex-5-en-yl)-amide (88%).

$^1$H-NMR(CDCl$_3$ 400 MHz): δ 2.15–2.35 (m., 4H), 2.29 (s, 6H), 3.09 (s, 3H), 3.26 (quint, J=7.2 Hz, 1H), 4.88 (d, J=7.6 Hz, 1H), 4.92 (s, 1H), 5.5 (m, 1H), 6.45 (s, 2H), 6.91 (dd, J=2 Hz, 7 Hz, 1H), 6.93 (s, 1H), 7.30 (d, J=8.3 Hz, 1H).

Step 4) 3-(R)-(3,4-Dichlorophenyl)-5-(N-(3,5-dimethylphenyl)-methylamino)-5-oxo-pentanal To 386mg (1.03mmol) of the product from the previous step was oxidized by osmium tetroxiide to corresponding diol as described in Example 1 to give 413mg of crude diol. 381mg of this material was then dissolved in 10 mL of benzene. To it was added lead tetraacetate 452 mg (1.02mmol). After stirring for 1 hr at rt, 5 mL of water was added to quench the reaction. The reaction mixture was extracted with two 10 mL portions of ethyl acetate. The combined organic phases were dried over anhydrous magnesium sulfate, filtered, and concentrated. The crude material was chromatographed on silica gel eluting with hexane:ethyl acetate=2:1 to give 329mg of 3-(R)-(3,4-dichlorophenyl)-5-(N-(3,5-dimethylphenyl)-methylamino)-5-oxo-pentanal (94% over two steps).

Step 5) 1'-(3-(R)-(3,4-Dichlorophenyl)-5-(N-3,5-dimethylphenyl-methylamino)-5-oxo-pentyl)-1-methanesulfonyl-spiro(indoline-3,4'-piperidine)

Following the procedure described in Example 2, 107 mg (0.287mmol) of this aldehyde was treated with 1-methanesulfonyl-spiro(indoline-3,4'-piperidine) hydrochloride to give 103 mg (58% yield) of the title compound.
$^1$H-NMR (CDCl$_3$ 400 MHz): δ 2.23 (s, 6H), 2.86 (s, 3H), 3.09 (s, 3H), 3.72 (s, 2H), 6.49 (s, 2H), 6.9–7.2 (s, 8H). MS(CI): 628 (M$^+$+1: $^{35}$C×2), 630 (M$^+$+1: $^{35}$Cl & $^{37}$Cl)

EXAMPLE 132

1'-(3-(R)-(3,4-Dichlorophenyl))-5-(3,5-dimethylphenyl)-5-oxo-pentyl)-1-methanesulfonyl-spiro(indoline-3,4'-piperidine)

Step 1) (N-Methoxy-N-methyl)-(3-(R)-(3,4-dichlorophenyl)-4-hexenyl)-amide

To a solution of 3-(R)-(3,4-dichlorophenyl)-5-hexenoic acid (Example 132, Step 1) 744mg (2.87mmol) was added 1-hydroxybenzotriazole hydrate 465mg (3.44mmol), and 1-(3-dimethylaminopropyl)-3-ethylcarbodiimide hydrochloroide 660mg (3.44mmol) with cooling in an ice-water bath. The cooling bath was then removed. After stirring at rt for 1 hr, to it was added 5mL dichiloromethane suspension of N,O-dimethylhydroxyl amine hydrochloride 840 mg (8.61 mmol) and triethylamine 1.2 mL (8.6 mmol). After stirring overnight, the solvent was removed under vacuum, diluted with ethyl acetate and water. The organic phase was separated. Aqueous phase was extracted twice with ethyl acetate. Combined organic phases were washed with brine, dried over anhydrous magnesium sulfate, filtered, concentrated, chromatographed on silica gel eluting on a gradient of hexane:ethyl acetate=5:1 to 2:1 to give 762 mg (88%) of (N-methoxy-N-methyl)-(3-(R)-(3,4,-dichlorophenyl)-4--hexenyl)-amide.

$^1$H-NMR (CDCl$_3$ 400 MHz): δ 2.34(m, 1H), 2.69 (App. d, 2H), 3.09 (s, 3H), 3.23 (quint. J=7.3 Hz, 1H), 3.56 (s, 3H), 4.95 (s, 1H), 4.98 (app. d, 1H), 5.6 (m, 1H), 7.0 (dd, J=2.1 Hz, 8.4 Hz, 1H), 7.28 (d, J=2.1 Hz, 1H), 7.32 (d, J=8.3 Hz, 1H).

Step 2) 3-(R)-(3,4-Dichlorophenyl)-(N-methoxymethylamino)-5-oxo-pentanal

This above material was subjected to the osmium tetroxide oxidation to the corresponding diol as described in Example 1. The crude product was then treated with 1.23g (2.77mmol) of lead tetraacetate as described in example 131, Step 4. Chromatographic purification on silica gel (eluant; dichloromethane:ethyl acetate=5:1) afforded 618 mg (81% two steps)of 3-(R)-(3,4-dichlorophenyl)-(N-methoxymethylamino)-5-oxo-pentanal.

Step 3) 1'-(3-(R)-(3,4-Dichlorophenyl)-5-(N-methoxymethylamino)-5-oxo-pentyl)-1-methanesulfonyl-spiro (indoline-3,4'-piperidine)

A sample of 332 mg (1.09 mmol) of the aldehyde from Step 2 above was subjected to reductive amination with 1-methanesulfonyl-spiro(indoline-3,4'-piperidine) hydrochloride as described in Example 2 to give 369 mg (61%) of 1'-(3-(R)-(3,4-dichlorophenyl)-5-(N-methoxy)-N-(methyl)amino)-5-oxo-pentyl)-1-methanesulfonyl-spiro(indoline-3,4'-piperidine). $^1$H-NMR (CDCl3 400 MHz): δ 2.87 (s 3H), 3.10 (s, 3H), 3.60 (s, 3H), 7.0–7.4 (m, 7H).

Step 4) 1'-(3-(R)-(3,4-Dichlorophenyl))-5-(3,5-dimethylphenyl)-5-oxo-pentyl)-1-methanesulfonyl-spiro (indoline-3,4'-piperidine)

To a 1.2 mL THF solution of the amide from Step 3 above (73 mg, 0.13 mmol) was added 1.1 mL of 0.7M 3,5-dimethylphenylmagnesium bromide solution in THF (prepared from 5-bromo-m-xylene and magnesium turnings in THF). Then the reaction mixture was heated to 50° C. After stirring for 1.5 hr, the reaction mixture was allowed to cool down to rt and the reaction was quenched by sat NH$_4$Cl aq solution. THF was removed under reduced pressure, diluted with ethyl acetate. The organic phase was separated and the aqueous phase was extracted twice with ethyl acetate. Combined organic phases were dried over anhydrous magnesium sulfate, filtered, concentrated, chromatographed on silica gel eluting with a gradient of dichloromethane:ethyl acetate=10:1 to 1:1 to give 55mg (70%) of the title compound.

$^1$H-NMR (CDCl$_3$ 400 Mz): δ 2.34 (s, 6H), 2.86 (s, 3H), 3.23 (m, 2H), 3.74 (s, 2H), 7.0–7.5 (m, 10H).
MS (CI): 599 (M$^+$+1: $^{35}$Cl×2), 601 (M$^+$+1: $^{35}$Cl & $^{37}$Cl).

EXAMPLE 133

1'-(3-(R)-(3,4-Dichlorophenyl)-6-(3,5-dimethylphenyl)-5-oxo-hexyl)-1-methanesulfonyl-spiro(indoline-3,4'-piperidine)

70 mg (0.126 mmol) of 1'-(3-(R)-(3,4-dichlorophenyl)-5-(N-methoxy)-N-(methyl)amino)-5-oxo-pentyl)-1-methanesulfonyl-spiro(indoline-3,4'-piperidine) (Example 132, Step 3) was treated with 0.8M THF solution of 3,5-dimethyl benzylmagnesium chloride as in the case of Example 132. The crude material was chromatographed on silica gel in the same solvent system to afford 33mg of the title compound (43%). $^1$H-NMR (CDCl$_3$ 400 MHz): δ 2.24 (s, 6H), 2.86 (s, 3H), 3.47 (s, 2H), 3.72 (s, 2H), 6.64 (s, 2H), 6.8–7.4 (m, 8H). MS (CI): 613 (M$^+$+1: $^{35}$Cl×2), 615 (M$^+$+1: $^{35}$Cl & $^{37}$Cl).

EXAMPLE 134

1'-(3-(S)-(3,4-Dichlorophenyl)-6-(3,5-dimethylphenyl)-6-oxo-hexyl)-1-methanesulfonyl-spiro(indoline-3,4'-piperidine)

3-(R)-(3,4-Dichlorophenyl)-4-hexenoic acid (Example 131, Step 2) was converted into 4-(S)-(3,4-Dichlorophenyl)-5-heptenoic acid as in Example 131, Steps 1 and 2. 4-(S)-(3,4-dichlorophenyl)-4-heptenoic acid was converted to (N-methoxyl-N-methyl)-(4-(S)-(3,4-dichlorophenyl)-6-heptenyl)-amide followed by treatment with 3,5-dimethylphenyl-magnesium bromide as described in Example 132, Step 4 to give the title compound. $^1$H-NMR (CDCl$_3$ 400 MHz): δ 2.32 (s, 6H), 2.80 (s, 3H), 3.74 (s, 3H), 7.0–7.4 (m, 10H). MS (CI): 613 (M$^+$+1: $^{35}$Cl×2), 615 (M$^+$+1: $^{35}$Cl & $^{37}$Cl).

EXAMPLE 135

1'-(3-(S)-(3,4-Dichlorophenyl)-6-(3,5-dimethylphenyl)-5-(RS)-methyl-6-oxo-hexyl)-1-methanesulfonyl-spiro(indoline-3,4'-piperidine)

Step 1) 4-(S)-(3,4-Dichlorophenyl)-1-(3,5-dimethylphenyl)-hept-6-ene-1-one 1.42 g (4.50mmol) of (N-Methoxy-N-methyl)-(4-(S)-(3, 4-dichlorophenyl)-6-heptenyl)-amide (prepared in Example 134) was dissolved in 20 mL of dry THF. To it added 10 mL THF solution of 3,5-dimethylphenylmagnesium bromide prepared from 1.8 g (9.6 mmol) of 5-bromo-m-xylene and 463 mg of magnesium turnings. After stirring for 2 hr at rt, the reaction was quenched with saturated aqueous ammonium chloride solution. THF was removed under reduced pressure. The residual material was diluted with ethyl acetate. The organic phase was separated, aqueous phase was extracted twice with ethyl acetate. Combined organic phases were washed with brine, dried over anhydrous magnesium sulfate, filtered, concentrated, chromatogrpraphed on silica gel eluting with a gradient of hexane ethyl acetate= 10:1 to 5:1 to give 1.57 g of 4-(S)-(3,4-dichlorophenyl)-1-(3,5-dimethylphenyl)-hept-6-ene-1-one (97%).

Step 2) 4-(R)-(3,4-Dichlorophenyl)-1-(3,5-dimethylphenyl)-2-(RS)-methyl-hept-6-ene-1-one Hexamethyldisilazane (0.108 mL, 0.512 mmol), and 0.089 mL of hexamethylphosphoramide were dissolved in 2 mL of dry THF. To it was added 0.306 mL (0.49 mmol) of n-butyllithium (1.6M hexane solution) after cooling in an ice-water bath. After stirring for 20 min, the ice-water bath was replaced by a dry ice-acetone bath and 2 mL of a dry THF solution of 4-(S)-(3,4-dichlorophenyl)-1-(3,5-dimethylphenyl)-hept-6-ene-1-one (154 mg, 0.426 mmol) was added via syringe. After stirring for 1 hr, 0.066 mL (1.06 mmol) of iodomethane was added. The cooling bath was removed and the mixture stirred at rt overnight. The solvent was then removed under reduced pressure and the residual material was diluted in ethyl acetate and water. The organic phase was separated. The aqueous phase was extracted twice with ethyl acetate. The combined organic phases were washed with brine, dried over anhydrous magnesium sulfate, filtered, concentrated, and chromatographed on silica gel eluting with a gradient of hexane:ethyl acetate=10:1 to 7:1 to give 150mg of 4-(R)-(3,4-dichlorophenyl)-1-(3,5-dimethylphenyl)-2-(R&S)-methyl-hept-6-ene-1-one (94%). This was a 1 to 1 mixture of two diastereomers as revealed by proton NMR. $^1$H-NMR (CDCl$_3$ 400 MHz): δ 1.06 (d, J=7 Hz, 1.5H), 1.14 (d, J=6.7 Hz, 1.5H), 2.30, 2.31 (s, 6H), 2.5 (m, 0.5H), 2.6 (m, 0.5H), 3.1–3.2 (m, 1H), 4.9 (m, 2H), 5.5 (m, 1H), 6.8–7.4 (m, 6H).

Step 3) 3-(S)-(3,4-Dichlorophenyl)-5-(RS)-methyl-6-(3,5-dimethylphenyl)-6-oxo-hexanal The product from Step 2 above was subjected to osmium tetroxide oxidation followed by the treatment with sodium periodate as described in Example 1 to give 3-(S)-(3,4-dichlorophenyl)-5-(RS)-methyl-6-(3,5-dimethylphenyl)-6-oxo-hexanal.

Step 4) 1-(3-(S)-(3,4-Dichlorophenyl)-6-(3,5-dimethylphenyl)-5-(RS)-methyl-6-oxo-hexyl)-1-methane sulfonyl-spiro(indoline-3,4'-piperidine)

This product from Step 3 above was subjected to reductive amination with 1-methanesulonyl-spiro(indoline-3,4'-piperidine) as described in Example 2 to give the title compound.
$^1$H-NMR (CDCl$_3$ 400 MHz): δ 1.05 (d, J=7 Hz), 1.08 (d, J=6.7 Hz), 2.30 & 2.32 (s, 6H), 2.89 (s, 3H), 3.72 (S, 2H), 6.8–7.0 (mn, 10H).
MS (CI): 627 (M$^+$+1: $^{35}$Cl×2), 629 (M$^+$+1: $^{35}$Cl& $^{37}$Cl).

EXAMPLE 136

1'-(3-(S)-(3,4-Dichlorophenyl)-4-(3,5-(bistrifluoromethyl)benzyloxy)-1-acetyl-spiro(indoline-3,4'-piperidine)

Step A: 2-(S)-(3,4-Dichlorophenyl)-4-penten-1-ol

To a solution of 2-(S)-(3,4-dichlorophenyl)-4-pentenoic acid (7.0 gm) (prepared as described by J. Hale et. al., *Bioorganic & Medicinal Chemistry Letters* 1993,3, 319–322.) in ether (50 mL) at r.t. was added portionwise over 5 min solid lithium aluminum hydride (700 mg). The reaction was heated to 40° C. for 3 hr and then stirred at r.t. for 16 hr. The reaction was poured into water containing 25 mL of 2N NaOH and extracted twice with ether. The ether layers were washed with brine, combined and dried over Na$_2$SO$_4$. Flash chromatograghy afforded the title compound (4.5 gm) as an oil. [α]$_D$=+14 (EtOH, c=1.5).

Step B: 2-(S)-(3,4-Dichlorophenyl)-1-(3,5-(bistrifluoromethyl)-benzyloxy)-4-pentene To a solution of 2-(S)-(3,4-dichlorophenyl)-4-penten-1-ol (1.0 gm) in DMF (25 mL) was added sodium hydride (175 mg) while cooled in an ice bath. After 1 min, 3,5-(bistrifluoromethyl)benzyl bromide (2.0 gm) was added followed by a second portion of sodium hydride (175 mg). After 1 hr, the reaction was poured into water and extracted twice with ether. The ether layers were washed with brine, combined and dried over Na$_2$SO$_4$. Flash chromatograghy (hexanes, then 2 and 5% ethyl acetate/hexanes) afforded the title compound (2.0 gm) as an oil. NMR (CDCl$_3$): δ 2.30–2.40 and 2.50–2.60 (2 m, 2H), 2.90–3.00 (m, 1H), 3.55–3.65 (d of AB q, 2H, J=6 and 9 Hz), 4.54 (AB q, 2H, J=13 Hz), 4.90–5.00 (m, 2H), 5.55–5.70 (m, 1H), 7.04 (dd, 1H, J=2 and 8 Hz), 7.30 (d, 1 h, J=2 Hz), 7.36 (d, 1 h, J=8 Hz), 7.64 (s, 2 h), 7.76 (s, 1H).

Step C: 3-(S)-(3,4-Dichlorophenyl)-4-(3,5-(bistrifLuoromethyl)-benzyloxy)butan-1-ol A solution of 2-(S)-(3,4-dichlorophenyl)-1-(3,5-(bistrifluoromethyl)benzyloxy)-4-pentene (1.5 gm) in methanol (50 mL) was cooled to −70° C. in a dry ice/acetone bath and ozone bubbled thru for 15 min until a blue coloration was seen. The solution was purged with N$_2$ for 10 min and sodium borohydride was added. The reaction was allowed to warm to r.t. and was stirred for 2 hr. The volatiles were removed in vacuo and the residue was flash chromatograghed (30 then 50% ethyl acetate/hex anes) to give the title compound as a clear oil.
NMR (CDCl$_3$): δ 1.78–1.88 and 2.00–2.10 (2 m, 2H), 3.05–3.15 (m, 1H), 3.45–3.55 (m, 1H), 3.55–3.68 (2 m, 3H), 4.55 (AB q, 2H, J=13 Hz), 7.04 (dd, 1H, J=2 and 8 Hz), 7.32 (d, 1 h, J=2 Hz), 7.36 (d, 1 h, J=8 Hz), 7.65 (s, 2 h), 7.76 (s, 1H).

Step D: 4-Bromo-2-(S)-(3,4-dichlorophenyl)-1-(3,5-(bistrifluoro-methyl)benzyloxy)butane 3-(S)-(3,4-Dichlorophenyl)-4-(3,5-(bistrifluoromethyl)-benzyloxy)butan-1-ol from Step C (500 mg) was converted to the title compound (530 mg) with Ph$_3$P-Br$_2$ as described in Example 20, Step B.

Step E: 1'-(3-(S)-(3,4-Dichlorophenyl)-4-(3,5-(bistrifluoromethyl)-benzyloxy)-1-acetyl-spiro(indoline-3,4'-piperidine)

4-Bromo-2-(S)-(3,4-dichlorophenyl)-1-(3,5-(bistrifluoromethyl)benzyloxy)butane (30 mg) from Step D was converted to the title compound (42 mg) as described in Example 20, Step C. NMR (CDCl$_3$): δ 1.48–2.05 (m, 10H), 2.14 and 2.34 (2 s, 3H), 2.10–2.25 (m, 2H), 2.70–2.85 (m, 2H), 2.90 (m, 1H), 3.48–3.58 (m, 2H), 3.70 and 3.84 (2 s, 2H), 4.55 (AB q, 2H, J=13 Hz), 6.90–7.15 (m, 4 h), 7.33 (d, 1 h, J=2 Hz), 7.37 (d, 1 h ,J=8 Hz), 7.66 (s, 2 h), 7.76 (s, 1H), 8.18 (d, 1 h, 8 Hz).

EXAMPLE 137

1'-(3-((S)-(3-Chlorophenyl))-4-(N-(phenylsulfonyl)(methylamino))butyl)-spiro(2,3-dihydrobenzothiophene-3,4'-piperidine)

A mixture of 3-((S)-(3-chlorophenyl))-4-(N-(phenylsulfonyl)-(methylamino))butanal (40 mg, 0.113 mmol) (prepared according to the procedure of Hale, J. J.; Finke, P. E.; MacCoss, M. *Bioorganic & Medicinal Chemistry Letters* 1993,3, 319–322 except using phenylsulfonyl chloride in place of the benzoyl chloride in the acylation), spiro(2,3-dihydrobenzo-thiophene-3,4'-piperidine hydrochloride (41 mg, 0.17 mmol), 4A molecular sieves (25 mg) and DIPEA (0.018 mL, 0.17 mmol) in THF (1.5 mL) was stirred at rt for 30 min. Sodium triacetoxyborohydride (48 mg, 0.227 mmol) was then added and the reaction was stirred at rt for 16–40 h. The mixture was poured into a water containing excess sodium carbonate and was extracted twice with ethyl acetate. The organic layers were washed with brine, dried, combined and concentrated in vacuo. The residue was purified by prep TLC using 5% methanol in methylene chloride as eluent to afforded the title compound (19 mg). Mass Spectrum (ESI) M+H=541, 543

EXAMPLE 138

1'-(3-((S)-(3-Chlorophenyl))-4-(N-(phenylsulfonyl)(methylamino))butyl)-spiro(2,3-dihydrobenzothiophene-3,4'-piperidine)-1-oxide Using essentially the same procedure as in Example 53, 1'-(3-((S)-(3-chlorophenyl))-4-(N-(phenylsulfonyl)(methylamino))butyl)-spiro(2,3-dihydrobenzothiophene-3,4'-piperidine) (20 mg, 0.037 mmol) from Example 137 was oxidized to the title compound (12.5 mg). Mass Spectrum (ESI) M+H=557, 559

EXAMPLE 139

1'-(3-((S)-(3-Chlorophenyl))-4-(N-(phenylsulfonyl)(methylamino))butyl)-spiro(2,3-dihydrobenzothiophene-3,4'-piperidine)-1,-dioxide Using essentially the same procedure as in Example 51, 1'-(3-((S)-(3-chlorophenyl))-4-(N-(phenylsulfonyl)

(methylamino))butyl)-spiro(2,3-dihydrobenzothiophene-3,4'-piperidine) (13.3 mg, 0.026 mmol) from Example 137 was oxidized to the title compound (8.6 mg).
Mass Spectrum (ESI) M+H=573, 575

Using essentially the same procedures as in Example 137 but using the appropriate phenyl- or thienylacetic acid as the starting material, Examples 140–145 were prepared.

EXAMPLE 140

1'-(3-((R,S)-(Phenyl))-4-(N-(phenylsulfonyl)(methylamino))butyl)-spiro(2,3-dihydrobenzothiophene-3,4'-piperidine)
Mass Spectrum (NH$_3$/CI) M+H=507

EXAMPLE 141

1'-(3-((R,S)-(3-Thienyl))-4-(N-(phenylsulfonyl)(methylamino))butyl)-spiro(2,3-dihydrobenzothiophene-3,4'-piperidine)
Mass Spectrum (ESI) M+H=513

EXAMPLE 142

1'-(3-((R,S)-(2-Thienyl))-4-(N-(phenylsulfonyl)(methylamino))butyl)-spiro(2,3-dihydrobenzothiophene-3,4'-piperidine)
Mass Spectrum (ESI) M+H=513

EXAMPLE 143

1'-(3-((S)-(4-Fluorophenyl))-4-(N-(phenylsulfonyl)(methylamino))butyl)-spiro(2,3-dihydrobenzothiophene-3,4'-piperidine)
Mass Spectrum (ES:) M+H=525

EXAMPLE 144

1'-(3-((R,S)-(3,5-Dichlorophenyl))-4-(N-(phenylsulfonyl)(methylamino))-butyl)-spiro(2,3-dihydrobenzothiophene-3,4'-piperidine)
Mass Spectrum (ESI) M+H=575

EXAMPLE 145

1'-(3-((S)-(3,4-1Dichlorophenyl))-4-(N-(phenylsulfonyl)(ethylamino))butyl)-spiro(2,3-dihydrobenzothiophene-3,4'-piperidine)
Mass Spectrum (NH$_3$/CI) M+H=589

Using essentially the same procedures as in Example 53 but using the appropriate 2,3-dihydrobenzothiophene as the starting material, Examples 146–151 were prepared.

EXAMPLE 146

1'-(3-((R,S)-(Phenyl))-4-(N-(phenylsulfonyl)(methylamino))butyl)-spiro(2,3-dihydrobenzothiophene-3,4'-piperidine)-1-oxide
Mass Spectrum (NH$_3$/CI) M+H=523, 507 (100%, M+1−16)

EXAMPLE 147

1'-(3-((R,S)-(3-Thienyl))-4-(N-(phenylsulfonyl)(methylamino))butyl)-spiro(2,3-dihydrobenzothiophene-3,4'-piperidine)-1-oxide
Mass Spectrum (ESI) M+H=529

EXAMPLE 148

1'-(3-((R,S)-(2-Thienyl))-4-(N-(phenylsulfonyl)(methylamino))butyl)-spiro(2,3-dihydrobenzothiophene-3,4'-piperidine)-1-oxide
Mass Spectrum (ESI) M+H=529

EXAMPLE 149

1'-(3-((S)-(4-Fluorophenyl))-4-(N-(phenylsulfonyl)(methylamino))butyl)-spiro(2,3-dihydrobenzothiophene-3,4'-piperidine)-1-oxide
Mass Spectrum (NH$_3$/CI) M+H−16=525

EXAMPLE 150

1'-(3-((R,S)-(3,5-Dichlorophenyl))-4-(N-(phenylsulfonyl)(methylamino))-butyl)-spiro(2,3-dihydrobenzothiophene-3,4'-piperidine)-1-oxide
Mass Spectrum (NH$_3$/CI) M+H=591

EXAMPLE 151

1'-(3-((S)-(3,4-Dichlorophenyl))-4-(N-(phenylsulfonyl)(ethylamino))butyl)-spiro(2,3-dihydrobenzothiophene-3,4'-piperidine)-1-oxide
Mass Spectrum (NH$_3$/CI) M+H=605

Using essentially the same procedures as in Example 51 but using the appropriate 2,3-dihydrobenzothiophene as the starting material, Examples 152–158 were prepared.

EXAMPLE 152

1'-(3-((R,S)-(Phenyl))-4-(N-(phenylsulfonyl)(methylamino))butyl)-spiro(2,3-dihydrobenzothiophene-3,4'-piperidine)-1,1-dioxide
Mass Spectrum (NH$_3$/CI) M+H=539

EXAMPLE 153

1'-(3-((R,S)-(2-Chlorophenyl))-4-(N-(phenylsulfonyl)(methylamino))butyl)-spiro(2,3-dihydrobenzothiophene-3,4'-piperidine)-1,1-dioxide
Mass Spectrum (NH$_3$/CI) M+H=573, 575

EXAMPLE 154

1'-(3-((R,S)-(3-Thienyl))-4-(N-(phenylsulfonyl)(methylamino))butyl)-spiro(2,3-dihydrobenzothiophene-3,4'-piperidine)-1,1-dioxide
Mass Spectrum (ESI) M+H=545

EXAMPLE 155

1'-(3-((R,S)-(2-Thienyl))-4-(N-(phenylsulfonyl)(methylamino))butyl)-spiro(2,3-dihydrobenzothiophene-3,4'-piperidine)-1,1-dioxide
Mass Spectrum (ESI) M+H=545

EXAMPLE 156

1'-(3-((S)-(4-Fluorophenyl))-4-(N-(phenylsulfonyl)(methylamino))butyl)-spiro(2,3-dihydrobenzothiophene-3,4'-piperidine)-1,1-dioxide
Mass Spectrum (NH$_3$/CI) M+H=557

EXAMPLE 157

1'-(3-((R, S)-(3,5-Dichlorophenyl))-4-(N-(phenylsulfonyl)(methylamino))-butyl)-spiro(2,3-dihydrobenzothiophene-3,4'-piperidine)-1,1-dioxide
Mass Spectrum (NH$_3$/CI) M+H=607

EXAMPLE 158

1'-(3-((S)-(3,4-Dichlorophenyl))-4-(N-(phenylsulfonyl)(ethylamino))butyl)-spiro(2,3-dihydrobenzothiophene-3,4'-piperidine)-1,1-dioxide
Mass Spectrum (NH$_3$/CI) M+H=621

Using essentially the same procedures as Example 3 but substituting the appropriate phenylacetyl chloride in Step B and the procedures of Example 51 and 53 for the sulfide oxidations, Examples 159–167 were prepared.

EXAMPLE 159

1'-(3-((R,S)-Phenyl)-4-(N-(phenylacetyl)(methylamino))butyl)-spiro(2,3-dihydrobenzothiophene-3,4'-piperidine)
Mass Spectrum (NH$_3$/CI) M+H=485

EXAMPLE 160

1'-(3-((R,S)-Phenyl)-4-(N-(phenylacetyl)(methylamino))butyl)-spiro(2,3-dihydrobenzothiophene-3,4'-piperidine)-1-oxide
Mass Spectrum (NH$_3$/CI) M+H=501

EXAMPLE 161

1'-(3-((R,S)-Phenyl)-4-(N-(phenylacetyl)(methylamino))butyl)-spiro(2,3-dihydrobenzothiophene-3,4'-piperidine)-1,1-dioxide
Mass Spectrum (NH$_3$/CI) M+H=517

EXAMPLE 162

1'-(3-((R,S)-Phenyl)-4-(N-((R)-α-methylphenylacetyl)(methylamino))butyl)-spiro(2,3-dihydrobenzothiophene-3,4'-piperidine)
Mass Spectrum (NH$_3$/CI) M+H=499

EXAMPLE 163

1'-(3-((R,S)-Phenyl)-4-(N-((R)-α-methylphenylacetyl)(methylamino))butyl)-spiro(2,3-dihydrobenzothiophene-3,4'-piperidine)-1-oxide
Mass Spectrum (NH$_3$/CI) M+H=515

EXAMPLE 164

1'-(3-((R,S)-Phenyl)-4-(N-((R)-α-methyl phenylacetyl)(methylamino))butyl)-spiro(2,3-dihydrobenzothiophene-3,4'-piperidine)-1,1-dioxide
Mass Spectrum (NH$_3$/CI) M+H=531

EXAMPLE 165

1'-(3-((R,S)-Phenyl)-4-(N-((S)-α-methyl phenylacetyl)(methylamino))butyl)-spiro(2,3-dihydrobenzothiophene-3,4'-piperidine)
Mass Spectrum (NH$_3$/CI) M+H=499

EXAMPLE 166

1'-(3-((R,S)-Phenyl)-4-(N-((S)-α-methylphenylacetyl)(methylamino))butyl)-spiro(2,3-dihydrobenzothiophene-3,4'-piperidine)-1-oxide
Mass Spectrum (NH$_3$/CI) M+H=515

EXAMPLE 167

1'-(3-((R,S)-Phenyl)-4-(N-((S)-α-methyl phenylacetyl)(methylamino))butyl)-spiro(2,3-dihydrobenzothiophene-3,4'-piperidine)-1,1-dioxide
Mass Spectrum (NH$_3$/CI) M+H=531

Using essentially the same procedure as Example 137 but substituting the appropriate substituted spiropiperidine in the reductive amination, Examples 168–170 were prepared.

EXAMPLE 168

1'-(3-((S)-(3-Chlorophenyl))-4-(N-(phenylsulfonyl)(methylamino))butyl)-spiro(indoline-3,4'-piperidine)
Mass Spectrum (NH$_3$/CI) M+H=524

EXAMPLE 169

1'-(3-((S )-(3-Chlorophenyl))-4-(N-(phenylsulfonyl)(methylamino))butyl)-spiro(1-oxoisoindoline-3,4'-piperidine)
Mass Spectrum (NH$_3$/CI) M+H=538

EXAMPLE 170

1'-(3-((S)-(3-Chlorophenyl))-4-(N-(phenylsulfonyl)(methylamino))butyl)-spiro(1-oxo-2-methylisoindoline-3,4'-piperidine)
Mass Spectrum (NH$_3$/CI) M+H=552

EXAMPLE 171

1'-(3-((R,S)-Phenyl)-4-(N-(benzyl)(methylamino))butyl)-spiro(2,3-dihydrobenzothiophene-3,4'-piperidine)

Using the procedure of Example 137, 1'-(3-((R,S)-phenyl)-4-(methylamino)-butyl)-spiro(2,3-dihydrobenzothiophene-3,4'-piperidine) (1209 mg, 0.33 mmol) was reductively alkylated with benzaldehyde to afford the title compound (129 mg). Mass Spectrum (NH$_3$/CI) M+H=457

EXAMPLE 172

1'-(3-((R,S)-Phenyl)-4-(N-(benzyl)(methylamino))butyl)-spiro(2,3-dihydrobenzothiophene-3,4'-piperidine)-1-oxide Using the procedure of Example 53, 1'-(3-((R,S)-phenyl)-4-(N-(benzyl)(methylamino))butyl)-spiro(2,3-dihydrobenzothiophene-3,4'-piperidine) (31 mg, 0.069 mmol) from Example 171 was oxidized to the title compound (25 mg). Mass Spectrum (NH$_3$/CI) M+H=473

EXAMPLE 173

1'-(3-((R,S)-Phenyl)-4-(N-(benzyl)(methylamino))butyl)-spiro(2,3-dihydrobenzothiophene-3,4'-piperidine)-1,1-dioxide Using the procedure of Example 53, 1'-(3-((R,S)-phenyl)-4-(N-(benzyl)(methylamino))butyl)-spiro(2,3-dihydrobenzothiophene-3,4'-piperidine) (30 mg, 0.066 mmol) from Example 171 was oxidized to the title compound (23 mg). Mass Spectrum (NH$_3$/CI) M+H=489

EXAMPLE 174

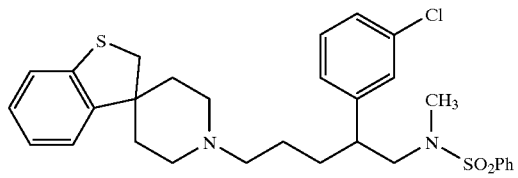

N-(2-(3-Chlorophenyl)-5-(spiro(benzo[b]thiophene-3(2H),4'-piperidin)-1'-yl)pentyl)-N-methylbenzenesulfonamide Step A: 2-(3-Chlorophenyl)pent-4-enenitrile A solution of 3-chlorobenzyl cyanide (2.00 g, 13.2 mmol) in 15 mL of THF was added over 30 min to a suspension of sodium hydride (60% dispersion in mineral oil, 636 mg, 15.9 mmol) in 5.0 mL of dry THF. After stirring 2 h at room temperature, the mixture was cooled to −20 °C., a solution of allyl bromide (1.14 mL, 1.59 g, 13.2 mmol) in 3.0 mL of THF was added, and the mixture was allowed to warm to room temperature. After 2 h, the reaction was quenched with a solution of 1.6 g of ammonium chloride in 100 mL of water. The aqueous layer was extracted with 3×50 mL of ethyl ether and the combined organic layers were washed with 50 mL of brine, dried over sodium sulfate and concentrated. The residue was purified by flash column chromatography on silica gel, eluting with 20–40% dichloromethane in hexane. Additional purification by flash column chromatography on silica gel, eluting with 5% ethyl ether in hexane gave 897 mg of the title compound as an amber oil. $^1$NMR (400 MHz, CDCl$_3$): δ 7.36–7.30 (m, 3H), 7.25–7.21 (m, 2H), 5.78 (ddt, 1H, J=17, 10, 7 Hz), 5.21 (bd, 1H, J=10 Hz), 5.20 (dq, 1H, J=17, 1 Hz), 3.84 (t, 1H, J=7 Hz), 2.70–2.57 (m, 2K). Mass spectrum (EI): m/z=191 (M$^+$).

Step B: 2-(3-Chlorophenyl)pent-4-enal

A 1.5 M solution of diisobutylaluminum hydride in toluene (3.66 mL, 5.49 mmol) was added dropwise to a solution of 2-(3-chlorophenyl)pent-4-enenitrile (877 mg, 4.58 mmol) in 35 mL of THF at −30 °C. The reaction was allowed to slowly warm to room temperature and stirred an additional 5 h before being quenched with 3.0 mL of saturated aqueous Rochelle salt. The resulting mixture was partitioned between 20 mL of 2.0 N aqueous HCl and 50 mL of ethyl acetate. The organic layer was washed with 20 mL of saturated sodium bicarbonate, followed by 20 mL of brine. Drying over sodium sulfate and evaporation gave the crude product which was purified by flash column chromatography on silica gel, eluting with 20% ethyl acetate in hexane to give 504 mg of a mixture containing the title compound. $^1$NMR (400 MHz, CDCl$_3$): δ 9.68 (s, 1H), 7.35–7.26 (m, 2H), 7.20 (s, 1H), 7.10–7.06 (m, 1H), 5.70 (ddt, 1H, J=16, 10, 7 Hz), 5.06 (d, 1H, J=16 Hz), 5.02 (d, 1H, J=10 Hz), 3.60 (t, 1H, J=7 Hz), 2.83 (dt, 1H, J=14, 7 Hz), 2.49 (dt, 1H, J=14, 7 Hz). Mass spectrum (EI): m/z=194 (M$^+$).

Step C: N-Methyl-(2-(3-chlorophenyl)pent-4-enyl)amine

Methylamine hydrochloride (595 mg, 8.81 mmol), triethylamine (1.23 mL, 893 mg, 8.82 mmol) and acetic acid (0.290 mL, 304 mg, 4.98 mmol) were added to a stirred solution of of 2-(3-chlorophenyl)pent-4-enal (350 mg, 1.80 mmol) in 8 mL of methanol at room temperature. After 10 min, sodium cyanoborohydride (97 mg, 1.6 mmol) was added and stirring was continued overnight. The mixture was then diluted with 100 mL of ethyl acetate and washed with a mixture of 30 mL of saturated sodium bicarbonate and 10 mL of brine, followed by 40 mL of brine. The organic layer was dried over sodium sulfate, decanted, and evaporated. The residue was partitioned between 25 mL of ethyl ether and 20 mL of 2.0 N aqueous HCl. The aqueous layer was washed with 25 mL of ethyl ether, made basic with 15 mL of 2.5 N aqueous sodium hydroxide, and extracted with 3×25 mL of ethyl acetate. The ethyl acetate layers were dried over sodium sulfate and evaporated to give 180 mg of the title compound as a colorless syrup. $^1$NMR (400 MHz, CDCl$_3$): δ 7.26–7.17 (m, 3H), 7.08 (dt, 1H, J=8, 1 Hz), 5.67 (ddt, 1H, J=17, 10, 7 Hz), 4.99 (dq, 1H, J=17, 1 Hz), 4.96 (dm, 1H, J=10 Hz), 2.90–2.80 (m, 2H), 2.78–2.70 (m, 1H), 2.45–2.28 (m, 2H), 2.38 (s, 3H).

Step D: N-(2-(3-Chlorophenyl)pent-4-enyl)-N-methylbenzenesulfonamide

N-Methyl-(2-(3-chlorophenyl)pent-4-enyl)amine (202 mg, 1.03 mmol) was dissolved in 10 mL of ethyl acetate. A solution of sodium bicarbonate (766 mg, 10.3 mmol) in water (10 mL) was added followed by benzenesulfonyl chloride (363 mg, 4.06 mmol), and the heterogeneous mixture was stirred overnight at room temperature. The mixture was extracted with 5 mL of ethyl acetate followed by an additional 2×15 mL of ethyl acetate. The combined organic layers were dried over sodium sulfate, decanted, and evaporated. The residue was purified by flash column chromatography on silica gel, eluting with 10–20% ethyl ether in hexane to give 223 mg the title compound. $^1$NMR (400 MHz, CDCl$_3$): δ 7.72 (d, 2H, J=8 Hz), 7.58 (tt, 1H, J=8, 1 Hz), 7.50 (t, 2H, J=8 Hz), 7.24 (d, 1H, J=8 Hz), 7.20 (dt, 1H, J=8, 1 Hz), 7.14 (t, 1H, J=1 Hz), 7.10 (dt, 1H, J=8, 1 Hz), 5.63 (ddt, 1H, J=17, 10, 7 Hz), 5.00 (dm, 1H, J=17 Hz), 4.97 (dm, 1H, J=10 Hz) 3.42–3.34 (m, 1H), 3.00–2.90 (m, 2H), 2.61 (s, 3H), 2.56 (dtm, 1H, J=14, 6 Hz), 2.36 (dtm, 1H, J=14, 7 Hz). Mass spectrum (NH$_3$/CI): m/z=350 (M+1).

Step E: N-(2-(3-Chlorophenyl)-5-hydroxypentyl)-N-methylbenzenesulfonamide

9-BBN (119 mg, 0.488 mmol) was added in one portion to an ice cold solution of N-(2-(3-chlorophenyl)pent-4-enyl)-N-methylbenzenesulfonamide (100 mg, 0.286 mmol) in 1.0 mL of THF, and the mixture was allowed to warm to room temperature. After 15 h, an additional portion of 9-BBN (26 mg, 0.11 mmol) was added and stirring was continued for another 1 h. Aqueous 2.5 N sodium hydroxide solution (0.29 mL, 0.73 mmol) and aqueous 30% hydrogen peroxide solution (0.176 mL) were added and the mixture was stirred 45 min at room temperature, 5 h at 50 °C., and overnight at room temperature. The reaction was concentrated and the residue was partitioned between 25 mL of ethyl acetate and a mixture of 20 mL of water and 5 mL of brine. The aqueous layer was extracted with 2×25 mL of ethyl acetate. The combined organic layers were washed with 25 mL of brine, dried over sodium sulfate, and concentrated. The residue was purified by flash column chromatography on silica gel, eluting with 5–50% ethyl acetate in dichloromethane to give 39 mg the title compound. $^1$NMR (400 MHz, CD$_3$OD): δ 7.72 (d, 2H, J=8 Hz), 7.63 (tt, 11H, J=8, 1 Hz), 7.56 (t, 2H, J=8 Hz), 7.29 (dd, 1H, J=9, 8 Hz), 7.24–7.20 (m, 2H), 7.16 (dt, 1H, J=8, 1 Hz), 3.49 (t, 2H, J=7 Hz), 3.24 (dd, 1H, J=13, 8 Hz), 3.13 (dd, 1H, J=13, 7 Hz), 2.97–2.88 (m, 1H), 2.59 (s, 3H), 1.87–1.77 (m, 1H), 1.65–1.54 (m, 1H), 1.45–1.27 (m, 2H). Mass spectrum (NH$_3$/CI): m/z=368 (M+1).

Step 1F: N-(5-Bromo-2-(3-chlorophenyl)pentyl)-N-methylbenzenesulfonamide

Bromine was added to a solution of triphenylphosphine (41.4 mg, 0.158 mmol) in 0.50 mL of acetonitrile until the red color persisted, and a small additional quantity of triphenylphorsphine was then added to consume the excess bromine. A solution of N-(2-(3-chlorophenyl)-5-hydroxypentyl)-N-methylbenzenesulfonamide (38.7 mg, 0.105 mmol) in 0.3 mL of acetonitrile was added. After stirring for 1 h, the reaction was quenched by a solution of sodium sulfite (20 mg) dissolved in 1.0 mL of water. The mixture was diluted with 15 mL of sodium bicarbonate and extracted with 2×20 mL of ethyl acetate. The organic layers were washed with 15 mL of brine, dried over sodium sulfate and concentrated. The crude product was purified by flash column chromatography on silica gel, eluting with of 10% ethyl acetate in hexane to give 23 mg the title compound. $^1$NMR (400 MHz, CD$_3$OD): δ 7.73 (d, 2H, J=8 Hz), 7.63 (tt, 1H, J=8, 1 Hz), 7.56 (t, 2H, J=8 Hz), 7.30 (dd, H, J=9, 8 Hz), 7.26–7.22 (m, 2H), 7.16 (dt, 1H, J=8, 1 Hz), 3.38 (t, 2H, J=6 Hz), 3.26 (dd, 1H, J=13, 7 Hz), 3.11 (dd, 1H, J=13, 8 Hz), 2.98–2.90 (m, 1H), 2.60 (s, 3H), 1.95–1.86 (m, 1H), 1.76–1.60 (m, 3H).

141

Step G: N-(2-(3-Chlorophenyl)-5-(spiro(benzo[b]thiophene-3(2H),4'-piperidin)-1'-yl)pentyl)-N-methylbenzenesulfonamide Spiro(benzo[b] thiophene-3(2H),4'-piperidine) hydrochloride (16.5 mg, 0.068 mmol) and N,N-diisopropylethylamine (0.036 mL, 27 mg, 0.21 mmol) were added to a solution of N-(5-bromo-2-(3-chlorophenyl)pentyl)-N-methylbenzenesulfonamide (24.6 mg, 0.057 mmol) in 0.30 mL of acetonitrile, and the mixture was heated in an oil bath at 52° C. After 2 days, tetrabutylammonium iodide (5.5 mg, 0.011 mmol) was added and the reaction was continued for an additional 24 h. Without work-up, the reaction mixture was purified by preparative TLC. Elution with 30% ethyl acetate in dichloromethane gave 13.5 mg the title compound. 1NMR (400 MHz, CD₃OD): δ 7.74 (d, 2H, J=8 Hz), 7.64 (tt, 1H, J=8, 1 Hz), 7.57 (t, 2H, J=8 Hz), 7.33–7.22 (m, 3H), 7.18 (d, 1H, J=8 Hz), 7.13–7.01 (m, 4H), 3.32–3.25 (m, 3H), 3.11 (dd, 1H, J=13, 8 Hz), 3.00–2.84 (m, 3H), 2.61 (s, 3H), 2.48–2.35 (m, 2H), 2.21 (bq, 2H, J=12 Hz), 1.99 (tt, 2H, J=13, 4 Hz), 1.84–1.75 (m, 3H), 1.67–1.56 (m, 1H), 1.52–1.34 (m, 2H). Mass spectrum (ESI): m/z=555 (M+1).

EXAMPLE 175

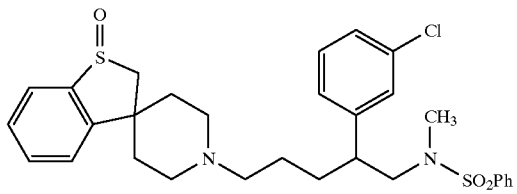

N-(2-(3-Chlorophenyl)-5-(spiro(benzo[b]thiophene-3(2H),4'-piperidin)-1-oxide-1'-yl)pentyl)-N-methylbenzenesulfonamide A solution of Oxone®(2KHSO₅.KHSO₄.K₂SO₄, 12.2 mg, 0.0198 mmol) in 0.50 mL of water was quickly added to solution of N-(2-(3-chlorophenyl)-5-(spiro(benzo[b]thiophene-3(2H),4'-piperidin)-1'-yl)pentyl)-N-methylbenzenesulfonamide (9.5 mg, 0.018 mmol) in 0.50 mL of methanol at 0° C. After 5 min, the reaction was quenched by the addition of 0.50 mL of saturated aqueous sodium sulfite solution and stirred at room temperature for 10 min. The mixture was made basic by the addition of 0.30 mL of 2.5 N aqueous sodium hydroxide solution, concentrated to a small volume, and extracted with 3×10 mL of dichloromethane. The combined organic layers were washed with 10 mL of brine, dried over sodium sulfate, and evaporated. Purification by preparative TLC, eluting with 5% methanol in dichloromethane, gave 8.4 mg of the title compound.

¹NMR (400 MHz, CD₃OD): δ 7.86 (d, 1H, J=8 Hz), 7.74 (d, 2H, J=8 Hz), 7.70–7.62 (m, 2H), 7.60–7.51 (m, 4H), 7.33–7.17 (m, 4H), 3.44 (d, 1H, J=14 Hz), 3.36–3.26 (m, 2H), 3.12 (dd, 1H, J=13, 8 Hz), 3.02–2.90 (m, 3H), 2.62 (s, 3H), 2.52–2.40 (m, 2H), 2.35–2.19 (m, 3H), 2.13–1.98 (m, 2H), 1.87–1.78 (m, 1H), 1.69–1.58 (m, 1H), 1.54–1.37 (m, 3H). Mass spectrum (ESI): m/z=571 (M+1).

142

EXAMPLE 176

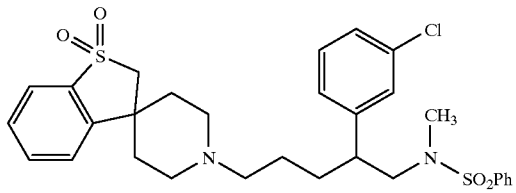

N-(2-(3-Chlorophenyl)-5-(spiro(benzo[b]thiophene-3(2H),4'-piperidin)-1 1-dioxide-1'-yl)pentyl)-N-methylbenzenesulfonamide A solution of Oxone®(2KHSO₅.KHSO₄.K₂SO₄, 7.7 mg, 0.013 mmol) in 0.40 mL of water was added to solution of N-(2-(3-chlorophenyl)-5-(spiro(benzo[b]thiophene-3(2H),4'-piperidin)-1'-yl)pentyl)-N-methylbenzenesulfonamide (6.5 mg, 0.011 mmol) in 0.40 mL of methanol at 0° C. The mixture was allowed to warm to room temperature and stirred for 2.5 h. A second portion of Oxone® (2KHSO₅.KHSO₄.K₂SO₄, 2.2 mg, 0.0036 mmol) was added and the reaction was stirred for an additional 1 h. The reaction was quenched with 0.20 mL of saturated aqueous sodium sulfite solution. After 10 min, 0.30 mL of 2.5 N aqueous sodium hydroxide solution was added. The mixture was concentrated in vacuo and extracted with 3×10 mL of dichloromethane. The combined organic layers were washed with 10 mL of brine, dried over sodium sulfate, and evaporated. Purification by preparative TLC, eluting with ethyl acetate, gave 4.3 mg the title compound as a white solid.
¹NMR (400 MHz, CD₃OD): δ 7.76–7.52 (m, 9H), 7.33–7.24 (m, 3H), 7.19 (dt, 1H, J=8 Hz), 3.42 (s, 2H), 3.29 (dd, 1H, J=13, 7 Hz), 3.11 (dd, 1H, J=13, 8 Hz), 3.01–2.91 (m, 3H), 2.62 (s, 3H), 2.48–2.36 (m, 2H), 2.24–2.07 (m, 4H), 1.86–1.75 (m, 3H), 1.68–1.57 (m, 1H), 1.51–1.37 (m, 2H). Mass spectrum (NH₃/CI): m/z=587 (M+1).

EXAMPLE 177

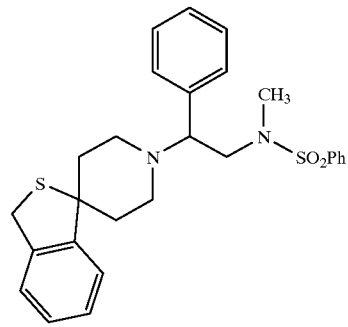

N-Methyl-N-(2-phenyl-2-(spiro(benzo[b]thiophene-3(2H),4'-piperidin)-1'-yl)ethyl)benzenesulfonamide Step A: N-(2-Hydroxy-2-phenylethyl)-N-methylbenzenesulfonamide A solution of α-(methylaminomethyl)benzyl alcohol (1.00 g, 6.61 mmol) in 15 mL of THF was cooled in an ice bath. Benzenesulfonyl chloride (0.886 mL, 1.23 g, 6.94 mmol) and N,N-diisopropylethylamine (2.3 mL, 1.7 g, 13 mmol) were added and mixture was allowed to warm to room temperature. After 30 min, the solvent was evaporated and the residue was partitioned between 50 mL of ethyl acetate and 40 mL of saturated aqueous sodium bicarbonate. The aqueous layer was extracted with 2×50 mL of ethyl acetate. The combined organic layers were washed with 50 mL of brine, dried over sodium sulfate, and evaporated. Purification by flash column chromatography on silica gel, eluting with 20–50% ethyl acetate in hexane, gave the title compound in quantitative yield.
¹NMR (400 MHz, CDCl₃): δ 7.79 (d, 2H, J=8 Hz), 7.59 (tt, 1H, J=8, 1 Hz), 7.52 (t, 2H, J=8 Hz), 7.41–7.28 (m, 5H), 4.94 (dd, 1H, J=9, 3 Hz), 3.31 (dd, 1H, J=14, 9 Hz), 3.05 (dd, 1H, J=14, 3 Hz), 2.83 (s, 3H).
Mass spectrum (NH₃/CI): m/z=292 (M+1).

Step B: N-Methyl-N-(2-phenyl-2-(spiro(benzo[b]thiophene-3(2H),4'-piperidin)-1'-yl)ethyl)benzenesulfonamide Methanesulfonyl chloride (0.028 mL, 41 mg, 0.36 mmol) was added dropwise over 5 min to a 0° C. solution of N-(2-hydroxy-2-phenylethyl)-N-methylbenzenesulfonamide (100 mg, 0.357 mmol) and triethylamine (0.075 mL, 54 mg, 0.054 mmol) in 1.0 mL of ethyl acetate. After 15 min., the resulting suspension was poured into 40 mL of ice cold ethyl acetate and washed succesively with 20 mL of ice water, 20 mL of ice cold 2.0 N HCl, 20 mL of ice water and 20 mL of brine. The ethyl acetate layer was dried over sodium sulfate and evaporated to give 128 mg of crude N-(2-methanesulfonyloxy-2-phenylethyl)-N-methylbenzenesulfonamide.

N-(2-Methanesulfonyloxy-2-phenylethyl)-N-methylbenzenesulfonamide (128 mg, 0.346 mmol), spiro(benzo[b]thiophene-3(2H),4'-piperidine) (142 mg, 0.693 mmol), and sodium carbonate (167 mg, 1.04 mmol) were combined in 1.0 mL of dry DMF. The mixture was stirred under nitrogen 1 h at room temperature and 1.5 h at 40° C., then slowly warmed to 65° C. and maintained at that temperature for 5 h. After cooling to room temperature and stirring overnight, the mixture was partitioned between 50 mL of ethyl acetate and 25 mL of saturated aqueous sodium bicarbonate. The organic layer was washed with 25 mL of brine, dried over sodium sulfate and concentrated. Purification by preparative TLC, eluting with 5% ethyl ether in dichloromethane, gave 103 mg of the title compound as a viscous oil. ¹NMR (400 MHz, CDCl₃): δ 7.77 (d, 2H, J=8 Hz), 7.58 (tt, 1H, J=8, 1 Hz), 7.51 (t, 2H, J=8 Hz), 7.39–7.28 (m, 3H), 7.23 (d, 2H, J=8 Hz), 7.17–7.03 (m, 4H), 3.77 (t, 1H, J=7 Hz), 3.71 (dd, 1H, J=13, 7 Hz), 3.30 (dd, 1H, J=13, 7 Hz), 3.12 (d, 1H, J=11 Hz), 3.08 (d, 1H, J=11 Hz), 2.94 (bd, 1H, J=12 Hz), 2.84 (bd, 1H, J=12 Hz), 2.65 (s, 3H), 2.34 (td, 1H, J=12, 3 Hz), 1.99 (td, 1H, J=12, 3 Hz), 1.96–1.73 (m, 4H). Mass spectrum (ESE): m/z=479 (M+1).

EXAMPLE 178

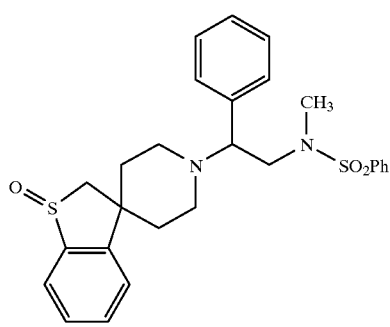

N-Methyl-N-(2-phenyl-2-(spiro(benzo[b]thiophene-3(2H),4'-piperidin)-1-oxide-1-yl)ethyl)benzenesulfonamide The title compound was prepared according to the procedure of Example 175, replacing N-(2-(3-chlorophenyl)-5-(spiro(benzo[b]thiophene-3(2H),4'-piperidin)-1'-yl)pentyl)-N-methylbenzenesulfonamide with N-methyl-N-(2-phenyl-2-(spiro(benzo[b]thiophene-3(2H),4'-piperidin)-1'-yl)ethyl)benzene-sulfonamide. ¹NMR (400 MHz, CDCl₃) showed a 1:1 mixture of diastereomers: δ 7.80–7.72 (m, 3H), 7.59–7.26 (m, 9H), 7.21 (t, 2H, J=8 Hz), 3.82–3.66 (m, 2H), 3.30–3.17 (m, 1H), 3.17 and 3.13 (two doublets, 1H, J=14 Hz), 3.04–2.82 (m, 2H), 3.00 and 2.91 (two doublets, 1H, J=14 Hz), 2.67 and 2.65 (two singlets, 3H), 2.48–1.93 (m, 5H), 1.44 and 1.39 (two broad doublets, 1H, J=12 Hz). Mass spectrum (NE₃/CI): m/z=495 (M+1).

EXAMPLE 179

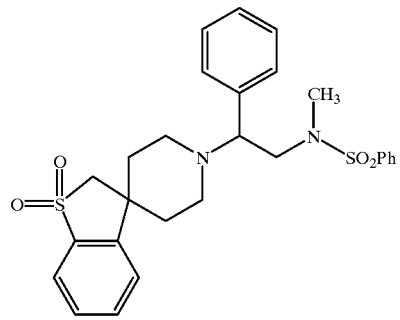

N-Methyl-N-2-(phenyl-2-(spiro(benzo[b]thiophene-3(2H)1,4'-piperidin)-1,1-dioxide-1-yl)ethyl)benzenesufonamide The title compound was prepared according to the procedure of Example 176 replacing N-(2-(3-chlorophenyl)-5-(spiro(benzo[b]thiophene-3(2H),4'-piperidin)-1'-yl)pentyl)-N-methylbenzenesulfonamide with N-methyl-N-(2-phenyl-2-(spiro(benzo[b]thiophene-3(2H),4'-piperidin)-1-yl)ethyl)benzene-sulfonamide. ¹NMR (400 MHz, CDCl₃): δ 7.78 (d, 2H, J=8 Hz), 7.71–7.45 (m, 7H), 7.42–7.33 (m, 3H), 7.22 (d, 2H, J=8 Hz), 3.86–3.76 (m, 2H), 3.29–3.15 (m, 3H), 3.02 (bd, 1H, J=12 Hz), 2.98 (bd, 1H, J=12 Hz), 2.68 (s, 3H), 2.31 (td, 1H, J=12, 2 Hz), 2.22–2.04 (m, 2H), 1.93 (td, 1H, J=12, 2 Hz), 1.83 (dm, 1H, J=12 Hz), 1.75 (dm, 1H, J=12 Hz). Mass spectrum (NH₃/CI): m/z=511 (M+1).

EXAMPLE 180

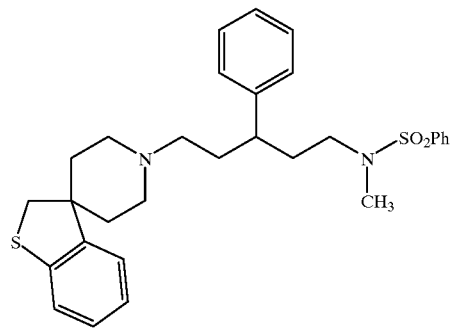

N-Methyl-N-(3-phenyl-5-(spiro(benzo[b]thiophene-3(2H),4'-piperidin)-1'-yl)pentyl)benzenesulfonamide Step A: 4-(N-Methylcarbamoyl)-3-phenylbutyric acid A solution of 3-phenylglutaric anhydride (500 mg, 2.63 mmol) in THF was added to a mixture of methylamine hydrochloride (266 mg, 3.94 mmol) and triethylamine (1.1 mL, 0.80 g, 7.9 mmol) in 4.0 mL of THEF. After 1.5 h, additional methylamine hydrochloride (177 mg, 2.62 mmol) and triethylamine (0.36 mL, 0.26 g, 2.6 mmol) were added and stirring was continued overnight at room temperature. The reaction was partitioned between 50 mL of ethyl acetate and 25 mL of 2.0 N aqueous HCl. The aqueous layer was extracted with 2×25 mL of ethyl acetate. The combined ethyl acetate layers were washed with 50 mL of brine, dried over sodium sulfate, and evaporated to give 518 mg of the title compound as a white solid. $^1$NMR (400 MHz, CD$_3$OD): δ 7.29–7.22 (m, 4H), 7.20–7.14 (m, 1H), 3.58 (tt, 1H, J=9, 7 Hz), 2.68 (dd, 1H, J=15, 7 Hz), 2.59 (dd, 1H, J=15, 9 Hz), 2.57 (s, 3H), 2.55 (dd, 1H, J=15, 7 Hz), 2.44 (dd, 1H, J=15, 9 Hz). Mass spectrum (NH$_3$/CI): m/z=222 (M+1).

Step 1B: 5-(Methylamino)-3-phenylpentan-1-ol

A suspension of 4-(N-methylcarbamoyl)-3-phenylbutyric acid (250 mg, 1.13 mmol) in 5.0 mL of THF was stirred in an ice bath as a 1.0 M solution of LAH (4.5 mL, 4.5 mmol) in THF was added dropwise over 10 min. The mixture was stirred 1 h at room temperature followed by 3 h at reflux. The reaction was then cooled in the ice bath and quenched with 0.70 mL of saturated aqueous Rochelle salt. The resulting precipitate was filtered and washed with 100 mL of ethyl acetate, and the combined filtrates were concentrated under reduced pressure. The residue was purified by flash column chromatography on silica gel, eluting with 10–15% methanol in dichloromethane containing 1% ammonium hydroxide, to give 151 mg of the title compound as a viscous oil. $^1$NMR (400 MHz, CD$_3$OD): δ 7.32–7.26 (m, 2H), 7.22–7.16 (m, 3H), 3.45–3.32 (m, 2H). 2.80–2.70 (m, 1H), 2.44 (ddd, 1H, J=12, 10, 6 Hz), 2.32 (ddd, 1H, J=12, 10, 6 Hz), 2.28 (s, 3H), 1.94–1.74 (m, 4H). Mass spectrum (NH$_3$/CI): m/z=194 (M+1).

Step C: N-(5-Hydroxy-3-phenylpentyl)-N-methylbenzenesulfonamide

The title compound was prepared according to the procedure of Example 177, Step A, replacing α-(methylaminomethyl)benzyl alcohol with 5-(methylamino)-3-phenylpentan-1-ol. $^1$NMR (400 MHz, CD$_3$OD): δ 7.67 (d, 2H, J=7 Hz), 7.62 (tt, 1H, J=7, 1 Hz), 7.54 (t, 2H, J=7 Hz), 7.29 (t, 2H, J=7 Hz), 7.22–7.16 (m, 3H), 3.42–3.28 (m, 2H), 2.91 (ddd, 1H, J=14, 9, 7 Hz), 2.80–2.69 (m, 2H), 2.66 (s, 3H), 1.96–1.72 (m, 4H). Mass spectrum (NH$_3$/CI): m/z=334 (M+1).

Step D: N-Methyl-N-(3-phenyl-5-(spiro(benzo[b]thiophene-3(2H)14'-piperidin)-1'-yl)pentyl)benzenesulfonamide The title compound was prepared according to the procedure of Example 177, Step B, replacing N-(2-hydroxy-2-phenylethyl)-N-methylbenzenesulfonamide with N-(5-hydroxy-3-phenylpentyl)-N-methylbenzenesulfonamide, and replacing DMF with isobutyronitrile. $^1$NMR (400 Mhz, CD$_3$OD): δ 7.69 (d, 2H, J=8 Hz), 7.62 (tt, 1H, J=8, 1 Hz), 7.55 (t, 2H, J=8 Hz), 7.30 (t, 2H, J=8 Hz), 7.24–7.18 (m, 3H), 7.13–7.01 (m, 4H), 3.26 (s, 2H), 2.94–2.78 (m, 4H), 2.70–2.61 (m, 1H), 2.67 (s, 3H), 2.34 (td, 1H, J=12, 5 Hz), 2.22–2.09 (m, 3H), 2.02–1.75 (m, 8H). Mass spectrum (NH$_3$/CI): m/z=521 (M+1).

EXAMPLE 181

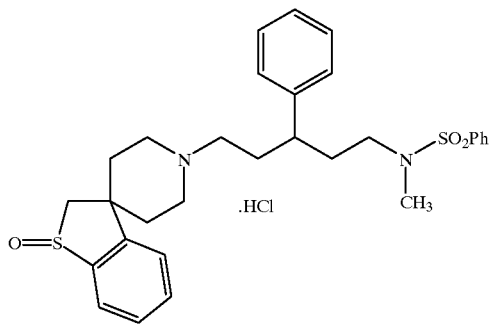

N-Methyl-N-(3-phenyl-5-spiro(benzo[b]thiophene-3(2H),4'-piperidin)-1-oxide-1'-yl)pentyl)benzenesulfonamide hydrochloride The free base corresponding to the title compound was prepared according to the procedure of Example 175, replacing N-(2-(3-chlorophenyl)-5-(spiro(benzo[b]thiophene-3(2H),4'-piperidin)-1'-yl)pentyl)-N-methylbenzenesulfonamide with N-methyl-N-(3-phenyl-5-(spiro(benzo[b]thiophene-3(2H),4'-piperidin)-1'-yl)pentyl)benzenesulfonamide. $^1$NMR (400 MHz, CD$_3$OD): δ 7.86 (d, 1H, J=7 Hz), 7.68 (t, 3H, J=7 Hz), 7.63 (tt, 1H, J=7, 1 Hz), 7.59–7.51 (m, 4H), 7.31 (t, 2H, J=7 Hz), 7.26–7.18 (m, 3H), 3.44 and 3.40 (two doublets, 1H, J=14), 3.34–3.28 (m, 1H), 3.00–2.80 (m, 4H), 2.73–2.64 (m, 1H), 2.67 (s, 3H), 2.42–1.78 (m, 11H), 1.54–1.47 (m, 1H). Mass spectrum (NK$_3$/CI): m/z=537 (M+1).

The free base was dissolved in dichloromethane and treated with a small excess of 1.0 M KCl in ether. Removal of the solvent at reduced pressure gave the title compound. $^1$NMR (400 MHz, CD$_3$OD): δ 7.93 (d, 1H, J=8 Hz), 7.76–7.70 (m, 3H), 7.66–7.54 (m, 5H), 7.37 (t, 2H, J=7 Hz), 7.33–7.24 (m, 3H), 3.73–3.56 (m, 3H), 3.34 (d, 1h, J=14 Hz), 3.26–3.08 (m, 2H), 3.01–2.76 (m, 4H), 2.69 (s, 3H), 2.56–2.43 (m, 1H), 2.36–2.23 (m, 3H), 2.18–2.09 (m, 1H), 2.03–1.78 (m, 3H).

EXAMPLE 182

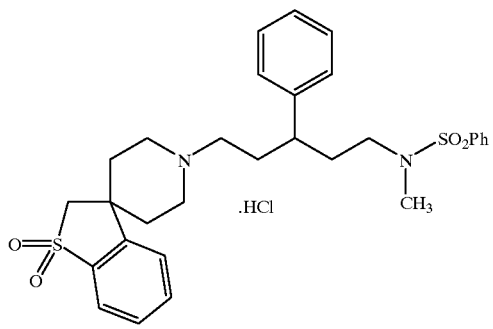

N-Methyl-N-(3-phenyl-5-spiro(benzo[b]thiophene-3(2H),4'-piperidin)-1,1-dioxide-1'-yl)pentyl)benzenesulfonamide hydrochloride The free base corresponding to the title compound was prepared according to the procedure of Example 176 replacing N-(2-(3-chlorophenyl)-5-(spiro(benzo[b] thiophene-3 (2H) ,4'-piperidin)-1'-yl)pentyl)-N-methylbenzenesulfonamide with N-methyl-N-(3-phenyl-5-(spiro(benzo[b]thiophene-3(2H),4'-piperidin)-1'-yl)pentyl) benzenesulfonamide. ¹NMR (400 MHz, CD₃OD): δ 7.74–7.60 (m, 6H), 7.58–7.52 (m, 3H), 7.31 (t, 2H, J=7 Hz), 7.24–7.18 (m, 3H), 3.51 (s, 2H), 2.98–2.80 (m, 4H), 2.73–2.64 (m, 1H), 2.67 (s, 3H), 2.35 (td, 1H, J=12, 5 Hz), 2.24–2.07 (m, 5H), 2.04–1.95 (m, 6H). Mass spectrum (NH₃/CI): m/z=553 (M+1).

The free base was dissolved in dichloromethane and treated with a small excess of 1.0 M HCl in ether. Removal of the solvent at reduced pressure gave the title compound. ¹NMR (400 MHz, CD₃OD): δ 7.80–7.69 (m, 4H), 7.67–7.54 (m, 5H), 7.38 (t, 2H, J=7 Hz), 7.32–7.24 (m, 3H), 3.67 (s, 2H), 3.66–3.58 (m, 2H), 3.22–2.76 (m, 7H), 2.68 (s, 3H), 2.42–2.24 (m, 3H), 2.17–2.06 (m, 3H), 2.02–1.88 (m, 2H).

EXAMPLE 183

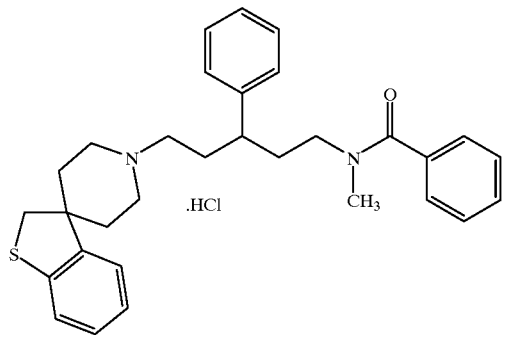

N-Methyl-N-(3-phenyl-5-(spiro(benzo[b]thiophene-3(2H),4'-piperidin)-1'-yl)pentyl)benzamide hydrochloride Step A: N-(5-Hydroxy-3-phenylpentyl)-N-methylbenzamide N,N-Diisopropylethylamine (0.352 mL, 261 mg, 2.02 mmol) and 5-(methylamino)-3-phenylpentan-1-ol (300 mg, 1.68 mmol) from Example 180, Step B, were dissolved in 4.0 mL of dichloromethane. The solution was cooled to 0° C., benzoyl chloride (0.205 mL, 248 mg, 1.77 mmol) was added dropwise, and the mixture was stirred for an additional 30 min. The mixture was then partitioned between 15 mL of dichloromethane and 15 mL of saturated aqueous sodium bicarbonate solution. The aqueous layer was extracted with 2×15 mL of dichloromethane. The combined organic extracts were washed with 20 mL of brine, dried over sodium sulfate, and evaporated. The crude product was purified by flash column chromatography on silica gel, eluting with 10% ethyl acetate in dichloromethane, to give 467 mg of the title compound. ¹NMR (400 MHz, CD₃OD) was complicated by the presence of a mixture of rotamers: δ 7.45–7.06 (m, 9H), 6.97 (d, 1H, J=8 Hz), 3.53–3.23 (m, 2H), 3.17–3.00 (m, 2H), 3.02 and 2.85 (two singlets, 3H), 2.88–2.78 and 2.57–2.49 (two multiplets, 1H), 2.07–1.64 (m, 4H). Mass spectrum (ESI): m/z=298 (M+1).
Step B: N-Methyl-N-(3-phenyl-5-(spiro(benzo[b]thiophene-3(2H),4'-piperidin)-1'-yl)pentyl)benzamide hydrochloride The free base corresponding to the title compound was prepared according to the procedure of Example 177, Step B, replacing N-(2-hydroxy-2-phenylethyl)-N-methylbenzenesulfonamide with N-(5-hydroxy-3-phenylpentyl)-N-methylbenzamide. Ethyl acetate was replaced by dichloromethane as the solvent for preparation of the methanesulfonate ester intermediate, and DMF was replaced by isobutyronitrile in the subsequent displacement reaction. ¹NMR (400 MHz, CD₃OD) was complicated by the presence of a mixture of rotamers: δ 7.46–6.95 (m, 14H), 3.53–3.44 and 3.39–3.29 (two multiplets, 1H), 3.27 and 3.25 (two singlets, 2H), 3.15–3.05 (m, 1H), 3.02 and 2.86 (two singlets, 3H), 2.97–2.65 (m, 3H), 2.46–2.35 (m, 1H), 2.32–1.97 (m, 5H), 1.95–1.71 (m, 6H). Mass spectrum (ESI): m/z=485 (M+1).

The free base was dissolved in 95% ethanol and treated with a small excess of aqueous HCl. Removal of the solvent at reduced pressure gave the title compound: ¹NMR (400 MHz, CD₃OD) was complicated by the presence of a mixture of rotamers: δ 7.49–7.01 (m, 14H), 3.56–3.43 (m, 2H), 3.38 and 3.36 (two singlets, 2H), 3.24–3.00 (m, 5H), 3.04 and 2.88 (two singlets, 3H), 2.92–2.66 (m, 2H), 2.52–2.42 and 2.37–2.26 (two multiplets, 1H), 2.19–1.84 (m, 8H).

EXAMPLE 184

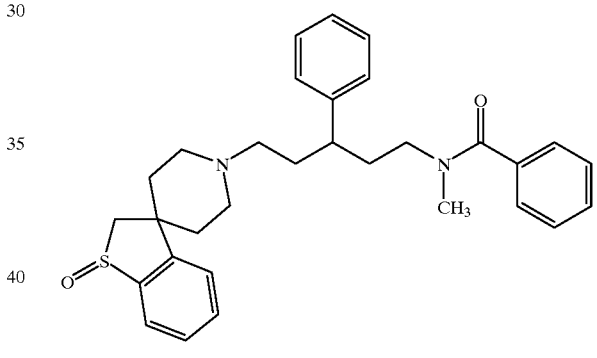

N-Methyl-N-(3-phenyl-5-(spiro(benzo[b] thiophene-3(2H),4'-piperidin)-1-oxide-1'-yl)pentyl)benzamide The title compound was prepared according to the procedure of Example 175, replacing N-(2-(3-chlorophenyl)-5-(spiro(benzo[b] thiophene-3(2H) ,4'-piperidin)-1'-yl) pentyl)-N-methylbenzenesulfonamide with N-methyl-N-(3-phenyl-5-(spiro(benzo[b]thiophene-3(2H),4'-piperidin)-1'yl)pentyl)benzamide. ¹NMR (400 MHz, CD₃OD) was complicated by the presence of a mixture of rotamers: δ 7.87 (d, 1H, J=7 Hz), 7.68 (t, 1H, J=7 Hz), 7.58–7.51 (m, 2H), 7.48–7.09 (m, 9H), 7.01 (d, 1H, J=7 Hz), 3.53–3.26 (m, 3H), 3.17–2.94 (m, 2H), 3.03 and 2.86 (two singlets, 3H), 2.92–2.83 and 2.76–2.67 (two multiplets, 1H), 2.50–1.70 (m, 12H), 1.56–1.45 (m, 1H). Mass spectrum (ESI): m/z= 501 (M+1).

EXAMPLE 185

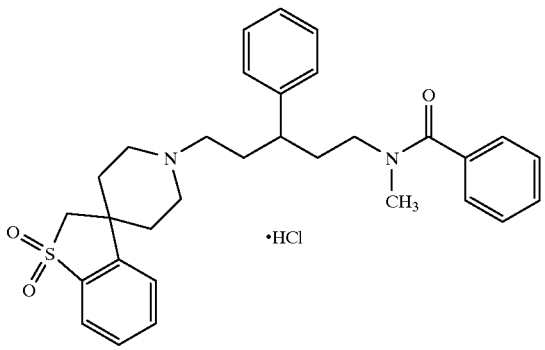

N-Methyl-N-(3-phenyl-5-(spiro(benzo[b]thiophene-3(2),4'-piperidin)-1,1-dioxide-1'-yl)pentyl)benzamide hydrochloride The free base corresponding to the title compound was prepared according to the procedure of Example 176 replacing N-(2-(3-chlorophenyl)-5-(spiro(benzo[b]thiophene-3(2H),4'-piperidin)-1'-yl)pentyl)-N-methylbenzenesulfonamide with N-methyl-N-(3-phenyl-5-(spiro(benzo [b]thiophene-3(2H),4'-piperidin)-1'-yl)pentyl)benzamide. $^1$NMR (400 MHz, CD$_3$OD) was complicated by the presence of a mixture of rotamers: δ 7.72 (t, 1H, J=8 Hz), 7.66 (d, 1H, J=8 Hz), 7.61 (d, 1H, J=8 Hz), 7.55 (t, 1H, J=8 Hz), 7.46–7.08 (m, 7H), 7.00 (d, 1H, J=8 Hz), 3.51 and 3.49 (two singlets, 2H), 3.53–3.44 and 3.40–3.33 (two multiplets, 1H), 3.16–2.94 (m, 3H), 3.03 and 2.86 (two singlets, 3H), 2.76–2.66 (m, 1H), 2.46–2.35 (m, 1H), 2.32–1.96 (m, 6H), 1.93–1.69 (m, 4H). Mass spectrum (ESI): m/z=517 (M+1).

The free base was dissolved in 95% ethanol and treated with a small excess of aqueous HCl. Removal of the solvent at reduced pressure gave the title compound. $^1$NMR (400 MHz, CD$_3$OD) was complicated by the presence of a mixture of rotamers: δ 7.79–7.00 (m, 14H), 3.71–3.43 (m, 4H), 3.24–3.03 (m, 5H), 3.05 and 2.88 (two singlets, 3H), 2.80–2.69 and 2.54–2.43 (two multiplets, 1H), 2.43–2.28 (m, 3H), 2.18–2.00 (m, 6H).

EXAMPLE 186

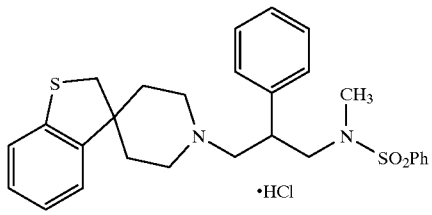

N-Methyl-N-(2-phenyl-3-(spiro(benzo[b]thiophene-3(2H),4'-piperidin)-1'-yl)propyl)benzenesulfonamide hydrochloride Step A: 2-Phenyl-3-(tert-butyldimethylsilyloxy)-1-propanol Sodium hydride (60% dispersion in mineral oil, 525 mg, 13 mmol) was added to a round bottom flask and washed with 3×5 mL of dry hexane. Dry THF (25 mL) was then added, followed by 2-phenyl-1,3-propanediol (2.0 g, 13 mmol). Another 25 mL of dry THF was added to facilitate stirring of the resulting thick suspension. After 45 min., tert-butyldimethylsilyl chloride was added in one portion. After stirring for 2 h, the mixture was partitioned between 100 mL of ethyl ether and 60 mL of 10% aqueous potassium carbonate. The aqueous layer was extracted with 2×30 mL of ethyl ether. The combined organic layers were washed with 40 mL of brine, dried over sodium sulfate, and evaporated. Purification by flash column chromatography, eluting with 10% ethyl acetate in hexane, gave the 3.36 g of the title compound as a colorless liquid. $^1$NMR (400 MHz,CD$_3$OD): δ 7.30–7.16(m, 5H), 3.90 (dd, 1H, J=11, 7 Hz), 3.88 (dd, 1H, J=10, 6 Hz), 3.83 (dd, 1H, J=10, 6 Hz), 3.76 (dd, 1H, J=11, 7 Hz), 2.91 (quintet, 1H, J=6 Hz), 0.84 (s, 9H),–0.04 (s, 3H),–0.05 (s, 3H). Mass spectrum (NH$_3$/Cl): m/z=267 (M+1).

Step B: N-(3-(tert-butyldimethylsilyloxy)-2-phenylpropyl)-N-methylbenzenesulfonamide Diethyl azodicarboxylate (0.059 mL, 65 mg, 0.37 mmol) was added to a solution of 2-phenyl-3-(tert-butyldimethylsilyloxy)-1-propanol (100 mg, 0.375 mmol), N-methylbenzenesulfonamide (77 mg, 0.45 mmol), and triphenylphosphine (98.4 mg, 0.38 mmol) in 1.0 mL of dry THEF, and the mixture was stirred 4 h at room temperature. Additional triphenylphosphine (48 mg, 0.18 mmol) and diethyl azodicarboxylate (0.030 mL, 33 mg, 0.19 mmol) were added and stirring was continued overnight at room temperature. After concentrating in vacuo, the residue was dissolved in 50 mL of dichloromethane and washed with 25 mL of 10% aqueous sodium hydroxide and 25 mL of brine. The organic layer was dried over sodium sulfate, decanted, and concentrated. The residue was purified by flash column chromatography on silica gel, eluting with 5% ethyl ether in hexane to give 83 mg of the title compound as a colorless syrup. $^1$NMR (400 MHz, CDCl$_3$): δ 7.73 (d, 2H, J=7 Hz), 7.57 (tt, 1H, J=7, 1 Hz), 7.49 (t, 2H, J=7 Hz), 7.33–7.20 (m, 5H), 3.84 (dd, 1H, J=10, 6 Hz), 3.77 (dd, 1H, J=10, 6 Hz), 3.48 (dd, 1H, J=13, 7 Hz), 3.20 (dd, 1H, J=13, 8 Hz), 3.08 (quintet, 1H, J=7 Hz), 2.64 (s, 3H), 0.84 (s, 9H),–0.05 (s, 3H),–0.06 (s, 3H). Mass spectrum (ESI): m/z=420 (M+1).

Step C: N-(3-Hydroxy-2-phenylpropyl)-N-methylbenzenesulfonamide

A THF solution of tetrabutylammonium fluoride (1.0 M, 3.9 mL, 3.9 mmol) was added to dropwise to a solution of N-(3-(tert-butyldimethylsilyloxy)-2-phenylpropyl)-N-methylbenzenesulfonamide (570 mg, 1.31 mmol) in 5.0 mL of THF. After stirring for 30 min at room temperature, the mixture was diluted with 50 mL of ethyl acetate and washed in sucession with 30 mL of 2.0 N aqueous HCl, 30 mL of saturated aqueous sodium bicarbonate, and 30 mL of brine. The organic layer was dried over sodium sulfate, decanted and concentrated. The residue was purified by flash column chromatography on silica gel, eluting with 20–30% of ethyl acetate in hexanes to give 393 mg of the title compound as a colorless syrup. $^1$NMR (400 MHz, CD$_3$OD): δ 7.74 (d, 2H, J=7 Hz), 7.64 (tt, 1H, J=7, 1 Hz), 7.56 (t, 2H, J=7 Hz), 7.33–7.20 (m, 5H), 3.79–3.71 (m, 2H), 3.41 (dd, 1H, J=13, 7 Hz), 3.24 (dd, 1H, J=13, 8 Hz), 3.13–3.04 (m, 1H), 2.58 (s, 3H).

Step D: N-Methyl-N-(2-phenyl-3-(spiro(benzo[b]thiophene-3(2H),4'-piperidin)-1'-yl)propyl)benzenesulfonamide hydrochloride The free base corresponding to the title compound was prepared according to the procedure of Example 177, Step B, replacing N-(2-hydroxy-2-phenylethyl)-N-methylbenzenesulfonamide with N-(3-hydroxy-2- phenylpropyl)-N-methylbenzenesulfonamide, and replacing DMF with isobutyronitrile. ¹NMR (400 MHz, CDCl₃): δ 7.72 (d, 2H, J=7 Hz), 7.55 (tt, 1H, J=7, 1 Hz), 7.48 (t, 2H, J=7 Hz), 7.30 (t, 2H, J=7 Hz), 7.24–7.00 (m, 7H), 3.67 (dd, 1H, J=14, 6 Hz), 3.23 (s, 2H), 3.17 (quintet, 1H, J=7 Hz), 2.98–2.88 (m, 2H), 2.82–2.69 (m, 2H), 2.59–2.50 (m, 1H), 2.54 (s, 3H), 2.21 (td, 1H, J=12, 3 Hz), 2.06 (td, 1H, J=12, 3 Hz), 1.90–1.74 (m, 4H). Mass spectrum (ESI): m/z=493 (M+1).

The free base was dissolved in 95% ethanol and treated with a small excess of aqueous HCl. Removal of the solvent at reduced pressure gave the title compound. ¹NMR (400 MHz, CD₃OD): δ 7.80 (d, 2H, J=7 Hz), 7.66 (tt, 1H, J=7, 1 Hz), 7.59 (t, 2H, J=7 Hz), 7.50–7.34 (m, 5H), 7.20–7.12 (m, 2H), 7.11–7.06 (m, 2H), 3.78–3.68 (m, 3H), 3.66–3.39 (m, 3H), 3.41 (s, 2H), 3.34–3.16 (m, 2H), 3.95 (dd, 1H, J=14, 6 Hz), 2.68 (s, 3H), 2.21–2.08 (m, 3H), 2.00 (bd, 1H, J=15 Hz).

EXAMPLE 187

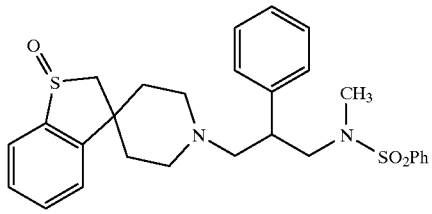

N-Methyl-N-(2-phenyl-3-(spiro(benzo[b]thiophene-3(2H),4'-piperidin)-1-oxide-1-yl)propyl)benzenesulfonamide The title compound was prepared according to the procedure of Example 175, replacing N-(2-(3-chlorophenyl)-5-(spiro(benzo[b]thiophene-3(2H),4'-piperidin)-1'-yl)pentyl)-N-methylbenzenesulfonamide with N-methyl-N-(2-phenyl-3-(spiro(benzo[b]thiophene-3(2H),4'-piperidin)-1'-yl)propyl)benzenesulfonamide. ¹NMR (400 MHz, CD₃OD) showed a 1:1 mixture of diastereomers: δ 7.86 (d, 1H, J=8 Hz), 7.79–7.73 (m, 2H), 7.70–7.62 (m, 2H), 7.61–7.50 (m, 4H), 7.35–7.21 (m, 5H), 3.58 (m, 1H), 3.44 (d, 1H, J=14 Hz), 3.33 (d, 1H, J=14 Hz), 3.26 (quintet, 1H, J=7 Hz), 3.08–2.91 (m, 3H), 2.82 (m, 1H), 2.67 (m, 1H), 2.58 and 2.57 (two singlets, 3H), 2.37 (td, 1H, J=13, 3 Hz), 2.34–2.17 (m, 2H), 2.12–1.94(m, 2H), 1.48 (bd, 1H, J=12 Hz). Mass spectrum (ESI): m/z=509 (M+1).

EXAMPLE 188

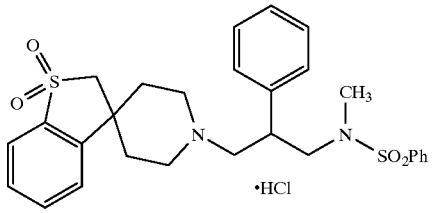

N-Methyl-N-(2-phenyl-3-(spiro(benzo[b]thiophene-3(2H),4'-piperidin)-1,1-dioxide-1-yl)propyl)benzenesulfonamide hydrochloride The free base corresponding to the title compound was prepared according to the procedure of Example 176 replacing N-2-(3-chlorophenyl)-5-(spiro(benzo[b]thiophene-3(2H),4'-piperidin)-1'-yl)pentyl)-N-methylbenzenesulfonamide with N-methyl-N-(2-phenyl-3-(spiro(benzo[b]thiophene-3(2H),4'-piperidin)-1'-yl)propyl)benzene-sulfonamide. ¹NMR (400 MHz, CDCl₃): δ 7.4 (d, 2H, J=8 Hz), 7.71 (d, 1H, J=8 Hz), 7.64 (t, 1H, J=7 Hz), 7.59 (tt, 1H, J=7, 1 Hz), 7.55–7.46 (m, 4H), 7.36–7.19 (m, 5H), 3.71 (dd, 1H, J=13, 6 Hz), 3.39 (s, 2H), 3.17 (quintet, 1H, J=7 Hz), 3.04–2.87 (m, 3H), 2.79 (dd, 1H, J=13, 8 Hz), 2.62 (dd, 1H, J=13, 7 Hz), 2.56 (s, 3H), 2.22–2.01 (m, 4H), 1.78 (d, 2H, J=13 Hz). Mass spectrum (ESI): m/z=525 (M+1).

The free base was dissolved in 95% ethanol and treated with a small excess of aqueous HCl1. Removal of the solvent at reduced pressure gave the title compound. ¹NMR (400 MHz, CD₃OD): δ 7.84–7.71 (m, 4H), 7.69–7.55 (m, 5H), 7.48–7.35 (m, 5H), 3.85–3.49 (m, 6H), 3.70 (s, 2H), 3.37–3.15 (m, 2H), 2.96 (dd, 1H, J=14, 6 Hz), 2.68 (s, 3H), 2.49–2.34 (m, 2H), 2.12 (bd, 1H, J=15), 2.02 (bd, 1H, J=14 Hz).

EXAMPLE 189

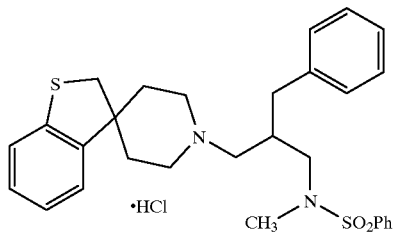

N-(2-Benzyl-3-(spiro(benzo[b]thiophene-3(2H),4'-piperidin)-1'-yl)propyl)-N-methylbenzenesulfonamide hydrochloride The free base corresponding to the title compound was prepared according to the procedures of Example 186, Steps A–D, replacing 2-phenyl-1,3-propanediol with 2-benzyl-1,3-propanediol. In Step D, ethyl acetate was replaced by dichloromethane as the solvent for preparation of the methanesulfonate ester intermediate. ¹NMR (400 MHz, CD₃OD): δ 7.81 (d, 2H, J=7 Hz), 7.72 (tt, 1H, J=7, 1 Hz), 7.65 (t, 2H, J=7 Hz), 7.34 (t, 2H, J=7 Hz), 7.30–7.21 (m, 3H), 7.19–7.07 (m, 4H), 3.25 (s, 2H), 2.99 (dd, 1H, J=13, 6 Hz), 2.90–2.78 (m, 3H), 2.78 (dd, 1H, J=14, 6 Hz), 2.71 (s, 3H), 2.66 (dd, 1H, J=14, 7 Hz), 2.42–2.24 (m, 3H), 2.15 (td, J=12, 2 Hz), 2.05 (td, 1H, J=12, 2 Hz), 2.05 (td, 1H, J=13, 2 Hz), 1.92–1.82 (m, 2H), 1.76 (d, 2H, J=14 Hz). Mass spectrum (EI): m/z=506 (M+).

The free base was dissolved in 95% ethanol and treated with a small excess of aqueous HCl. Removal of the solvent at reduced pressure gave the title compound. ¹NMR (400 MHz, CD₃OD): δ 7.73 (d, 2H, J=7 Hz), 7.68 (tt, 1H, J=7, 1 Hz), 7.59 (t, 2H, J=7 Hz), 7.34 (t, 2H, J=7 Hz), 7.31–7.24 (3, 3H), 7.22–7.09 (m, 4H), 3.76 (bd, 1H, J=12 Hz), 3.67 (bd, 1H, J=12 Hz), 3.50 (dd, 1H, J=13, 6 Hz), 3.46 (d, 1H, J=11 Hz), 3.42 (d, 1H, J=11 Hz), 3.36–3.13 (m, 4H), 2.98–2.90 (m, 1H), 2.85 (dd, 1H, J=14, 3 Hz), 2.72 (s, 3H), 2.77–2.64 (m, 2H), 2.34–2.22 (m, 2H), 2.20–2.08 (m, 2H).

EXAMPLE 190

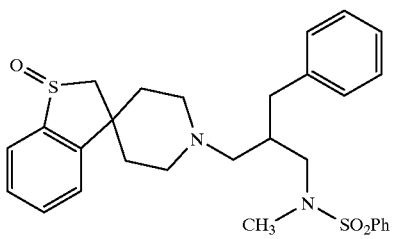

N-(2-Benzyl-3-(spiro(benzo[b]thiophene-3(2H), 4'-piperidin)-1-oxide-1'-yl)propyl)-N-methylbenzenesulfonamide The title compound was prepared according to the procedure of Example 175, replacing N-(2-(3-chlorophenyl)-5-(spiro(benzo[b]thiophene-3(2H),4'-piperidin)-1'-yl)pentyl)-N-methylbenzenesulfonamide with N-(2-benzyl-3-(spiro (benzo[b]-thiophene-3(2H),4'-piperidin)-1'-yl)propyl)-N-methylbenzene-sulfonamide. $^1$NMR (400 MHz, CD$_3$OD): δ 7.86 (d, 1H, J=7 Hz), 7.78–7.72 (m, 2H), 7.70–7.63 (m, 2H), 7.62–7.50 (m, 4H), 7.31–7.15 (m, 5H), 3.41 (dd, 1H, J=14, 3 Hz), 3.34–3.27 (m, 1H), 3.00 (td, 1H, J=13, 6 Hz), 2.95–2.84 (m, 3H), 2.82–2.75 (m, 1H), 2.72 and 2.71 (two singlets, 3H), 2.71–2.63 (m, 1H), 2.47–2.38 (m, 1H), 2.35–1.93 (m, 7H), 1.47 (bd, 1H, J=11 Hz). Mass spectrum (EI): m/z=522 (M+).

EXAMPLE 191

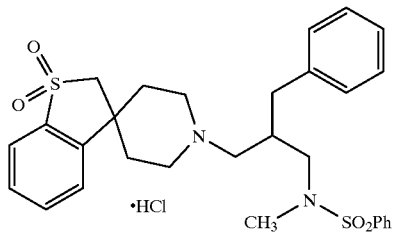

N-(2-Benzyl-3-(spiro(benzo[b]thiophene-3(2H),4'-piperidin)-1,1-dioxide-1'-yl)propyl)-N-methylbenzenesulfonamide hydrochloride The free base corresponding to the title compound was prepared according to the procedure of Example 176 replacing N-(2-(3-chlorophenyl)-5-(spiro(benzo[b]thiophene-3 (2H),4'-piperidin)-1'-yl)pentyl)-N-methylbenzenesulfonamide with N-(2-benzyl-3-(spiro (benzo[b]thiophene-3(2H),4'-piperidin)-1'-yl)propyl)-N-methylbenzenesulfonamide. $^1$NMR (400 MHz, CD$_3$OD): δ 7.76–7.51 (m, 9H), 7.27 (t, 2H, J=7 Hz), 7.24–7.15 (m, 3H), 3.49 (s, 2H), 3.00 (dd, 1H, J=14, 6 Hz), 2.96–2.88 (m, 2H), 2.87 (dd, 1H, J=14, 6 Hz), 2.78 (dd, 1H, J=14, 6 Hz), 2.71 (s, 3H), 2.67 (dd, 1H, J=14, 7 Hz), 2.46–2.38 (m, 1H), 2.35–2.26 (m, 2H), 2.19–2.02 (m, 4H), 1.75 (d, 2H, J=12 Hz). Mass spectrum (EI): m/z=538 (M+).

The free base was dissolved in 95% ethanol and treated with a small excess of aqueous HCl. Removal of the solvent at reduced pressure gave the title compound. $^1$NMR (400 MHz, CD$_3$OD): δ 7.82–7.56 (m, 9H), 7.37–7.23 (m, 5H), 3.84 (d, 1H, J=12 Hz), 3.78–3.59 (m, 3H), 3.52 (bd, 1H, J=13 Hz), 3.35–3.13 (m, 3H), 3.03–2.95 (m, 1H), 2.88 (dd, 1H, J=14, 3 Hz), 2.77–2.56 (m, 5H), 2.72 (s, 3H), 2.20–2.09 (m, 2H).

EXAMPLE 192

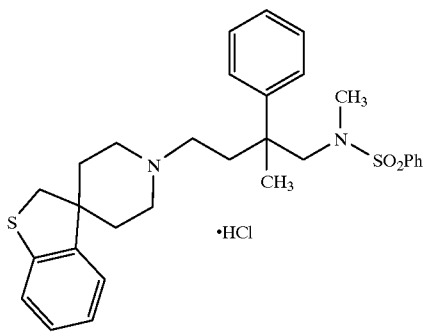

N-Methyl-N-(2-methyl-2-phenyl-4-(spiro(benzo[b] thiophene-3(2H),4'-piperidin)-1'-yl)butyl) benzenesulfonamide hydrochloride Step A: N-Methyl-(2,5-dimethyl-2-phenylhex-4-enyl)amine Methylamine hydrochloride (500 mg, 7.41 mmol), triethylamine (1.00 mL, 725 mg, 7.17 mmol), and 3 Å molecular sieve pellets (1.05 g) were added to a stirred solution of 2,5-dimethyl-2-phenylhex-4-enal (500 mg, 2.47 mmol) in 5.0 mL of methanol at room temperature. After 1 h, the mixture was cooled in an ice bath and acetic acid (0.29 mL, 0.30 g, 5.1 mmol) was added followed by sodium cyanoborohydride (310 mg, 4.93 mmol). The mixture was allowed to slowly come to room temperature and stirred 16 h before being diluted with ethyl acetate (50 mL) and washed with saturated aqueous sodium bicarbonate (30 mL) and saturated aqueous sodium chloride (30 mL). The aqueous layers were extracted with ethyl acetate (30 mL) and the combined organic layers were dried over sodium sulfate, decanted, and evaporated. The residue was purified by flash column chromatography on silica gel, eluting with 5% methanol in ethyl acetate to give 415 mg the title compound. $^1$H NMR (400 MHz, CD$_3$OD): δ 7.36–7.28 (m, 4H), 7.18 (t, 1H, J=7 Hz), 4.88 (t, 1H, J=7.5 Hz), 2.87 (d, 1H, J=12 Hz), 2.66 (d, 1H, J=12 Hz), 2.39 (dd, 1H, J=14, 7.5 Hz), 2.30 (dd, 1H, J=14, 8 Hz), 2.27 (s, 3H), 1.59 (s, 3H), 1.54 (s, 3H), 1.34 (s, 3H). Mass spectrum (NH$_3$/CI): m/z=218 (M+1).

Step B: N-Methyl-N-(2,5-dimethyl-2-phenylhex-4-en-1-yl) benzenesulfonamide

The title compound was prepared according to the procedure of Example 177, Step A, replacing α-(methylaminomethyl)benzyl alcohol with N-methyl-(2,5-dimethyl-2-phenylhex-4-enyl)amine. $^1$H NMR (400 MHz, CDCl$_3$): δ 7.72 (d, 2H, J=7.5 Hz), 7.55 (t, 1H, J=7.5 Hz), 7.48 (t, 2H, J=7.5 Hz), 7.33–7.23 (m, 4H), 7.17 (t, 1H, J=7 Hz), 4.83 (bt, 1H, J=7 Hz), 3.40 (d, 1H, J=13 Hz), 2.94 (d, 1H, J=13 Hz), 2.50 (dd, 1H, J=15, 6 Hz), 2.33 (dd, 1H, J=15, 8 Hz), 2.09 (s, 3H), 1.59 (s, 6H), 1.42 (s, 3H). Mass spectrum (NH$_3$/CI): m/z=$358$ (M+1).

Step C: N-Methyl-N-(2-methyl-2-phenyl-4-oxobut-1-yl) benzenesulfonamide

To a solution of N-methyl-N-(2,5-dimethyl-2-phenylhex-4-en-1-yl)benzenesulfonamide (300 mg, 0.839 mmol) in 6.0 mL of acetone, 3.0 mL of t-butanol and 1.5 mL of water was added 0.145 mL (118 mg, 0.012 mmol) of 2.5% osmium tetroxide in t-butanol followed by 433 mg (3.70 mmol) of N-methylmorpholine-N-oxide. The reaction was stirred at room temperature for 18 h and was then quenched with 3 g of aqueous sodium bisulfite and concentrated in vacuo. The residue was partitioned between dichloromethane (20 mL) and water (10 mL). The aqueous layer was extracted with dichloromethane (2×20 mL) and the combined organic layers were dried over sodium sulfate, decanted, and evaporated to give the diol intermediate.

The diol intermediate was dissolved in 9.0 mL of THF and 3.0 mL of water, and treated with 323 mg (1.51 mmol) of sodium periodate. After 2 h, additional sodium periodate (150 mg, 0.70 mmol) was added and the mixture was stirred 1 h longer. Most of the THF was removed in vacuo and the residue was patitioned between ethyl acetate (20 mL) and water (10 mL). The aqueous layer was extracted with ethyl acetate (2×20 mL) and the combined organic layers were dried (sodium sulfate), decanted, and evaporated. The residue was dissolved in 9.0 mL of THF and 3.0 mL of water, and sodium periodate (450 mg, 2.1 mmol) was added in three equal portions at 1.5 h intervals. The mixture was stirred for 1.5 h after the addition of the last portion, and then worked up as before. Flash column chromatography on silica gel, eluting with 20% ethyl acetate in hexane gave 210 mg of the title compound as a colorless syrup. $^1$H NMR (400 MHz, CDCl$_3$): δ 9.62 (t, 1H, J=2.5 Hz), 7.74 (d, 2H, J=7.5 Hz), 7.59 (t, 1H, J=7.5 Hz), 7.52 (t, 2H, J=7.5 Hz), 7.40–7.32 (m, 4H), 7.28–7.23 (m, 1H), 3.23 (d, 1H, J=13 Hz), 3.19 (dd, 1H, J=16, 2.5 Hz), 3.15 (d, 1H, J=13 Hz), 2.78 (dd, 1H, J=16, 2.5 Hz), 2.21 (s, 3H), 1.64 (s, 3H). Mass spectrum (ESI): m/z=332 (M+1).

Step D: N-Methyl-N-(2-methyl-2-phenyl-4-(spiro(benzo[b]-thiophene-3(2H),4'-piperidin)-1'-yl)butyl)benzenesulfonamide hydrochloride N-Methyl-N-(2-methyl-2-phenyl-4-oxobut-1-yl)benzenesulfonamide (100 mg, 0.302 mmol), spiro(benzo[b]thiophene-3(2H),4'-piperidine) hydrochloride (109 mg, 0.451 mmol), and N,N-diisopropylethylamine (0.084 mL, 62 mg, 0.48 mmol) were combined in 3.0 mL of THF with 3 Å molecular sieve pellets (0.30 g). After 20 minutes, sodium triacetoxyborohydride (127 mg, 0.60 mmol) was added and the mixture was stirred at room temperature for 1.5 h. The reaction was partitioned between 25 mL of ethyl acetate and 15 mL of saturated aqueous sodium bicarbonate, and the aqueous layer was extracted with 2×25 mL of ethyl acetate. The combined organic layers were dried over sodium sulfate and evaporated. The residue was purified by preparative TLC, eluting with 5% methanol in dichloromethane, to give 95 mg of the free base corresponding to the title compound. $^1$NMR (400 MHz, CD$_3$OD): δ 7.76 (d, 2H, J=7 Hz), 7.64 (t, 1H, J=7 Hz), 7.57 (t, 2H, J=7 Hz), 7.42 (d, 2H, J=7 Hz), 7.34 (t, 2H, J=7 Hz), 7.22 (t, 1H, J=7 Hz), 7.15–7.02 (m, 4H), 3.41 (d, 1H, J=14 Hz), 3.33–3.22 (m, 3H), 3.03 (d, 1H, J=14 Hz), 3.03–2.88 (m, 2H), 2.50–2.40 (m, 1H), 2.33–2.05 (m, 3H), 2.12 (s, 3H), 1.97–1.76 (m, 5H), 1.50 (s, 3H). Mass spectrum (ESI): m/z=521 (M+1).

The free base was dissolved in 95% ethanol and treated with a small excess of aqueous HCl. Removal of the solvent at reduced pressure gave the title compound. $^1$NMR (400 MHz, CD$_3$OD): δ 7.79 (d, 2H, J=7 Hz), 7.66 (tt, 1H, J=7, 1 Hz), 7.59 (t, 2H, J=7 Hz), 7.46 (d, 2H, J=7 Hz), 7.40 (t, 2H, J=7 Hz), 7.28 (t, 1H, J=7 Hz), 7.21–7.08 (m, 4H), 3.67–3.57 (m, 2H), 3.40 (s, 2H), 3.35 (d, 1H, J=14 Hz), 3.28–3.10 (m, 3H), 3.16 (d, 1H, J=14 Hz), 2.86 (td, 1H, J=13,4 Hz), 2.58 (td, 1H, J=13,4 Hz), 2.25–2.06 (m, 5H), 2.18 (s, 3H), 1.52 (s, 3H).

EXAMPLE 193

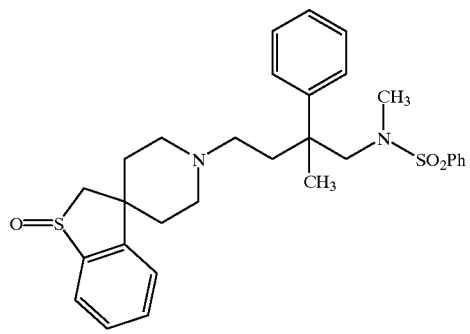

N-Methyl-N-(2-methyl-2-phenyl-4-(spiro(benzo[b]thiophene-3(2H), 4'-piperidin)-1-oxide-1'-yl)butyl)benzenesulfonamide The title compound was prepared according to the procedure of Example 175, replacing N-(2-(3-chlorophenyl)-5-(spiro(benzo[b]thiophene-3(2H),4'-piperidin)-1'-yl)pentyl)-N-methylbenzenesulfonamide with N-methyl-N-(2-methyl-2-phenyl-4-(spiro(benzo[b]thiophene-3(2H),4'-piperidin)-1'-yl)butyl)benzenesulfonamide. $^1$NMR (400 MHz, CD$_3$OD): δ 7.87 (d, 1H, J=7 Hz), 7.76 (d, 2H, J=7 Hz), 7.69 (t, 1H, J=7 Hz), 7.64 (tt, 1H, J=7 Hz), 7.61–7.52 (m, 4H), 7.43 (d, 2H, J=7 Hz), 7.35 (t, 2H, J=7 Hz), 7.23 (t, 1H, J=7 Hz), 3.47–3.40 (m, 2H), 3.35–3.30 (m, 1H), 3.08–2.94 (m, 3H), 2.48 (td, 1H, J=12, 4 Hz), 2.40–1.99 (m, 7H), 2.12 (s, 3H), 1.88 (td, 1H, J=12, 5 Hz), 1.57–1.48 (m, 1H), 1.51 (s, 3H). Mass spectrum (ESI): m/z=537 (M+1).

EXAMPLE 194

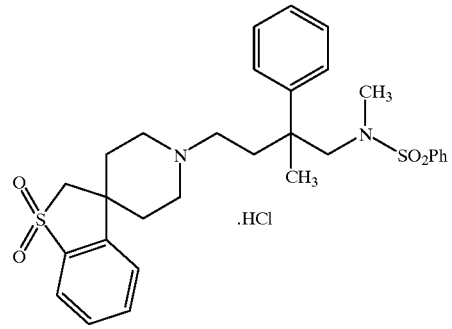

N-Methyl-N-(2-methyl-2-phenyl-4-(spiro(benzo[b]thiophene-3(2H),4'-piperidin)-1,1-dioxide-1'-yl)butyl)benzenesulfonamide hydrochloride The free base corresponding to the title compound was prepared according to the procedure of Example 176 replacing N-2-(3-chlorophenyl)-5-(spiro(benzo[b]thiophene-3(2H),4'-piperidin)-1'-yl)pentyl)-N-methylbenzenesulfonamide with N-methyl-N-(2-methyl-2-phenyl-4-(spiro(benzo[b]thiophene-3(2H),4'-piperidin)-1'-yl)butyl)benzenesulfonamide. $^1$NMR (400 MHz, CD$_3$OD): δ 7.78–7.53 (m, 9H), 7.42 (d, 2H, J=7 Hz), 7.34 (t, 2H, J=7 Hz), 7.21 (t, 1H, J=7 Hz), 3.52 (s, 2H), 3.42 (d, 1H, J=14 Hz), 3.04–2.94 (m, 2H), 3.03 (d, 1H, J=14 Hz), 2.44 (td, 1H, J=12, 5 Hz), 2.28 (td, 1H, J=12, 4 Hz), 2.25–2.06 (m, 5H), 2.12 (s, 3H), 1.91–1.74 (m, 3H), 1.50 (s, 3H). Mass spectrum (ESI): m/z=553 (M+1).

The free base was dissolved in 95% ethanol and treated with a small excess of aqueous HCl. Removal of the solvent at reduced pressure gave the title compound. $^1$NMR (400 MHz, CD$_3$OD): δ 7.82–7.56 (m, 9Hz), 7.47 (d, 2H, J=7 Hz), 7.40 (t, 2H, J=7 Hz), 7.29 (t, 1H, J=7 Hz), 3.75–3.66 (m, 2H), 3.69 (s, 2H), 3.36 (d, 1H, J=14 Hz), 3.30–3.10 (m, 4H), 2.87 (td, 1H, J=13,4 Hz), 2.60 (td, 1H, J=13,4 Hz), 2.51–2.40 (m, 2H), 2.27–2.07 (m, 3H), 2.18 (s, 3H), 1.53 (s, 3H).

Examples 195–198 were prepared from 1'-(3-((S)-(3,4-dichlorophenyl))-4-(methylamino)butyl)-1-methanesulfonyl-spiro(2,3 -dihydrobenzothiophene-3,4'-piperidine) by analogy to Example 3, Step 3, using commerically available sulfonylating agents. The intermediate 1'-(3-((S)-(3,4-dichlorophenyl))-4-(methylamino) butyl)-1-methanesulfonyl-spiro(2,3-dihydrobenzothiophene-3,4'-piperidine) was prepared from 1'-(3-(S)-(3,4-dichlorophenyl)-4-(N-(t-butoxycarbonyl) (methylamino))butyl)-1-methanesulfonyl-spiro(2,3-dihydrobenzothiophene-3,4'-piperidine) according to the procedure given in Example 3, step A. 1'-(3-(S)-(3,4-dichlorophenyl)-4-(N-(t-butoxycarbonyl)(methylamino)) butyl)-1-methanesulfonyl-spiro(2,3-dihydrobenzothiophene-3,4'-piperidine) was prepared according to the procedures given in Hale, J. J.; Finke, P. E.; MacCoss, M. *Bioorganic & Medicinal Chemistry Letters* 1993,3, 319–322.

EXAMPLE 195

1'-(3-((S)-(3,4-Dichlorophenyl))-4-(N-(phenylmethylsulfonyl) (methylamino))-butyl)-spiro(2,3-dihydrobenzothiophene-3,4'-piperidine)

Mass spectrum (ESI): m/z=589.3 ($^{35}$Cl+$^{35}$Cl isotope+H$^+$), 591.3 ($^{37}$Cl+$^{35}$Cl isotope+H$^+$).

EXAMPLE 196

1'-(3-((S)-(3,4-Dichlorophenyl))-4-(N-(quinoline-8-sulfonyl) (methylamino))-butyl)-spiro(2.3-dihydrobenzothiophene-3,4'-piperidine)

Mass spectrum (ESI): m/z=626.3 ($^{35}$Cl+$^{35}$Cl isotope+H$^+$), 628.3 ($^{37}$Cl+$^{35}$Cl isotope+H$^+$).

EXAMPLE 197

1'-(3-((R)-(3,4-Dichlorophenyl))-4-(N-(benzenesulfonyl) (methylamino))-butyl)-spiro(2,3-dihydrobenzothiophene-3 4'-piperidine)

Mass spectrum (ESI): m/z=575.3 ($^{35}$Cl+$^{35}$Cl isotope+H$^+$), 577.3 ($^{37}$Cl+$^{35}$Cl isotope +H$^+$).

EXAMPLE 198

1'-(3-((R)-(3,4-Dichlorophenyl))-4-(N-(thiophene-2-sulfonyl) (methylamino))-butyl)-spiro(2,3-dihydrobenzothiophene-3,4'-piperidine)

Mass spectrum (ESI): m/z=581.3 ($^{35}$Cl+$^{35}$Cl isotope+H$^+$), 583.3 ($^{37}$Cl+$^{35}$Cl isotope+1H$^+$).

EXAMPLE 199

1'-(3-((S)-(3,4-Dichlorophenyl))-4-(N-(benzenesulfonyl)-(methylamino))butyl)-spiro(2,3-dihydrobenzothiophene-3,4'-piperidine)-1,1-dioxide The title compound was prepared by analogy to the procedure given in example 49, starting from 1'-(3-((R)-(3,4-Dichlorophenyl))-4-(N-(benzenesulfonyl) (methylamino))-butyl)-spiro(2,3-dihydrobenzothiophene-3,4'-piperidine). Mass spectrum (CI): m/z=607.0 ($^{35}$Cl+$^{35}$Cl isotope+H$^+$), 609.0 ($^{37}$Cl+$^{35}$Cl isotope+H$^+$).

Examples 200–209 were prepared according to the procedure given in Example 53.

EXAMPLE 200

1'-(3-((S)-(4-Chlorophenyl))-4-(N-(benzenesulfonyl)-(methylamino))-butyl)-spiro(2,3-dihydrobenzothiophene-3, 4'-piperidine)-1-oxide Mass spectrum (EI): m/z=591.2 ($^{35}$Cl+$^{35}$Cl isotope+H$^+$), 593.2 ($^{37}$Cl+$^{35}$Cl isotope+H$^+$).

EXAMPLE 201

1'-(3-((S)-(4-Chlorophenyl))-4-(N-(methanesulfonyl)-(methylamino))-butyl)-spiro(2,3-dihydrobenzothiophene-3, 4'-piperidine)-1-oxide Mass spectrum (ESI): m/z=529.2 ($^{35}$Cl+$^{35}$Cl isotope+H$^+$), 531.3 ($^{37}$Cl+$^{35}$Cl isotope+H$^+$).

EXAMPLE 202

1'-(3-((S)-(4-Chlorophenyl))-4-(N-(phenylmethylsulfonyl)-(methylamino))butyl)-spiro(2,3-dihydrobenzothiophene-3, 4'-piperidine)-1-oxide Mass spectrum (ESI): m/z=605.2 ($^{35}$Cl+$^{35}$Cl isotope+H$^+$), 607.2 ($^{37}$Cl+$^{35}$Cl isotope+H$^+$).

EXAMPLE 203

1'-(3-((S)-(4-Chlorophenyl))-4-(N-(quinoline-8-sulfonyl)-(methylamino))butyl)-spiro(2,3-dihydrobenzothiophene-3, 4'-piperidine)-1-oxide Mass spectrum (ESI): m/z=642.3 ($^{35}$Cl+$^{35}$Cl isotope+H$^+$),644.3 ($^{37}$Cl+$^{35}$Cl isotope+H$^+$).

EXAMPLE 204

1'-(3-((R)-(4-Chlorophenyl))-4-(N-(benzenesulfonyl)-(methylamino))-butyl)-spiro(2,3-dihydrobenzothiophene-3, 4'-piperidine)-1-oxide Mass spectrum (EI): m/z=591.0 ($^{35}$Cl+$^{35}$Cl isotope+H$^+$), 593.0 ($^{37}$Cl+$^{35}$Cl isotope+H$^+$).

EXAMPLE 205

1'-(3-((R)-(4-Chlorophenyl))-4-(N-(thiophene-2-sulfonyl)-(methylamino))butyl)-spiro(2,3-dihydrobenzothiophene-3, 4'-piperidine)-1-oxide Mass spectrum (EI): m/z=597.4 ($^{35}$Cl+$^{35}$Cl isotope+H$^+$), 599.1 ($^{37}$Cl+$^{35}$Cl isotope+H$^+$).

EXAMPLE 206

1'-(3-((S)-(4-Chlorophenyl))-4-(N-(quinoline-3-sulfonyl)-(methylamino))butyl)-spiro(2,3-dihydrobenzothiophene-3, 4'-piperidine)-1-oxide Mass spectrum (CI): m/z=642.0 ($^{35}$Cl+$^{35}$Cl isotope+H$^+$), 644.0 ($^{37}$Cl+$^{35}$Cl isotope+H$^+$).

EXAMPLE 207

1'-(3-((S)-(4-Chlorophenyl))-4-(N-(phenoxycarbonyl)-(methylamino))butyl)-spiro(2,3-dihydrobenzothiophene-3, 4'-piperidine)-1-oxide Mass spectrum (CI): m/z=570.9 ($^{35}$Cl+$^{35}$Cl isotope+H$^+$), 572.9 ($^{37}$Cl+$^{35}$Cl isotope+H$^+$).

EXAMPLE 208

1'-(3-((S)-(4-Chlorophenyl))-4-(N-(phenylaminocarbonyl)-(methylamino))butyl)-spiro(2,3-dihydrobenzothiophene-3, 4'-piperidine)-1-oxide Mass spectrum (CI): m/z=570.0 ($^{35}$Cl+$^{35}$Cl isotope+H$^+$), 572.0 ($^{37}$Cl+$^{35}$Cl isotope+H$^+$).

EXAMPLE 209

1'-(3-((S)-(4-Chlorophenyl))-4-(N-(benzoylformyl)-(methylamino))butyl)-spiro(2,3-dihydrobenzothiophene-3, 4'-piperidine)-1-oxide Mass spectrum (ESE): m/z=583.1 ($^{35}$Cl+$^{35}$Cl isotope+H$^+$),585.1 ($^{37}$Cl+$^{35}$Cl isotope+H$^+$).

EXAMPLE 210

1'-(3-((S)-(4-Chlorophenyl))-4-(N-(pyridine-3-sulfonyl)-(methylamino))butyl)-spiro(2,3-dihydrobenzothiophene-3, 4'-piperidine)-1-oxide Mass spectrum (ESI): m/z=592.3 ($^{35}Cl+^{35}Cl$ isotope+H$^+$),594.3 ($^{37}Cl+^{35}Cl$ isotope+H$^+$).

Examples 211 through 218 were prepared as noted above for examples 195–198, followed by the procedures noted in the individual examples.

EXAMPLE 211

1'-(3-((S)-(3,4-Dichlorophenyl))-4-(N-(4-chlorobenzenesulfonyl)-(methylamino))butyl)-spiro(2,3-dihydrobenzothiophene-3,4'-piperidine)-1-oxide The title compound was prepared by the Oxone®oxidation method described in Example 53. $^1$H NMR (500 MHz, CDCl$_3$): δ 1.27–3.34 (16H), 7.09 (d, J=7.6 Hz, 1H), 7.29 (d, J=1.4 Hz, 1H), 7.41 (dd, J=1.8 & 8.2 Hz, 1H), 7.46–7.50 (m, 3H), 7.61 (t, J=7.6 Hz, 1H), 7.65 (d, J=8.4 Hz, 2H), 7.84 (d, J=7.8 Hz, 2H). Mass Spectrum (NH$_3$-CI): 609 (M+1).

EXAMPLE 212

1'-(3-((S)-(3,4-Dichlorophenyl))-4-(N-(3-nitrobenzenesulfonyl)-(methylamino))butyl)-spiro(2,3-dihydrobenzothiophene-3,4'-piperidine)-1,1-dioxide The title compound was prepared by the Oxone®oxidation method described in Example 49. $^1$H NMR (500 MHz, CDCl$_3$): δ 1.27–3.41 (16H), 7.09 (d, J=8.2 Hz, 1H), 7.28 (d, J=1.6 Hz, 1H), 7.40 (dd, J=1.8 & 8.2 Hz, 1H), 7.45–7.50 (m, 2H), 7.60 (t, J=7.5 Hz, 1H), 7.72 (t, J=8.0 Hz, 1H), 7.84 (d, J=7.7 Hz, 1H), 8.00 (d, J=7.6 Hz, 1H), 8.43 (d, J=8.0 Hz, 1H), 8.55 (s, 1H). Mass Spectrum (NH$_3$-CI): 636 (M+1).

EXAMPLE 213

1'-(3-((S)-(3,4-Dichlorophenyl))-4-(N-(4-nitrobenzenesulfonyl)-(methylamino))butyl)-spiro(2,3-dihydrobenzothiophene-3,4'-piperidine)-1,1-dioxide The title compound was prepared by the Oxone®oxidation method described in Example 49. $^1$H NMR (500 MHz, CDCl$_3$): δ 1.27–3.41 (16H), 7.10 (d, J=7.3 Hz, 1H), 7.28 (d, J=4.6 Hz, 1H), 7.41 (d, J=8.0 Hz, 1H), 7.48–7.51 (m, 2H), 7.61 (t, J=7.3 Hz, 1H), 7.84 (d, J=7.8 Hz, 1H), 7.89 (d, J=8.7 Hz, 2H), 8.35 (d, J=8.7 Hz, 2H). Mass Spectrum (NH$_3$-CI): 636 (M+1).

EXAMPLE 214

1'-(3-((S)-(3,4-Dichlorophenyl))-4-(N-(2-chlorobenzenesulfonyl)-(methylamino))butyl)-spiro(2,3-dihydrobenzothiophene-3,4'-piperidine)-1-oxide The title compound was prepared by the Oxone®oxidation method described in Example 53. 1H NMR (500 MHz, CDCl$_3$): δ 1.27–3.38 (16H), 7.09 (d, J=8.2 Hz, 1H), 7.30 (d, J=1.6 Hz, 1H), 7.41 (dd, J=1.8 & 8.2 Hz, 1H), 7.44–7.61 (m, 6H), 7.71 (s, 1H), 7.83 (d, J=7.5 Hz, 1H). Mass Spectrum (NH$_3$-CI): 609 (M+1).

EXAMPLE 215

1'-(3-((S)-(3,4-Dichlorophenyl))-4-(N-(3-chlorobenzenesulfonyl)-(methylamino))butyl)-spiro(2,3-dihydrobenzothiophene-3,4'-piperidine)-1-oxide The title compound was prepared by the Oxone®oxidation method described in Example 53. $^1$H NMR (500 MHz, CDCl$_3$): δ 1.27–3.63 (16H), 7.04–7.61 (9H), 7.84 (d, J=7.6 Hz, 16H), 8.02 (dd, J=1.0 & 8.0 Hz, 1H). Mass Spectrum (NH$_3$-CI): 609 (M+1).

EXAMPLE 216

1'-(3-((S)-(3,4-Dichlorophenyl))-4-(N-(2,3,4,5,6-pentafluoro-benzenesulfonyl)-(methylamino))butyl)-spiro(2,3-dihydrobenzothiophene-3,4'-piperidine)-1-oxide The title compound was prepared by the Oxone®oxidation method described in Example 53. $^1$H NMR (500 MHz, CDCl$_3$): δ 1.27–3.56 (16H), 7.10–7.87 (7H). Mass Spectrum (NH$_3$-CI): 665 (M+1).

EXAMPLE 217

1'-(3-((S)-(3,4-Dichlorophenyl))-4-(N-(4-biphenylsulfonyl)-(methylamino))butyl)-spiro(2,3-dihydrobenzothiophene-3,4'-piperidine)-1-oxide The title compound was prepared by the Oxone®oxidation method described in Example 53. $^1$NMR (500 MHz, CDCl$_3$): δ 1.27–3.41 (16H), 7.10–7.86 (16H). Mass Spectrum (NH$_3$-CE): 651 (M+1).

EXAMPLE 218

1'-(3-((S)-(3,4-Dichlorophenyl))-4-(N-(4-methoxybenzenesulfonyl)-(methylamino))butyl)-spiro(2,3-dihydrobenzothiophene-3,4'-piperidine)-1-oxide The title compound was prepared by the Oxone®oxidation method described in Example 53. $^1$H NMR (500 MHz, CDCl$_3$): δ 1.27–3.36 (16H), 3.88 (s, 3H), 6.97–7.86 (11H). Mass Spectrum (NH$_3$-CI): 605 (M+1).

EXAMPLE 219

(+/−) N-methyl-N-phenylsulfonyl-2-(3-chloro-4-benzyloxy)-4-(spiro[2,3-dihydrobenzothiophene-3,4'-piperdin-1'-yl)butanamine Step A: Benzyl-3-chloro-4-benzyloxy phenylacetate To a solution of 3-chloro-4-hydroxyphenyl acetic acid (500 mg, 2.68 mmols) in DMF (10 mL) was added K$_2$CO$_3$ (926 mg, 6.7 mmols), followed by benzyl bromide (1.15 g, 6.7 mmols). After stirring at room temperature for 12 hrs. the reaction was diluted with H$_2$O (100 mL) and extracted with CH$_2$Cl$_2$ (3×100 mL). The combined organic extracts were washed with brine, dried (Na$_2$SO$_4$), and concentrated in vacuo. The residue was purified by column chromatography (20 g silica gel 60, 100 mm col. diam., 5–25% EtOAc/Hex) to afford the dialkylated compound (940 mg, 96%) as a light yellow oil. $^1$H NMR (500 MHz, CDCl$_3$) δ 7.49 (d, 2H, J=8.3

Hz), 7.43–7.44 (m, 11H), 7.11–7.13 (m, 1H), 6.94 (dd, 1H, J=1.1, 8.2 Hz), 5.17 (d, 2H, J=2.7 Hz), 3.61 (s, 2H) ppm.

Step B: (+/−) Benzyl-2(3-chloro-4-benzyloxy)-4-pentenoate

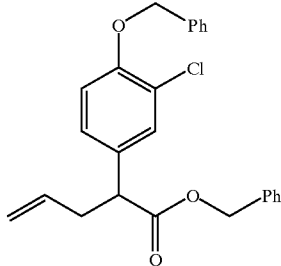

To a solution of benzyl-3-chloro-4-benzyloxy phenylacetate (3.6 g, 9.8 mmols),from Step A, in THF (30 mL) at −78° C. was added LHMDS (10.8 mL, 1M THF solution). The reaction was stirred at −78° C. for 30 minutes then added dropwise via cannula to a solution of allyl bromide (1.8 g, 14.7 mmols) in THF (10 ml) at −78° C. After stirring for 1.5 hours at −78° C. the reaction was quenched with a saturated solution of NH$_4$Cl and diluted with H$_2$O (150 mL). The mixture was extracted with EtOAc (3×100 mL) and the combined organic extracts were washed with brine, dried (Na$_2$SO$_4$), and concentrated in vacuo . The residue was purified by column chromatography (150 g silica gel 60, 100 mm col. diam., 50% CH$_2$Cl$_2$/Hexanes) to afford the racemate (2.54 g, 65%) as a light yellow oil. $^1$H NMR (CDCl$_3$, 500 MHz) δ 7.48 (d, 2H, J=7.1 Hz), 7.26–7.43 (m, 9H), 7.14 (dd, 1H, J=2.1, 8.5 Hz), 6.29 (d, 1H, J=8.5 Hz), 5.63–5.73 (m, 1H), 5.01–5.18 (m, 6H),3.63 (t, 1H, J=8.0 Hz), 2.78–2.85 (m, 1H), 2.48–2.55 (m, 1H) ppm.

Step C: (+/−) N-methyl-2-(3-chloro-4-benzyloxy)-4-pentenamide

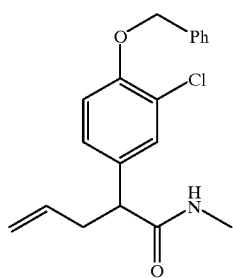

To a solution of (+/−) benzyl-2(3-chloro-4-benzyloxy)-4-pentenoate (1.27 g, 3.12 mmols), from step B, in MeOH (75 mL) at room temperature was added methyl amine (75 mL, 40% aqueous solution). After stirring for 2 days the reaction mixture was concentrated in vacuo to a white solid. The white solid was dissolved in CH$_2$Cl$_2$ (100 mL) and diluted with H$_2$O (100 mL). The mixture was extracted with CH$_2$Cl$_2$ (3×100 mL). The combined organic extracts were washed with brine, dried (Na$_2$SO$_4$), and concentrated in vacuo. The residue was purified by column chromatography (40 g silica gel 60, 100 mm col. diam., 40–50% EtOAc/Hex) to afford the methyl amide (704 mg, 68%) as a white solid. $^1$H NMR (CDCl$_3$, 500 MHz) δ 7.47 (d, 2H, J=7.0 Hz), 7.41 (t, 2H, J=7.7 Hz), 7.33–7.36 (m, 2H), 7.14 (dd, 1H, J=2.3, 8.5 Hz), 6.94 (d, 1H, J=8.4 Hz), 5.66–5.72 (m, 1H), 5.40 (bs, 1H), 5.16 (s, 2H), 5.06 (dd, 1H, J=1.3, 17 Hz), 5.0 (dd, 1H, J=1.0, 10.3 Hz), 3.30 (t, 1H, J=7.8 Hz), 2.86–2.92 (m, 1H), 2.77 (d, 3H, J=5.0 Hz), 2.46–2.52 (m, 1H) ppm.

Step D: (+/−) N-methyl-N-phenylsulfonyl-2-(3-chloro-4-benzyloxy)-4-pentenamine

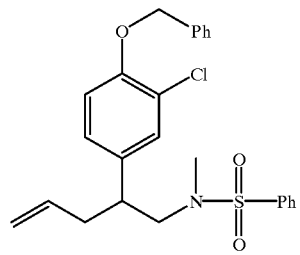

To a solution of (+/−) N-methyl-2-(3-chloro-4-benzyloxy)-4-pentenamide (704 mg, 2.13 mmols) in CH$_2$Cl$_2$ (50 mL) at 0° C. was added DIBAL (8.5 mL, 1M CH$_2$Cl$_2$ solution). The reaction was allowed to warm slowly to room temperature. After stirring for 12 hours the reaction was quenched with MeOH (10 mL), diluted with H$_2$O (100 mL), a saturated solution of Rochelle salts (100 mL) and CH$_2$Cl$_2$ (150 mL). After stirring for 30 minutes the mixture was extracted with CH$_2$Cl$_2$ (3×100 mL). The combined organic extracts were washed with brine, dried (Na$_2$SO$_4$), and concentrated in vacuo to afford the methyl amine as an orange oil. The oil was used directly below.

To a solution of the methyl amine (400 mg, 1.27 mmols), obtained above, in CH$_2$Cl$_2$ (30 mL) at 0° C. was added Et$_3$N (390 mg, 3.81 mmols) followed by benzenesulfonyl chloride (270 mg, 1.52 mmols). The reaction was stirred at 0° C. for 30 minutes, warmed to room temperature and stirred for an additional 2 hours. The reaction was diluted with H$_2$O (100 mL), a saturated solution of NaHCO$_3$ (100 mL) and then extracted with CH$_2$Cl$_2$ (3×100 mL). The combined organic extracts were washed with brine, dried (Na$_2$SO$_4$), and concentrated in vacuo. The residue was purified by column chromatography (20 g silica gel 60, 100 mm col. diam., 10–15% EtOAc/Hex) to afford the N-methyl sulfonamide (395 mg, 68%) as an oil. $^1$H NMR (CDCl$_3$, 500 MHz) 6 7.73–7.74 (m, 2H), 7.36–7.59 (m, 8H) 7.18 (d, 1H, J=2.1 Hz), 7.02 (dd, 1H, J=2.1, 8.4 Hz), 6.92 (d, 1H, J=8.5 Hz) 5.63–5.69 (m, 1H), 5.15 (s, 2H), 4.96–5.03 (m, 2H) 3.37 (dd, 1H, J=7.1,13 Hz), 2.88–2.97 (m, 2H), 2.62 (s, 3H) 2.52–2.56 (m, 1H), 2.32–2.36 (m, 1H) ppm.

Step E: (+/−) 4-(N-methyl-N-phenylsulfonyl)amino-3-(3-chloro-4-benzyloxy)-butanecarboxaldehyde

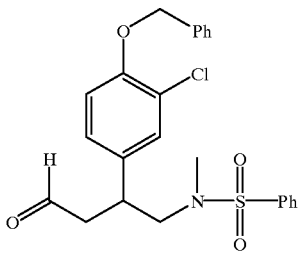

To a mixture of (+/−) N-methyl-N-phenylsulfonyl-2-(3-chloro-4-benzyloxy)-4-pentenamine (395 mg, 0.87 mmols), from Example 4, in a 2:1:1 acetone/t-butanol/H$_2$O (9 mL) mixture at room temperature was added OsO$_4$ (2.25 mL, 2.5% t-butanol solution). After stirring for 5 minutes, NMMO (152 mg, 1.3 mmols) was added and the reaction was stirred at room temperature. After 4 hours solid sodium bisulfite (300 mg, 2.88 mmols) was added as a single portion and the reaction was stirred for 15 mins. The reaction was diluted with H₂O (100 mL) and extracted with CH₂Cl₂ (3×100 mL). The combined organic extracts were washed with brine, dried (Na₂SO₄), and concentrated in vacuo to afford the diol as a colorless oil. The oil was carried on directly as described below.

To a solution of the diol obtained above, in a 3:1 THF/H₂O (13 mL) mixture at room temperature was added NaIO₄ (333 mg, 1.56 mmols). After stirring for 12 hours the reaction mixture was diluted with H₂O (100 mL) and the mixture was extracted with EtOAc (3×100 mL). The combined organic extracts were washed with brine, dried (Na₂SO₄), and concentrated in vacuo . The residue was purified by column chromatography (25 g silica gel 60, 100 mm col. diam., 25–40% EtOAc/Hex) to afford the aldehyde (280 mg, 70%) as an oil. ¹H NMR (CDCl₃, 500 MHz) δ 9.79 (s,1H) 7.74 (d, 1H, J=7.3 Hz), 7.57–7.59 (m, 1H), 7.50–7.53 (m, 2H), 7.45–7.47 (m, 2H), 7.38–7.42 (m, 2H), 7.33–7.35 (m, 2H), 7.24 (d, 1H, J=2.1 Hz), 7.06 (dd, 1H, J=2.0, 8.5 Hz), 6.91 (d, 1H, J=8.2 Hz), 5.15 (s, 2H), 3.50–3.56 (m, 1H), 3.35 (dd, 1H, J=9.4, 13.5 Hz), 3.12 (dd, 1H, J=6.1,17.6 Hz), 2.86 (dd, 1H, J=5.7, 13.3 Hz), 2.78 (dd, 1H, J=7.6, 17.7 Hz), 2.66 (s, 3H) ppm.

Step F: (+/−) N-methyl-N-phenylsulfonyl-2-(3-chloro-4-benzyloxy)-4-(spiro[2,3-dihydrobenzothiophene-3,4'-piperdin-1'-yl)butanamine

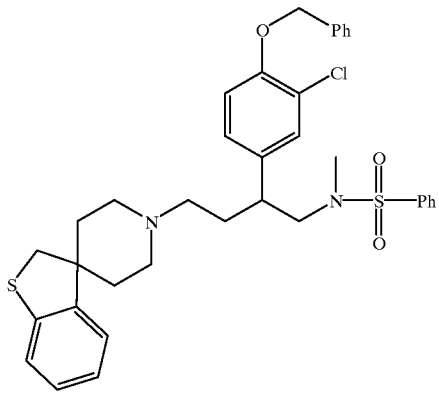

To a solution of (+/−) 4-(N-methyl-N-phenylsulfonyl) amino-3-(3-chloro-4-benzyloxy)-butanecarboxaldehyde, from Step E,(200 mg, 0.44 mmol) in MeOH (10 mL) at room temperature was added 3 A mol sieves (400 mg) followed by spiro-2,3-dihydrobenzothiophene-3,4'-piperdin-1'-yl hydrochloride (128 mg, 0.53 mmols). After stirring for 2 hours, solid NaCNBH₃ (111 mg, 1.76 mmols) was added as a single portion. The mixture was stirred at room temperature for 3 hours whereupon it was filtered thru celite, washed with MeOH, and the filtrate concentrated in vacuo. The residue was partitioned between H₂O (50 mL) and EtOAc (50 mL), followed by extraction with EtOAc (3×50 mL). The combined organic extracts were washed with brine, dried (Na₂SO₄) and concentrated in vacuo. The residue was purified by column chromatography (30 g silica gel 60, 30 mm col. diam., 2.5–8% MeOH/CH₂Cl₂) to afford the amine (270 mg, 95%) as a white solid. Mass spectrum (EI): m/e=647 (M+1).

EXAMPLE 220
(+/−) N-methyl-N-phenylsulfonyl-2-(3-chloro-4-benzyloxy)-4-(spiro[2,3-dihydrobenzothiophene-3,4'-piperdin-1'-yl)butamine, S-oxide

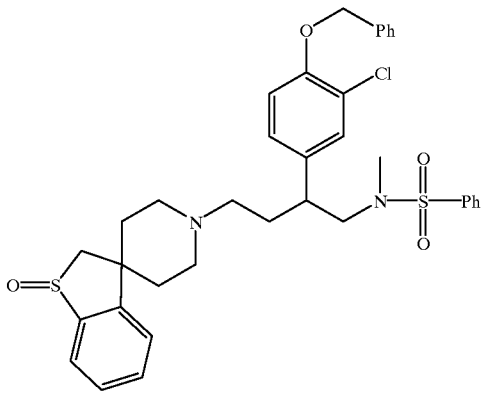

To a solution of(+/−) N-methyl-N-phenylsulfonyl-2-(3-chloro-4-benzyloxy)-4-(spiro[2,3-dihydrobenzothiophene-3,4'-piperdin-1'-yl)butanamine (50 mg, 0.08 mmol), from Example 219, Step F, in a 1:1 MeOH/H₂O (2 mL) mixture at 0° C. was added Oxone®(8 mg, 0.013). After stirring for 3 minutes the reaction was quenched with 20% aqueous sodium bisulfite (3 mL) and stirred for 10 minutes. The reaction was then diluted with H₂O (50 mL) and extracted with CH₂Cl₂ (3×50 mL). The combined organic extracts were washed with brine, dried (Na₂SO₄) and concentrated in vacuo. The residue was purified by column chromatography (10 g silica gel 60, 18 mm col. diam., 2.5–8% MeOH/CH₂Cl₂) to afford the sulfoxide (51 mg, 96%) as a colorless glass. Mass spectrum (EI): m/e=663 (M+1).

EXAMPLE 221
(+/−) N-methyl-N-phenylsulfonyl-2-(3-chloro-4-benzyloxy)-4-(spiro[2,3-dihydrobenzothiophene-3'-piperdin-1'-yl)butamine, S-dioxide

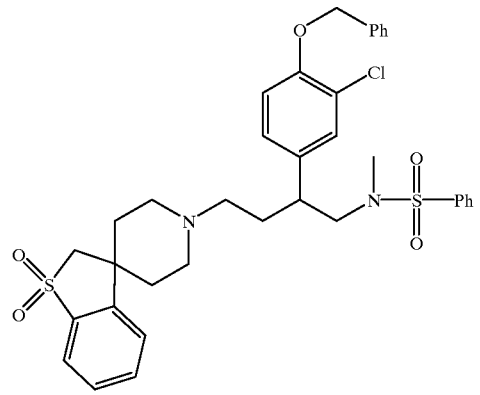

To a solution of (+/−) N-methyl-N-phenylsulfonyl-2-(3-chloro-4-benzyloxy)-4-(spiro[2,3-dihydrobenzothiophene-3,4'-piperdin-1'-yl)butanamine(40 mg, 0.06 mmol), from Example 219, Step F, in a 1:1 MeOH/H₂O (4 mL) mixture at 0° C. was added Oxone®(8 mg, 0.013). The cooling bath was removed and the reaction was allowed to warm to room temperature. After stirring for 1 hour the reaction was quenched with 20% aqueous sodium bisulfite (3 mL) and stirred for 10 minutes. The reaction was then diluted with H₂O (50 mL) and extracted with CH₂Cl₂ (3×50 mL). The combined organic extracts were washed with brine, dried (Na₂SO₄) and concentrated in vacuo. The residue was purified by column chromatography (20 g silica gel 60, 18 mm col. diam., 5% MeOH/CH$_2$Cl$_2$) to afford the sulfone (45 mg, 99%) as a colorless glass. Mass spectrum (EI): m/e=679 (M+1).

EXAMPLE 222

(+/−) N-methyl-N-phenylsulfonyl-2-(3-chloro-4-hydroxy)-4-(spiro[2,3-dihydrobenzothiophene-3,4'-piperdin-1'-yl) butanamine

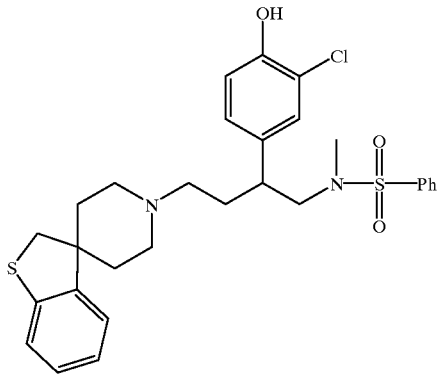

To a solution of the (+/−) N-methyl-N-phenylsulfonyl-2-(3-chloro-4-benzyloxy)-4-(spiro[2,3-dihydrobenzothiophene-3,4'-piperdin-1'-yl)butanamine, from Example 219, Step F,(5 mg, 0.01 mmol) in ethanethiol (1 mL) at room temperature was added BF$_3$.Et$_2$O (23 mg, 0.17 mmols). After stirring for 3 hours the reaction was diluted with H$_2$O (50 mL) and extracted with CH$_2$Cl$_2$ (3×50 mL). The combined organic extracts were washed with brine, dried (Na$_2$SO$_4$) and concentrated in vacuo. The residue was purified by column chromatography (5 g silica gel 60, 18 mm col. diam., 5% MeOH/CH$_2$Cl$_2$) to afford the phenol (5 mg, 99%) as a colorless oil. Mass spectrum (EI): m/e=557 (M+1).

EXAMPLE 223

(+/−) N-methyl-N-phenylsulfonyl-2-(3-chloro-4-hydroxy)-4-(spiro[2,3-dihydrobenzothiophene-3,4'-piperdin-1'-yl) butanamine, S-oxide

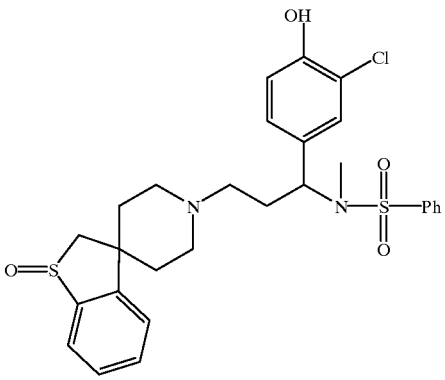

To a solution of the (+/−) N-methyl-N-phenylsulfonyl-2-(3-chloro-4-benzyloxy)-4-(spiro[2,3-dihydrobenzothiophene-3,4'-piperdin-1'-yl)butamine, S-oxide, from Example 220,(26 mg, 0.04 mmol) in ethanethiol (2 mL) at room temperature was added BF$_3$.Et$_2$O (111 mg, 0.78 mmols). After stirring for 3 hours the reaction was diluted with H$_2$O (50 mL) and extracted with CH$_2$Cl$_2$ (3×50 mL). The combined organic extracts were washed with brine, dried (Na$_2$SO$_4$) and concentrated in vacuo. The residue was purified by column chromatography (5 g silica gel 60, 18 mm col. diam., 2.5–8% MeOH/CH$_2$Cl$_2$) to afford the phenol (16 mg, 73%) as a colorless oil. Mass spectrum (EI): m/e=572 (M).

EXAMPLE 224

(+/−) N-methyl-N-phenylsulfonyl-2-(3-chloro-4-hydroxy)-4-(spiro[2,3-dihydrobenzothiophene-3,4'-piperdin-1'-yl) butanamine, S-dioxide

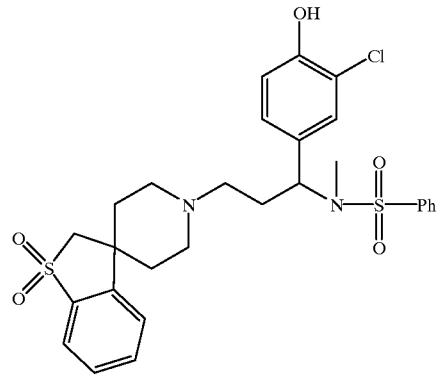

To a solution of (+/−) N-methyl-N-phenylsulfonyl-2-(3-chloro-4-benzyloxy)-4-(spiro[2,3-dihydrobenzothiophene-3'-piperdin-1'-yl)butamine, S-dioxide, from Example 221, (30 mg, 0.04 mmol) in ethanethiol (2 mL) at room temperature was added BF$_3$.Et$_2$O (125 mg, 0.88 mmols). After stirring for 3 hours the reaction was diluted with H$_2$O (50 mL) and extracted with CH$_2$Cl$_2$ (3×50 mL). The combined organic extracts were washed with brine, dried (Na$_2$SO$_4$) and concentrated in vacuo. The residue was purified by column chromatography (5 g silica gel 60, 18 mm col. diam., 2.5–8% MeOH/CH$_2$Cl$_2$) to afford the phenol (16 mg, 62%) as a colorless oil. Mass spectrum (EI): m/e=589 (M+1).

EXAMPLE 225

(+/−) N-methyl-N-phenylsulfonyl-2-(4-benzyloxy)-4-(spiro [2,3-dihydrobenzothiophene-3,4'-piperdin-1'-yl)butanamine Step A: Benzyl-4-benzyloxy phenylacetate

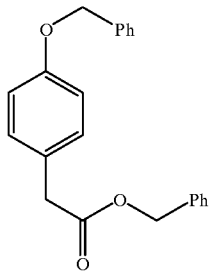

To a solution of 4-benzyloxy phenyl acetic acid (2.0 g, 8.25 mmols) in DMF (30 mL) at room temperature was added K$_2$CO$_3$ (1.36 mgs, 9.9 mmols), followed by benzyl bromide (1.7 g, 9.9 mmols). After stirring at room temperature for 12 hrs. the reaction was diluted with H$_2$O (100 mL) and extracted with EtOAc (3×100 mL). The combined organic extracts were washed with brine, dried (Na$_2$SO$_4$), and concentrated in vacuo. The light yellow solid was used directly in the next step. $^1$H NMR (500 MHz, CDCl$_3$) δ 7.43–7.44 (m, 10H), 7.26 (d, 2H, J=8.5 Hz), 6.96 (d, 2H, J=8.5 Hz), 5.15 (s, 2H), 5.08 (s, 2H), 3.64 (s, 2H) ppm.

Step B: (+/−) Benzyl-2(4-benzyloxy)-4-pentenoate

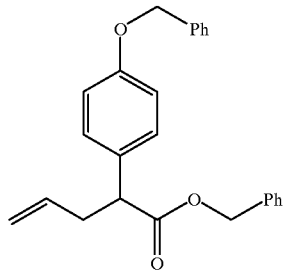

To a solution of benzyl-4-benzyloxy phenylacetate (2.3 g, 6.92 mmols), from Step A, in THF (20 mL) at −78° C. was added LHMDS (7.6 mL, 1M THF solution). The reaction was stirred at −78° C. for 30 minutes then added dropwise via cannula to a solution of allyl bromide (919 mg, 7.6 mmols) in THF (10 ml) at −78° C. After stirring for 1.5 hours at −78° C. the reaction was quenched with a saturated solution of $NH_4Cl$ and diluted with $H_2O$ (150 mL). The mixture was extracted with EtOAc (3×100 mL) and the combined organic extracts were washed with brine, dried ($Na_2SO_4$), and concentrated in vacuo. The residue was purified by column chromatography (150 g silica gel 60, 100 mm col. diam., 50% $CH_2Cl_2$/Hexanes) to afford the racemate (825 mg, 23%) as a light yellow oil. $^1H$ NMR ($CDCl_3$, 500 MHz) δ 7.22–7.46 (m, 10H), 6.95 (d, 4H, J=8.4 Hz), 5.71–5.76 (m, 1H), 4.99–5.17 (m, 6H), 3.68 (t, 1H, J=8.0 Hz), 2.81–2.87 (m, 1H), 2.51–2.56 (m, 1H) ppm.

Step C: (+/−) N-methyl-2-(4-benzyloxy)-4-pentenamide

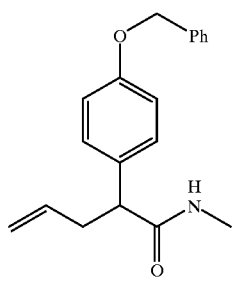

To a solution of (+/−) benzyl-2(4-benzyloxy)-4-pentenoate (400 mg, 1.07 mmols), from Step C, in MeOH (25 mL) at room temperature was added methylamine (25 mL, 40% aqueous solution). After stirring for 2 days the reaction mixture was concentrated in vacuo to a white solid. The white solid was dissolved in $CH_2Cl_2$ (100 mL) and diluted with $H_2O$ (100 mL). The mixture was extracted with $CH_2Cl_2$ (3×100 mL). The combined organic extracts were washed with brine, dried ($Na_2SO_4$), and concentrated in vacuo. The residue was purified by column chromatography (40 g silica gel 60, 100 mm col. diam., 40% EtOAc/Hex) to afford the methyl amide (168 mg, 53%) as a white solid. $^1H$ NMR ($CDCl_3$, 500 MHz) δ 7.33–7.45 (m, 5H), 7.22 (d, 2H, J=8.7 Hz), 6.96 (d, 2H, J=8.7 Hz), 5.66–5.72 (m, 1H), 5.37 (bs, 1H), 5.07 (s, 2H), 5.04 (dd, 1H, J=1.4, 9.1 Hz), 4.97 (dd, 1H, J=1.0, 10.0 Hz), 3.36 (t, 1H, J=7.6 Hz), 2.93–2.96 (m, 1H), 2.76 (d, 3H, J=4.8 Hz), 2.48–2.55 (m, 1H) ppm.

Step D: (+/−) N-methyl-N-phenylsulfonyl-2-(4-benzyloxy)-4-pentenamine

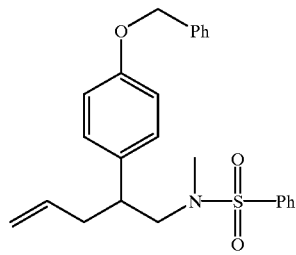

To a solution of (+/−) N-methyl-2-(4-benzyloxy)-4-pentenamide (168 mg, 0.57 mmols) in $CH_2Cl_2$ (10 mL) at 0° C. was added DIBAL (2.28 mL, 1M $CH_2Cl_2$ solution). The reaction was allowed to warm slowly to room temperature. After stirring for 12 hours the reaction was quenched with MeOH (10 mL), diluted with $H_2O$ (100 mL), a saturated solution of Rochelle salts (100 mL) and $CH_2Cl_2$ (150 mL). After stirring for 30 minutes the mixture was extracted with $CH_2Cl_2$ (3×100 mL). The combined organic extracts were washed with brine, dried ($Na_2SO_4$), and concentrated in vacuo to afford the methyl amine as an orange oil. The oil was used directly as described in the next paragraph.

To a solution of the methyl amine (100 mg, 0.36 mmols), from above, in $CH_2Cl_2$ (10 mL) at 0° C. was added $Et_3N$ (109 mg, 1.08 mmols) followed by sulfonyl chloride (76 mg, 0.43 mmols). The reaction was stirred at 0° C. for 30 minutes, warmed to room temperature and stirred for an additional 2 hours. The reaction was diluted with $H_2O$ (100 mL), a saturated solution of $NaHCO_3$ (100 mL) and then extracted with $CH_2Cl_2$ (3×100 mL). The combined organic extracts were washed with brine, dried ($Na_2SO_4$), and concentrated in vacuo. The residue was purified by column chromatography (20 g silica gel 60, 100 mm col. diam., 10–15% EtOAc/Hex) to afford the N-methyl sulfonamide (100 mg, 66%) as an oil. $^1H$ NMR ($CDCl_3$, 500 MHz) δ 7.74 (d, 2H, J=7.5 Hz), 7.33–7.59 (m, 8H), 7.11 (d, 2H, J=8.5 Hz), 6.94 (d, 2H, J=8.4 Hz), 5.66–5.68 (m, 1H), 5.06 (s, 2H), 4.96–5.04 (m, 2H), 3.39–3.44 (m, 1H), 2.92–2.96 (m, 2H), 2.62 (s, 3H), 2.54–2.59 (m, 1H), 2.36–2.41 (m, 1H) ppm.

Step E: (+/−) 4-(N-methyl-N-phenylsulfonyl)amino-3-(4-benzyloxy)-butanecarboxaldehyde

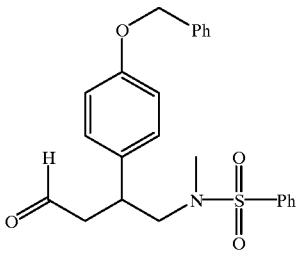

To a mixture of (+/−) N-methyl-N-phenylsulfonyl-2-(4-benzyloxy)-4-pentenamine (20 mg, 0.05 mmols), from Step D, in a 2:1:1 acetone/t-butanol/$H_2O$ (2 mL) mixture at room temperature was added $OsO_4$ (0.125 mL, 2.5% t-butanol solution). After stirring for 10 minutes, NMMO (9 mg, 0.75 mmols) was added and the reaction was stirred at room temperature. After 2 hours the reaction was quenched with an aqueous solution of 20% sodium bisulfite (3 mL) and the reaction was stirred for 15 mins. The reaction was diluted with $H_2O$ (50 mL) and extracted with $CH_2Cl_2$ (3×25 mL). The combined organic extracts were washed with brine, dried ($Na_2SO_4$), and concentrated in vacuo to afford the diol as a colorless oil. The oil was used directly below.

To a solution of the diol described above, in a 4:1 THF/H₂O (2 mL) mixture at room temperature was added NaIO₄ (16 mg, 0.08 mmols). After stirring for 2 hours the reaction mixture was diluted with H₂O (100 mL) and the mixture was extracted with EtOAc (3×100 mL). The combined organic extracts were washed with brine, dried (Na₂SO₄), and concentrated in vacuo. The residue was purified by column chromatography (5 g silica gel 60, 100 mm col. diam., 25–40% EtOAc/Hex) to afford the aldehyde (18 mg, 86%) as an oil. ¹H NMR (CDCl₃, 500 MHz) δ 9.79 (s, 1H) 7.74 (d, 2H, J=8.2 Hz), 7.34–7.59 (m, 8H), 7.15 (d, 2H, J=8.5 Hz), 6.94 (d, 2H, J=8.7 Hz), 5.05 (s, 2H), 3.54–3.57 (m, 1H), 3.38 (dd, 1H, J=9.6, 13.5 Hz), 3.12 (dd, 1H, J=6.2, 17.4 Hz), 2.86 (dd, 1H, J=5.7, 13.2 Hz), 2.81 (dd, 1H, J=7.6, 17.4 Hz), 2.65 (s, 3H) ppm.

Step F: (+/−) N-methyl-N-phenylsulfonyl-2-(4-benzyloxy)-4-(spiro[2,3-dihydrobenzothiophene-3,4'-piperdin-1'-yl)butanamine

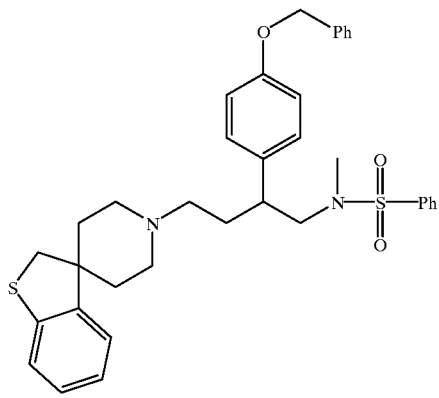

To a solution of (+/−) 4-(N-methyl-N-phenylsulfonyl) amino-3-(4-benzyloxy)-butanecarboxaldehyde, from Step E, (30 mg, 0.07 mmol) in MeOH (2 mL) at room temperature was added 3 A mol sieves (60 mg) followed by spiro-2,3-dihydrobenzothiophene-3,4'-piperdine hydrochloride (22 mg, 0.09 mmols). After stirring for 2 hours, solid NaCNBH₃ (18 mg, 0.28 mmols) was added as a single portion. The mixture was stirred at room temperature for 12 hours whereupon it was filtered thru celite, washed with MeOH, and the filtrate concentrated in vacuo. The residue was partitioned between H₂O (50 mL) and EtOAc (50 mL), followed by extraction with EtOAc (3×50 mL). The combined organic extracts were washed with brine, dried (Na₂SO₄) and concentrated in vacuo. The residue was purified by column chromatography (5 g silica gel 60, 30 mm col. diam., 5–8% MeOH/CH₂Cl₂) to afford the amine (25 mg, 58%) as an oil. Mass spectrum (CI): m/e=613 (M+1).

EXAMPLE 226

(+/−) N-methyl-N-phenylsulfonyl-2-(4-benzyloxy)-4-(spiro[2,3-dihydrobenzothiophene-3,4'-piperdin-1'-yl)butanamine, S-oxide

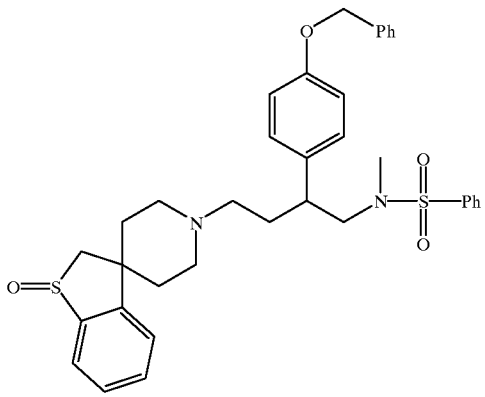

To a solution of (+/−) N-methyl-N-phenylsulfonyl-2-(4-benzyloxy)-4-(spiro[2,3-dihydrobenzothiophene-3,4'-piperdin-1'-yl)butanamine (15 mg, 0.03 mmol), from Example 225, Step F, in a 1:1 MeOH/H₂O (2 mL) at 0C was added Oxone®(20 mg, 0.013). After stirring for 3 minutes the reaction was quenched with 20% aqueous sodium bisulfite (3 mL) and stirred for 10 minutes. The reaction was then diluted with 1H₂O (50 mL) and extracted with CH₂Cl₂ (3×50 mL). The combined organic extracts were washed with brine, dried (Na₂SO₄) and concentrated in vacuo. The residue was purified by column chromatography (10 g silica gel 60, 18 mm col. diam., 2.5–8% MeOH/CH₂Cl₂) to afford the sulfoxide (9 mg, 60%) as a colorless glass. Mass spectrum (CI): m/e=629 (M+1).

EXAMPLE 227

(+/−) N-methyl-N-phenylsulfonyl-2-(4-hydroxy)-4-(spiro[2,3-dihydrobenzothiophene-3,4'-piperdin-1'-yl)butanamine

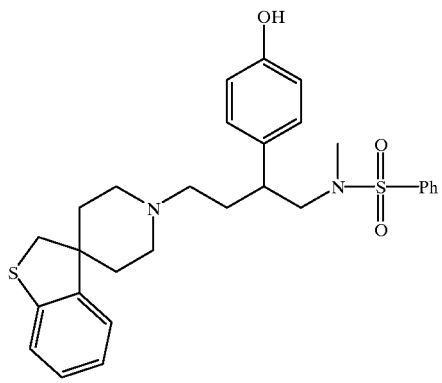

To a solution of (+/−) N-methyl-N-phenylsulfonyl-2-(4-benzyloxy)-4-(spiro[2,3-dihydrobenzothiophene-3,4'-piperdin-1'-yl)butanamine, from Example 225, Step F,(5 mg, 0.01 mmol) in ethanethiol (2 mL) at room temperature was added BF₃.Et₂O (16 mg, 0.12 mmols). After stirring for 2 hours the reaction was diluted with H₂O (50 mL) and extracted with CH₂Cl₂ (3×50 mL). The combined organic extracts were washed with brine, dried (Na₂SO₄) and concentrated in vacuo. The residue was purified by column chromatography (2 g silica gel 60, 18 mm col. diam., 2.5–8% MeOH/H₂Cl₂) to afford the phenol (2 mg, 50%) as a colorless oil.

Mass spectrum (CI): m/e=523 (M+1).

EXAMPLE 228

(+/−) N-methyl-N-phenylsulfonyl-2-(4-benzyloxy)-4-(spiro[2,3-dihydrobenzothiophene-3,4'-1piperdin-1'-yl)butanamine,S-oxide

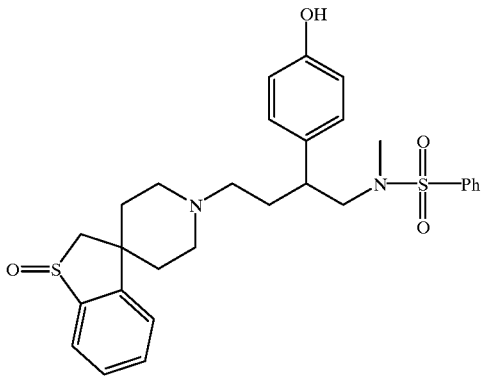

To a solution of (+/−) N-methyl-N-phenylsulfonyl-2-(4-benzyloxy)-4-(spiro[2,3-dihydrobenzothiophene-3,4'-piperdin-1'-yl)butanamine, S-oxide, from Example 226,(10 mg, 0.02 mmol) in ethanethiol (2 mL) at room temperature was added $BF_3.Et_2O$ (32 mg, 0.22 mmols). After stirring for 1 hour the reaction was diluted with $H_2O$ (50 mL) and extracted with $CH_2Cl_2$ (3×50 mL). The combined organic extracts were washed with brine, dried ($Na_2SO_4$) and concentrated in vacuo. The residue was purified by preparative TLC (500 um plate, 20×20 cm., 5% $MeOH/CH_2Cl_2$) to afford the phenol (10 mg, 99%) as a colorless oil. Mass spectrum (CI): m/e=539 (M+1).

EXAMPLE 229

(+/−) N-methyl-N-phenylsulfonyl-2-(4-benzyloxy)-4-(spiro[2,3-dihydrobenzothiophene-3,4'-piperdin-1-yl)butamine, S-dioxide

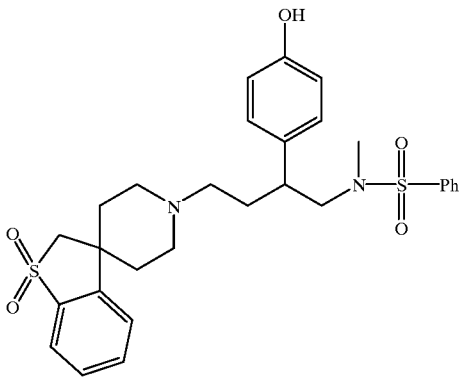

To a solution of the (+/−) N-methyl-N-phenylsulfonyl-2-(4-benzyloxy)-4-(spiro[2,3-dihydrobenzothiophene-3,4'-piperdin-1'-yl)butanamine, S-oxide (9 mg, 0.02 mmol), from Example 228, in a 1:1 $MeOH/H_2O$ (2 mL) at 0C was added Oxone®(12 mg, 0.02). The cooling bath was removed and the reaction was allowed to warm to room temperature. After stirring for 2 hours the reaction was quenched with 20% aqueous sodium bisulfite (3 mL) and stirred for 10 minutes. The reaction was then diluted with $H_2O$ (50 mL) and extracted with $CH_2Cl_2$ (3×50 mL). The combined organic extracts were washed with brine, dried ($Na_2SO_4$) and concentrated in vacuo. The residue was purified by column chromatography (2 g silica gel 60, 18 mm col. diam., 2.5–8% $MeOH/CH_2Cl_2$) to afford the sulfone (3 mg, 33%) as a colorless glass. Mass spectrum (CI): m/e=555 (M+1).

EXAMPLE 230

N-phenylsulfonyl-2(S)-(3,4-dichloro)-4-(spiro[2,3-dihydrobenzothiophene-3,4'-piperdin-1'-yl)butanamine Step A: 2(S)-(3,4-dichlorophenyl)-4-pentenamide

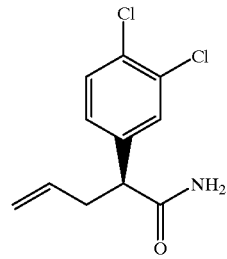

To a solution of the acid (200 mg, 0.82 mmols), described in Hale,J. J.; Finke, P. E.; MacCoss, M. *Bioorganic and Medicinal Chemistry Letters*, 2, (February 1993), from Example, $CH_2Cl_2$ in (2 mL) at room temperature was added oxalyl chloride (0.5 mL) and one drop of DMF. After stirring for 20 minutes, the reaction mixture was concentrated and then reconcentrated from $CH_2Cl_2/Et_2O$ in vacuo (3×) to afford a yellow oil. The yellow oil was dissolved in toluene (2 mL) and added to a rapidly stirred 1:1 mixture of toluene/sat'd aqueous $NH_4Cl$ solution (2 mL). After stirring for 30 minutes diluted with $H_2O$ (10 mL) and $CH_2Cl_2$ (10 mL). The mixture was extracted with $CH_2Cl_2$ (3×50 mL). The combined organic extracts were washed with brine, dried ($Na_2SO_4$), and concentrated in vacuo to yield a yellow solid which was used directly in the next step. $^1H$ NMR ($CDCl_3$, 500 MHz) δ 7.40–7.42 (m, 2H), 7.16 (dd, 1H, J=2.1, 8.5 Hz), 6.18 (bs, 1H), 5.75 (bs, 1H), 5.65–5.72 (m, 1H), 5.01–5.08 (m, 2H), 3.42 (t, 1H, J=7.5 Hz), 2.78–2.84 (m, 1H), 2.44–2.49 (m, 1H) ppm.

Step B: 2(S)-(3,4-dichlorophenyl)-4-pentenamine

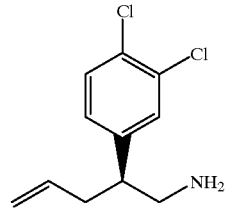

To a solution of 2(S)-(3,4-dichlorophenyl)-4-pentenamide (1.00 g, 4.1 mmols), from Step A, in $CH_2Cl_2$ (20 mL) at 0° C. was added DIBAL (31.4 mL, 1M PhMe solution). The reaction was allowed to warm slowly to room temperature. Mter stirring for 72 hours the reaction was quenched with MeOH (5 mL), diluted with $H_2O$ (100 mL), a saturated solution of Rochelle salts (100 mL) and EtOAc (150 mL). After stirring for 30 minutes the mixture was extracted with EtOAc (3×100 mL). The combined organic extracts were washed with brine, dried ($Na_2SO_4$), and concentrated in vacuo to afford the amine as yellow oil. The oil was dissolved in $Et_2O$ (50 mL) and treated with a 1M HCl solution, to pHB=2, and extracted with $Et_2O$ (3×50 mL). The aqueous was then basified with to a pH=12 with 5N NaOH, and extracted with EtOAc (3×50 mL), washed with brine, dried (Na$_2$SO$_4$) and concentrated in vacuo to yield a pale yellow oil (464 mg, 49%). $^1$ NMR (CDCl$_3$, 500 MHz) δ 7.36 (dd, 1H, J=2.5, 8.2 Hz), 7.27 (d, 1H, J=2.3 Hz), 7.02 (dd, 1H, J=2.0, 8.2 Hz), 5.58–5.67 (m, 1H), 4.93–4.99 (m, 2H), 2.53–2.94 (m, 5H), 2.36–2.42 (m, 1H), 2.26–2.31 (m, 1H) ppm.

Step C: N-phenylsulfonyl-2(S)-(3,4-dichlorophenyl)-4-pentenamine

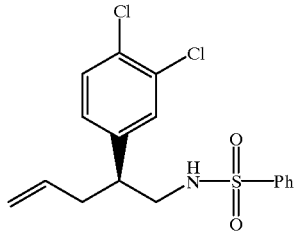

To a solution of 2(S)-(3,4-dichlorophenyl)-4-pentenamine (218 mg, 0.95 mmols), from Step B, in CH$_2$Cl$_2$ (10 mL) at 0° C. was added Et$_3$N (191 mg, 1.90 mmols) followed by sulfonyl chloride (186 mg, 1.05 mmols) The reaction was stirred at 0C for 30 minutes, warmed to room temperature and stirred for an additional 2 hours. The reaction was diluted with H$_2$O (100 mL), a saturated solution of NaHCO$_3$ (100 mL) and then extracted with CH$_2$Cl$_2$ (3×100 mL). The combined organic extracts were washed with brine, dried (Na$_2$SO$_4$), and concentrated in vacuo. The residue was purified by column chromatography (30 g silica gel 60, 100 mm col. diam., 15–25% EtOAc/Hex) to afford the sulfonamide (242 mg, 69%) as an oil. $^1$H NMR (CDCl$_3$, 500 MHz) δ 7.76 (dd, 2H, J=1.4, 7.3 Hz), 7.60–7.62 (m, 1H), 7.51–7.59 (m, 2H), 7.34 (dd, 1H, J=3.4, 8.2 Hz), 7.09 (d, 1H, J=2.1 Hz), 6.90 (d, 1H, J=2.0, 8.2 Hz), 5.54–5–59 (m, 1H), 4.96–5.00 (m, 2H), 4.38–4.41 (m, 1H), 3.30–3.35 (m, 1H), 3.01–3.29 (m, 1H), 2.75–2.81 (m, 1H), 2.30–2.39 (m, 1H), 2.24–2.29 (m, 1H)ppm.

Step D: N-tert-butylcarbamoyl-N-phenylsulfonyl-2(S)-(3,4-dichlorophenyl)-4-pentenamine

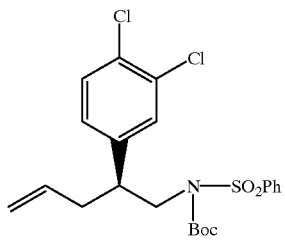

To a solution of the N-phenylsulfonyl-2(S)-(3,4-dichlorophenyl)-4-pentenamine ($^{35}$ mg, 0.08 mmol), from Step C, in CH$_2$Cl$_2$ (10 mL) at room temperature was added Et$_3$N (72 mg, 0.71 mmols), DMAP (8 mg, 0.07 mmols) followed by BOC anhydride (156 mg, 0.71 mmols) in a solution of CH$_2$Cl$_2$ (0.75 mL). After stirring for 2 hours, the reaction was quenched with H$_2$O (5 mL) and stirred for 10 minutes. The reaction was then diluted with H$_2$O (50 mL) and extracted with CH$_2$Cl$_2$ (3×50 mL). The combined organic extracts were washed with brine, dried (Na$_2$SO$_4$) and concentrated in vacuo. The residue was purified by column chromatography (30g silica gel 60, 30 mm col. diam., 10–25% EtOAc/Hex) to afford the tiltle compound (270 mg, 89%) as a oil. $^1$H NMR (CDCl$_3$, 500 MHz) δ 7.72 (dd, 2H, J=1.1, 7.3 Hz), 7.58–7.61 (m, 1H), 7.40–7.49 (m, 2H), 7.39 (d, 1H, J=8.2 Hz), 7.31 (d, 1H, J=1.8 Hz), 7.12 (dd, 1H, J=2.1, 8.1 Hz), 5.64–5.69 (m, 1H), 5.05 (dd, 1H, J=1.6, 17.2 Hz), 5.00 (d, 1H, J=10.1 Hz), 4.01–4.06 (m, 2H), 3.24–3.27 (m, 1H), 2.52–2.56 (m, 1H), 2.42–2.47 (m, 1H), 1.24 (s, 9H), ppm.

Step E: 3(S)-(3,4-dichlorophenyl)-4-(N-tert-butylcarbamoyl-N-phenylsulfonyl)amino butanecarboxaldehyde

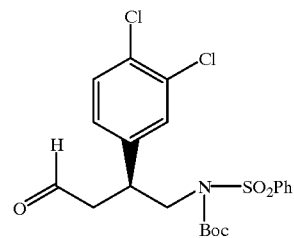

To a mixture of N-tert-butylcarbamoyl-N-phenylsulfonyl-2(S)-(3,4-dichlorophenyl)-4-pentenamine (265 mg, 0.56 mmols), from Step D, in a 2:1:1 acetone/t-butanol/H$_2$O (6 mL) mixture at room temperature was added OsO$_4$ (1.5 mL, 2.5% t-butanol solution). After stirring for 10 minutes, NMMO (99 mg, 0.85 mmols) was added and the reaction was stirred at room temperature. After 2 hours the reaction was quenched with an aqueous solution of 20% sodium bisulfite (3 mL) and the reaction was stirred for 15 mins. The reaction was diluted with H$_2$O (50 mL) and extracted with CH$_2$Cl$_2$ (3×25 mL). The combined organic extracts were washed with brine, dried (Na$_2$SO$_4$), and concentrated in vacuo to afford the diol as a colorless oil. The oil was used directly as described in the next paragraph.

To a solution of the diol, in a 3:1 THF/H$_2$O (9 mL) mixture at room temperature was added NaIO$_4$ (220 mg, 1.03 mmols). After stirring for 12 hours the reaction mixture was diluted with H$_2$O (100 mL) and the mixture was extracted with EtOAc (3×100 mL). The combined organic extracts were washed with brine, dried (Na$_2$SO$_4$), and concentrated in vacuo . The residue was purified by column chromatography (28 g silica gel 60, 30 mm col. diam., 25–40% EtOAc/Hex) to afford the aldehyde (199 mg, 75%) as an oil. $^1$H NMR (CDCl$_3$, 500 MHz) δ 9.72 (s, 1H) 7.75 (d, 2H, J=1.2 Hz), 7.59–7.62 (m, 1H), 7.47–7.50 (m, 2H), 7.40 (d, 1H, J=8.5 Hz), 7.37 (d, 1H, J=2.0 Hz), 7.15 (dd, 1H, J=2.0, 8.2 Hz), 4.01–4.06 (m, 2H), 3.79–3.83 (m, 1H), 2.99 (dd, 1H, J=5.4, 17.6 Hz), 2.90 (ddd, 1H, J=1.6, 9.2, 17.7 Hz), 1.27 (s, 9H) ppm.

Step F: N-tert-butylcarbamoyl-N-phenylsulfonyl-2(S)-(3,4-dichloro)-4-(spiro[2,3-dihydrobenzothiophene-3,4'-piperdin-1'-yl)butanamine

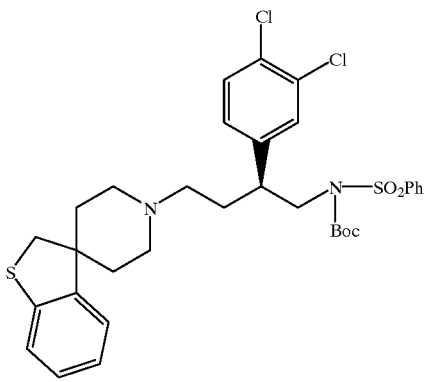

To a solution of 3(S)-(3,4-dichlorophenyl)-4-(N-tert-butylcarbamoyl-N-phenylsulfonyl)amino butanecarboxaldehyde, from Step E,(197 mg, 0.42 mmol) in MeOH (5 mL) at room temperature was added 3 A mol sieves (200 mg) followed by spiro-2,3-dihydrobenzothiophene-3,4'-piperdin-1'-yl hydrochloride (121 mg, 0.51 mmols). After stirring for 2 hours, solid NaCNBH$_3$ (105 mg, 1.67 mmols) was added as a single portion. The mixture was stirred at room temperature for 12 hours whereupon it was filtered thru celite, washed with MeOH, and the filtrate concentrated in vacuo. The residue was partitioned between H$_2$O (50 mL) and EtOAc (50 mL), followed by extraction with EtOAc (3×50 mL). The combined organic extracts were washed with brine, dried (Na$_2$SO$_4$) and concentrated in vacuo. The residue was purified by column chromatography (5 g silica gel 60, 30 mm col. diam., 2.5–8% MeOH/CH$_2$Cl$_2$) to afford the amine (222 mg, 81%). $^1$H NMR (CDCl$_3$, 500 MHz) δ 7.74–7.77 (m, 2H), 7.58–7.63 (m, 1H), 7.46–7.52 (m, 2H), 7.38–7.42 (m, 1H), 7.36–7.38 (m, 1H), 7.06–7.22 (m, 5H), 4.03–4.01 (m, 2H), 3.15–3.38 (m, 3H), 2.75–2.95 (m, 2H), 1.79–2.35 (m, 10H), 1.25 (s, 9H) ppm.

Step G: N-phenylsulfonyl-2(S)-(3,4-dichloro)-4-(spiro[2,3-dihydrobenzothiophene-3 4'-piperdin-1'-yl)butanamine

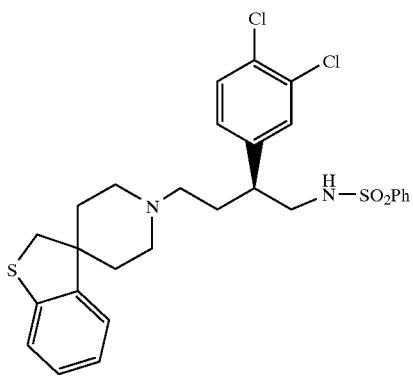

To a solution of N-tert-butylcarbamoyl-N-phenylsulfonyl-2(S)-(3,4-dichloro)-4-(spiro[2,3-dihydrobenzothiophene-3,4'-piperdin-1'-yl)butanamine (110 mg, 0.17 mmols), from Step F, in CH$_2$Cl$_2$ (5 mL) at 0° C. was added anisole (18 mg, 0.17 mmols) followed by TFA (2 ml). The reaction was stirred at 0° C. for 2.5 hours and then warmed to room temperature. The reaction was diluted with H$_2$O (100 mL), a saturated solution of NaHCO$_3$ (100 mL) and then extracted with CH$_2$Cl$_2$ (3×100 mL). The combined organic extracts were washed with brine, dried (Na$_2$SO$_4$), and concentrated in vacuo. The residue was purified by column chromatography (5 g silica gel 60, 20 mm col. diam., 2.5–8% MeOH/CH$_2$Cl$_2$) to afford the sulfonamide (78 mg, 84%) as an oil. $^1$H NMR (CDCl$_3$, 500 MHz) δ 7.84 (d, 2H, J=7.3 Hz), 7.57–7.61 (m, 1H), 7.50–7.53 (m, 2H), 7.34 (d, 1H, J=8.2 Hz), 7.27–7.28 (m, 1H), 7.10–7.26 (m, 4H), 6.93 (dd, 1H, J=1.8, 8.2 Hz), 3.29 (s, 2H), 2.94–3.16 (m, 5H), 1.76–2.52 (m, 11H) ppm.

EXAMPLE 231

N-phenylsulfonyl-2(S)-(3,4-dichloro)-4-(spiro[2,3-dihydrobenzothiophene-3,4'-piperdin-1'-yl)butanamine, S-oxide

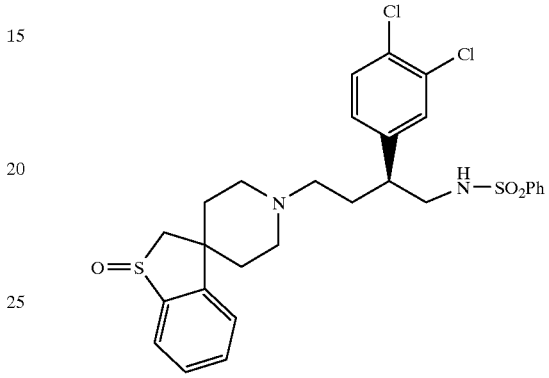

To a solution of N-phenylsulfonyl-2(S)-(3,4-dichloro)-4-(spiro[2,3-dihydrobenzothiophene-3,4'-piperdin-1'-yl) butanamine (32 mg, 0.06 mmol), from Example 230, Step G, in a 1:1 MeOH/H$_2$O (3 mL) mixture at 0° C. was added Oxone® (45 mg, 0.07 mmols). After stirring for 3 minutes the reaction was quenched with 20% aqueous sodium bisulfite (3 mL) and stirred for 10 minutes. The reaction was then diluted with H$_2$O (50 mL) and extracted with CH$_2$Cl$_2$ (3×50 mL). The combined organic extracts were washed with brine, dried (Na$_2$SO$_4$) and concentrated in vacuo. The residue was purified by preparative TLC (500 um plate, 20×20 cm., 2.5% MeOH/CH$_2$Cl$_2$) to afford the sulfoxide (19 mg, 59%) as a colorless solid. $^1$H NMR (CDCl$_3$, 500 MHz) δ 7.83–7.86 (m, 3H), 7.48–7.67 (m, 6H), 7.35 (d, 1H, J=8.2 Hz), 7.15–7.18 (m, 1H), 6.94 (d, 1H, J=8.2 Hz), 3.37–3.43 (m, 2H), 3.07–3.19 (m,4H), 2.75–2.79 (m, 1H), 1.76–2.52 (m, 11H) ppm.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in the responsiveness of the mammal being treated for any of the indications with the compounds of the invention indicated above. Likewise, the specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A compound of the Formula II:

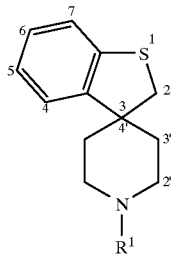

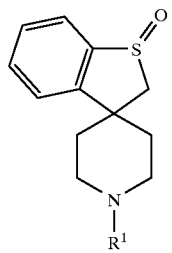

or

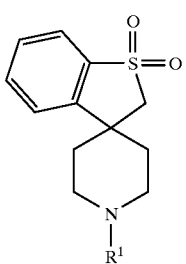

II wherein the optional substitutents residing at the positions numbered #2, #2', #3', #4, #5, #6 or #7 on the above structures, are independently selected from the group consisting of:

(a) hydroxy,
(b) oxo,
(c) cyano,
(d) chloro,
(e) fluoro,
(f) -CF$_3$,
(g) -phenyl;

R$_1$ is:

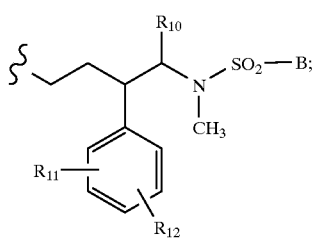

where B is phenyl, or mono di or trisubstituted phenyl, wherein the substitutents on phenyl are independents selected from:
chloro, fluoro, methyl, phenyl or CF$_3$;

R$_{10}$ is selected from: hydrogen, C$_{1-3}$alkyl, and phenyl;
R$_{11}$ and R$_{12}$ are independently selected from:
hydrogen, halogen, methyl, phenyl or CF$_3$;
and pharmaceutically acceptable salts thereof.

2. A compound which is selected from the group consisting of:

1'-(3-((S)-(3-Chlorophenyl))-4-(N-(phenylsulfonyl)(methylamino))butyl)-spiro(2,3-dihydrobenzothiophene-3,4'-piperidine);

1'-(3-((S)-(3-Chlorophenyl))-4-(N-(phenylsulfonyl)(methylamino))butyl)-spiro(2,3-dihydrobenzothiophene-3,4'-piperidine)-1-oxide;

1'-(3-((S)-(3-Chlorophenyl))-4-(N-(phenylsulfonyl)(methylamino))butyl)-spiro(2,3-dihydrobenzothiophene-3,4'-piperidine)-1,1-dioxide;

1'-(3-((R,S)-(Phenyl))-4-(N-(phenylsulfonyl)(methylamino))butyl)-spiro(2,3-dihydrobenzothiophene-3,4'-piperidine);

1'-(3-((R,S)-(3-Thienyl))-4-(N-(phenylsulfonyl)(methylamino))butyl)-spiro(2,3-dihydrobenzothiophene-3,4'-piperidine);

1'-(3-((R,S)-(2-Thienyl))-4-(N-(phenylsulfonyl)(methylamino))butyl)-spiro(2,3-dihydrobenzothiophene-3,4'-piperidine);

1'-(3-((S)-(4-Fluorophenyl))-4-(N-(phenylsulfonyl)(methylamino))butyl)-spiro(2,3-dihydrobenzothiophene-3,4'-piperidine);

1'-(3-((1R,S)-(3, 5-Dichlorophenyl))-4-(N-(phenylsulfonyl)(methylamino))butyl)-spiro(2,3-dihydrobenzothiophene-3,4'-piperidine);

1'-(3-((S)-(3,4-Dichlorophenyl))-4-(N-(phenylsulfonyl)(ethylamino))butyl)-spiro(2,3-dihydrobenzothiophene-3,4'-piperidine);

1'-(3-((R,S)-(Phenyl))-4-(N-(phenylsulfonyl)(methylamino))butyl)-spiro(2,3-dihydrobenzothiophene-3,4'-piperidine)1-oxide;

1'-(3-((R,S)-(3-Thienyl))-4-(N-(phenylsulfonyl)(methylamino))butyl)-spiro(2,3-dihydrobenzothiophene-3 4'-piperidine)-1-oxide;

1'-(3-((R,S)-(2-Thienyl))-4-(N-(phenylsulfonyl)(methylamino))butyl)-spiro(2,3-dihydrobenzothiophene-3,4'-piperidine)-1-oxide;

1'-(3-((S)-(4-Fluorophenyl))-4-(N-(phenylsulfonyl)(methylamino))butyl)-spiro(2,3-dihydrobenzothiophene-3,4'-piperidine)-1-oxide;

1'-(3-((R,S)-(3,5-Dichlorophenyl))-4-(N-(phenylsulfonyl)(methylamino))butyl)-spiro(2,3-dihydrobenzothiophene-3,4'-piperidine)-1-oxide;

1'-(3-((S)-(3,4-Dichlorophenyl))-4-(N-(phenylsulfonyl)(ethylamino))butyl)-spiro(2,3-dihydrobenzothiophene-3,4'-piperidine)-1-oxide;

1'-(3-((R,S)-(Phenyl))-4-(N-(phenylsulfonyl)(methylamino))butyl)-spiro(2,3-dihydrobenzothiophene-3,4'-piperidine)-1, 1-dioxide;

1'-(3-((R,S)-(2-Chlorophenyl))-4-(N-(phenylsulfonyl)(methylamino))butyl)-spiro(2,3-dihydrobenzothiophene-3,4'-piperidine)-1,1-dioxide;

1'-(3-((R,S)-(3-Thienyl))-4-(N-(phenylsulfonyl)(methylamino))butyl)-spiro(2,3-dihydrobenzothiophene-3,4'-piperidine)-1,1-dioxide;

1'-(3-((R,S)-(2-Thienyl))-4-(N-(phenylsulfonyl)(methylamino))butyl)-spiro(2,3-dihydrobenzothiophene-3,4'-piperidine)-1,1-dioxide;

1'-(3-((S)-(4-Fluorophenyl))-4-(N-(phenylsulfonyl)(methylamino))butyl)-spiro(2,3-dihydrobenzothiophene-3,4'-piperidine)-1,1-dioxide;

1'-(3-((R,S)-(3,5-Dichlorophenyl))-4-(N-(phenylsulfonyl)(methylamino))butyl)-spiro(2,3-dihydrobenzothiophene-3,4'-piperidine)-1,1-dioxide;

1'-(3-((S)-(3,4-Dichlorophenyl))-4-(N-(phenylsulfonyl)(ethylamino))butyl)-spiro(2,3-dihydrobenzothiophene-3,4'-piperidine)-1,1-dioxide;

1'-(3-((R,S)-Phenyl)-4-(N-(phenylacetyl)(methylamino))butyl)-spiro(2,3-dihydrobenzothiophene-3,4'-piperidine);

1'-(3-((R,S)-Phenyl)-4-(N-(phenylacetyl)(methylamino))butyl)-spiro(2,3-dihydrobenzothiophene-3,4'-piperidine)-1-oxide;

1'-(3-((R,S)-Phenyl)-4-(N-(phenylacetyl)(methylamino))butyl)-spiro(2,3-dihydrobenzothiophene-3,4'-piperidine)-1,1-dioxide;

1'-(3-((R,S)-Phenyl)-4-(N-((R)-α-methyl phenylacetyl)(methylamino))butyl)-spiro(2,3-dihydrobenzothiophene-3,4'-piperidine);

1'-(3-((R,S)-Phenyl)-4-(N-((R)-α-methylphenylacetyl)(methylamino))butyl)-spiro(2,3-dihydrobenzothiophene-3,4'-piperidine)-1-oxide;

1'-(3-((R,S)-Phenyl)-4-(N-((R)-α-methyl phenylacetyl)(methylamino))butyl)-spiro(2,3-dihydrobenzothiophene-3,4'-piperidine)-1,1-dioxide;

1'-(3-((R,S)-Phenyl)-4-(N-((S)-α-methyl phenylacetyl)(methylamino))butyl)-spiro(2,3-dihydrobenzothiophene-3,4'-piperidine);

1'-(3-((R,S)-Phenyl)-4-(N-((S)-α-methylphenylacetyl)(methylamino))butyl)-spiro(2,3-dihydrobenzothiophene-3,4'-piperidine)-1,1-oxide;

1'-(3-((R,S)-Phenyl)-4-(N-((S)-α-methyl phenylacetyl)(methylamino))butyl)-spiro(2,3-dihydrobenzothiophene-3,4'-piperidine)-1,1-dioxide;

1'-(3-((S)-(3-Chlorophenyl))-4-(N-(phenylsulfonyl)(methylamino))butyl)-spiro(indoline-3,4'-piperidine);

1'-(3-((S)-(3-Chlorophenyl))-4-(N-(phenylsulfonyl)(methylamino))butyl)-spiro(1-oxoisoindoline-3,4'-piperidine);

1'-(3-((S)-(3-Chlorophenyl))-4-(N-(phenylsulfonyl)(methylamino))butyl)-spiro(1-oxo-2-methylisoindoline-3,4'-piperidine);

1'-(3-((R,S)-Phenyl)-4-(N-(benzyl)(methylamino))butyl)-spiro(2,3-dihydrobenzothiophene-3,4'-piperidine);

1'-(3-((R,S)-Phenyl)-4-(N-(benzyl)(methylamino))butyl)-spiro(2,3-dihydrobenzothiophene-3,4'-piperidine)-1-oxide;

1'-(3-((R,S)-Phenyl)-4-(N-(benzyl)(methylamino))butyl)-spiro(2,3-dihydrobenzothiophene-3,4'-piperidine)-1,1-dioxide;

N-(2-(3-Chlorophenyl)-5-(spiro(benzo[b]thiophene-3(2H),4'-piperidin)-1'-yl)pentyl)-N-methylbenzenesulfonamide;

N-(2-(3-Chlorophenyl)-5-(spiro(benzo[b]thiophene-3(2H),4'-piperidin)-1-oxide-1'-yl)pentyl)-N-methylbenzenesulfonamide;

N-(2-(3-Chlorophenyl)-5-(spiro(benzo[b]thiophene-3(2H),4'-piperidin)-1,1-dioxide-1'-yl)pentyl)-N-methylbenzenesulfonamide;

N-Methyl-N-(2-phenyl-2-(spiro(benzo[b]thiophene-3(2H),4'-piperidin)-1,1-yl)ethyl)benzenesulfonamide;

N-Methyl-N-(2-phenyl-2-(spiro(benzo[b]thiophene-3(2H),4'-piperidin)-1-oxide-1'-yl)ethyl)benzenesulfonamide;

N-Methyl-N-(2-(phenyl-2-(spiro(benzo[b]thiophene-3(2H),4'-piperidin)-1,1-dioxide-1'-yl)ethyl)benzenesulfonamide;

N-Methyl-N-(3-phenyl-5-(spiro(benzo[b]thiophene-3(2H),4'-piperidin)-1'-yl)pentyl)benzenesulfonamide;

N-Methyl-N-(3-phenyl-5-spiro(benzo[b]thiophene-3(2H),4'-piperidin)-1-oxide-1'-yl)pentyl)benzenesulfonamide;

N-Methyl-N-(3-phenyl-5-spiro(benzo[b]thiophene-3(2H),4'-piperidin)-1,1-dioxide-1'-yl)pentyl)benzenesulfonamide;

N-Methyl-N-(3-phenyl-5-(spiro(benzo[b]thiophene-3(2H),4'-piperidin)-1'-yl)pentyl)benzamide;

N-Methyl-N-(3-phenyl-5-(spiro(benzo[b]thiophene-3(2H),4-piperidin)-1-oxide-1'-yl)pentyl)benzamide;

N-Methyl-N-(3-phenyl-5-spiro(benzo[b]thiophene-3(2H),4'-piperidin)-1-oxide-1'-yl)pentyl)benzenesulfonamide;

N-Methyl-N-(3-phenyl-5-spiro(benzo[b]thiophene-3(2H),4'-piperidin)-1,1-dioxide-1'-yl)pentyl)benzenesulfonamide;

N-Methyl-N-(3-phenyl-5-(spiro(benzo[b]thiophene-3(2H),4'-piperidin)1'-yl)pentyl)benzamide;

N-Methyl-N-(3-phenyl-5-(spiro(benzo[b]thiophene-3(2H),4'-piperidin)-1-oxide-1'-yl)pentyl)benzamide;

N-Methyl-N-(3-phenyl-5-(spiro(benzo[b]thiophene-3(2H),4'-piperidin)-1,1-dioxide-1'-yl)pentyl)benzamide;

N-Methyl-N-(2-phenyl-3-(spiro(benzo[b]thiophene-3(2H),4'-piperidin)-1-oxide-1'-yl)propyl)benzenesulfonamide;

N-Methyl-N-(2-phenyl-3-(spiro(benzo[b]thiophene-3(2H),4'-piperidin)-1,1-dioxide-1'-yl)propyl)benzenesulfonamide;

N-(2-Benzyl-3-(spiro(benzo[b]thiophene-3(2H),4'-piperidin)-1'-yl)propyl)-N-methylbenzenesulfonamide;

N-(2-Benzyl-3-(spiro(benzo[b]thiophene-3(2H),4'-piperidin)-1-oxide-1'-yl)propyl)-N-methylbenzenesulfonamide;

N-(2-Benzyl-3-(spiro(benzo[b]thiophene-3(2H),4'-piperidin)-1,1-dioxide-1'-yl)propyl)-N-methylbenzenesulfonamide;

N-Methyl-N-(2-methyl-2-phenyl-4-(spiro(benzo[b]thiophene-3(2H),4'-piperidin)-1'-yl)butyl)benzenesulfonamide;

N-Methyl-N-(2-methyl-2-phenyl-4-(spiro(benzo[b]thiophene-3(2H), 4'-piperidin)-1-oxide-1'-yl)butyl)benzenesulfonamide;

N-Methyl-N-(2-methyl-2-phenyl-4-(spiro(benzo[b]thiophene-3(2H),4'-piperidin)-1,i-dioxide-1'-yl)butyl)benzenesulfonamide;

1'-(3-((S)-(3,4-Dichlorophenyl))-4-(N-(phenylmethylsulfonyl)(methylamino))-butyl)-spiro(2,3-dihydrobenzothiophene-3,4'-piperidine);

1'-(3-((S)-(3,4-Dichlorophenyl))-4-(N-(quinoline-8-sulfonyl)(methylamino))-butyl)-spiro(2,3-dihydrobenzothiophene-3,4'-piperidine);

1'-(3-((R)-(3,4-Dichlorophenyl))-4-(N-(benzenesulfonyl)(methylamino))butyl)-spiro(2,3-dihydrobenzothiophene-3,4'-piperidine);

1'-(3-((R)-(3,4-Dichlorophenyl))-4-(N-(thiophene-2-sulfonyl)(methylamino))-butyl)-spiro(2,3-dihydrobenzothiophene-3,4'-piperidine);

1'-(3-((S)-(3,4-Dichlorophenyl))-4-(N-(benzenesulfonyl)-(methylamino))butyl)-spiro(2,3-dihydrobenzothiophene-3,4'-piperidine)-1,1-dioxide;

1'-(3-((S)-(4-Chlorophenyl))-4-(N-(benzenesulfonyl)-(methylamino))butyl)-spiro(2,3-dihydrobenzothiophene-3,4'-piperidine)-1-oxide;

1'-(3-((S)-(4-Chlorophenyl))-4-(N-(methanesulfonyl)-(methylamino))butyl)-spiro(2,3-dihydrobenzothiophene-3,4'-piperidine)-1-oxide;

1'-(3-((S)-(4-Chlorophenyl))-4-(N-(phenylmethylsulfonyl)-(methylamino))butyl)-spiro(2,3-dihydrobenzothiophene-3,4'-piperidine)-1-oxide;

1'-(3-((S)-(4-Chlorophenyl))-4-(N-(quinoline-8-sulfonyl)-(methylamino))butyl)-spiro(2,3-dihydrobenzothiophene-3,4'-piperidine)-1-oxide;

1'-(3-((R)-(4-Chlorophenyl))-4-(N-(benzenesulfonyl)-(methylamino))butyl)-spiro(2,3-dihydrobenzothiophene-3,4'-piperidine)-1-oxide;

1'-(3-((R)-(4-Chlorophenyl))-4-(N-(thiophene-2-sulfonyl)-(methylamino))butyl)-spiro(2,3-dihydrobenzothiophene-3,4'-piperidine)-1-oxide;

1'-(3-((S)-(4-Chlorophenyl))-4-(N-(quinoline-3-sulfonyl)-(methylamino))butyl)-spiro(2,3-dihydrobenzothiophene-3,4'-piperidine)-1-oxide;

1'-(3-((S)-(4-Chlorophenyl))-4-(N-(phenoxycarbonyl)-(methylamino))butyl)-spiro(2,3-dihydrobenzothiophene-3,4'-piperidine)-1-oxide;

1'-(3-((S)-(4-Chlorophenyl))-4-(N-(phenylaminocarbonyl)-(methylamino))butyl)-spiro(2,3-dihydrobenzothiophene-3,4'-piperidine)-1-oxide;

1'-(3-((S)-(4-Chlorophenyl))-4-(N-(benzoylformyl)-(methylamino))butyl)spiro(2,3-dihydrobenzothiophene-3,4'-piperidine)-1-oxide;

1'-(3-((S)-(4-Chlorophenyl))-4-(N-(pyridine-3-sulfonyl)-(methylamino))butyl)-spiro(2,3-dihydrobenzothiophene-3,4'-piperidine)-1-oxide;

1'-(3-((S)-(3,4-Dichlorophenyl))-4-(N-(4-chlorobenzenesulfonyl)-(methylamino))butyl)-spiro(2,3-dihydrobenzothiophene-3,4'-piperidine)-1-oxide;

1'-(3-((S)-(3,4-Dichlorophenyl))-4-(N-(3-nitrobenzenesulfonyl)-(methylamino))butyl)-spiro(2,3-dihydrobenzothiophene-3,4'-piperidine)-1,1-dioxide;

1'-(3-((S)-(3,4-Dichlorophenyl))-4-(N-(4-nitrobenzenesulfonyl)-(methylamino))butyl)-spiro(2,3-dihydrobenzothiophene-3,4'-piperidine)-1,1-dioxide;

1'-(3-((S)-(3,4-Dichlorophenyl))-4-(N-(2-chlorobenzenesulfonyl)-(methylamino))butyl)-spiro(2,3-dihydrobenzothiophene-3,4'-piperidine)-1-oxide;

1'-(3-((S)-(3,4-Dichlorophenyl))-4-(N-(3-chlorobenzenesulfonyl)-(methylamino))butyl)-spiro(2,3-dihydrobenzothiophene-3,4'-piperidine)1-oxide;

1'-(3-((S)-(3,4-Dichlorophenyl))-4-(N-(2,3,4,5,6-pentafluorobenzenesulfonyl)-(methylamino))butyl)-spiro(2,3-dihydrobenzothiophene-3,4'-piperidine)-1-oxide;

1'-(3-((S)-(3,4-Dichlorophenyl))-4-(N-(4-biphenylsulfonyl)-(methylamino))butyl)-spiro(2,3-dihydrobenzothiophene-3,4'-piperidine)-1-oxide;

1'-(3-((S)-(3,4-Dichlorophenyl))-4-(N-(4-methoxybenzenesulfonyl)-(methylamino))butyl)-spiro(2,3-dihydrobenzothiophene-3,4'-piperidine)-1-oxide;

(+/-) N-methyl-N-phenylsulfonyl-2-(3-chloro-4-benzyloxy)-4-(spiro[2,3-dihydrobenzothiophene-3,4'-piperdin-1'-yl)butanamine;

(+/-) N-methyl-N-phenylsulfonyl-2-(3-chloro-4-benzyloxy)-4-(spiro[2,3-dihydrobenzothiophene-3,4'-piperdin-1'-yl)butamine, S-oxide;

(+/-) N-methyl-N-phenylsulfonyl-2-(3-chloro-4-benzyloxy)-4-(spiro[2,3-dihydrobenzothiophene-3'-piperdin-1'-yl)butamine, S-dioxide;

(+/-) N-methyl-N-phenylsulfonyl-2-(3-chloro-4-hydroxy)-4-(spiro[2,3-dihydrobenzothiophene-3,4'-piperdin-1'-yl)butanamine;

(+/-) N-methyl-N-phenylsulfonyl-2-(3-chloro-4-hydroxy)-4-(spiro[2,3-dihydrobenzothiophene-3,4'-piperdin-1'-yl)butanamine, S-oxide;

(+/-) N-methyl-N-phenylsulfonyl-2-(3-chloro-4-hydroxy)-4-(spiro[2,3-dihydrobenzothiophene-3,4'-piperdin-1'-yl)butanamine, S-dioxide;

(+/-) N-methyl-N-phenylsulfonyl-2-(4-benzyloxy)-4-(spiro[2,3-dihydrobenzothiophene-3,4'-piperdin-1'-yl)butanamine;

(+/-) N-methyl-N-phenylsulfonyl-2-(4-benzyloxy)-4-(spiro[2,3-dihydrobenzothiophene-3,4'-piperdin-1'-yl)butanamine, S-oxide;

(+/-) N-methyl-N-phenylsulfonyl-2-(4-hydroxy)-4-(spiro[2,3-dihydrobenzothiophene-3,4'-piperdin-1'-yl)butanamine;

(+/-) N-methyl-N-phenylsulfonyl-2-(4-benzyloxy)-4-(spiro[2,3-dihydrobenzothiophene-3,4'-piperdin-1'-yl)butanamine,S-oxide;

(+/-) N-methyl-N-phenylsulfonyl-2-(4-benzyloxy)-4-(spiro[2,3-dihydrobenzothiophene-3,4'-piperdin-1'-yl)butamine,S-dioxide;

N-phenylsulfonyl-2(S)-(3,4-dichloro)-4-(spiro[2,3-dihydrobenzothiophene-3,4'-piperdin-1'-yl)butanamine;

N-phenylsulfonyl-2(S)-(3,4-dichloro)-4-(spiro[2,3-dihydrobenzothiophene-3,4'-piperdin-1'-yl)butanamine, S-oxide;

and pharmaceutically acceptable salts thereof.

3. A method for modulation of chemokine receptor activity in a mammal comprising the administration of an effective amount of a compound of Formula II:

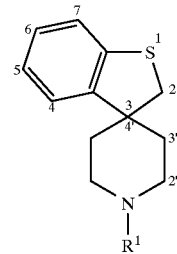

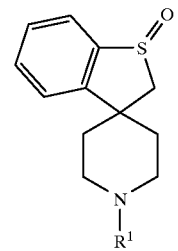

or

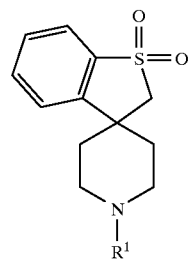

wherein the optional substitutents residing at the positions numbered #2, #2', #3', #4, #5, #6 or #7 on the above structures, are independently selected from the group consisting of:

(a) hydroxy, (b) oxo, (c) cyano, (d) chloro, (e) fluoro, (f) -CF$_3$, (g) -phenyl;

$R_1$ is:

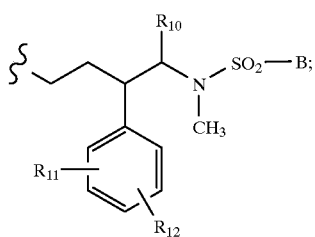

where B is phenyl, or mono di or trisubstituted phenyl, wherein the substitutents on phenyl are independently selected from:
chloro fluoro, methyl, phenyl or $CF_3$;
$R_{10}$ is selected from: hydrogen, $C_{1-3}$alkyl, and phenyl;
$R_{11}$ and $R_{12}$ are independently selected from:
hydrogen, halogen, methyl, phenyl or $CF_3$.
and pharmaceutically acceptable salts thereof.

4. The method of claim 3 wherein the compound of Formula II, B is phenyl or mono di or trisubstituted phenyl wherein the substitutents on phenyl are independently selected from:
chloro, methyl, phenyl and $CF_3$.

5. The method of claim 3 wherein the compound of Formula II, B is unsubstituted phenyl, 3-chlorophenyl or 3-fluorophenyl.

6. The method of claim 3 wherein the compound is selected from the group consisting of:
1'-(3-((S)-(3-Chlorophenyl))-4-(N-(phenylsulfonyl)(methylamino))butyl)-spiro(2,3-dihydrobenzothiophene-3,4'-piperidine);
1'-(3-((S)-(3-Chlorophenyl))-4-(N-(phenylsulfonyl)(methylamino))butyl)-spiro(2,3-dihydrobenzothiophene-3,4'-piperidine)-1-oxide;
1'-(3-((S)-(3-Chlorophenyl))-4-(N-(phenylsulfonyl)(methylamino))butyl)-spiro(2,3-dihydrobenzothiophene-3,4'-piperidine)-1,1-dioxide;
1'-(3-((R,S)-(Phenyl))4-(N-(phenylsulfonyl)(methylamino))butyl)-spiro(2,3-dihydrobenzothiophene-3,4'-piperidine);
1'-(3-((R,S)-(3-Thienyl))-4-(N-(phenylsulfonyl)(methylamino))butyl)-spiro(2,3-dihydrobenzothiophene-3,4'-piperidine);
1'-(3-((R,S)-(2-Thienyl))-4-(N-(phenylsulfonyl)(methylamino))butyl)-spiro(2,3-dihydrobenzothiophene-3,4'-piperidine);
1'-(3-((S)-(4-Fluorophenyl))-4-(N-(phenylsulfonyl)(methylamino))butyl)-spiro(2,3-dihydrobenzothiophene-3,4'-piperidine);
1'-(3-((R,S)-(3,5-Dichlorophenyl))-4-(N-(phenylsulfonyl)(methylamino))butyl)-spiro(2,3-dihydrobenzothiophene-3,4'-piperidine);
1'-(3-((S)-(3,4-Dichlorophenyl))-4-(N-(phenylsulfonyl)(ethylamino))butyl)-spiro(2,3-dihydrobenzothiophene-3,4'-piperidine);
1-(3-((1R,S)-(Phenyl))-4-(N-(phenylsulfonyl)(methylamino))butyl)-spiro(2,3-dihydrobenzothiophene-3,4'-piperidine)-1-oxide;
1'-(3-((R,S)-(3-Thienyl))-4-(N-(phenylsulfonyl)(methylamino))butyl)-spiro(2,3-dihydrobenzothiophene-3,4'-piperidine)1-oxide;
1'-(3-((R,S)-(2-Thienyl))-4-(N-(phenylsulfonyl)(methylamino))butyl)-spiro(2,3-dihydrobenzothiophene-3,4'-piperidine)-1-oxide;
1'-(3-((S)-(4-Fluorophenyl))-4-(N-(phenylsulfonyl)(methylamino))butyl)-spiro(2,3-dihydrobenzothiophene-3,4'-piperidine)1-oxide;
1'-(3-((R,S)-(3,5-Dichlorophenyl))-4-(N-(phenylsulfonyl)(methylamino))butyl)-spiro(2,3-dihydrobenzothiophene-3,4'-piperidine)-1-oxide;
1-(3-((S)-(3,4-Dichlorophenyl))-4-(N-(phenylsulfonyl)(ethylamino))butyl)-spiro(2,3-dihydrobenzothiophene-3,4'-piperidine)-1 1-oxide;
1'-(3-((R,S)-(Phenyl))-4-(N-(phenylsulfonyl)(methylamino))butyl)-spiro(2,3-dihydrobenzothiophene-3,4'-piperidine)-1,1-dioxide;
1'-(3-((1R,S)-(2-Chlorophenyl))-4-(N-(phenylsulfonyl)(methylamino))butyl)-spiro(2,3-dihydrobenzothiophene-3,4'-piperidine)-1,1-dioxide;
1'-(3-((R,S)-(3-Thienyl))-4-(N-(phenylsulfonyl)(methylamino))butyl)-spiro(2,3-dihydrobenzothiophene-3,4'-piperidine)-1,1-dioxide;
1'-(3-((R,S)-(2-Thienyl))-4L-(N-(phenylsulfonyl)(methylamino))butyl)-spiro(2,3-dihydrobenzothiophene-3,4'-piperidine)-1,1-dioxide;
1'-(3-((S)-(4-Fluorophenyl))-4-(N-(phenylsulfonyl)(methylamino))butyl)-spiro(2,3-dihydrobenzothiophene-3,4'-piperidine)-1,1-dioxide;
1'-(3-((R,S)-(3,5-Chlorophenyl))-4-(N-(phenylsulfonyl)(methylamino))butyl)-spiro(2,3-dihydrobenzothiophene-3,4'-piperidine)-1,1-dioxide;
1-(3-((S)-(3,4-Chlorophenyl))-4-(N-(phenylsulfonyl)(ethylamino))butyl)-spiro(2,3-dihydrobenzothiophene-3,4'-piperidine)-1,1-dioxide;
1'-(3-((R,S)-Phenyl)-4-(N-(phenylacetyl)(methylamino))butyl)-spiro(2,3-dihydrobenzothiophene-3,4'-piperidine);
1'-(3-((R,S)-Phenyl)-4-(N-(phenylacetyl)(methylamino))butyl)-spiro(2,3-dihydrobenzothiophene-3,4'-piperidine)-1-oxide;
1'-(3-((R,S)-Phenyl)-4-(N-(phenylacetyl)(methylamino))butyl)-spiro(2,3-dihydrobenzothiophene-3,4'-piperidine)-1,1-dioxide;
1'-(3-((R,S)-Phenyl)-4-(N-((R)-a-methyl phenylacetyl)(methylamino))butyl)-spiro(2,3-dihydrobenzothiophene-3,4'-piperidine); 1'-(3-((R,S)-Phenyl)-4-(N-((R)-a-methylphenylacetyl)(methylamino))-butyl)-spiro(2,3-dihydrobenzothiophene-3,4'-piperidine)-1-oxide;
1'-(3-((R,S)-Phenyl)-4-(N-((R)-a-methyl phenylacetyl)(methylamino))butyl)-spiro(2,3-dihydrobenzothiophene-3,4'-piperidine)-1,1-dioxide;
1'-(3-((R,S)-Phenyl)-4-(N-((S)-a-methyl phenylacetyl)(methylamino))butyl)-spiro(2,3-dihydrobenzothiophene-3,4'-piperidine);
1'-(3-((R,S)-Phenyl)-4-(N-((S)-a-methylphenylacetyl)(methylamino))-butyl)-spiro(2,3-dihydrobenzothiophene-3,4'-piperidine)1-dioxide;
1'-(3-((R,S)-Phenyl)-4-(N-((S)-a-methyl phenylacetyl)(methylamino))-butyl)-spiro(2,3-dihydrobenzothiophene-3,4'-piperidine)-1,1-dioxide;
1'-(3-((S)-(3-Chlorophenyl))-4-(N-(phenylsulfonyl)(methylamino))butyl)-spiro(indoline-3,4'-piperidine);
1'-(3-((S)-(3-Chlorolphenyl))-4-(N-(phenylsulfonyl)(methylamino))butyl)-spiro(1-oxoisoindoline-3,4'-piperidine);
1'-(3-((S)-(3-Chlorophenyl))-4-(N-(phenylsulfonyl)(methylamino))butyl)-spiro(1-oxo-2-methylisoindoline-3,4'-piperidine);
1'-(3-((R,S)-Phenyl)-4-(N-(benzyl)(methylamino))butyl)-spiro(2,3-dihydrobenzothiophene-3,4'-piperidine);
1'-(3-((RS)-Phenyl)-4-(N-(benzyl)(methylamino))butyl)-spiro(2,3-dihydrobenzothiophene-3,4'-piperidine)-1-oxide;
1'-(3-((R,S)-Phenyl)-4-(N-(benzyl)(methylamino))butyl)-spiro(2,3-dihydrobenzothiophene-3,4'-piperidine)-1,1-dioxide;

N-(2-(3-Chorophenyl)-5-(spiro(benzo[b]thiophene-3(2H), 4'-piperidin)1'-yl)pentyl)-N-methylbenzenesulfonamide;

N-(2-(3-Chlorophenyl)-5-(spiro(benzo[b]thiophene-3(2H), 4'-piperidin)-1-oxide-1'-yl)pentyl)-N-methylbenzenesulfonamide;

N-(2-(3-Chlorophenyl)-5-(spiro(benzo[b]thiophene-3(2H), 4'piperidin)-1,1-dioxide-1'-yl)pentyl)-N-methylbenzenesulfonamide;

N-Methyl-N-(2-phenyl-2-(spiro(benzo[b]thiophene-3(2H), 4'-piperidin)1'-yl)ethyl)benzenesulfonamide;

N-Methyl-N-(2-phenyl-2-(spiro(benzo[b]thiophene-3(2H), 4'-piperidin)-1-oxide-1'-yl)ethyl)benzenesulfonamide;

N-Methyl-N-[2-(phenyl-2-(spiro(benzo[b]thiophene-3(2H), 4'-piperidin)-1,1-dioxide-1'-yl)ethyl)benzenesulfonamide;

N-Methyl-N-(3-phenyl-5-(spiro(benzo[b]thiophene-3(2H), 4'-piperidin)1'-yl)pentyl)benzenesulfonamide;

N-Methyl-N-(3-phenyl-5-spiro(benzo[b]thiophene-3(2H), 4'-piperidin)-1-oxide-1'-yl)pentyl)benzenesulfonamide;

N-Methyl-N-(3-phenyl-5-(spiro(benzo[b]thiophene-3(2H), 4'-piperidin)-1,1-dioxide-1'-yl)pentyl)benzenesulfonamide;

N-Methyl-N-(3-phenyl-5-(spiro(benzo[b]thiophene-3(2H), 4'-piperidin)1'-yl)pentyl)benzamide;

N-Methyl-N-(3-phenyl-5-(spiro(benzo[b]thiophene-3(2H), 4'-piperidin)1-oxide-1'-yl)pentyl)benzamide;

N-Methyl-N-(3-phenyl-5-spiro(benzo[b]thiophene-3(2H), 4'-piperidin)1-oxide-1'-yl)pentyl)benzenesulfonamide;

N-Methyl-N-(3-phenyl-5-spiro(benzo[b ]thiophene-3(2H[), 4'-piperidin)-1,1-dioxide-1'-yl)pentyl)benzenesulfonamide;

N-Methyl-N-(3-phenyl-5-(spiro(benzo[b]thiophene-3(2H), 4'-piperidin)1'-yl)pentyl)benzamide;

N-Methyl-N-(3-phenyl-5-(spiro(benzo[b]thiophene-3(2H), 4'-piperidin)1-dioxide-1'-yl)pentyl)benzamide;

N-Methyl-N-(3-phenyl-5-(spiro(benzo[b]thiophene-3(2H), 4'-piperidin)-1,1-dioxide-1'-yl)pentyl)benzamide;

N-Methyl-N-(2-phenyl-3-(spiro(benzo[b]thiophene-3(2H), 4'-piperidin)1-oxide-1'-yl)propyl)benzenesulfonamide;

N-Methyl-N-(2-phenyl-3-(spiro(benzo[b]thiophene-3(2H), 4'-piperidin)-1,1-dioxide-1'-yl)propyl)benzenesulfonamide;

N-(2-Benzyl-3-(spiro(benzo[b]thiophene-3(2H),4'-piperidin)1'-yl)propyl)-N-methylbenzenesulfonamide;

N-(2-Benzyl-3-(spiro(benzo[b]thiophene-3(2H),4'-piperidin)1-oxide-1'-yl)propyl)-N-methylbenzenesulfonamide;

N-(2-Benzyl-3-(spiro(benzo[b]thiophene-3(2H),4'-piperidin)-1,1-dioxide-1'-yl)propyl)-N-methylbenzenesulfonamide;

N-Methyl-N-(2-methyl-2-phenyl -4-(spiro(benzo[b]thiophene-3(2H),4'-piperidin)1'-yl)butyl)benzenesulfonamide;

N-Methyl-N-(2-methyl-2-phenyl-4-(spiro(benzo[b]thiophene-3(2H),4'-piperidin)-1-oxide-1'-yl)butyl)benzenesulfonamide;

N-Methyl-N-(2-methyl-2-phenyl-4-(spiro(benzo[b]thiophene-3(2H),4'-piperidin)-1,1-dioxide-1'-yl)butyl)benzenesulfonamide;

1'-(3-((S)-(3,4-Dichlorophenyl))-4-(N-(phenylmethylsulfonyl)(methylamino))-butyl)-spiro(2,3-dihydrobenzothiophene-3,4'-piperidine);

1'-(3-((S)-(3,4-Dichlorophenyl))-4-(N-(quinoline-8-sulfonyl)(methylamino))-butyl)-spiro(2,3-dihydrobenzothiophene-3,4'-piperidine);

1'-(3-((R)-(3,4-Dichlorophenyl))-4-(N-(benzenesulfonyl)(methylamino))-butyl)-spiro(2,3-dihydrobenzothiophene-3,4'-piperidine);

1'-(3-((R)-(3,4-Dichlorophenyl))-4-(N-(thiophene-2-sulfonyl)(methylamino))-butyl)-spiro(2,3-dihydrobenzothiophene-3,4'-piperidine);

1'-(3-((S)-(3,4-Dichlorophenyl))-4-(N-(benzenesulfonyl)-(methylamino))-butyl)-spiro(2,3-dihydrobenzothiophene-3,4'-piperidine)-1,1-dioxide;

1'-(3-((S)-(4-Chorophenyl))-4-(N-(benzenesulfonyl)-(methylamino))-butyl)-spiro(2,3-dihydrobenzothiophene-3,4'-piperidine)-1-oxide;

1'-(3-((S)-(4-Chlorophenyl))-4-(N-(methanesulfonyl)-(methylamino))-butyl)-spiro(2,3-dihydrobenzothiophene-3,4'-piperidine)-1-oxide;

1'-(3-((S)-(4-Chlorophenyl))-4-(N-(phenylmethylsulfonyl)-(methylamino))butyl)-spiro(2,3-dihydrobenzothiophene-3,4'-piperidine)-1-oxide;

1'-(3-((S)-(4-Chorophenyl))-4-(N-(quinoline-8-sulfonyl)-(methylamino))-butyl)-spiro(2,3-dihydrobenzothiophene-3,4'-piperidine)-1-oxide;

1'-(3-((1)-(4-Chorophenyl))-4-(N-(benzenesulfonyl)-(methylamino))-butyl)-spiro(2,3-dihydrobenzothiophene-3,4'-piperidine)1-oxide; 1'-(3-((R)-(4-Chlorophenyl))-4-(N-(thiophene-2-sulfonyl)-(methylamino))-butyl)-spiro(2,3-dihydrobenzothiophene-3,4'-piperidine)1-oxide;

1-(3-((S)-(4-Chlorophenyl))-4-(N-(quinoline-3-sulfonyl)-(methylamino))-butyl)-spiro(2,3-dihydrobenzothiophene-3,4'-piperidine)-1-oxide;

1'-(3-((S)-(4-Chlorophenyl))-4-(N-(phenoxycarbonyl)-(methylamino))-butyl)-spiro(2,3-dihydrobenzothiophene-3,4'-piperidine)1-oxide;

1'-(3-((S)-(4-Chlorophenyl))-4-(N-(phenylaminocarbonyl)-(methylamino))-butyl)-spiro(2,3-dihydrobenzothiophene-3,4'-piperidine)-1-oxide;

1'-(3-((S)-(4-Chlorophenyl))-4-(N-(benzoylformyl)-(methylamino))butyl)-spiro(2,3-dihydrobenzothiophene-3,4'-piperidine)1-oxide;

1'-(3-((S)-(4-Chlorophenyl))-4-(N-(pyridine-3-sulfonyl)-(methylamino))-butyl)-spiro(2,3-dihydrobenzothiophene-3,4'-piperidine)-1-oxide;

1'-(3-((S)-(3,4-Dichlorophenyl))-4-(N-(4-chlorobenzenesulfonyl)-(methylamino))butyl)-spiro(2,3-dihydrobenzothiophene-3,4'-piperidine)1-oxide;

1'-(3-((S)-(3,4-Dichlorophenyl))-4-(N-(3-nitrobenzenesulfonyl)-(methylamino))butyl)-spiro(2,3-dihydrobenzothiophene-3,4'-piperidine)-1,1-dioxide;

1'-(3-((S)-(3,4-Dichlorophenyl))-4-(N-(3-nitrobenzenesulfonyl)-(methylamino))butyl)-spiro(2,3-dihydrobenzothiophene-3,4'-piperidine)-1,1-dioxide;

1-(3-((S)-(3,4-Dichlorophenyl))-4-(N-(2-chlorobenzenesulfonyl)-(methylamino))butyl)-spiro(2,3-dihydrobenzothiophene-3,4'-piperidine)-1-oxide;

1'-(3-((S)-(3,4–1Dichlorophenyl))-4-(N-(3-chlorobenzenesulfonyl)-(methylamino))butyl)-spiro(2,3-dihydrobenzothiophene-3,4'-piperidine)-1 -oxide;

1'-(3-((S)-(3,4-Dichlorophenyl))-4-(N-(2,3,4,5,6-pentafluorobenzenesulfonyl)-(methylamino))butyl)-spiro(2,3-dihydrobenzothiophene-3,4'-piperidine)-1-oxide;

1'-(3-((S)-(3,4-Dichlorophenyl))-4-(N-(4-biphenylsulfonyl)-(methylamino))butyl)-spiro(2,3-dihydrobenzothiophene-3,4'-piperidine)-1-oxide;

1'-(3-((S)-(3,4-]Dichlorophenyl))-4-(N-(4-methoxybenzenesulfonyl)-(methylamino))butyl)-spiro(2,3-dihydrobenzothiophene-3,4'-piperidine)1-oxide;

(+/−) N-methyl-N-phenylsulfonyl-2-(3-chloro-4-benzyloxy-4-(spiro[2,3-dihydrobenzothiophene-3,4'-piperdin-1'-yl)butanamine;

(+/−) N-methyl-N-phenylsulfonyl-2-(3-chloro-4-benzyloxy-4-(spiro[2,3-dihydrobenzothiophene-3,4'-piperdin-1'-yl)butamine, S-oxide;

(+/-) N-methyl-N-phenylsulfonyl-2-(3-chloro-4-benzyloxy)-4-(spiro[2,3-dihydrobenzothiophene-3'-piperdin-1'-yl)butamine, S-dioxide;

(+/-) N-methyl-N-phenylsulfonyl-2-(3-chloro-4-hydroxy)-4-(spiro[2,3-dihydrobenzothiophene-3,4'-piperdin-1'-yl)butanamine;

(+/-) N-methyl-N-phenylsulfonyl-2-(3-chloro-4-hydroxy)-4-(spiro[2,3-dihydrobenzothiophene-3,4'-piperdin-1'-yl)butanamine, S-oxide;

(+/-) N-methyl-N-phenylsulfonyl-2-(3-chloro-4-hydroxy)-4-(spiro[2,3-dihydrobenzothiophene-3,4'-piperdin-1'-yl)butanamine, S-dioxide;

(+/-) N-methyl-N-phenylsulfonyl-2-(4-benzyloxy)-4-(spiro[2,3-dihydrobenzothiophene-3,4'-piperdin-1'-yl)butanamine;

(+/-) N-methyl-N-phenylsulfonyl-2-(4-benzyloxy)-4-(spiro[2,3-dihydrobenzothiophene-3,4'-piperdin-1'-yl)butanamine, S-oxide;

(+/-) N-ethyl-N-phenylsulfonyl-2-(4-hydroxy)-4-(spiro[2,3-dihydrobenzothiophene-3,4'-piperdin-1'-yl)butanamine;

(+/-) N-methyl-N-phenylsulfonyl-2-(4-benzyloxy)-4-(spiro[2,3-dihydrobenzothiophene-3,4'-piperdin-1'-yl)butanamine,S-oxide;

(+/-) N-methyl-N-phenylsulfonyl-2-(4-benzyloxy)-4-(spiro[2,3-dihydrobenzothiophene-3,4'-piperdin-1'-yl)butamine,S-dioxide; N-phenylsulfonyl-2(S)-(3,4-dichloro)-4-(spiro[2,3-dihydrobenzothiophene-3,4'-piperdin-1'-yl)butanamine;

N-phenylsulfonyl-2(S)-(3,4-dichloro)-4-(spiro[2,3-dihydrobenzothiophene-3,4'-piperdin-1'-yl)butanamine, S-oxide;

and pharmaceutically acceptable salts thereof.

7. A method for treating infection by HIV, delaying of the onset of AIDS, or treating AIDS comprising the administration to a patient of an effective amount of a compound of the Formula II:

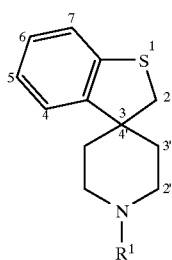

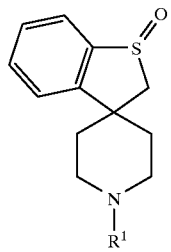

or

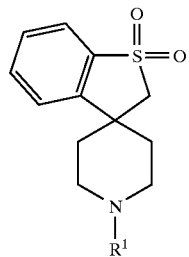

wherein the optional substitutents residing at the positions numbered #2, #2', #3', #4, #5, #6, or #7 on the above structures, are independently selected from the group consisting of:
(a) hydroxy,
(b) oxo,
(c) cyano,
(d) chloro,
(e) fluoro
(f) -$CF_3$,
(g) -phenyl;

$R_1$ is:

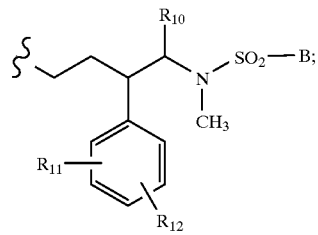

where B is phenyl, or mono di or trisubstituted phenyl, wherein the substitutents on phenyl are independently selected from:
chloro, fluoro, methyl, phenyl or $CF_3$;
$R_1$ is selected from: hydrogen, $C_{1-3}$alkyl, and phenyl;
$R_{11}$ and $R_{12}$ are independently selected from:
hydrogen, halogen, methyl, phenyl or $CF_3$;
and pharmaceutically acceptable salts thereof.

8. The method of claim 7 wherein the compound of Formula II, B is phenyl, or mono di or trisubstituted phenyl wherein the substitutents on phenyl are independently selected from:
chloro, methyl, phenyl and -$CF_3$.

9. The method of claim 7 wherein the compound of Formula II, B is unsubstituted phenyl, 3-chlorophenyl or 3-fluorophenyl.

10. The method of claim 7 wherein the compound is selected from the group consisting of:
1'-(3-((S)-(3-Chlorophenyl))-4-(N-(phenylsulfonyl)(methylamino))butyl)-spiro(2,3-dihydrobenzothiophene-3,4'-piperidine);
1'-(3-((S)-(3-Chlorophenyl))-4-(N-(phenylsulfonyl)(methylamino))butyl)-spiro(2,3-dihydrobenzothiophene-3,4'-1piperidine)-1-oxide;
1'-(3-((S)-(3-Chlorophenyl))-4-(N-(phenylsulfonyl)(methylamino))butyl)-spiro(2,3-dihydrobenzothiophene-3,4'-piperidine)-1,1-dioxide;
1'-(3-((R,S)-(Phenyl))-4-(N-(phenylsulfonyl)(methylamino))butyl)-spiro(2,3-dihydrobenzothiophene-3,4'-piperidine);

1'-(3-((R,S)-(3-Thienyl))-4-(N-(phenylsulfonyl)
(methylamino))butyl)-spiro(2,3-dihydrobenzothiophene-
3,4'-piperidine);

1'-(3-((R,S)-(2-Thienyl))-4-(N-(phenylsulfonyl)
(methylamino))butyl)-spiro(2,3-dihydrobenzothiophene-
3,4'-piperidine);

1'-(3-((S)-(4-Fluorophenyl))-4-(N-(phenylsulfonyl)
(methylamino))butyl)-spiro(2,3-dihydrobenzothiophene-
3,4'-piperidine);

1'-(3-((R,S)-(3,65-Dichlorophenyl))-4-(N-(phenylsulfonyl)
(methylamino))-butyl)-spiro(2,3-
dihydrobenzothiophene-3,4'-piperidine);

1'-(3-((S)-(3,4-Dichlorophenyl))-4-(N-(phenylsulfonyl)
(ethylamino))butyl)-spiro(2,3-dihydrobenzothiophene-3,
4'-piperidine);

1'-(3-((R,S)-(Phenyl))-4-(N-(phenylsulfonyl)
(methylamino))butyl)-spiro(2,3-dihydrobenzothiophene-
3,4'-piperidine)-1-oxide;

1'-(3-((R,S)-(3-Thienyl))-4-(N-(phenylsulfonyl)
(methylamino))butyl)-spiro(2,3-dihydrobenzothiophene-
3,4'-piperidine)1-oxide;

1'-(3-((R,S)-(2-Thienyl))-4-(N-(phenylsulfonyl)
(methylamino))butyl)-spiro(2,3-dihydrobenzothiophene-
3,4'-piperidine)-1-oxide;

1'-(3-((S)-(4-Fluorophenyl))-4-(N-(phenylsulfonyl)
(methylamino))butyl)-spiro(2,3-dihydrobenzothiophene-
3,4'-piperidine)-1-oxide;

1'-(3-((R,S)-(3,5-Dichlorophenyl))-4-(N-(phenylsulfonyl)
(methylamino))-butyl)-spiro(2,3-
dihydrobenzothiophene-3,4'-piperidine)-1-oxide;

1'-(3-((S)-(3,4–1Dichlorophenyl))-4-(N-(phenylsulfonyl)
(ethylamino))butyl)-spiro(2,3-dihydrobenzothiophene-3,
4'-piperidine)1-oxide;

1'-(3-((R,S)-(Phenyl))-4-(N-(phenylsulfonyl)
(methylamino))butyl)-spiro(2,3-dihydrobenzothiophene-
3,4'-piperidine)-1,1-dioxide;

1'-(3-((R,S)-(2-Chlorolphenyl))-4-(N-(phenylsulfonyl)
(methylamino))butyl)-spiro(2,3-dihydrobenzothiophene-
3,4'-piperidine)-1,1-dioxide;

1'-(3-((R,S)-(3-Thienyl))-4-(N-(phenylsulfonyl)
(methylamino))butyl)-spiro(2,3-dihydrobenzothiophene-
3,4'-piperidine)-1,1-dioxide;

1'-(3-((R,S)-(2-Thienyl))-4-(N-(phenylsulfonyl)
(methylamino))butyl)-spiro(2,3-dihydrobenzothiophene-
3,4'-piperidine)-1,1-dioxide;

1'-(3-((S)-(4-Fluorophenyl))-4-(N-(phenylsulfonyl)
(methylamino))butyl)-spiro(2,3-dihydrobenzothiophene-
3,4'-piperidine)-1,1-dioxide;

1'-(3-((R,S)-(3,5-Dichlorophenyl))-4-(N-(phenylsulfonyl)
(methylamino))-butyl)-spiro(2,3-
dihydrobenzothiophene-3,4'-piperidine)-1,1-dioxide;

1'-(3-((S)-(3,4-Dichlorophenyl))-4-(N-(phenylsulfonyl)
(ethylamino))butyl)-spiro(2,3-dihydrobenzothiophene-3,
4'-piperidine)-1,1-dioxide;

1'-(3-((R,S)-Phenyl)-4-(N-(phenylacetyl)(methylamino))
butyl)-spiro(2,3-dihydrobenzothiophene-3,4'-piperidine);

1'-(3-((R,S)-Phenyl)-4-(N-(phenylacetyl)(methylamino))
butyl)-spiro(2,3-dihydrobenzothiophene-3,4'-piperidine)
1-oxide;

1'-(3-((R,S)-Phenyl)-4-(N-(phenylacetyl)(methylamino))
butyl)-spiro(2,3-dihydrobenzothiophene-3,4'-piperidine)-
1,1-dioxide;

1'-(3-((1R,S)-Phenyl)-4-(N-((R)-a-methyl phenylacetyl)
(methylamino))-butyl)-spiro(2,3-
dihydrobenzothiophene-3,4'-piperidine);

1'-(3-((R,S)-Phenyl)-4-(N-((R)-a-methylphenylacetyl)
(methylamino))-butyl)-spiro(2,3-
dihydrobenzothiophene-3,4'-piperidine)1-oxide;

1'-(3-((R,S)-Phenyl)-4-(N-((R)-a-methyl phenylacetyl)
(methylamino))-butyl)-spiro(2,3-
dihydrobenzothiophene-3,4'-piperidine)-1,1-dioxide;

1'-(3-((R,S)-Phenyl)-4-(N-((S)-a-methyl phenylacetyl)
(methylamino))-butyl)-spiro(2,3-
dihydrobenzothiophene-3,4'-piperidine);

1'-(3-((RS)-Phenyl)-4-(N-((S)-a-methylphenylacetyl)
(methylamino))-butyl)-spiro(2,3-
dihydrobenzothiophene-3,4'-piperidine)-1-oxide;

1'-(3-((R,S)-Phenyl)-4-(N-((S)-a-methyl phenylacetyl)
(methylamino))-butyl)-spiro(2,3-
dihydrobenzothiophene-3,4'-piperidine)-1,1-dioxide;

1'-(3-((S)-(3-Chlorophenyl))-4-(N-(phenylsulfonyl)
(methylamino))butyl)-spiro(indoline-3,4'-piperidine);

1'-(3-((S)-(3-Chlorophenyl))-4-(N-(phenylsulfonyl)
(methylamino))butyl)-spiro(1-oxoisoindoline-3,4'-
piperidine);

1'-(3-((S)-(3-Chlorophenyl))-4-(N-(phenylsulfonyl)
(methylamino))butyl)-spiro(1-oxo-2-methylisoindoline-
3,4'-piperidine);

1'-(3-((R,S)-Phenyl)-4-(N-(benzyl)(2methylamino))butyl)-
spiro(2,3-dihydrobenzothiophene-3,4'-piperidine);

1'-(3-((R,S)-Phenyl)-4-(N-(benzyl)(methylamino))butyl)-
spiro(2,3-dihydrobenzothiophene-3,4'-piperidine)-1-
oxide;

1'-(3-((R,S)-Phenyl)-4-(N-(benzyl)(methylamino))butyl)-
spiro(2,3-dihydrobenzothiophene-3,4'-piperidine)-1,1-
dioxide;

N-(2-(3-Chlorophenyl)-5-(spiro(benzo[b]thiophene-3(2H),
4'-piperidin-1'-yl)pentyl)-N-methylbenzenesulfonamide;

N-(2-(3-Chlorophenyl)-5-(spiro(benzo[b]thiophene-3(2H),
4'-piperidin)1-oxide-1'-yl)pentyl)-N-
methylbenzenesulfonamide;

N-(2-(3-Chlorophenyl)-5-(spiro(benzo[b]thiophene-3(2H),
4'-piperidin)-1,1-dioxide-1'-yl)pentyl)-N-
methylbenzenesulfonamide;

N-Methyl-N-(2-phenyl-2-(spiro(benzo[b]thiophene-3(2H),
4'-piperidin)1'-yl)ethyl)benzenesulfonamide;

N-Methyl-N-(2-phenyl-2-(spiro(benzo[b]thiophene-3(2H),
4'-piperidin)1-oxide-1'-yl)ethyl)benzenesulfonamide;

N-Methyl-N-[2-(phenyl-2-(spiro(benzo[b]thiophene-3(2H),
4'-piperidin)-1,1-dioxide-1'-yl)ethyl)
benzenesulfonamide;

N-Methyl-N-(3-phenyl-5-(spiro(benzo[b]thiophene-3(2H),
4'-piperidin)1'-yl)pentyl)benzenesulfonamide;

N-Methyl-N-(3-phenyl-5-spiro(benzo[b]thiophene-3(2H),
4'-piperidin)1-oxide-1'-yl)pentyl)benzenesulfonamide;

N-Methyl-N-(3-phenyl-5-(spiro(benzo[b]thiophene-3(2H),
4'-piperidin)-1,1-dioxide-1'-yl)pentyl)
benzenesulfonamide;

N-Methyl-N-(3-phenyl-5-(spiro(benzo[b]thiophene-3(2H),
4'-piperidin)1'-yl)pentyl)benzamide;

N-Methyl-N-(3-phenyl-5-spiro(benzo[b]thiophene-3(2),4'-
piperidin)1-oxide-1'-yl)pentyl)benzamide;

N-Methyl-N-(3-phenyl-5-spiro(benzo[b]thiophene-3(2H),
4'-piperidin)1-oxide-1'-yl)pentyl)benzenesulfonamide;

N-Methyl-N-(3-phenyl-5-spiro(benzo[b]thiophene-3(2H),
4'-piperidin)-1,1-dioxide-1'-yl)pentyl)
benzenesulfonamide;

N-Methyl-N-(3-phenyl-5-(spiro(benzo[b]thiophene-3(2H),
4'-piperidin)1'-yl)pentyl)benzamide;

N-Methyl-N-(3-phenyl-5-(spiro(benzo[b]thiophene-3(2H),
4'-piperidin)-1-oxide-1'-yl)pentyl)benzamide;

N-Methyl-N-(3-phenyl-5-(spiro(benzo[b]thiophene-3(2H),
4'-piperidin)-1,1-dioxide-1'-yl)pentyl)benzamide;

N-Methyl-N-(2-phenyl-3-(spiro(benzo[b]thiophene-3(2H),
4'-piperidin)-1-oxide-1'-yl)propyl)benzenesulfonamide;

N-Methyl-N-(2-phenyl-3-(spiro(benzo[b]thiophene-3(2H), 4'-1piperidin)-1,1-dioxide-1'-yl)propyl) benzenesulfonamide;

N-(2-]Benzyl-3-(spiro(benzo[b]thiophene-3(2H),4'-piperidin)1'-yl)propyl)-N-methylbenzenesulfonamide;

N-(2-Benzyl-3-(spiro(benzo[b]thiophene-3(2H),4'-piperidin)-1-oxide-1'-yl)propyl)-N-methylbenzenesulfonamide;

N-(2-Benzyl-3-(spiro(benzo[b]thiophene-3(2H),4'-piperidin)-1,1-dioxide-1'-yl)propyl)-N-methylbenzenesulfonamide;

N-Methyl-N-(2-methyl-2-phenyl-4-(spiro(benzo[b]thiophene-3(2H),4'-piperidin)1'-yl)butyl) benzenesulfonamide;

N-Methyl-N-(2-methyl-2-phenyl-4-(spiro(benzo[b]thiophene-3(2H), 4'-piperidin)-1-oxide-1'-yl)butyl) benzenesulfonamide;

N-Methyl-N-(2-methyl-2-phenyl-4-(spiro(benzo[b]thiophene-3(2H),4'-piperidin)-1,1-dioxide-1'-yl)butyl) benzenesulfonamide;

1'-(3-((S)-(3,4-Dichlorophenyl))-4-(N-(phenylmethylsulfonyl)(methylamino))-butyl)-spiro(2,3-dihydrobenzothiophene-3,4'-piperidine);

1'-(3-((S)-(3,4-Dichlorophenyl))-4-(N-(quinoline-8-sulfonyl) (methylamino))-butyl)-spiro(2,3-dihydrobenzothiophene-3,4'-piperidine);

1'-(3-((R)-(3,4-Dichlorophenyl))-4-(N-(benzenesulfonyl) (methylamino))-butyl)-spiro(2,3-dihydrobenzothiophene-3,4'-piperidine);

1'-(3-((R)-(3,4-Dichlorophenyl))-4-(N-(thiophene-2-sulfonyl) (methylamino))-butyl)-spiro(2,3-dihydrobenzothiophene-3,4'-piperidine);

1'-(3-((S)-(3,4-Dichlorophenyl))-4-(N-(benzenesulfonyl)-(methylamino))-butyl)-spiro(2,3-dihydrobenzothiophene-3,4'-piperidine)-1,1-dioxide;

1'-(3-((S)-(4-Chlorophenyl))-4-(N-(benzenesulfonyl)-(methylamino))-butyl)-spiro(2,3-dihydrobenzothiophene-3,4'-piperidine)-1-oxide;

1'-(3-((S)-(4-Chlorophenyl))-4-(N-(methanesulfonyl)-(methylamino))-butyl)-spiro(2,3-dihydrobenzothiophene-3,4'-piperidine)-1-oxide;

1'-(3-((S)-(4-Chlorophenyl))-4-(N-(phenylmethylsulfonyl)-(methylamino))butyl)-spiro(2,3-dihydrobenzothiophene-3,4'-piperidine)1-oxide;

1'-(3-((S)-(4-Chlorophenyl))-4-(N-(quinoline-8-sulfonyl)-(methylamino))-butyl)-spiro(2,3-dihydrobenzothiophene-3,4'-piperidine)-1-oxide;

1'-(3-((R)-(4-Chlorophenyl))-4-(N-(benzenesulfonyl)-(methylamino))-butyl)-spiro(2,3-dihydrobenzothiophene-3,4'-piperidine)-1-oxide;

1'-(3-((R)-(4-Chlorophenyl))-4-(N-(thiophene-2-sulfonyl)-(methylamino))-butyl)-spiro(2,3-dihydrobenzothiophene-3,4'-piperidine)1-oxide;

1'-(3-((S)-(4-Chlorophenyl))-4-(N-(quinoline-3-sulfonyl)-(methylamino))-butyl)-spiro(2,3-dihydrobenzothiophene-3,4'-piperidine)-1-oxide;

1'-(3-((S)-(4-Chlorophenyl))-4-(N-(phenoxycarbonyl)-(methylamino))-butyl)-spiro(2,3-dihydrobenzothiophene-3,4'-piperidine)1-oxide;

1'-(3-((S)-(4-Chlorophenyl))-4-(N-(phenylaminocarbonyl)-(methylamino))-butyl)-spiro(2,3-dihydrobenzothiophene-3,4'-piperidine)-1-oxide;

1'-(3-((S)-(4-Chlorophenyl))-4-(N-(benzoylformyl)-(methylamino))butyl)-spiro(2,3-dihydrobenzothiophene-3,4'-piperidine)1-oxide;

1'-(3-((S)-(4-Chlorophenyl))-4-(N-(pyridine-3-sulfonyl)-(methylamino))-butyl)-spiro(2,3-dihydrobenzothiophene-3,4'-piperidine)1-oxide;

1'-(3-((S)-(3,4-Dichlorophenyl))-4-(N-(4-chlorobenzenesulfonyl)-(methylamino))butyl)-spiro(2,3-dihydrobenzothiophene-3,4'-piperidine)-1-oxide;

1'-(3-((S)-(3,4-Dichlorophenyl))-4-(N-(3-nitrobenzenesulfonyl)-(methylamino))butyl)-spiro(2,3-dihydrobenzothiophene-3,4'-piperidine)-1,1-dioxide;

1'-(3-((S)-(3,4-Dichlorophenyl))-4-(N-(4-nitrobenzenesulfonyl)-(methylamino))butyl)-spiro(2,3-dihydrobenzothiophene-3.4'-piperidine)-1,1-dioxide;

1'-(3-((S)-(3,4-Dichlorophenyl))-4-(N-(2-chlorobenzenesulfonyl)-(methylamino))butyl)-spiro(2,3-dihydrobenzothiophene-3,4'-piperidine)-1-oxide;

1'-(3-((S)-(3,4-Dichlorophenyl))-4-(N-(3-chlorobenzenesulfonyl)-(methylamino))butyl)-spiro(2,3-dihydrobenzothiophene-3,4'-piperidine)1-oxide;

1'-(3-((S)-(3,4-Dichlorophenyl))-4-(N-(2,3,4,5,6-pentafluorobenzenesulfonyl)-(methylamino))butyl)-spiro(2,3-dihydrobenzothiophene-3,4'-piperidine)-1-oxide;

1'-(3-((S)-(3,4-Dichlorophenyl))-4-(N-(4-biphenylsulfonyl)-(methylamino))butyl)-spiro(2,3-dihydrobenzothiophene-3,4'-piperidine)1-oxide;

1'-(3-((S)-(3,4-Dichlorophenyl))-4-(N-(4-methoxybenzenesulfonyl)-(methylamino))butyl)-spiro(2, 3-dihydrobenzothiophene-3,4'-piperidine)1-oxide;

(+/-) N-methyl-N-phenylsulfonyl-2-(3-chloro-4-benzyloxy)-4-(spiro[2,3-dihydrobenzothiophene-3,4'-piperdin-1'-yl)butanamine;

(+/-) N-methyl-N-phenylsulfonyl-2-(3-chloro-4-benzyloxy)-4-(spiro[2,3-dihydrobenzothiophene-3,4'-piperdin-1'-yl)butamine, S-oxide;

(+/-) N-methyl-N-phenylsulfonyl-2-(3-chloro-4-benzyloxy)-4-(spiro[2,3-dihydrobenzothiophene-3'-piperdin-1'-yl)butamine, S-dioxide;

(+/-) N-methyl-N-phenylsulfonyl-2-(3-chloro-4-hydroxy)-4-(spiro[2,3-dihydrobenzothiophene-3,4'-piperdin-1'-yl) butanamine;

(+/-) N-methyl-N-phenylsulfonyl-2-(3-chloro-4-hydroxy)-4-(spiro[2,3-dihydrobenzothiophene-3,4'-piperdin-1'-yl) butanamine, S-oxide;

(+/-) N-methyl-N-phenylsulfonyl-2-(3-chloro-4-hydroxy)-4-(spiro[2,3-dihydrobenzothiophene-3,4'-piperdin-1'-yl) butanamine, S-dioxide;

(+/-) N-methyl-N-phenylsulfonyl-2-(4-benzyloxy)-4-(spiro[2,3-dihydrobenzothiophene-3,4'-piperdin-1'-yl) butanamine;

(+/-) N-methyl-N-phenylsulfonyl-2-(4-benzyloxy)-4-(spiro[2,3-dihydrobenzothiophene-3,4'-piperdin-1'-yl) butanamine, S-oxide;

(+/-) N-methyl-N-phenylsulfonyl-2-(4-hydroxy)-4-(spiro[2,3-dihydrobenzothiophene-3,4'-piperdin-1'-yl) butanamine;

(+/-) N-methyl-N-phenylsulfonyl-2-(4-benzyloxy)-4-(spiro[2,3-dihydrobenzothiophene-3,4'-piperdin-1'-yl) butanamine,S-oxide;

(+/-) N-methyl-N-phenylsulfonyl-2-(4-benzyloxy)-4-(spiro[2,3-dihydrobenzothiophene-3,4'-piperdin-1'-yl) butamine,S-dioxide;

N-phenylsulfonyl-2(S)-(3,4-dichloro-4-(spiro[2,3-dihydrobenzothiophene-3,4'-piperdin-1'-yl)butanamine;

N-phenylsulfonyl-2(S)-(3,4-dichloro-4-(spiro[2,3-dihydrobenzothiophene-3,4'-piperdin-1'-yl)butanamine, S-oxide;

and pharmaceutically acceptable salts thereof.

\* \* \* \* \*